US012806287B2

(12) United States Patent
Panzner et al.

(10) Patent No.: US 12,806,287 B2
(45) Date of Patent: Nov. 24, 2026

(54) NUCLEIC ACID COMPOSITIONS COMPRISING A MULTIVALENT ANION, SUCH AS AN INORGANIC POLYPHOSPHATE, AND METHODS FOR PREPARING, STORING AND USING THE SAME

(71) Applicant: BIONTECH SE, Mainz (DE)

(72) Inventors: Steffen Panzner, Halle (DE); Gholan-Martin Hamraz, Halle (DE); Martin Kirchberg, Halle (DE); Christian Reinsch, Halle (DE); Patrick Kreideweiß, Halle (DE)

(73) Assignee: BIONTECH SE, Mainz, GA (US)

( * ) Notice: Subject to any disclaimer, the term of this patent is extended or adjusted under 35 U.S.C. 154(b) by 219 days.

(21) Appl. No.: 18/853,663

(22) PCT Filed: Apr. 5, 2023

(86) PCT No.: PCT/EP2023/059066
§ 371 (c)(1),
(2) Date: Oct. 2, 2024

(87) PCT Pub. No.: WO2023/194508
PCT Pub. Date: Oct. 12, 2023

(65) Prior Publication Data

US 2025/0222132 A1 Jul. 10, 2025

(30) Foreign Application Priority Data

Apr. 5, 2022 (WO) ................ PCT/EP2022/059023

(51) Int. Cl.
*A61K 48/00* (2006.01)
*A61K 9/1272* (2025.01)
(Continued)

(52) U.S. Cl.
CPC ........ *A61K 48/0041* (2013.01); *A61K 9/1272* (2013.01); *A61K 39/39* (2013.01); *A61K 48/0091* (2013.01); *C12N 15/88* (2013.01); *A61K 2039/53* (2013.01); *A61K 2039/55555* (2013.01)

(58) Field of Classification Search
CPC .. A61K 48/0041; A61K 9/1272; A61K 39/39; A61K 39/00; A61K 48/0091; A61K 2039/55555; C12N 15/88
See application file for complete search history.

(56) References Cited

FOREIGN PATENT DOCUMENTS

| | | | | |
|---|---|---|---|---|
| EP | 2760477 | * 8/2018 | ............ | A61K 47/60 |
| WO | 2016/115198 | 7/2016 | | |

(Continued)

OTHER PUBLICATIONS

The International Search Report (ISR) with Written Opinion for PCT/EP2023/059066 dated Jun. 21, 2023, pp. 1-13.

*Primary Examiner* — Trevor Love
(74) *Attorney, Agent, or Firm* — McDonnell Boehnen Hulbert & Berghoff

(57) ABSTRACT

The present disclosure relates generally to the field of nucleic acid (such as DNA or RNA, in particular mRNA or inhibitory RNA, e.g., siRNA) compositions comprising a multivalent anion (e.g., an inorganic polyphosphate), methods for preparing and storing such compositions, and the use of such compositions in therapy.

22 Claims, 10 Drawing Sheets

Specification includes a Sequence Listing.

(51) Int. Cl.

| | |
|---|---|
| ***A61K 39/00*** | (2006.01) |
| ***A61K 39/39*** | (2006.01) |
| ***C12N 15/88*** | (2006.01) |

(56) References Cited

FOREIGN PATENT DOCUMENTS

| | | |
|---|---|---|
| WO | 2017/075531 | 5/2017 |
| WO | 2017/212494 | 12/2017 |
| WO | 2020/070040 | 4/2020 |
| WO | 2021/191265 | 9/2021 |

* cited by examiner

Fig. 1 (contin.)

Fig. 2
A
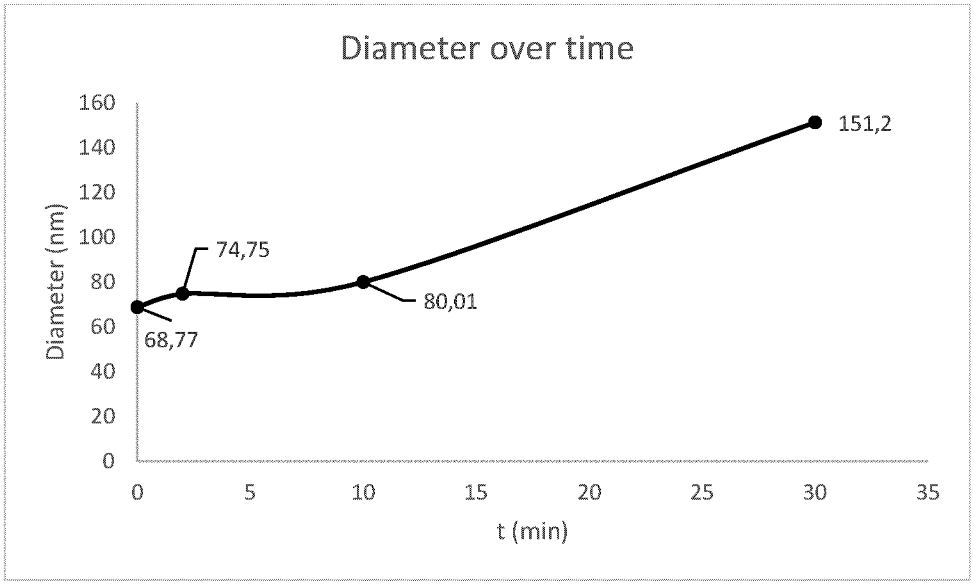
B
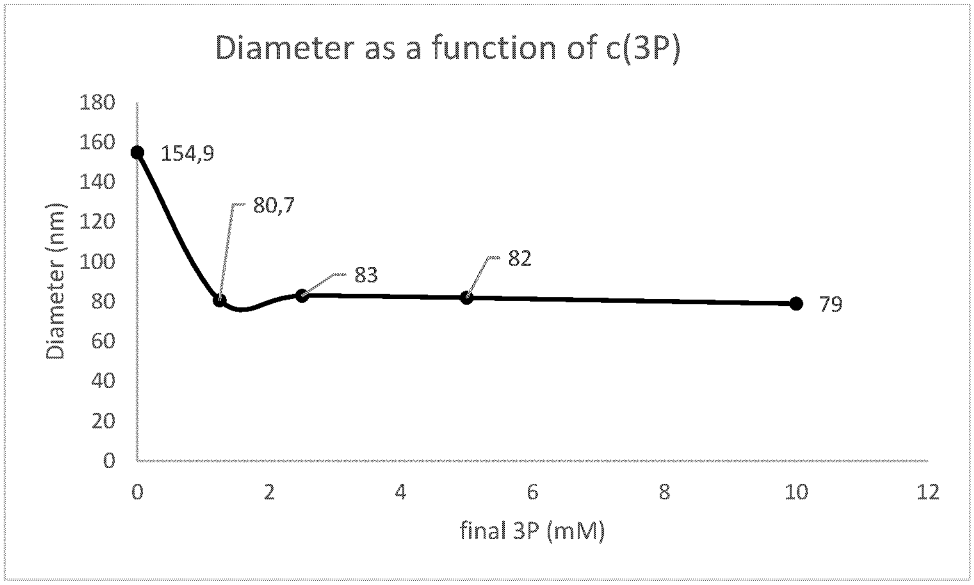

Fig. 3
A
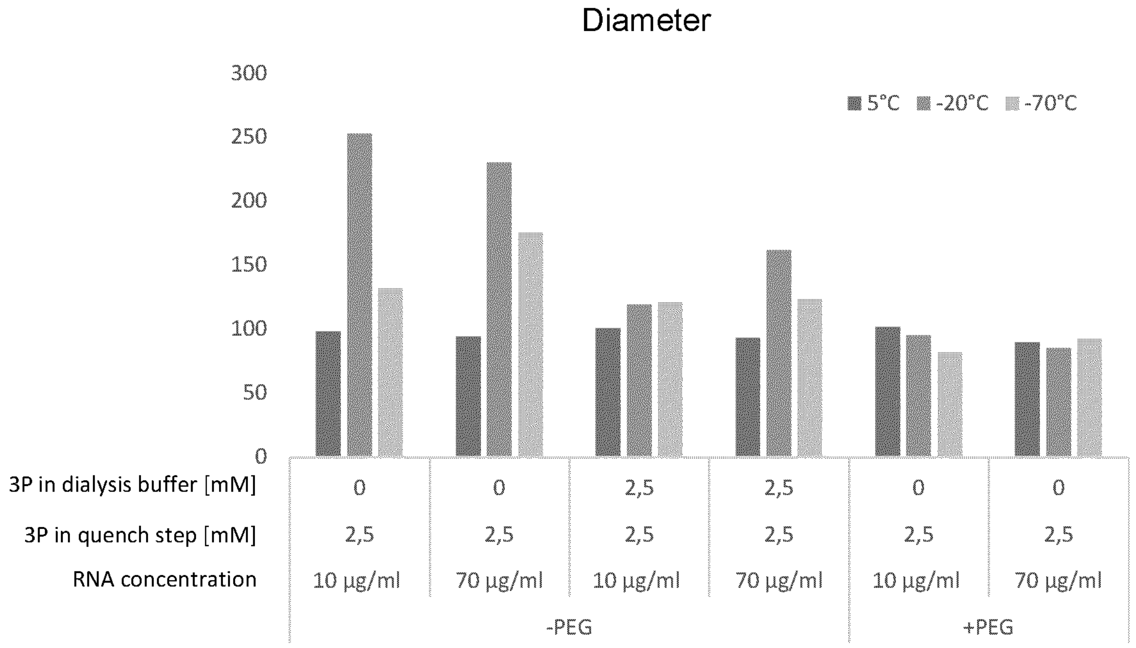
B
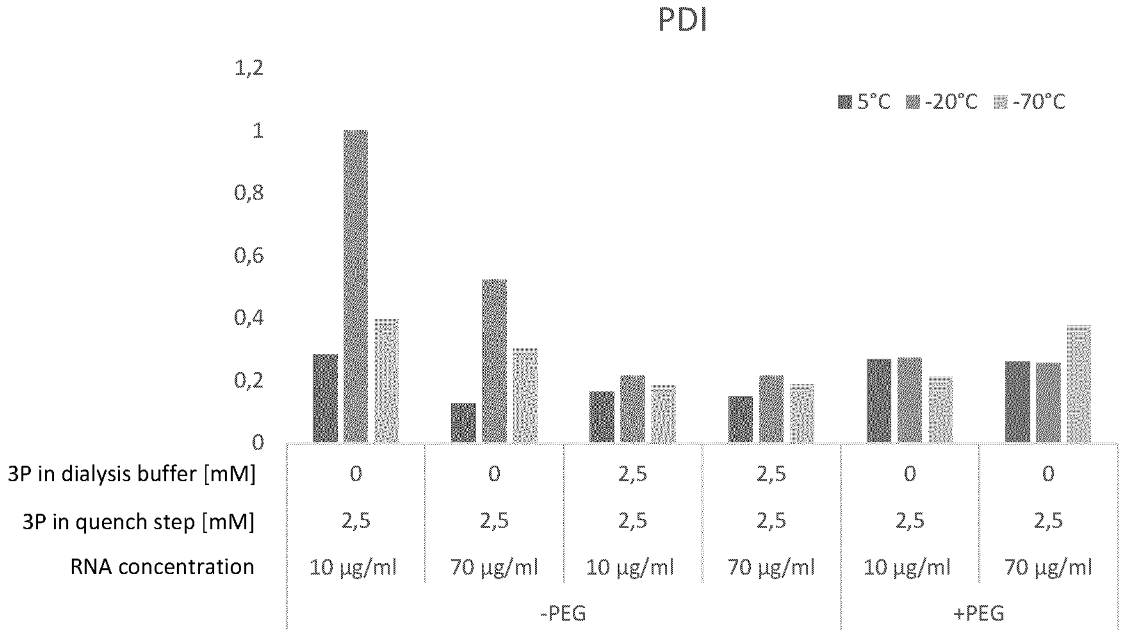

Fig. 4

A

| XIV-3 | CHOL/ION | (-Serum) DSPC [%] | | | | (+Serum) DSPC [%] | | | | log10 (+S/-S) DSPC [%] | | | |
|---|---|---|---|---|---|---|---|---|---|---|---|---|---|
| | | 10 | 14 | 17 | 21 | 10 | 14 | 17 | 21 | 10 | 14 | 17 | 21 |
| | 1.71 | 8E+05 | 1E+06 | 4E+06 | 6E+06 | 2E+05 | 6E+05 | 1E+07 | 2E+07 | -0.67 | -0.33 | 0.42 | 0.44 |
| | 1.42 | 1E+06 | 3E+06 | 2E+06 | 4E+06 | 5E+05 | 4E+06 | 1E+07 | 1E+07 | -0.34 | 0.14 | 0.60 | 0.56 |
| | 1.18 | 2E+06 | 2E+06 | 2E+06 | 4E+06 | 2E+06 | 1E+07 | 1E+07 | 2E+07 | -0.02 | 0.70 | 0.70 | 0.60 |
| | 0.99 | 3E+06 | 1E+06 | 2E+06 | 3E+06 | 6E+06 | 1E+07 | 1E+07 | 1E+07 | 0.29 | 1.12 | 0.94 | 0.60 |
| | 0.82 | 2E+06 | 1E+06 | 2E+06 | 2E+06 | 1E+07 | 8E+06 | 1E+07 | 1E+07 | 0.65 | 0.82 | 0.87 | 0.71 |
| | 0.68 | 6E+05 | 9E+05 | 1E+06 | 2E+06 | 8E+06 | 1E+07 | 1E+07 | 1E+07 | 1.13 | 1.20 | 1.01 | 0.71 |
| | 0.56 | 2E+06 | 4E+05 | 6E+05 | 1E+06 | 1E+07 | 1E+07 | 1E+07 | 1E+07 | 0.70 | 1.50 | 1.31 | 0.88 |
| | 0.46 | 3E+05 | 7E+05 | 3E+05 | 1E+06 | 1E+07 | 1E+07 | 1E+07 | 1E+07 | 1.57 | 1.24 | 1.52 | 0.94 |
| | 0.37 | 2E+05 | 2E+05 | 5E+05 | 9E+05 | 1E+07 | 1E+07 | 9E+06 | 7E+06 | 1.76 | 1.83 | 1.25 | 0.91 |

B

| XIV-1 | CHOL/ION | (-Serum) DSPC [%] | | | | (+Serum) DSPC [%] | | | | log10 (+S/-S) DSPC [%] | | | |
|---|---|---|---|---|---|---|---|---|---|---|---|---|---|
| | | 10 | 14 | 17 | 21 | 10 | 14 | 17 | 21 | 10 | 14 | 17 | 21 |
| | 1.71 | 1E+05 | 5E+05 | 4E+05 | 4E+05 | 1E+04 | 4E+04 | 9E+04 | 1E+05 | -1.01 | -1.07 | -0.68 | -0.53 |
| | 1.42 | 2E+05 | 2E+06 | 1E+06 | 6E+05 | 1E+04 | 3E+05 | 6E+05 | 7E+05 | -1.22 | -0.86 | -0.23 | 0.11 |
| | 1.18 | 3E+05 | 4E+06 | 6E+05 | 1E+06 | 2E+04 | 3E+06 | 7E+05 | 2E+06 | -1.19 | -0.19 | 0.08 | 0.26 |
| | 0.99 | 2E+06 | 2E+06 | 1E+06 | 8E+05 | 9E+04 | 8E+05 | 2E+06 | 1E+06 | -1.33 | -0.42 | 0.37 | 0.20 |
| | 0.82 | 2E+06 | 4E+06 | 7E+05 | 4E+05 | 3E+05 | 7E+06 | 2E+06 | 2E+06 | -0.79 | 0.20 | 0.32 | 0.61 |
| | 0.68 | 3E+06 | 4E+06 | 1E+06 | 1E+06 | 5E+05 | 5E+06 | 8E+06 | 9E+06 | -0.76 | 0.16 | 0.81 | 0.82 |
| | 0.56 | 1E+07 | 4E+06 | 6E+05 | 6E+05 | 3E+06 | 5E+06 | 3E+06 | 8E+06 | -0.53 | 0.15 | 0.65 | 1.16 |
| | 0.46 | 3E+06 | 4E+06 | 6E+05 | 5E+05 | 2E+06 | 9E+06 | 6E+06 | 2E+06 | -0.32 | 0.32 | 0.97 | 0.68 |
| | 0.37 | 6E+06 | 2E+06 | 7E+05 | 3E+05 | 5E+06 | 4E+06 | 4E+06 | 5E+06 | -0.10 | 0.25 | 0.82 | 1.19 |

Fig. 4 (contin.)

C

| XIV-2 | CHOL/ION | (-Serum) DSPC [%] | | | | (+Serum) DSPC [%] | | | | log10 (+S/-S) DSPC [%] | | | |
|---|---|---|---|---|---|---|---|---|---|---|---|---|---|
| | | 10 | 14 | 17 | 21 | 10 | 14 | 17 | 21 | 10 | 14 | 17 | 21 |
| | 1.71 | 1E+07 | 8E+06 | 6E+06 | 6E+06 | 1E+07 | 1E+07 | 1E+07 | 1E+07 | 0.08 | 0.13 | 0.24 | 0.33 |
| | 1.42 | 1E+07 | 8E+06 | 6E+06 | 9E+06 | 1E+07 | 2E+07 | 1E+07 | 1E+07 | 0.08 | 0.37 | 0.38 | 0.15 |
| | 1.18 | 1E+07 | 1E+07 | 1E+07 | 3E+06 | 2E+07 | 2E+07 | 2E+07 | 4E+06 | 0.11 | 0.24 | 0.19 | 0.18 |
| | 0.99 | 1E+07 | 2E+07 | 1E+07 | 9E+06 | 2E+07 | 2E+07 | 2E+07 | 2E+07 | 0.29 | 0.13 | 0.27 | 0.27 |
| | 0.82 | 1E+07 | 1E+07 | 9E+06 | 6E+06 | 2E+07 | 2E+07 | 2E+07 | 9E+06 | 0.14 | 0.33 | 0.43 | 0.22 |
| | 0.68 | 1E+07 | 1E+07 | 8E+06 | 5E+06 | 2E+07 | 2E+07 | 2E+07 | 1E+07 | 0.10 | 0.26 | 0.42 | 0.47 |
| | 0.56 | 1E+07 | 1E+07 | 1E+07 | 3E+06 | 2E+07 | 2E+07 | 1E+07 | 2E+07 | 0.18 | 0.25 | 0.09 | 0.70 |
| | 0.46 | 9E+06 | 6E+06 | 9E+06 | 3E+06 | 1E+07 | 2E+07 | 2E+07 | 1E+07 | 0.19 | 0.39 | 0.23 | 0.57 |
| | 0.37 | 5E+06 | 3E+06 | 3E+06 | 1E+06 | 1E+07 | 1E+07 | 1E+07 | 7E+06 | 0.38 | 0.64 | 0.66 | 0.80 |

D

| G | CHOL/ION | (-Serum) DSPC [%] | | | | (+Serum) DSPC [%] | | | | log10 (+S/-S) DSPC [%] | | | |
|---|---|---|---|---|---|---|---|---|---|---|---|---|---|
| | | 10 | 14 | 17 | 21 | 10 | 14 | 17 | 21 | 10 | 14 | 17 | 21 |
| | 1.71 | 1E+06 | 7E+06 | 1E+07 | 1E+07 | 3E+05 | 7E+06 | 3E+07 | 3E+07 | -0.68 | -0.01 | 0.41 | 0.30 |
| | 1.42 | 3E+06 | 3E+06 | 3E+06 | 1E+07 | 9E+05 | 8E+06 | 2E+07 | 2E+07 | -0.56 | 0.39 | 0.71 | 0.29 |
| | 1.18 | 4E+06 | 5E+06 | 6E+06 | 9E+06 | 2E+06 | 1E+07 | 3E+07 | 3E+07 | -0.20 | 0.46 | 0.73 | 0.56 |
| | 0.99 | 7E+06 | 2E+06 | 8E+06 | 7E+06 | 7E+06 | 1E+07 | 3E+07 | 3E+07 | 0.05 | 0.85 | 0.59 | 0.59 |
| | 0.82 | 5E+06 | 8E+06 | 5E+06 | 6E+06 | 1E+07 | 3E+07 | 3E+07 | 3E+07 | 0.43 | 0.55 | 0.80 | 0.69 |
| | 0.68 | 4E+06 | 6E+06 | 3E+06 | 2E+06 | 2E+07 | 4E+07 | 3E+07 | 2E+07 | 0.72 | 0.77 | 1.01 | 0.97 |
| | 0.56 | 7E+06 | 7E+06 | 2E+06 | 2E+06 | 4E+07 | 5E+07 | 2E+07 | 2E+07 | 0.72 | 0.81 | 1.15 | 1.00 |
| | 0.46 | 5E+06 | 6E+05 | 6E+05 | 1E+06 | 3E+07 | 8E+06 | 9E+06 | 1E+07 | 0.76 | 1.10 | 1.16 | 0.91 |
| | 0.37 | 2E+06 | 7E+05 | 5E+05 | 9E+05 | 1E+07 | 8E+06 | 8E+06 | 1E+07 | 0.80 | 1.11 | 1.17 | 1.04 |

SEQUENCE LISTING

```
Sequence total quantity: 10
SEQ ID NO: 1            moltype = RNA  length = 47
FEATURE                 Location/Qualifiers
misc_feature            1..47
                        note = 5'-UTR
source                  1..47
                        mol_type = other RNA
                        organism = synthetic construct
SEQUENCE: 1
aactagtatt cttctggtcc ccacagactc agagagaacc cgccacc                47

SEQ ID NO: 2            moltype = RNA  length = 278
FEATURE                 Location/Qualifiers
misc_feature            1..278
                        note = 3'-UTR
source                  1..278
                        mol_type = other RNA
                        organism = synthetic construct
SEQUENCE: 2
ctggtactgc atgcacgcaa tgctagctgc ccctttcccg tcctgggtac cccgagtctc  60
ccccgacctc gggtcccagg tatgctccca cctccacctg ccccactcac cacctctgct  120
agttccagac acctcccaag cacgcagcaa tgcagctcaa aacgcttagc ctagccacac  180
ccccacggga aacagcagtg attaaccttt agcaataaac gaaagtttaa ctaagctata  240
ctaaccccag ggttggtcaa tttcgtgcca gccacacc                          278

SEQ ID NO: 3            moltype = RNA  length = 110
FEATURE                 Location/Qualifiers
misc_feature            1..110
```

```
                         note = A30L70
source                   1..110
                         mol_type = other RNA
                         organism = synthetic construct
SEQUENCE: 3
aaaaaaaaaa aaaaaaaaaa aaaaaaaaaa gcatatgact aaaaaaaaaa aaaaaaaaaa  60
aaaaaaaaaa aaaaaaaaaa aaaaaaaaaa aaaaaaaaaa aaaaaaaaaa             110

SEQ ID NO: 4             moltype = AA  length = 26
FEATURE                  Location/Qualifiers
REGION                   1..26
                         note = Secretory sequence
source                   1..26
                         mol_type = protein
                         organism = synthetic construct
SEQUENCE: 4
MRVMAPRTLI LLLSGALALT ETWAGS                                       26

SEQ ID NO: 5             moltype = AA  length = 55
FEATURE                  Location/Qualifiers
REGION                   1..55
                         note = MITD
source                   1..55
                         mol_type = protein
                         organism = synthetic construct
SEQUENCE: 5
IVGIVAGLAV LAVVVIGAVV ATVMCRRKSS GGKGGSYSQA ASSDSAQGSD VSLTA       55

SEQ ID NO: 6             moltype = AA  length = 65
FEATURE                  Location/Qualifiers
REGION                   1..65
                         note = P2P16
source                   1..65
                         mol_type = protein
                         organism = synthetic construct
SEQUENCE: 6
KKQYIKANSK FIGITELKKL GGGKRGGGKK MTNSVDDALI NSTKIYSYFP SVISKVNQGA  60
QGKKL                                                              65

SEQ ID NO: 7             moltype = AA  length = 10
FEATURE                  Location/Qualifiers
REGION                   1..10
                         note = Linker
source                   1..10
                         mol_type = protein
                         organism = synthetic construct
SEQUENCE: 7
GGSGGGGSGG                                                         10

SEQ ID NO: 8             moltype = AA  length = 14
FEATURE                  Location/Qualifiers
REGION                   1..14
                         note = Linker
source                   1..14
                         mol_type = protein
                         organism = synthetic construct
SEQUENCE: 8
GSSGGGGSPG GGSS                                                    14

SEQ ID NO: 9             moltype = AA  length = 15
FEATURE                  Location/Qualifiers
REGION                   1..15
                         note = P2
source                   1..15
                         mol_type = protein
                         organism = synthetic construct
SEQUENCE: 9
QYIKANSKFI GITEL                                                   15

SEQ ID NO: 10            moltype = AA  length = 32
FEATURE                  Location/Qualifiers
REGION                   1..32
                         note = P16
source                   1..32
                         mol_type = protein
                         organism = synthetic construct
SEQUENCE: 10
MTNSVDDALI NSTKIYSYFP SVISKVNQGA QG                                32
```

NUCLEIC ACID COMPOSITIONS COMPRISING A MULTIVALENT ANION, SUCH AS AN INORGANIC POLYPHOSPHATE, AND METHODS FOR PREPARING, STORING AND USING THE SAME

CROSS-REFERENCE TO RELATED APPLICATION

This application is a U.S. national phase filing of International Application No. PCT/EP2023/059066, filed Apr. 5, 2023, which claims priority to International Application No. PCT/EP2022/05902, filed Apr. 5, 2022, the disclosure of each of which is hereby incorporated by reference in their entireties.

TECHNICAL FIELD

The present disclosure relates generally to the field of nucleic acid (such as DNA or RNA, in particular mRNA or inhibitory RNA, e.g., siRNA) compositions comprising a multivalent anion (such as an inorganic polyphosphate), methods for preparing and storing such compositions, and the use of such compositions in therapy.

BACKGROUND

The use of a recombinant nucleic acid (such as DNA or RNA) for delivery of foreign genetic information into target cells is well known. A recombinant nucleic acid may be administered in naked form to a subject in need thereof; however, usually a recombinant nucleic acid is administered using a composition. For example, nucleic acid, such as RNA, may be delivered to a subject using different delivery vehicles, based mostly on cationic polymers or lipids which together with the nucleic acid form nanoparticles. The nanoparticles are intended to protect the nucleic acid, such as RNA, from degradation, enable delivery of the nucleic acid, such as RNA, to the target site and facilitate cellular uptake and processing by the target cells. The efficiency of the nucleic acid delivery depends, in part, on the molecular composition of the nanoparticle and can be influenced by numerous parameters, including particle size, formulation, and charge or grafting with molecular moieties, such as polyethylene glycol (PEG) or other ligands. The fate of such nanoparticle formulations is controlled by diverse key-factors (e.g., size and size distribution of the nanoparticles; etc.). These factors are, e.g., referred to in the FDA "Liposome Drug Products Guidance" from 2018 as specific attributes which should be analyzed and specified. The advantages of using RNA include transient expression and a non-transforming character. Furthermore, RNA does not need to enter the nucleus in order to be expressed and moreover cannot integrate into the host genome, thereby eliminating diverse risks such as oncogenesis.

Grafting with PEG is considered to reduce serum interactions, to increase serum stability and to increase circulation time, which can be helpful for certain targeting approaches. Ligands which bind to receptors at the target site can help to improve targeting efficacy. Furthermore, PEGylation can be used for particle engineering. For example, if lipid nanoparticles (LNPs) are manufactured by mixing an aqueous phase of the nucleic acid, such as RNA, with an organic phase of the lipids a certain fraction of PEG-conjugated lipid in the lipid mixture is required, otherwise the particles aggregate during or after the mixing step. It has been shown that by variation of the molar fraction of PEG-lipids comprising PEG at different molar masses the size of the particles can be adjusted. As well, the particle size may be adjusted by variation of the molar mass of the PEG moiety of the PEGylated lipids. Typical sizes which are accessible are in the range between 30 and 200 nm (Belliveau et al., 2012, Molecular Therapy—Nucleic Acids 1, e37). So-formed particles have additionally the advantage, that, due to the PEG fraction, they interact less with serum components, and have a longer circulation half-life, which is desirable in many drug delivery approaches. Without PEG-lipids, no particles with discrete size can be formed; the particles form large aggregates and precipitate. Thus, one of the primary roles of PEG-lipids is to facilitate particle self-assembly by providing a steric barrier at the surface of nascent particles formed when nucleic acids are rapidly mixed in ethanol solutions containing lipids to bind the nucleic acid, such as RNA. PEG steric hindrance prevents inter-particle fusion and promotes the formation of a homogeneous population of LNPs where diameters <100 nm can be achieved.

PEG is the most widely used and gold standard "stealth" polymer in drug delivery. PEG-lipids are typically incorporated into systems to prepare a homogenous and colloidally stable nanoparticle population due to its hydrophilic steric hindrance property (PEG shell prevents electrostatic or Van der Waals attraction that leads to aggregation). PEGylation enables to attract a water shell around the polymer shielding the particles from opsonization with serum proteins, increasing serum half-life which results in an improvement of the pharmacokinetic behavior. Variation of the length of the acyl chains ($C_{18}$, $C_{16}$ or $C_{14}$) of the lipids modifies the stability of the incorporation of the PEG-lipid in the particles which leads to a modulation of the pharmacokinetics. The use of a PEG-lipid containing short ($C_{14}$) acyl chains that dissociates from LNPs in vivo with a halftime <30 min results in optimum hepatocyte gene-silencing potency (Chen et al., 2014, J. Control Release 196:106-12; Ambegia et al., 2005, Biochimica et Biophysica Acta 1669:155-163). In addition, tight control of particle size can be obtained by varying the PEG-lipid parameter: higher PEG MW or higher molar fraction of PEG-lipids in the particles lead to smaller particles.

Despite these advantages, PEGylation of nanoparticles may lead as well to several effects which are detrimental to the intended use for drug delivery. PEGylation of liposomes and LNPs is known to reduce the cellular uptake and endosomal escape, thus reducing at the end the overall transfection efficiency. Indeed, the PEG shell provides a steric barrier to efficient binding of particles to the cell and also hinders endosomal release by preventing membrane fusion between the liposome and the endosomal membrane. This is why the type of PEG-lipid and the amount of PEG-lipid used must be always carefully adjusted. It should provide sufficient stealth effect for in vivo and stabilization aspects on the one hand, while not hindering transfection on the other. This phenomenon is known as the "PEG Dilemma".

Besides lowering transfection efficiency, PEGylation has been associated with accelerated blood clearance (ABC) phenomenon induced by anti-PEG antibodies and/or complement activation as well as storage diseases (Bendele A et al., 1998, Toxicolocical Sciences 42, 152-157; Young M A et al., 2007, Translational Research 149(6), 333-342; S. M. Moghimi, J. Szebeni, 2003, Progress in Lipid Research 42:463-478). Ishida et al. and Laverman et al. reported that intravenous injection in rats of PEG-grafted liposomes may significantly alter the pharmacokinetic behavior of a second dose when this second dose is administered after an interval of several days (Laverman P et al., 2001, J. Pharmacol. Exp. Ther. 298(2), 607-12; Ishida et al., 2006, J. Control Release 115(3), 251-8). The phenomenon of "accelerated blood clearance" (ABC) appears to be related to the PEG content of liposomes. The presence of anti-PEG antibodies in the plasma induces a higher clearance of the particles by the Monophagocyte System (MPS) which at the end reduces the efficacy of the drug.

PEG is also supposed to induce complement activation, which can lead to hypersensitivity reaction, also known as Complement-Activation Related Pseudo-Allergy (CARPA). It is still not clear from the literature if the activation of complement is due to the nanoparticle in general or to the presence of PEG in particular.

The presence of PEG in other lipidic particles may also induce a specific immune response. Semple et al. (2005, J. Pharmacol. Exp. Ther. 312(3), 1020-6) reported that liposomes containing PEG-lipid derivatives and encapsulated antisense oligodeoxynucleotide or plasmid DNA elicit a strong immune response that results in the rapid blood clearance of subsequent doses in mice. The magnitude of this response was sufficient to induce significant morbidity and, in some instances, mortality. Rapid elimination of liposome-encapsulated oligodeoxynucleotides from blood depended on the presence of PEG-lipid in the membrane because the use of non-pegylated liposomes or liposomes containing rapidly exchangeable PEG-lipid abrogated the response. The generation of anti-PEG antibody and the putative complement activation were a likely explanation for the rapid elimination of the vesicles from the blood.

As PEG may induce immune responses there is a need to avoid it for certain applications where multiple injections are needed. Examples are therapies using nucleic acid (such as RNA, in particular mRNA), for example for protein replacement therapy. Here, the risk can be particularly high due to the potential intrinsic immunogenicity of nucleic acid (in particular RNA). Other examples are protein knock-down therapies using inhibitory RNA (such as siRNA), antisense oligonucleotides or DNA based therapies.

Thus, there remains a need in the art for efficient compositions and methods for introducing nucleic acid, such as RNA, into cells which avoid the disadvantages accompanied by use of PEG. Ideally, these compositions and methods should be such that (i) the compositions are stable and can be stored in a temperature range compliant to regular technologies in pharmaceutical practice, in particular at a temperature of about −20° C. or even in liquid form at temperatures between +2 and +20° C.; (ii) the compositions can repeatably be frozen and thawed; (iii) the compositions are ready to use; (iv) the compositions being free of PEG maintain high biological efficacy; and/or (v) the nucleic acid contained in the compositions is in a stable form and is not significantly degraded upon storage. The present disclosure addresses these and other needs.

The inventors surprisingly found that the compositions and methods described herein fulfill the above-mentioned requirements. In particular, it is demonstrated that by using a multivalent anion, such as an inorganic polyphosphate, inorganic phosphate or citrate, it is possible to prepare compositions which are stable (in particular with respect to the colloidal size of the particles contained in said compositions), which can be stored in liquid form, which can repeatably be frozen and thawed, which contain nucleic acid that is in a stable form, and which maintain high biological efficacy, even if the composition/particles does/do not comprise a PEG lipid or any other stealth lipid.

SUMMARY

In a first aspect, the present disclosure provides a composition comprising (i) a nucleic acid; (ii) a cationically ionizable lipid; (iii) a steroid; (iv) a neutral lipid; and (v) a multivalent anion, such as an inorganic polyphosphate.

As demonstrated in the present application, the aggregation of particles (such as lipid nanoparticles (LNPs), liposomes, lipoplexes (LPXs), or mixtures thereof) contained in a composition (in particular an aqueous composition) and formed from a nucleic acid (in particular RNA, such as mRNA), a cationically ionizable lipid, a steroid, and a neutral lipid can be prevented by adding to the composition a multivalent anion, such as an inorganic polyphosphate, even if the composition/particles does/do not contain a PEG lipid or any other stealth lipid. Furthermore, the present application demonstrates that, surprisingly, in presence of a multivalent anion, such as an inorganic polyphosphate, and by adjusting the amounts of lipids to each other, it is possible to obtain nucleic acid (such as RNA) compositions exhibiting different biological performance: when used for transfecting cells, nucleic acid compositions containing higher relative amounts of ionizable and neutral lipids and a lower relative amount of steroid result in higher expression of the nucleic acid in the transfected cells if the transfection is carried out in the presence of serum compared to the expression obtained if the transfection is carried out in the absence of serum (this effect is called "serum stimulation" herein and resembles the biological performance of standard nucleic acid compositions containing a PEG lipid). In contrast, nucleic acid compositions containing lower relative amounts of ionizable and neutral lipids and a higher relative amount of steroid and used for transfecting cells result in comparable or reduced expression of the nucleic acid in the transfected cells if the transfection is carried out in the presence of serum (i.e., these compositions show some or no serum inhibition, but do not show serum stimulation). Thus, the claimed composition is stable, can be stored in a temperature range compliant to regular technologies in pharmaceutical practice, provides a ready-to-use composition, and maintains high biological efficacy, even if the composition/particles does/do not comprise a PEG lipid or any other stealth lipid. Furthermore, depending on the relative amounts of lipids to each other, the claimed composition may exhibit a different biological performance, i.e., may be stimulable by serum or not.

The term "multivalent anion" as used herein may be understood to refer to an ion having multiple (i.e., more than one) negative charges. For example, the multivalent anion may be a dianion, i.e., having a charge of 2-, or having two negative charges. In another example the multivalent anion may be a trianion, i.e. having a charge of 3- or having three negative charges. In yet another example the multivalent anion may be a tetraanion, i.e. having a charge of 4- or having four negative charges. In further examples the multivalent anion may have a plurality of negative charges. Typically, the multivalent anion is not, or does not comprise, a nucleic acid, such as DNA or RNA. In some embodiments, the multivalent anion has no more than 20 negative charges (i.e., a charge of 20−), preferably no more than 10 negative charges (i.e., a charge of 10−), or most preferably no more than 5 negative charges (i.e., a charge of 5−). The multivalent anion may have 2-20, 2-15, 2-10, 2-8, 2-5, 3-20, 3-15, 3-10, 3-8, or 3-5 negative charges, optionally 2-10 negative charges, preferably 2-5 negative charges.

The multivalent anion may be selected from the group consisting of: an inorganic polyphosphate (as further defined herein), an inorganic phosphate (e.g., $PO_4^{3-}$), sulfate, sulfite, pyrosulfate, dithionate, dithionite, metabisulfite, thiosulfate, trithionate or tetrathionate, a dicarboxylic acid (e.g., oxalic, malonic, succinic, glutaric, adipic, pimelic, sebacic, phthalic, isophthalic or terephthalic acid), a substituted dicarboxylic acid (e.g., tartronic, mesoxalic, malic, tartaric, aspartic, glutamic, hydroxyglutaric or saccharinic acid), a tricarboxylic acid (e.g., citric, isocitric, propane-1,2,3-tricarboxylic or trimesic acid), or mixtures thereof. Typically, the multivalent anion in water is molecularly dissolved as a solute and does not form supramolecular assemblies such as micelles. Structurally, the multivalent anion is not, or does not comprise, a negatively charged amphiphile having a hydrophilic portion and a lipophilic portion (e.g., the multivalent anion is not a negatively charged lipid).

In some embodiments, the multivalent anion is an inorganic polyphosphate. The inorganic polyphosphate can be any linear, cyclic, or branched inorganic polyphosphate. In some embodiments of the first aspect, the inorganic polyphosphate is a linear inorganic polyphosphate (such as a linear inorganic triphosphate).

In some embodiments of the first aspect, the inorganic polyphosphate comprises the formula $[P_xO_{(3x+1)}]^y$, wherein x is an integer and is at least 2, preferably at least 3; and y is the anionic charge. For example, if x is 3, the inorganic polyphosphate is a linear inorganic triphosphate comprising the formula $[P_3O_{10}]^{5-}$. Likewise, if x is 4, the inorganic polyphosphate is a linear or branched inorganic tetraphosphate comprising the formula $[P_4O_{13}]^{6-}$.

In some embodiments of the first aspect, the inorganic polyphosphate is selected from the group consisting of diphosphate, triphosphate, tetraphosphate, pentaphosphate, hexaphosphate, heptaphosphate, and mixtures thereof, such as from the group consisting of triphosphate, tetraphosphate, pentaphosphate, hexaphosphate, heptaphosphate, and mixtures thereof. In some preferred embodiments of the first aspect, the inorganic polyphosphate is selected from the group consisting of triphosphate, tetraphosphate, pentaphosphate, and mixtures thereof. In some preferred embodiments of the first aspect, the inorganic polyphosphate is triphosphate.

In some embodiments, the multivalent anion is an inorganic phosphate (e.g., $PO_4^{3-}$), sulfate, sulfite, pyrosulfate, dithionate, dithionite, metabisulfite, thiosulfate, trithionate or tetrathionate. In some embodiments, the multivalent anion is an inorganic phosphate (e.g., $PO_4^{3-}$).

In some embodiments, the multivalent anion is a dicarboxylic acid (e.g., oxalic, malonic, succinic, glutaric, adipic, pimelic, sebacic, phthalic, isophthalic or terephthalic acid), or a substituted dicarboxylic acid (e.g., tartronic, mesoxalic, malic, tartaric, aspartic, glutamic, hydroxyglutaric or saccharinic acid).

In some embodiments, the multivalent anion is a tricarboxylic acid (e.g., citric, isocitric, propane-1,2,3-tricarboxylic or trimesic acid).

In some preferred embodiments, the multivalent anion is selected from the group consisting of: an inorganic polyphosphate (as defined herein), an inorganic phosphate (e.g., $PO_4^{3-}$), sulfate, succinate, glutarate, tartrate, malate, citrate, or mixtures thereof. In some embodiments, the multivalent anion is an inorganic polyphosphate (as defined herein), an inorganic phosphate or citrate. In some most preferred embodiments, the multivalent anion is an inorganic polyphosphate (as defined herein).

In some embodiments of the first aspect, the molar ratio of (v) the multivalent anion (such as the inorganic polyphosphate) to (ii) the cationically ionizable lipid is at least about 1:2. For example, the molar ratio of (v) the multivalent anion (such as the inorganic polyphosphate) to (ii) the cationically ionizable lipid may be at least about 0.55, at least about 0.60, at least about 0.65, at least about 2:3, at least about 0.7, at least about 0.75, at least about 0.80, at least about 0.85, at least about 0.90, at least about 0.95, at least about 1.00, at least about 1.10, at least about 1.20, at least about 1.30, at least about 4:3, at least about 1.40, at least about 1.50, at least about 1.60, at least about 1.70, at least about 1.80, at least about 1.90, or at least about 2.0. In some preferred embodiments of the first aspect, the molar ratio of (v) the multivalent anion (such as the inorganic polyphosphate) to (ii) the cationically ionizable lipid is at least about 2:3. In some preferred embodiments of the first aspect, the molar ratio of (v) the multivalent anion (such as the inorganic polyphosphate) to (ii) the cationically ionizable lipid is at least about 4:3.

In some embodiments of the first aspect, the composition is substantially free of a lipid comprising polyethyleneglycol (PEG). In some embodiments, the composition is substantially free of any compound comprising PEG. In some embodiments, the composition is substantially free of PEG. Thus, in some embodiments of the first aspect, the composition comprises (i) a nucleic acid; (ii) a cationically ionizable lipid; (iii) a steroid; (iv) a neutral lipid; and (v) a multivalent anion, wherein the composition is substantially free of a lipid comprising PEG, substantially free of any compound comprising PEG or substantially free of PEG. In some of these embodiments, the multivalent anion is selected from the group consisting of an inorganic polyphosphate, an inorganic phosphate, sulfate, succinate, glutarate, tartrate, malate, citrate, and mixtures thereof. In some of these embodiments, the multivalent anion is selected from the group consisting of an inorganic polyphosphate, an inorganic phosphate and citrate. In some of these embodiments, the multivalent anion is an inorganic polyphosphate.

In some embodiments of the first aspect, the composition is also substantially free of another polymer-conjugated lipid. In some embodiments, the another polymer-conjugated lipid is a polysarcosine-conjugated lipid. In some embodiments, the composition is substantially free of any polymer-conjugated lipid (including PEG lipids and polysarcosine-conjugated lipids). Thus, in some embodiments of the first aspect, the composition comprises (i) a nucleic acid; (ii) a cationically ionizable lipid; (iii) a steroid; (iv) a neutral lipid; and (v) a multivalent anion, wherein the composition is substantially free of any polymer-conjugated lipid (including PEG lipids and polysarcosine-conjugated lipids). In some of these embodiments, the multivalent anion is selected from the group consisting of an inorganic polyphosphate, inorganic phosphate (e.g., $PO_4^{3-}$), sulfate, sulfite, pyrosulfate, dithionate, dithionite, metabisulfite, thiosulfate, trithionate or tetrathionate, a dicarboxylic acid (e.g., oxalic, malonic, succinic, glutaric, adipic, pimelic, sebacic, phthalic, isophthalic or terephthalic acid), a substituted dicarboxylic acid (e.g., tartronic, mesoxalic, malic, tartaric, aspartic, glutamic, hydroxyglutaric or saccharinic acid), or a tricarboxylic acid (e.g., citric, isocitric, propane-1,2,3-tricarboxylic or trimesic acid). In some of these embodiments, the multivalent anion is selected from the group consisting of an inorganic polyphosphate, inorganic phosphate, sulfate, succinate, glutarate, tartrate, malate, citrate, and mixtures thereof. In some of these embodiments, the multivalent anion is selected from the group consisting of an inorganic polyphosphate, an inorganic phosphate and citrate. In some of these embodiments, the multivalent anion is an inorganic polyphosphate.

In some embodiments of the first aspect, the pH of the composition is between about 4.0 and about 8.0. In some embodiments of the first aspect, the pH of the composition is between about 4.5 and about 8.0, such as between about 5.0 and about 8.0, between about 5.5 and about 8.0, between about 6.0 and about 8.0, between about 6.5 and about 8.0, between about 6.8 and about 7.9, or between about 7.0 and about 7.8.

In some embodiments of the first aspect, water is the main component in the composition and/or the total amount of solvent(s) other than water contained in the composition is less than about 1.0% (v/v), such as less than about 0.5% (v/v). For example, the amount of water contained in the composition may be at least 50% (w/w), such as at least at least 55% (w/w), at least 60% (w/w), at least 65% (w/w), at least 70% (w/w), at least 75% (w/w), at least 80% (w/w), at least 85% (w/w), at least 90% (w/w), or at least 95% (w/w). In particular, if the composition comprises a cryoprotectant, the amount of water contained in the composition may be at least 50% (w/w), such as at least at least 55% (w/w), at least 60% (w/w), at least 65% (w/w), at least 70% (w/w), at least 75% (w/w), at least 80% (w/w), at least 85% (w/w), or at least 90% (w/w). If the composition is substantially free of a cryoprotectant, the amount of water contained in the composition may be at least 95% (w/w). Additionally, or alternatively, the total amount of solvent(s) other than water contained in the composition may be less than about 0.5% (v/v), such as less than about 0.4% (v/v), less than about 0.3% (v/v), less than about 0.2% (v/v), less than about 0.1% (v/v), less than about 0.05% (v/v), less than about 0.01% (v/v), or less than about 0.005% (v/v). In this respect, a cryoprotectant which is liquid under normal conditions will not be considered as a solvent other than water but as cryoprotectant. In other words, the above optional limitation that the total amount of solvent(s) other than water contained in the composition may be less than about 0.5% (v/v), such as less than about 0.4% (v/v), does not apply to cryoprotectants which are liquids under normal conditions.

In some embodiments of the first aspect, the osmolality of the composition is at most about $1000\times10^{-3}$ osmol/kg. In some embodiments of the first aspect, the osmolality of the composition is at most about $1000\times10^{-3}$ osmol/kg. In some embodiments, the osmolality of the composition is at most about $500\times10^{-3}$ osmol/kg, such as at most about $490\times10^{-3}$ osmol/kg, at most about $480\times10^{-3}$ osmol/kg, at most about $470\times10^{-3}$ osmol/kg, at most about $460\times10^{-3}$ osmol/kg, at most about $450\times10^{-3}$ osmol/kg, at most about $440\times10^{-3}$ osmol/kg, at most about $430\times10^{-3}$ osmol/kg, at most about $420\times10^{-3}$ osmol/kg, at most about $410\times10^{-3}$ osmol/kg, at most about $400\times10^{-3}$ osmol/kg, at most about $390\times10^{-3}$ osmol/kg, at most about $380\times10^{-3}$ osmol/kg, at most about $370\times10^{-3}$ osmol/kg, at most about $360\times10^{-3}$ osmol/kg, at most about $350\times10^{-3}$ osmol/kg, at most about $340\times10^{-3}$ osmol/kg, at most about $330\times10^{-3}$ osmol/kg, at most about $320\times10^{-3}$ osmol/kg, at most about $310\times10^{-3}$ osmol/kg, or at most about $300\times10^{-3}$ osmol/kg. In some embodiments of the first aspect, the osmolality of the composition is between about $100\times10^{-3}$ osmol/kg and about $500\times10^{-3}$ osmol/kg, such as about $300\times10^{-3}$ osmol/kg. If the composition does not comprise a cryoprotectant, the osmolality of the composition may be below $300\times10^{-3}$ osmol/kg, such as at most about $250\times10^{-3}$ osmol/kg, at most about $200\times10^{-3}$ osmol/kg, at most about $150\times10^{-3}$ osmol/kg, at most about $100\times10^{-3}$ osmol/kg, at most about $50\times10^{-3}$ osmol/kg, at most about $40\times10^{-3}$ osmol/kg, or at most about $30\times10^{-3}$ osmol/kg. If the composition comprises a cryoprotectant, it is preferred that the main part of the osmolality of the composition is provided by the cryoprotectant. For example, the cryoprotectant may provide at least 50%, such as at least 55%, at least 60%, at least 65%, at least 70%, at least 75%, at least 80%, at least 85%, or at least 90%, of the osmolality of the composition.

In some embodiments of the first aspect, the concentration of the nucleic acid (in particular RNA) in the composition is about 1 mg/l to about 500 mg/l. In some embodiments, the concentration of the nucleic acid (in particular RNA) in the composition is about 1 mg/l to about 100 mg/l. In some embodiments, the concentration of the nucleic acid (in particular RNA) in the composition is about 5 mg/l to about 500 mg/l, such as about 10 mg/l to about 400 mg/l, about 10 mg/l to about 300 mg/l, about 10 mg/l to about 200 mg/l, about 10 mg/l to about 150 mg/l, or about 10 mg/l to about 100 mg/l, preferably about 10 mg/l to about 140 mg/l, more preferably about 20 mg/l to about 130 mg/l, more preferably about 30 mg/l to about 120 mg/l. In some embodiments, the concentration of the nucleic acid (in particular RNA) in the composition is about 5 mg/l to about 150 mg/l, such as about 10 mg/l to about 140 mg/l, about 20 mg/l to about 130 mg/l, about 25 mg/l to about 125 mg/l, about 30 mg/l to about 120 mg/l, about 35 mg/l to about 115 mg/l, about 40 mg/l to about 110 mg/l, about 45 mg/l to about 105 mg/l, or about 50 mg/l to about 100 mg/l. In some embodiments, the concentration of the nucleic acid (in particular RNA) in the composition is 1 mg/l to about 50 mg/l or about 10 mg/l to about 100 mg/l. In some embodiments of the first aspect (in particular those, where the composition is in frozen form), the concentration of the nucleic acid (in particular RNA) in the composition is about 1 mg/l to about 50 mg/l. In some embodiments of the first aspect (in particular those, where the composition is in liquid form), the concentration of the nucleic acid (in particular RNA) in the composition is about 10 mg/l to about 100 mg/l.

In some embodiments of the first aspect, the composition comprises a cryoprotectant. In some embodiments of the first aspect, the composition is substantially free of a cryoprotectant.

In some embodiments of the first aspect, the molar ratio of the multivalent anion to the cationically ionizable lipid is at least about 1:2 (preferably at least about 2:3, such as at least about 1.00 or at least about 4:3), and the concentration of the nucleic acid (in particular RNA) in the composition is about 1 mg/l to about 100 mg/l (such as 1 mg/l to about 50 mg/l or about 10 mg/l to about 100 mg/l). In some embodiments of the first aspect (in particular those, where the composition is in frozen form), the molar ratio of the multivalent anion to the cationically ionizable lipid is at least about 1:2 (preferably at least about 2:3, such as at least about 1.00 or at least about 4:3), and the concentration of the nucleic acid (in particular RNA) in the composition is about 1 mg/l to about 50 mg/l. In some embodiments of the first aspect (in particular those, where the composition is in liquid form), the molar ratio of the multivalent anion to the cationically ionizable lipid is at least about 1:2 (preferably at least about 2:3, such as at least about 1.00 or at least about 4:3), and the concentration of the nucleic acid (in particular RNA) in the composition is about 10 mg/l to about 100 mg/l. In some of these embodiments, the multivalent anion is selected from the group consisting of an inorganic polyphosphate, an inorganic phosphate, sulfate, succinate, glutarate, tartrate, malate, citrate, and mixtures thereof. In some of these embodiments, the multivalent anion is selected from the group consisting of an inorganic polyphosphate, an inorganic phosphate and citrate.

In some embodiments of the first aspect, the multivalent anion is an inorganic polyphosphate which is a linear inorganic polyphosphate, in particular triphosphate, and the molar ratio of the inorganic polyphosphate to the cationically ionizable lipid is at least about 1:2, preferably at least about 2:3, such as at least about 1.00 or at least about 4:3. In some preferred embodiments of the first aspect, the inorganic polyphosphate is a linear inorganic polyphosphate (in particular triphosphate), the molar ratio of the inorganic polyphosphate to the cationically ionizable lipid is at least about 1:2 (preferably at least about 2:3, such as at least about 1.00 or at least about 4:3), and the concentration of the nucleic acid (in particular RNA) in the composition is about 1 mg/l to about 100 mg/l (such as 1 mg/l to about 50 mg/l or about 10 mg/l to about 100 mg/l). In some embodiments of the first aspect (in particular those, where the composition is in frozen form), the inorganic polyphosphate is a linear inorganic polyphosphate (in particular triphosphate), the molar ratio of the inorganic polyphosphate to the cationically ionizable lipid is at least about 1:2 (preferably at least about 2:3, such as at least about 1.00 or at least about 4:3), and the concentration of the nucleic acid (in particular RNA) in the composition is about 1 mg/l to about 50 mg/l. In some embodiments of the first aspect (in particular those, where the composition is in liquid form), the inorganic polyphosphate is a linear inorganic polyphosphate (in particular triphosphate), the molar ratio of the inorganic polyphosphate to the cationically ionizable lipid is at least about 1:2 (preferably at least about 2:3, such as at least about 1.00 or at least about 4:3), and the concentration of the nucleic acid (in particular RNA) in the composition is about 10 mg/l to about 100 mg/l.

In some embodiments of the first aspect, the cationically ionizable lipid comprises a head group which includes at least one tertiary amine moiety.

In some embodiments of the first aspect, the cationically ionizable lipid has the structure of Formula (X)

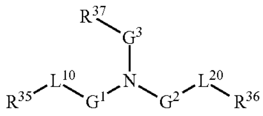

(X)

or a pharmaceutically acceptable salt, tautomer, prodrug or stereoisomer thereof, wherein $L^{10}$, $L^{20}$, $G^1$, $G^2$, $G^3$, $R^{35}$, $R^{36}$, and $R^{37}$ are as defined herein. In some embodiments, the cationically ionizable lipid is selected from the following: the structures X-1 to X-36 (shown herein); the structures A to G (shown herein); or N,N-dimethyl-2,3-dioleyloxypropylamine (DODMA), 1,2-dioleoyl-3-dimethylammonium-propane (DODAP), heptatriaconta-6,9,28,31-tetraen-19-yl-4-(dimethylamino)butanoate (DLin-MC3-DMA), and 4-((di ((9Z,12Z)-octadeca-9,12-dien-1-yl)amino)oxy)-N,N-dimethyl-4-oxobutan-1-amine (DPL-14). In some embodiments, the cationically ionizable lipid is the lipid having the structure X-3. In some embodiments, the cationically ionizable lipid is DPL-14 (i.e., the lipid having the structure G). In some embodiments, the cationically ionizable lipid is the lipid having the structure D.

In some embodiments of the first aspect, the cationically ionizable lipid has the structure of Formula (XI):

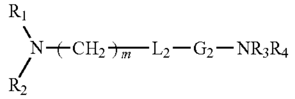

wherein $R_1$, $R_2$ $R_3$, $R_4$, $L_2$, $G_2$, and m are as defined herein. In some embodiments, the cationically ionizable lipid is selected from the structures (XIV-1), (XIV-2), and (XIV-3) (shown herein). In some embodiments, the cationically ionizable lipid is the lipid having the structure XIV-1 In some embodiments, the cationically ionizable lipid is the lipid having the structure XIV-2. In some embodiments, the cationically ionizable lipid is the lipid having the structure XIV-3.

In some embodiments of the first aspect, the cationically ionizable lipid is completely or partially replaced by a cationic lipid. In some embodiments, the cationic lipid is selected from the structures XV-1 to XV-6 (shown herein). In those embodiments, where the cationically ionizable lipid is completely replaced by a cationic lipid, the molar ratio of the multivalent anion (such as the inorganic polyphosphate) to the cationically ionizable lipid is replaced by the molar ratio of the multivalent anion (such as the inorganic polyphosphate) to the cationic lipid. In some embodiments, the molar ratio of the multivalent anion (such as the inorganic polyphosphate) to the cationic lipid is at least about 1:2 (such as at least about 0.55, at least about 0.60, at least about 0.65, at least about 2:3, at least about 0.7, at least about 0.75, at least about 0.80, at least about 0.85, at least about 0.90, at least about 0.95, at least about 1.00, at least about 1.10, at least about 1.20, at least about 1.30, at least about 4:3, at least about 1.40, at least about 1.50, at least about 1.60, at least about 1.70, at least about 1.80, at least about 1.90, or at least about 2.0, preferably the molar ratio of the multivalent anion (such as the inorganic polyphosphate) to the cationic lipid is at least about 2:3, such as at least about 4:3). In those embodiments, where the cationically ionizable lipid is partially replaced by a cationic lipid, the molar ratio of the multivalent anion (such as the inorganic polyphosphate) to the cationically ionizable lipid is replaced by the molar ratio of the multivalent anion (such as the inorganic polyphosphate) to the sum of cationic lipid and cationically ionizable lipid. Thus, in some embodiments, the molar ratio of the multivalent anion (such as the inorganic polyphosphate) to the sum of cationic lipid and cationically ionizable lipid is at least about 1:2 (such as at least about 0.55, at least about 0.60, at least about 0.65, at least about 2:3, at least about 0.7, at least about 0.75, at least about 0.80, at least about 0.85, at least about 0.90, at least about 0.95, at least about 1.00, at least about 1.10, at least about 1.20, at least about 1.30, at least about 4:3, at least about 1.40, at least about 1.50, at least about 1.60, at least about 1.70, at least about 1.80, at least about 1.90, or at least about 2.0, preferably the molar ratio of the multivalent anion (such as the inorganic polyphosphate) to the sum of cationic lipid and cationically ionizable lipid is at least about 2:3, such as at least about 4:3).

In some embodiments of the first aspect, the cationically ionizable lipid comprises from about 20 mol % to about 75 mol %, such as from about 40 mol % to about 70 mol %, from about 45 mol % to about 65 mol %, or from about 50 mol % to about 60 mol % (in particular for those embodiments having higher relative amounts of ionizable and neutral lipids and a lower relative amount of steroid); or from about 20 mol % to about 40 mol %, from about 25 mol % to about 40 mol %, or from about 25 mol % to about 35 mol % (in particular for those embodiments having lower relative amounts of ionizable and neutral lipids and a higher relative amount of steroid), of the total lipid present in the composition. In those embodiments, where the cationically ionizable lipid is partially or completely replaced by a cationic lipid, it is preferred that the same ranges as specified above for the cationically ionizable lipid (e.g., from about 20 mol % to about 75 mol %, etc.) apply to the sum of cationically ionizable lipid and cationic lipid.

In some embodiments of the first aspect, the steroid comprises a sterol. In some preferred embodiments of the first aspect, the steroid comprises or is cholesterol.

In some embodiments of the first aspect, the steroid comprises from about 15 mol % to about 60 mol 00 such as from about 15 mol % to about 40 mol %, from about 20 mol % to about 35 mol %, or from about 20 mol % to about 30 mol % (in particular for those embodiments having higher relative amounts of ionizable and neutral lipids and a lower relative amount of steroid); or from about 35 mol % to about 60 mol %, from about 40 mol % to about 60 mol %, or from about 45 mol % to about 60 mol % (in particular for those embodiments having lower relative amounts of ionizable and neutral lipids and a higher relative amount of steroid), of the total lipid present in the composition.

In some embodiments of the first aspect, the neutral lipid is a phospholipid. In some embodiments, the phospholipid is selected from the group consisting of phosphatidylcholines, phosphatidylethanolamines, phosphatidylglycerols, phosphatidic acids, phosphatidylserines and sphingomyelins. In some embodiments, the phospholipid is selected from the group consisting of phospholipids having a $T_g$ value of higher than 30° C. In some embodiments, the phospholipid is selected from the group consisting of distearoylphosphatidylcholine (DSPC), dipalmitoylphosphatidylcholine (DPPC), distearoyl-phosphatidylethanolamine (DSPE), and dipalmitoyl-phosphatidylethanolamine (DPPE). In some embodiments, the neutral lipid is DSPC.

In some embodiments of the first aspect, the neutral lipid comprises from about 5 mol % to about 25 mol %, such as from about 15 mol % to about 25 mol % or from about 17 mol % to about 21 mol % (in particular for those embodiments having higher relative amounts of ionizable and neutral lipids and a lower relative amount of steroid); or from about 5 mol % to about 15 mol % or from about 7 mol % to about 14 mol % (in particular for those embodiments having lower relative amounts of ionizable and neutral lipids and a higher relative amount of steroid), of the total lipid present in the composition.

In some embodiments of the first aspect, the cationically ionizable lipid comprises from about 20 mol % to about 70 mol % of the total lipid present in the composition; the steroid comprises from about 15 mol % to about 60 mol % of the total lipid present in the composition; and the neutral lipid (e.g., phospholipid) comprises from about 5 mol % to about 25 mol % of the total lipid present in the composition.

In some embodiments of the first aspect, the cationically ionizable lipid comprises from about 40 mol % to about 70 mol %, such as from about 45 mol % to about 65 mol % or from about 50 mol % to about 60 mol %, of the total lipid present in the composition; the steroid (which preferably is cholesterol) comprises from about 15 mol % to about 40 mol %, such as from about 20 mol % to about 35 mol %, or from about 20 mol % to about 30 mol %, of the total lipid present in the composition; and the neutral lipid (which preferably is a phospholipid) comprises from about 15 mol % to about 25 mol %, such as from about 17 mol % to about 21 mol %, of the total lipid present in the composition. These embodiments of the composition of the first aspect, i.e., compositions containing higher relative amounts of ionizable and neutral lipids and a lower relative amount of steroid, are especially suitable for transfecting cells in the presence of serum. In some of these embodiments, the steroid is cholesterol and the neutral lipid is a phospholipid.

In some embodiments of the first aspect, which contain higher relative amounts of ionizable and neutral lipids and a lower relative amount of steroid, the molar ratio of steroid to neutral lipid is at most 2.5, preferably said ratio is between 1 and 2.5. Thus, in some embodiments of the first aspect, the cationically ionizable lipid comprises from about 40 mol % to about 70 mol % (such as from about 45 mol % to about 65 mol % or from about 50 mol % to about 60 mol %) of the total lipid present in the composition; the steroid comprises from about 15 mol % to about 40 mol % (such as from about 20 mol % to about 35 mol % or from about 20 mol % to about 30 mol %) of the total lipid present in the composition; the neutral lipid comprises from about 15 mol % to about 25 mol % (such as from about 17 mol % to about 21 mol %) of the total lipid present in the composition; and the molar ratio of steroid to neutral lipid is at most 2.5, preferably said ratio is between 1 and 2.5. In some of these embodiments, the steroid is cholesterol and the neutral lipid is a phospholipid.

In some alternative embodiments of the first aspect, the cationically ionizable lipid comprises from about 20 mol % to about 40 mol %, such as from about 25 mol % to about 40 mol % or from about 25 mol % to about 35 mol %, of the total lipid present in the composition; the steroid (which preferably is cholesterol) comprises from about 35 mol % to about 60 mol %, such as from about 40 mol % to about 60 mol % or from about 45 mol % to about 60 mol %, of the total lipid present in the composition; and the neutral lipid (which preferably is a phospholipid) comprises from about 5 mol % to about 15 mol %, such as from about 7 mol % to about 14 mol %, of the total lipid present in the composition. These alternative embodiments of the composition of the first aspect, i.e., compositions containing lower relative amounts of ionizable and neutral lipids and a higher relative amount of steroid, are especially suitable for transfecting cells in the absence of serum. In some of these embodiments, the steroid is cholesterol and the neutral lipid is a phospholipid.

In some embodiments of the first aspect, which contain lower relative amounts of ionizable and neutral lipids and a higher relative amount of steroid, the molar ratio of steroid to neutral lipid is at least 3.0, preferably said ratio is between 3.0 and 10.0, such as between 5.0 and 7.0. Thus, in some embodiments of the first aspect, the cationically ionizable lipid comprises from about 20 mol % to about 40 mol % (such as from about 25 mol % to about 40 mol % or from about 25 mol % to about 35 mol %) of the total lipid present in the composition; the steroid comprises from about 35 mol % to about 60 mol % (such as from about 40 mol % to about 60 mol % or from about 45 mol % to about 60 mol %) of the total lipid present in the composition; the neutral lipid comprises from about 5 mol % to about 15 mol % (such as from about 7 mol % to about 14 mol %) of the total lipid present in the composition; and the molar ratio of steroid to neutral lipid is at least 3.0, preferably said ratio is between 3.0 and 10.0, such as between 5.0 and 7.0. In some of these embodiments, the steroid is cholesterol and the neutral lipid is a phospholipid.

In some embodiments of the first aspect, the composition further comprises one or more additional lipids. For example, the one or more additional lipids may comprise a cationic lipid. In these embodiments, where a cationic lipid is present, the sum of (1) the amount the cationically ionizable lipid and (2) the amount of cationic lipid is used for calculations. E.g., if the amount of cationically ionizable lipid in a composition should be from about 20 mol % to about 70 mol % and the composition should also contain a cationic lipid, then the sum of (1) the amount the cationically ionizable lipid and (2) the amount of cationic lipid is to be from about 20 mol % to about 70 mol %.

In some embodiments of the first aspect, the only lipids contained in the composition are the cationically ionizable lipid, the steroid and the neutral lipid, in particular the cationically ionizable lipid, the steroid and the phospholipid.

In some embodiments of the first aspect, the composition comprises particles dispersed in an aqueous phase, wherein the particles comprise at least a portion of the nucleic acid, at least a portion of the cationically ionizable lipid, at least a portion of the steroid, and at least a portion of the neutral lipid; and wherein at least a portion of the multivalent anion (such as the inorganic polyphosphate) is associated with the particles. In some embodiments, the particles comprise or are selected from lipid nanoparticles (LNPs), liposomes, lipoplexes (LPXs), and mixtures thereof. In some embodiments, the particles comprise or are LNPs. In some embodiments, the particles comprise or are liposomes. In some embodiments, the particles comprise or are LPXs. In some embodiments, the particles comprise or are mixtures of LNPs and liposomes. In some embodiments, the particles comprise or are mixtures of LNPs and LPXs. In some embodiments, the particles comprise or are mixtures of liposomes and LPXs. In some embodiments, the particles comprise or are mixtures of LNPs, liposomes, and LPXs.

In some embodiments of the first aspect, where the composition comprises particles dispersed in an aqueous phase, the particles comprise essentially all of lipids, (in particular all of the cationically ionizable lipid, the steroid, and the neutral lipid) present in the composition.

In some embodiments of the first aspect, where the composition comprises particles dispersed in an aqueous phase, the aqueous phase is substantially free of the cationically ionizable lipid, the steroid, and the neutral lipid (e.g., substantially free of lipids).

In some embodiments of the first aspect, where the composition comprises particles dispersed in an aqueous phase, the particles comprise at least 50% (such as at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%) of the nucleic acid (in particular RNA) present in the composition. In some embodiments, the particles comprise at least 75%, preferably at least 85% of the nucleic acid (in particular RNA) present in the composition.

In some embodiments of the first aspect, where the composition comprises particles dispersed in an aqueous phase, the aqueous phase is substantially free of the nucleic acid.

In some embodiments of the first aspect, where the composition comprises particles dispersed in an aqueous phase, the nucleic acid (such as RNA) is encapsulated within or associated with the particles.

In some embodiments of the first aspect, where the composition comprises particles dispersed in an aqueous phase, at least 10% (such as at least 15%, at least 20%, at least 25%, at least 30%, at least 35%, at least 40%, at least 45%, at least 50%, at least 55%, at least 60%) of the multivalent anion (such as the polyphosphate) present in the composition is associated with the particles. In some embodiments, at least 20%, and more preferably at least 50% of the multivalent anion (such as the polyphosphate) present in the composition is associated with the particles.

In some embodiments of the first aspect, where the composition comprises particles dispersed in an aqueous phase, the particles have a size of from about 30 nm to about 500 nm. In some embodiments, the particles have a size from about 50 nm to about 150 nm.

In some embodiments of the first aspect, the nucleic acid is DNA.

In some embodiments of the first aspect, the nucleic acid is RNA, preferably mRNA or inhibitory RNA, (e.g. siRNA).

In some embodiments of the first aspect, the nucleic acid is RNA (such as mRNA) and (i) comprises a modified nucleoside in place of uridine; (ii) has a coding sequence which is codon-optimized; and/or (iii) has a coding sequence whose G/C content is increased compared to the wild-type coding sequence. In some embodiments, the modified nucleoside is selected from pseudouridine (ψ), N1-methyl-pseudouridine (m1ψ), and 5-methyl-uridine (m5U).

In some embodiments of the first aspect, the nucleic acid is RNA (such as mRNA) and comprises at least one or more of the following: a 5' cap; a 5' UTR; a 3' UTR; and a poly-A sequence. In some embodiments, the RNA (such as mRNA) comprises all of the following: a 5' cap; a 5' UTR; a 3' UTR; and a poly-A sequence. In some embodiments, the poly-A sequence comprises at least 100 A nucleotides, wherein the poly-A sequence preferably is an interrupted sequence of A nucleotides. In some embodiments, the 5' cap is a cap1 or cap2 structure.

In some embodiments of the first aspect, the nucleic acid is RNA (such as mRNA) and encodes one or more polypeptides. In some embodiments, the one or more polypeptides are pharmaceutically active polypeptides and/or comprise an epitope for inducing an immune response against an antigen in a subject.

In some embodiments of the first aspect, the pharmaceutically active polypeptide and/or the antigen or epitope is derived from or is a protein of a pathogen, an immunogenic variant of the protein, or an immunogenic fragment of the protein or the immunogenic variant thereof. In some embodiments, the pathogen is a pathogen causing an infectious disease.

In some embodiments of the first aspect, the pharmaceutically active polypeptide and/or the antigen or epitope is derived from or is a SARS-CoV-2 spike (S) protein, an immunogenic variant thereof, or an immunogenic fragment of the SARS-CoV-2 S protein or the immunogenic variant thereof. In some embodiments, the RNA (such as mRNA) comprises an open reading frame (ORF) encoding an amino acid sequence comprising a SARS-CoV-2 S protein, an immunogenic variant thereof, or an immunogenic fragment of the SARS-CoV-2 S protein or the immunogenic variant thereof.

In some embodiments of the first aspect, the nucleic acid is inhibitory RNA (such as siRNA) and selectively hybridizes to and/or is specific for a target mRNA. In some embodiments, the target mRNA comprises an ORF encoding a pharmaceutically active peptide or polypeptide, in particular a pharmaceutically active peptide or polypeptide whose expression (in particular increased expression, e.g., compared to the expression in a healthy subject) is associated with a disease. In some embodiments, the target mRNA comprises an ORF encoding a pharmaceutically active peptide or polypeptide whose expression (in particular increased expression, e.g., compared to the expression in a healthy subject) is associated with cancer.

In some embodiments of the first aspect, the composition is in liquid form, preferably at a temperature of about 2° C. to about 10° C.

In some embodiments of the first aspect, the nucleic acid integrity (such as the RNA integrity) of the composition after storage for at least one week, preferably at a temperature of 0° C. or higher, such as about 2° C. to about 8° C., is such that the desired effect, e.g., to induce an immune response, can be achieved. In some embodiments, the nucleic acid integrity (such as the RNA integrity) of the composition after storage for at least one week (such as for at least 2 weeks, at least three weeks, at least four weeks, at least one month, at least two months, at least three months, at least 4 months, or at least 6 months), preferably at a temperature of 0° C. or higher, such as about 2° C. to about 8° C., is at least 90%, compared to the nucleic acid integrity before storage. In some embodiments, the nucleic acid integrity (such as the RNA integrity) of the composition after storage for at least four weeks, preferably at a temperature of 0° C. or higher, such as about 2° C. to about 8° C., is at least 90%, compared to the nucleic acid integrity before storage. In some embodiments, the nucleic acid integrity (such as the RNA integrity) of the composition after storage for at least three months, preferably at a temperature of 0° C. or higher, such as about 2° C. to about 8° C., is at least 90%, compared to the nucleic acid integrity before storage.

In some embodiments of the first aspect, the initial nucleic acid integrity (such as the initial RNA integrity) of the composition (i.e., after its preparation but before storage) is at least 50% and the nucleic acid integrity (such as the RNA integrity) of the composition after storage for at least one week (such as for at least 2 weeks, at least three weeks, at least four weeks, at least one month, at least two months, or at least 3 months), preferably at a temperature of 0° C. or higher, such as about 2° C. to about 8° C., is at least 90%, of the initial RNA integrity.

Additionally or alternatively, in some embodiments of the first aspect, the size ($Z_{average}$) (and/or size distribution and/or polydispersity index (PDI)) of the nucleic acid particles (such as the RNA particles) of the liquid composition after storage (e.g., for at least one week), preferably at a temperature of 0° C. or higher, such as about 2° C. to about 8° C., is such that the desired effect, e.g., to induce an immune response, can be achieved. In some embodiments, the size ($Z_{average}$) (and/or size distribution and/or polydispersity index (PDI)) of the nucleic acid particles (such as the RNA particles) of the liquid composition after storage (e.g., for at least one week), preferably at a temperature of 0° C. or higher, such as about 2° C. to about 8° C., is essentially equal to the size ($Z_{average}$) (and/or size distribution and/or PDI) of the nucleic acid particles (such as the RNA particles) of the initial composition, i.e., before storage. In some embodiments, the size ($Z_{average}$) of the nucleic acid particles (such as the RNA particles) after storage for at least one week (such as at least four weeks, or at least three months), preferably at a temperature of 0° C. or higher, such as about 2° C. to about 8° C., is between about 50 nm and about 500 nm, preferably between about 40 nm and about 200 nm, more preferably between about 40 nm and about 120 nm. In some embodiments, the PDI of the nucleic acid particles (such as the RNA particles) after storage for at least one week (such as at least four weeks, or at least three months), preferably at a temperature of 0° C. or higher, such as about 2° C. to about 8° C., is less than 0.3, preferably less than 0.2, more preferably less than 0.1. In some embodiments, the size ($Z_{average}$) of the nucleic acid particles (such as the RNA particles) after storage for at least one week (such as at least four weeks, or at least three months), preferably at a temperature of 0° C. or higher, such as about 2° C. to about 8° C., is between about 50 nm and about 500 nm, preferably between about 40 nm and about 200 nm, more preferably between about 40 nm and about 120 nm, and the size ($Z_{average}$) (and/or size distribution and/or PDI) of the nucleic acid particles (such as the RNA particles) after storage of the liquid composition for at least one week (such as at least four weeks, or at least three months), preferably at a temperature of 0° C. or higher, such as about 2° C. to about 8° C., is essentially equal to the size ($Z_{average}$) (and/or size distribution and/or PDI) of the nucleic acid particles (such as the RNA particles) before storage. In one embodiment, the size ($Z_{average}$) of the nucleic acid particles (such as the RNA particles) after storage of the liquid composition for at least one week (such as at least four weeks, or at least three months), preferably at a temperature of 0° C. or higher, such as about 2° C. to about 8° C., is between about 50 nm and about 500 nm, preferably between about 40 nm and about 200 nm, more preferably between about 40 nm and about 120 nm, and the PDI of the nucleic acid particles (such as the RNA particles) after storage of the liquid composition for at least one week (such as at least four weeks, or at least three months), preferably at a temperature of 0° C. or higher, such as about 2° C. to about 8° C., e.g., at 0° C. or higher for at least one week is less than 0.3 (preferably less than 0.2, more preferably less than 0.1).

In some embodiments of the first aspect, the composition is in frozen form (e.g., at −20° C.). In some embodiments, the nucleic acid integrity (such as the RNA integrity) after thawing the frozen composition is at least 90%, at least 95%, at least 97%, at least 98%, or substantially 100%, compared to the nucleic acid integrity (such as the RNA integrity) before the composition has been frozen. In some embodiments, the size ($Z_{average}$) and/or size distribution and/or polydispersity index (PDI) of nucleic acid particles (such as RNA particles), in particular LNPs, after thawing the frozen composition is essentially equal to the size ($Z_{average}$) and/or size distribution and/or PDI of the nucleic acid particles (such as the RNA particles) before the composition has been frozen.

In some embodiments of the first aspect, the initial nucleic acid integrity (such as the initial RNA integrity) of the composition (i.e., after its preparation but before freezing) is at least 50% and the nucleic acid integrity (such as the RNA integrity) of the composition after thawing the frozen composition is at least 90%, preferably at least 95%, more preferably at least 97%, more preferably at least 98%, more preferably substantially 100%, of the initial nucleic acid integrity (such as the initial RNA integrity).

Additionally or alternatively, in some embodiments of the first aspect, the size ($Z_{average}$) (and/or size distribution and/or polydispersity index (PDI)) of the nucleic acid particles (such as the RNA particles) after thawing the frozen composition is essentially equal to the size ($Z_{average}$) (and/or size distribution and/or PDI) of the nucleic acid particles (such as the RNA particles) before the composition has been frozen. In some embodiments, the size ($Z_{average}$) of the nucleic acid particles (such as the RNA particles) after thawing the frozen composition is between about 50 nm and about 500 nm, preferably between about 40 nm and about 200 nm, more preferably between about 40 nm and about 120 nm. In some embodiments, the PDI of the nucleic acid particles (such as the RNA particles) after thawing the frozen composition is less than 0.3, preferably less than 0.2, more preferably less than 0.1. In some embodiments, the size ($Z_{average}$) of the nucleic acid particles (such as the RNA particles) after thawing the frozen composition is between about 50 nm and about 500 nm, preferably between about 40 nm and about 200 nm, more preferably between about 40 nm and about 120 nm, and the size ($Z_{average}$) (and/or size distribution and/or PDI) of the nucleic acid particles (such as the RNA particles) after thawing the frozen composition is essentially equal to the size ($Z_{average}$) (and/or size distribution and/or PDI) of the nucleic acid particles (such as the RNA particles) before freezing. In some embodiments, the size ($Z_{average}$) of the nucleic acid particles (such as the RNA particles) after thawing the frozen composition is between about 50 nm and about 500 nm, preferably between about 40 nm and about 200 nm, more preferably between about 40 nm and about 120 nm, and the PDI of the nucleic acid particles (such as the RNA particles) after thawing the frozen composition is less than 0.3 (preferably less than 0.2, more preferably less than 0.1).

In some embodiments of the first aspect, the size of the nucleic acid particles (such as the RNA particles) and the nucleic acid integrity (such as the RNA integrity) of the composition after one freeze/thaw cycle, preferably after two freeze/thaw cycles, more preferably after three freeze/thaw cycles, more preferably after four freeze/thaw cycles, more preferably after five freeze/thaw cycles or more, are essentially equal to the size of the nucleic acid particles (such as the RNA particles) and the nucleic acid integrity (such as the RNA integrity) of the initial composition (i.e., before the composition has been frozen for the first time).

In a second aspect, the present disclosure provides a method of preparing a composition comprising particles dispersed in a final aqueous phase, wherein the composition comprises (i) a nucleic acid; (ii) a cationically ionizable lipid; (iii) a steroid; (iv) a neutral lipid; and (v) a multivalent anion (such as an inorganic polyphosphate); wherein the particles comprise at least a portion of the nucleic acid, at least a portion of the cationically ionizable lipid, and at least a portion of the steroid; wherein at least a portion of the multivalent anion (such as the inorganic polyphosphate) is associated with the particles; and wherein the final aqueous phase comprises a final buffer system;

wherein the method comprises:

(I) preparing a formulation comprising particles dispersed in the final aqueous phase, wherein the particles comprise at least a portion of the nucleic acid, at least a portion of the cationically ionizable lipid, at least a portion of the steroid, and at least a portion of the neutral lipid, and wherein at least a portion of the multivalent anion (such as the inorganic polyphosphate) is associated with the particles; and (II) optionally freezing the formulation to about −10° C. or below, thereby obtaining the composition, wherein step (I) comprises:

(a) providing (e.g., preparing) a nucleic acid solution containing water and a first buffer system;

(b) providing (e.g., preparing) an organic solution comprising the cationically ionizable lipid, the steroid, and the neutral lipid;

(c) mixing the nucleic acid solution provided under (a) with the organic solution provided under (b), thereby preparing a first intermediate formulation comprising the particles dispersed in a first aqueous phase comprising the first buffer system;

(d) mixing the first intermediate formulation prepared under (c) with a multivalent anion (such as an inorganic polyphosphate) or a salt thereof, thereby preparing a second intermediate formulation comprising the particles dispersed in a second aqueous phase comprising a second buffer system, wherein at least a portion of the multivalent anion (such as the inorganic polyphosphate) is associated with the particles; and (e) filtrating (e.g., dialyzing, tangential flow filtrating or diafiltrating) and/or diluting the second intermediate formulation prepared under (d) using a final aqueous buffer solution comprising the final buffer system, thereby preparing the formulation comprising the particles dispersed in the final aqueous phase.

As demonstrated in the present application, by using the method of the present application compositions comprising particles dispersed in a final aqueous phase can be prepared, wherein the compositions comprise (i) a nucleic acid; (ii) a cationically ionizable lipid; (iii) a steroid; (iv) a neutral lipid; and (v) a multivalent anion (such as an inorganic polyphosphate); and wherein the particles comprise at least a portion of the nucleic acid, at least a portion of the cationically ionizable lipid, and at least a portion of the steroid, wherein the aggregation of the particles can be prevented due to the presence of the multivalent anion (such as the inorganic polyphosphate), even if the composition/particles does/do not contain a PEG lipid or any other stealth lipid (polymer-conjugated lipid). Furthermore, the present application demonstrates that, surprisingly, by using the method of the present application, in particular by adjusting the amounts of lipids to each other, it is possible to obtain nucleic acid (such as RNA) compositions exhibiting different biological performances: when used for transfecting cells, nucleic acid compositions containing higher relative amounts of ionizable and neutral lipids and a lower relative amount of steroid result in higher expression of the nucleic acid in the transfected cells if the transfection is carried out in the presence of serum compared to the expression obtained if the transfection is carried out in the absence of serum (these compositions resemble standard nucleic acid compositions containing a PEG lipid). In contrast, nucleic acid compositions containing lower relative amounts of ionizable and neutral lipids and a higher relative amount of steroid and used for transfecting cells result in comparable or reduced expression of the nucleic acid in the transfected cells if the transfection is carried out in the presence of serum (i.e., these compositions show some or no serum inhibition, but do not show serum stimulation).

An exemplary flowchart of steps (c) to (e) according to the method of the second aspect is depicted in FIG. 1A. First, the aqueous nucleic acid solution (containing a first buffer system, e.g., a buffer system which has a pH below 6.0, such as a pH between about 3.5 and about 5.9) is mixed with the organic (e.g., ethanolic) lipids solution ("lipids in org. solution" in FIG. 1A) thereby forming the first intermediate formulation which comprises particles dispersed in a first aqueous phase comprising the first buffer system. Thereafter, the first intermediate formulation is mixed with a multivalent anion (such as an inorganic polyphosphate) or a salt thereof, thereby preparing a second intermediate formulation comprising the particles dispersed in a second aqueous phase comprising a second buffer system, wherein at least a portion of the multivalent anion (such as the inorganic polyphosphate) is associated with the particles. Then, the second intermediate formulation is filtrated (e.g., using dialysis, tangential flow filtration and/or diafiltration), and/or diluted using a final aqueous buffer solution comprising the final buffer system, thereby preparing the formulation comprising the particles dispersed in the final aqueous phase. For example, the second intermediate formulation is filtrated in order to remove unwanted compounds (e.g., organic solvent (such as ethanol) and/or one or more mono-, di- and/or polybasic organic acids and, optionally, respective countercations used for maintaining the pH below 6.0) from the second intermediate formulation and/or to increase the nucleic acid (such as RNA) concentration and/or to change the pH and/or to change the buffer system to the final buffer system.

In some embodiments of the second aspect, step (d) is conducted at most about 20 min after step (c). In some embodiments, step (d) is conducted at most about 19 min (such as at most about 18 min, at most about 17 min, at most about 16 min, at most about 15 min, at most about 14 min, at most about 13 min, at most about 12 min, at most about 11 min, at most about 10 min, at most about 9 min, at most about 8 min, at most about 7 min, at most about 6 min, or at most about 5 min) after step (c).

In some embodiments of the second aspect, step (I) further comprises one or more optional processing steps selected from diluting and filtrating, such as dialyzing, tangential flow filtrating and diafiltrating, after step (c) and/or step (d) and/or step (e) (preferably only after step (d) and/or step (e)). For example, a diluting step may comprise adding a dilution solution (e.g., water) to an intermediate formulation. Such dilution solution may comprise one or more additional compounds (e.g., a cryoprotectant) and optionally a buffer system (e.g., the final buffer system). The diluting step may be carried out to dilute unwanted compounds (e.g., organic solvent (such as ethanol) and/or one or more di- and/or polybasic organic acids) in the intermediate formulation and/or to change the pH and/or to change the buffer system and/or to add one or more additional compounds (e.g., a cryoprotectant). The one or more 25 filtrating steps (including steps (e), (h'), (i') and (j') as specified herein) may be used to remove unwanted compounds (e.g., organic solvent (such as ethanol) and/or one or more di- and/or polybasic organic acids) from an intermediate formulation and/or to increase the nucleic acid (such as RNA) concentration of an intermediate formulation and/or to change the pH and/or to change the buffer system of an intermediate formulation. To this end, an aqueous buffer solution can be used, which does not contain the unwanted compounds (such that the unwanted compounds are filtrated or washed out from the intermediate formulation and into the aqueous buffer solution) and/or which is hypertonic compared to the aqueous buffer solution (such that water flows from the intermediate formulation to the aqueous buffer solution) and/or which has a pH and/or buffer system other than the pH and/or buffer system of the intermediate formulation.

In some embodiments of the second aspect, step (a) comprises (a') providing an aqueous nucleic acid solution; (b') providing a first aqueous buffer solution comprising a first buffer system; and (c') mixing the aqueous nucleic acid solution provided under (a') with the first aqueous buffer solution provided under (b') thereby providing (e.g., preparing) a nucleic acid solution containing water and the first buffer system.

In some embodiments of the second aspect, the organic solution comprises an organic solvent selected from a lower alcohol, such as alcohols (in particular aliphatic alcohols) having up to 6 carbon atoms, and mixtures of two or more of these alcohols. In preferred embodiments, the organic solvent is completely miscible with water. In some embodiments, the organic solvent is selected from the group consisting of ethanol, propanol, isopropanol, 1,2-propanediol, and mixtures of two or more of these alcohols.

In some embodiments of the second aspect, step (I) comprises:

(a') providing an aqueous nucleic acid solution;

(b') providing a first aqueous buffer solution comprising a first buffer system;

(c') mixing the aqueous nucleic acid solution provided under (a') with the first aqueous buffer solution provided under (b') thereby preparing a nucleic acid solution containing water and the first buffer system;

(d') providing (e.g., preparing) an organic solution comprising the cationically ionizable lipid, the steroid, and the neutral lipid;

(e') mixing the nucleic acid solution prepared under (c') with the organic solution provided (e.g., prepared) under (d'), thereby preparing a first intermediate formulation comprising particles dispersed in a first aqueous phase comprising the first buffer system;

(f') optionally diluting the first intermediate formulation prepared under (e') using water or a further aqueous buffer solution comprising a further buffer system, thereby preparing a further intermediate formulation comprising the particles dispersed in a further aqueous phase comprising the first or further buffer system, wherein the further aqueous buffer solution may be identical to or different from the first aqueous buffer solution;

(g') mixing the first intermediate formulation obtained in step (e'), if step (f') is absent, or the further intermediate formulation obtained in step (f'), if step (f') is present, with a multivalent anion (such as an inorganic polyphosphate) or a salt thereof (as specified herein), thereby preparing a second intermediate formulation comprising the particles dispersed in a second aqueous phase, wherein at least a portion of the multivalent anion (such as the inorganic polyphosphate) is associated with the particles;

(h') optionally filtrating the second first intermediate formulation prepared under (g') using a further aqueous buffer solution comprising a further buffer system, thereby preparing a further intermediate formulation comprising the particles dispersed in a further aqueous phase comprising the further buffer system, wherein the further aqueous buffer solution may be identical to or different from the first and/or second aqueous buffer solution;

(i') optionally repeating step (h') once or two or more times, wherein the further intermediate formulation comprising the particles dispersed in the further aqueous phase comprising the further buffer system obtained after step (h') of one cycle is used as the second intermediate formulation of the next cycle, wherein in each cycle the further aqueous buffer solution may be identical to or different from the first and/or second aqueous buffer solution;

(j') filtrating the second intermediate formulation obtained in step (g'), if step (h') is absent, or the further intermediate formulation obtained in step (h'), if step (h') is present and step (i') is not present, or the further intermediate formulation obtained after step (i'), if steps (h') and (i') are present, using a final aqueous buffer solution comprising the final buffer system; and (k') optionally diluting the formulation obtained in step (j') with a dilution solution;

thereby preparing the formulation comprising the particles dispersed in the final aqueous phase.

An exemplary flowchart of steps (e'), (g'), and (j') according to these embodiments of the second aspect is depicted in FIG. 1B (also showing optional processing steps (f'), (h'), (i'), and (k')). First, in step (e'), the aqueous nucleic acid solution (containing a first buffer system, e.g., a buffer system which has a pH below 6.0, such as a pH between about 3.5 and about 5.9) is mixed with the organic lipids solution thereby forming the first intermediate formulation which comprises particles dispersed in a first aqueous phase comprising the first buffer system. Thereafter, optionally, the first intermediate formulation is (f') diluted using water or a further aqueous buffer solution comprising a further buffer system, thereby preparing a further intermediate formulation comprising the particles dispersed in a further aqueous phase comprising the first or further buffer system, wherein the further aqueous buffer solution may be identical to or different from the first aqueous buffer solution. Optional step (f') may be carried out to dilute unwanted compounds (e.g., organic solvent (such as ethanol) and/or one or more di- and/or polybasic organic acids) in the first intermediate formulation and/or to change the pH and/or to change the buffer system. In specific embodiments, step (f') is used to change the pH of the first intermediate formulation to a pH between 7 and 9, preferably between 7.5 and 8.5 and even more preferably between 7.5 and 8.0. Then, in step (g'), the first intermediate formulation (if step (f') is absent) or the respective further intermediate formulation (if step (f') is present) is mixed with a multivalent anion (such as an inorganic polyphosphate) or a salt thereof, thereby preparing a second intermediate formulation comprising the particles dispersed in a second aqueous phase comprising a second buffer system, wherein at least a portion of the multivalent anion (such as the inorganic polyphosphate) is associated with the particles. Then, optionally, the second intermediate formulation is (h') filtrated (e.g., dialyzed, tangential flow filtrated or diafiltrated) using a further aqueous buffer solution comprising a further buffer system, thereby preparing a further intermediate formulation comprising the particles dispersed in a further aqueous phase comprising the further buffer system, wherein the further aqueous buffer solution may be identical to or different from the first and/or the second aqueous buffer solution; and, optionally, under (i'), step (h') is repeated once or two or more times. Optional steps (h') and (i') may be carried out to remove unwanted compounds (e.g., organic solvent (such as ethanol) and/or one or more mono-, di- and/or polybasic organic acids and, optionally, their respective countercations) from the second intermediate formulation and/or to increase the nucleic acid (such as RNA) concentration and/or to change the pH and/or to change the buffer system. Then, in step (j'), the second intermediate formulation (if step (h') is absent) or the respective further intermediate formulation (if step (h') is present or both steps (h') and (i') are present) is filtrated (e.g., dialyzed, tangential flow filtrated or diafiltrated) using a final aqueous buffer solution comprising the final buffer system. Step (j') is carried out to remove unwanted compounds (e.g., organic solvent (such as ethanol) and/or one or more mono-, di- and/or polybasic organic acids and, optionally, their respective countercations) from the intermediate formulation and/or to increase the nucleic acid (such as RNA) concentration and/or to change the pH and/or to change the buffer system to the final buffer system. Optionally, in step (k'), the formulation obtained in step (j') is diluted with a dilution solution (e.g., for adding a cryoprotectant).

In some embodiments of the second aspect, step (f') is used to change the pH of the first intermediate formulation to a pH between 7 and 9, preferably between 7.5 and 8.5 and even more preferably between 7.5 and 8.0, and is conducted no later than 12 hours, preferably no later than 4 hours and more preferably no later than 30 minutes after step (e'). In specific embodiments of the second aspect, step (f') is used to change the pH of the first intermediate formulation to a pH between 7 and 9 followed by the addition of the multivalent anion in step (g') and the combined duration of steps (f') and (g') is no longer than 12 hours, preferably no longer than 4 hours and more preferably no longer than 30 minutes after step (e').

In some embodiments of the second aspect, step (g') is conducted at most about 20 min after step (e'). In some embodiments, step (g') is conducted at most about 19 min (such as at most about 18 min, at most about 17 min, at most about 16 min, at most about 15 min, at most about 14 min, at most about 13 min, at most about 12 min, at most about 11 min, at most about 10 min, at most about 9 min, at most about 8 min, at most about 7 min, at most about 6 min, or at most about 5 min) after step (e').

In some embodiments of the second aspect, step (f') is absent and step (g') is conducted at most about 20 min after step (e'). In some embodiments, step (g') is conducted at most about 19 min (such as at most about 18 min, at most about 17 min, at most about 16 min, at most about 15 min, at most about 14 min, at most about 13 min, at most about 12 min, at most about 11 min, at most about 10 min, at most about 9 min, at most about 8 min, at most about 7 min, at most about 6 min, or at most about 5 min) after step (e').

In some embodiments of the second aspect, step (f') is absent. An exemplary flowchart of steps (e'), (g'), and (j') according to these embodiments of the second aspect (i.e., where step (f') is absent) is depicted in FIG. 1C (also showing optional processing steps (h'), (i'), and (k')). These embodiments are especially preferred, when step (g') is conducted at most about 20 min after step (e').

In some embodiments of the second aspect, step (f') is present.

In some embodiments of the second aspect, the organic solution provided in step (e') comprises an organic solvent selected from a lower alcohol, such as alcohols (in particular aliphatic alcohols) having up to 6 carbon atoms, and mixtures thereof (such as mixtures of two or more of these alcohols). In preferred embodiments, the organic solvent is completely miscible with water. In some embodiments, the organic solvent is selected from the group consisting of ethanol, propanol, isopropanol, 1,2-propanediol, and mixtures of two or more of these alcohols.

In some embodiments of the second aspect, the multivalent anion or a salt thereof is an inorganic phosphate, sulfate, sulfite, pyrosulfate, dithionate, dithionite, metabisulfite, thiosulfate, trithionate, tetrathionate, or a salt thereof. In some embodiments, the multivalent anion is an inorganic phosphate (e.g., $PO_4^{3-}$).

In some embodiments of the second aspect, the multivalent anion or a salt thereof is a dicarboxylic acid (e.g., oxalic, malonic, succinic, glutaric, adipic, pimelic, sebacic, phthalic, isophthalic or terephthalic acid), a substituted dicarboxylic acid (e.g., tartronic, mesoxalic, malic, tartaric, aspartic, glutamic, hydroxyglutaric or saccharinic acid), or a salt thereof.

In some embodiments, the multivalent anion or a salt thereof is a tricarboxylic acid (e.g., citric, isocitric, propane-1,2,3-tricarboxylic or trimesic acid) or a salt thereof.

In some preferred embodiments of the second aspect, the multivalent anion or a salt thereof is selected from the group consisting of: an inorganic polyphosphate, an inorganic phosphate (e.g., $PO_4^{3-}$), sulfate, succinate, glutarate, tartrate, malate, citrate, salts thereof or mixtures thereof. In some embodiments, the multivalent anion or a salt thereof is an inorganic polyphosphate, an inorganic phosphate, citrate, or a salt thereof.

In some most preferred embodiments of the second aspect, the multivalent anion or a salt thereof is an inorganic polyphosphate or a salt thereof.

In some embodiments of the second aspect, where the multivalent anion or a salt thereof is an inorganic polyphosphate or a salt thereof, the inorganic polyphosphate or a salt thereof can be any linear, cyclic, or branched inorganic polyphosphate or a salt thereof. In some embodiments of the second aspect, the inorganic polyphosphate or a salt thereof is a linear inorganic polyphosphate (such as a linear inorganic triphosphate) or a salt thereof.

In some embodiments of the second aspect, where the multivalent anion or a salt thereof is an inorganic polyphosphate or a salt thereof, the inorganic polyphosphate or a salt thereof comprises or has the formula $[P_xO_{(3x+1)}]M_{y'}$, wherein x is an integer and is at least 2, preferably at least 3; each M is independently $H^+$ or a cation; and y' is the number of cations needed for charge equalization. M may be only of one type (e.g., only $Na^+$) or may be of two or more types (e.g., a mixture of $Na^+$ and $K^+$, or a mixture of $Na^+$ and $H^+$, or a mixture of $Na^+$ $K^+$, and $H^+$). In some embodiments, each M is independently selected from the group consisting of $H^+$, an alkaline cation (e.g., $Li^+$, $Na^+$, $K^+$), ammonium (i.e., $NH_4^+$), and a monovalent organic cation (e.g., a monovalent organic amine, such as trimethylamine, triethylamine, etc.). In some embodiments, each M is independently selected from the group consisting of $H^+$, $Na^+$, $K^+$, $Li^+$, and $NH_4^+$. For example, if x is 3, the inorganic polyphosphate or a salt thereof is a linear inorganic triphosphate or a salt comprising or having the formula $[P_3O_{10}]M_{y'}$ (such as $[P_3O_{10}]Na_5$). Likewise, if x is 4, the inorganic polyphosphate or a salt thereof is a linear or branched inorganic tetraphosphate or a salt thereof comprising or having the formula $[P_4O_{13}]M_{y'}$ (such as $[P_4O_{13}]Na_6$ or $[P_4O_{13}]Na_4K_2$).

In some embodiments of the second aspect, where the multivalent anion or a salt thereof is an inorganic polyphosphate or a salt thereof, the inorganic polyphosphate or a salt thereof is selected from the group consisting of diphosphate, triphosphate, tetraphosphate, pentaphosphate, hexaphosphate, heptaphosphate, salts and mixtures thereof, such as from the group consisting of triphosphate, tetraphosphate, pentaphosphate, hexaphosphate, heptaphosphate, and mixtures thereof. In some preferred embodiments of the second aspect, the inorganic polyphosphate or a salt thereof is selected from the group consisting of triphosphate, tetraphosphate, pentaphosphate, salts and mixtures thereof.

In some preferred embodiments of the second aspect, the inorganic polyphosphate or a salt thereof is triphosphate or a salt thereof.

In some embodiments of the second aspect, the molar ratio of (v) the multivalent anion (such as the inorganic polyphosphate) to (ii) the cationically ionizable lipid is at least about 1:2. For example, the molar ratio of (v) the multivalent anion (such as the inorganic polyphosphate) to (ii) the cationically ionizable lipid may be at least about 0.55, at least about 0.60, at least about 0.65, at least about 2:3, at least about 0.7, at least about 0.75, at least about 0.80, at least about 0.85, at least about 0.90, at least about 0.95, at least about 1.00, at least about 1.10, at least about 1.20, at least about 1.30, at least about 4:3, at least about 1.40, at least about 1.50, at least about 1.60, at least about 1.70, at least about 1.80, at least about 1.90, or at least about 2.0. In some preferred embodiments of the second aspect, the molar ratio of (v) the multivalent anion (such as the inorganic polyphosphate) to (ii) the cationically ionizable lipid is at least about 2:3. In some preferred embodiments of the second aspect, the molar ratio of (v) the multivalent anion (such as the inorganic polyphosphate) to (ii) the cationically ionizable lipid is at least about 4:3.

In some embodiments of the second aspect, in particular if it is desired to prepare a composition in frozen form, the method of the second aspect comprises (II) freezing the formulation to about −10° C. or below. Thus, in these embodiments, conducting the method of the second aspect results in a composition in frozen form.

In some alternative embodiments, in particular if it is desired to prepare a composition in liquid form, the method of the second aspect does not comprise step (II). Thus, in these embodiments, conducting the method of the second aspect results in a composition in liquid form.

In some embodiments of the second aspect, the organic solution provided (e.g., prepared) under (b) or (d'), respectively, additionally comprises an acid. In some embodiments, the acid is an inorganic acid (such as a monobasic inorganic acid, like hydrochloric acid, hydrobromic acid, or nitric acid) or an organic acid (such as a mono-, di- or polybasic organic acid, e.g., a monocarboxylic acid (like acetic acid, propionic acid, or lactic acid), a dicarboxylic acid (like oxalic acid, malonic acid, succinic acid, glutaric acid, adipic acid, maleic acid, fumaric acid, tartaric acid, or malic acid), or a polycarboxylic acid (like citric acid, isocitric acid, or trimesic acid)). In some preferred embodiments, the acid is a monobasic acid, such as such as a monobasic inorganic acid (like hydrochloric acid) or a monobasic organic acid (like acetic acid).

In some embodiments of the second aspect, the composition is substantially free of a lipid comprising polyethyleneglycol (PEG). In some embodiments, the composition is substantially free of any compound comprising PEG. In some embodiments, the composition is substantially free of PEG. In some of these embodiments, the multivalent anion or salt thereof is selected from the group consisting of an inorganic polyphosphate, inorganic phosphate, sulfate, succinate, glutarate, tartrate, malate, citrate, salts and mixtures thereof. In some of these embodiments, the multivalent anion or salt thereof is selected from the group consisting of an inorganic polyphosphate, an inorganic phosphate, citrate, and salts thereof. In some of these embodiments, the multivalent anion or salt thereof is an inorganic polyphosphate or salt thereof.

In some embodiments of the second aspect, the composition is also substantially free of another polymer-conjugated lipid. In some embodiments, the another polymer-conjugated lipid is a polysarcosine-conjugated lipid. Thus, in some embodiments, the composition is substantially free of PEG lipids and substantially free of polysarcosine-conjugated lipids. In some embodiments, the composition is substantially free of any polymer-conjugated lipid. In some of these embodiments, the multivalent anion or salt thereof is selected from the group consisting of an inorganic polyphosphate, inorganic phosphate, sulfate, succinate, glutarate, tartrate, malate, citrate, salts and mixtures thereof. In some of these embodiments, the multivalent anion or salt thereof is selected from the group consisting of an inorganic polyphosphate, an inorganic phosphate, citrate, and salts thereof. In some of these embodiments, the multivalent anion or salt thereof is an inorganic polyphosphate or a salt thereof.

In some embodiments of the second aspect, the pH of the final buffer system (and the pH of the composition) is between about 4.0 and about 8.0. For example, the pH of the final buffer system (and the pH of the composition) may be between about 4.5 and about 8.0, such as between about 5.0 and about 8.0, between about 5.5 and about 8.0, between about 6.0 and about 8.0, between about 6.5 and about 8.0, between about 6.8 and about 7.9, between about 7.0 and about 7.8 or about 7.5.

In some embodiments of the second aspect, the first buffer system (and the pH of the nucleic acid (such as RNA) solution provided/obtained in step (a) or (c')) has a pH of below 6.0, preferably at most about 5.5, such as at most about 5.0, at most about 4.9, at most about 4.8, at most about 4.7, at most about 4.6, or at most about 4.5. For example, the pH of first buffer system (and the pH of the nucleic acid (such as RNA) solution provided/obtained in step (a) or (c')) may be between about 3.5 and about 5.9, such as between about 4.0 and about 5.5, or between about 4.5 and about 5.0. To this end, the nucleic acid (such as RNA) solution provided/obtained in step (a) or (c') may further comprises one or more acids (e.g., selected from inorganic acids (such as hydrochloric acid, hydrobromic acid, or nitric acid) and organic acids (such as mono-, di- or polybasic organic acids, e.g., monocarboxylic acids (like acetic acid, propionic acid, or lactic acid), dicarboxylic acids (like oxalic acid, malonic acid, succinic acid, glutaric acid, adipic acid, maleic acid, fumaric acid, tartaric acid, or malic acid), or polycarboxylic acids (like citric acid, isocitric acid, or trimesic acid)). In some preferred embodiments, the acid is a monobasic acid, such as such as a monobasic inorganic acid (like hydrochloric acid) or a monobasic organic acid (like acetic acid). In some embodiments, it is preferred that step (e) is conducted under conditions which remove one or more unwanted substances (e.g., organic solvent (such as ethanol) and/or the one or more one or more acids) resulting in the formulation comprising the particles dispersed in a final aqueous phase with the final aqueous phase being substantially free of such one or more unwanted substances. For example, such conditions can include subjecting the intermediate formulation comprising the particles dispersed in the second intermediate aqueous phase obtained in step (d) to at least one step of filtrating, such as dialyzing, tangential flow filtrating or diafiltrating, using a final buffer solution comprising the final buffer system (i.e., the final buffer substance), wherein the final buffer solution does not contain the one or more unwanted substances. Alternatively, such conditions can include (1) subjecting the intermediate formulation comprising the particles dispersed in the second intermediate aqueous phase obtained in step (d) (i.e., a second intermediate formulation) to at least one step of diluting using water or a further aqueous buffer solution comprising a further buffer system, thereby preparing a further intermediate formulation comprising the particles dispersed in a further aqueous phase comprising the first or further buffer system, wherein the further buffer system of the further aqueous buffer solution may be identical to or different from the buffer system used in step (a); and (2) subjecting the further intermediate formulation obtained in step (1) to at least one step of filtrating, such as dialyzing, tangential flow filtrating or diafiltrating, using the final aqueous buffer solution, wherein at least the final aqueous buffer solution (preferably the intermediate and final aqueous buffer solutions) does not contain the one or more unwanted substances.

Similarly, in some embodiments of the second aspect, where step (I) comprises steps (a' to (e'), (g') and (j') (and optionally one or more of steps (f'), (h'), (i'), and (k')), the first aqueous buffer solution (and the pH of the nucleic acid (such as RNA) solution obtained under step (c')) has a pH of below 6.0, preferably at most about 5.5, such as at most about 5.0, at most about 4.9, at most about 4.8, at most about 4.7, at most about 4.6, or at most about 4.5. For example, the pH of the first aqueous buffer solution (and the pH of the nucleic acid (such as RNA) solution obtained under step (c')) may be between about 3.5 and about 5.9, such as between about 4.0 and about 5.5, or between about 4.5 and about 5.0. To this end, the first aqueous buffer solution provided under (b') (and the first aqueous phase) may further comprises one or more acids (e.g., one or more mono, di- or polybasic acids). In these embodiments, it is preferred that least one of steps (f' to (j') is conducted under conditions which remove one or more unwanted substances (e.g., organic solvent (such as ethanol) and/or the one or more mono-, di- or polybasic acids) from the first intermediate formulation and/or from the second intermediate formulation and/or from the further intermediate formulation resulting in a further intermediate formulation comprising the particles dispersed in a further aqueous phase or in the final aqueous phase with the further and/or final aqueous phase being substantially free of the one or more unwanted substances. For example, such conditions can include using a further aqueous buffer solution and/or a final buffer solution, wherein at least one of the further aqueous buffer solution(s) and the final buffer solution (preferably all of the further aqueous buffer solution(s) and the final buffer solution) does not contain the one or more unwanted substances. In some embodiments, the filtrating steps can be independently selected from dialyzing, tangential flow filtrating and diafiltrating, preferably from dialyzing and tangential flow filtrating.

In some embodiments of the second aspect, the first buffer system used in step (a) comprises the final buffer substance used in step (e), preferably the buffer system and pH of the first buffer system used in step (a) are identical to the buffer system and pH of the final aqueous buffer solution used in step (e). For example, only one aqueous buffer solution is used in this embodiment of the second aspect. In such cases, the pH of the second intermediate formulation may be adjusted through the addition of the multivalent anion (such as the inorganic polyphosphate) in combination with their respective countercations. For example, the pH of the second intermediate formulation may be reached through addition of solutions of pentasodiumtriphosphate, tetrasodiumdiphosphate, disodiumhydrogenphosphate or trisodiumcitrate.

Similarly, in some embodiments of the second aspect, where step (I) comprises steps (a') to (e'), (g') and (j') (and optionally one or more of steps (f'), (h'), (i'), and (k')), each of the first buffer system and every further buffer system used in steps (b'), (f'), (h'), and (i') comprises the final buffer substance used in step (j'), preferably the buffer system and pH of each of the first aqueous buffer solution and of every further aqueous buffer solution used in steps (b'), (f'), (h'), and (i') are identical to the buffer system and pH of the final aqueous buffer solution. In some embodiments, for example, the uniform buffer system (i.e., each of the first buffer system and every further buffer system used in the method) may comprise acetic acid and Tris-hydroxymethylaminomethane, wherein acetic acid prevails in steps (a') to (d') and Tris-hydroxymethylaminomethane is added in (e') in an amount to arrive at pH between 7 and 9, preferably between 7.5 and 8.5 before the addition of the multivalent anion in step (f'). In another example, the multivalent anion can be a constituent of the buffer system as is the case for a buffer composed of citric acid and Tris-hydroxymethylaminomethane, wherein citric acid is combined with between 0.1 and 2, preferably 0.2 and 1 equivalent of Tris-hydroxymethylaminomethane in steps (a') to (d') and Tris-hydroxymethylaminomethane is added in (e') in an amount to arrive at pH between 7 and 9, preferably between 7.5 and 8.5 and step (f') is used to add water or is absent. In this example, the materials used in steps (e') and (f) may be reversed, so that the first intermediate formulation is diluted with water before adjusting the pH using a solution of Tris-hydroxymethylaminomethane in step (f'). In some embodiments of the second aspect, the formulation obtained in step (I) and/or the composition comprise(s) a cryoprotectant. In some embodiments of the second aspect, the formulation obtained in step (I) and/or the composition is/are substantially free of a cryoprotectant.

In some embodiments of the second aspect, the formulation and/or composition comprise(s) water as the main component and/or the total amount of solvent(s) other than water contained in the composition is less than about 1.0% (v/v), such as less than about 0.5% (v/v). For example, the amount of water contained in the formulation and/or composition may be at least 50% (w/w), such as at least at least 55% (w/w), at least 60% (w/w), at least 65% (w/w), at least 70% (w/w), at least 75% (w/w), at least 80% (w/w), at least 85% (w/w), at least 90% (w/w), or at least 95% (w/w). If the formulation and/or composition comprise(s) a cryoprotectant, the amount of water contained in the formulation and/or composition comprise(s) may be at least 50% (w/w), such as at least at least 55% (w/w), at least 60% (w/w), at least 65% (w/w), at least 70% (w/w), at least 75% (w/w), at least 80% (w/w), at least 85% (w/w), or at least 90% (w/w). If the formulation and/or composition is/are substantially free of a cryoprotectant, the amount of water contained in the formulation and/or composition may be at least 95% (w/w). Additionally or alternatively, the total amount of solvent(s) other than water contained in the composition may be less than about 1.0% (v/v), such as less than about 0.9% (v/v), less than about 0.8% (v/v), less than about 0.7% (v/v), less than about 0.6% (v/v), less than about 0.5% (v/v), less than about 0.4% (v/v), less than about 0.3% (v/v), less than about 0.2% (v/v), less than about 0.1% (v/v), less than about 0.05% (v/v), less than about 0.01% (v/v), or less than about 0.005% (v/v). In this respect, a cryoprotectant which is liquid under normal conditions will not be considered as a solvent other than water but as cryoprotectant. In other words, the above optional limitation that the total amount of solvent(s) other than water contained in the composition may be less than about 1.0% (v/v), such as less than about 0.5% (v/v), does not apply to cryoprotectants which are liquids under normal conditions.

In some embodiments of the second aspect, the osmolality of the composition is at most about $1000\times10^{-3}$ osmol/kg. In some embodiments, the osmolality of the composition is at most about $500\times10^{-3}$ osmol/kg, such as at most about $490\times10^{-3}$ osmol/kg, at most about $480\times10^{-3}$ osmol/kg, at most about $470\times10^{-3}$ osmol/kg, at most about $460\times10^{-3}$ osmol/kg, at most about $450\times10^{-3}$ osmol/kg, at most about $440\times10^{-3}$ osmol/kg, at most about $430\times10^{-3}$ osmol/kg, at most about $420\times10^{-3}$ osmol/kg, at most about $410\times10^{-3}$ osmol/kg, at most about $400\times10^{-3}$ osmol/kg, at most about $390\times10^{-3}$ osmol/kg, at most about $380\times10^{-3}$ osmol/kg, at most about $370\times10^{-3}$ osmol/kg, at most about $360\times10^{-3}$ osmol/kg, at most about $350\times10^{-3}$ osmol/kg, at most about $340\times10^{-3}$ osmol/kg, at most about $330\times10^{-3}$ osmol/kg, at most about $320\times10^{-3}$ osmol/kg, at most about $310\times10^{-3}$ osmol/kg, or at most about $300\times10^{-3}$ osmol/kg. If the composition does not comprise a cryoprotectant, the osmolality of the composition may be below $300\times10^{-3}$ osmol/kg, such as at most about $250\times10^{-3}$ osmol/kg, at most about $200\times10^{-3}$ osmol/kg, at most about $150\times10^{-3}$ osmol/kg, at most about $100\times10^{-3}$ osmol/kg, at most about $50\times10^{-3}$ osmol/kg, at most about $40\times10^{-3}$ osmol/kg, or at most about $30\times10^{-3}$ osmol/kg. If the composition comprises a cryoprotectant, it is preferred that the main part of the osmolality of the composition is provided by the cryoprotectant. For example, the cryoprotectant may provide at least 50%, such as at least 55%, at least 60%, at least 65%, at least 70%, at least 75%, at least 80%, at least 85%, or at least 90%, of the osmolality of the composition.

In some embodiments of the second aspect, the concentration of the nucleic acid (such as RNA) in the composition is about 1 mg/l to about 500 mg/l, such as about 1 mg/l to about 100 mg/l. In some embodiments, the concentration of the nucleic acid (in particular RNA) in the composition is about 5 mg/l to about 500 mg/l, such as about 10 mg/l to about 400 mg/l, about 10 mg/l to about 300 mg/l, about 10 mg/l to about 200 mg/l, about 10 mg/l to about 150 mg/l, or about 10 mg/l to about 100 mg/l, preferably about 10 mg/l to about 140 mg/l, more preferably about 20 mg/l to about 130 mg/l, more preferably about 30 mg/l to about 120 mg/l. In some embodiments, the concentration of the nucleic acid (in particular RNA) in the composition is about 5 mg/l to about 150 mg/l, such as about 10 mg/l to about 140 mg/l, about 20 mg/l to about 130 mg/l, about 25 mg/l to about 125 mg/l, about 30 mg/l to about 120 mg/l, about 35 mg/l to about 115 mg/l, about 40 mg/l to about 110 mg/l, about 45 mg/l to about 105 mg/i, or about 50 mg/i to about 100 mg/i. In some embodiments, the concentration of the nucleic acid (in particular RNA) in the composition is 1 mg/i to about 50 mg/i or about 10 mg/l to about 100 mg/l.

In some embodiments of the second aspect (in particular those, where the method comprises (II) freezing the formulation to about −10° C. or below and, thus, the composition prepared by the method is in frozen form), the concentration of the nucleic acid (in particular RNA) in the composition is about 1 mg/i to about 50 mg/i.

In some embodiments of the second aspect (in particular those, where the method does not comprise step (II) and, thus, the composition prepared by the method is in liquid form), the concentration of the nucleic acid (in particular RNA) in the composition is about 10 mg/i to about 100 mg/l.

In some embodiments of the second aspect, the molar ratio of the multivalent anion or a salt thereof to the cationically ionizable lipid is at least about 1:2 (preferably at least about 2:3, such as at least about 1.00 or at least about 4:3), and the concentration of the nucleic acid (in particular RNA) in the composition is about 1 mg/l to about 100 mg/i (such as 1 mg/i to about 50 mg/i or about 10 mg/l to about 100 mg/i). In some embodiments of the second aspect (in particular those, where the method comprises (II) freezing the formulation to about −10° C. or below and, thus, the composition prepared by the method is in frozen form), the molar ratio of the multivalent anion or a salt thereof to the cationically ionizable lipid is at least about 1:2 (preferably at least about 2:3, such as at least about 1.00 or at least about 4:3), and the concentration of the nucleic acid (in particular RNA) in the composition is about 1 mg/i to about 50 mg/i. In some embodiments of the second aspect (in particular those, where the method does not comprises step (II) and, thus, the composition prepared by the method is in liquid form), the molar ratio of the multivalent anion or a salt thereof to the cationically ionizable lipid is at least about 1:2 (preferably at least about 2:3, such as at least about 1.00 or at least about 4:3), and the concentration of the nucleic acid (in particular RNA) in the composition is about 10 mg/l to about 100 mg/l. In some of these embodiments, the multivalent anion or a salt thereof is selected from the group consisting of an inorganic polyphosphate, an inorganic phosphate, sulfate, succinate, glutarate, tartrate, malate, citrate, salts and mixtures thereof. In some of these embodiments, the multivalent anion is selected from the group consisting of an inorganic polyphosphate, an inorganic phosphate, citrate, and salts thereof.

In some embodiments of the second aspect, the multivalent anion is an inorganic polyphosphate or a salt thereof. In some embodiments, the inorganic polyphosphate or a salt thereof is a linear inorganic polyphosphate or a salt thereof as defined herein (e.g., a linear triphosphate or a salt thereof), and the molar ratio of the inorganic polyphosphate or a salt thereof to the cationically ionizable lipid is at least about 1:2, preferably at least about 2:3, such as at least about 1.00 or at least about 4:3. In some preferred embodiments of the second aspect, the inorganic polyphosphate or a salt thereof is a linear inorganic polyphosphate (in particular triphosphate) or a salt thereof, the molar ratio of the inorganic polyphosphate or a salt thereof to the cationically ionizable lipid is at least about 1:2 (preferably at least about 2:3, such as at least about 1.00 or at least about 4:3), and the concentration of the nucleic acid (in particular RNA) in the composition is about 1 mg/l to about 100 mg/l (such as 1 mg/l to about 50 mg/l or about 10 mg/l to about 100 mg/l). In some embodiments of the second aspect (in particular those, where the method comprises (II) freezing the formulation to about −10° C. or below and, thus, the composition prepared by the method is in frozen form), the inorganic polyphosphate is a linear inorganic polyphosphate (in particular triphosphate) or a salt thereof, the molar ratio of the inorganic polyphosphate or a salt thereof to the cationically ionizable lipid is at least about 1:2 (preferably at least about 2:3, such as at least about 1.00 or at least about 4:3), and the concentration of the nucleic acid (in particular RNA) in the composition is about 1 mg/l to about 50 mg/l. In some embodiments of the second aspect (in particular those, where the method does not comprises step (II) and, thus, the composition prepared by the method is in liquid form), the inorganic polyphosphate or a salt thereof is a linear inorganic polyphosphate (in particular triphosphate) or a salt thereof, the molar ratio of the inorganic polyphosphate or a salt thereof to the cationically ionizable lipid is at least about 1:2 (preferably at least about 2:3, such as at least about 1.00 or at least about 4:3), and the concentration of the nucleic acid (in particular RNA) in the composition is about 10 mg/l to about 100 mg/l.

In some embodiments of the second aspect, the cationically ionizable lipid comprises a head group which includes at least one tertiary amine moiety.

In some embodiments of the second aspect, the cationically ionizable lipid has the structure of Formula (X):

(X)

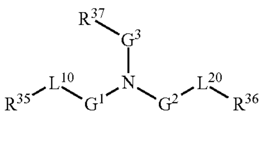

or a pharmaceutically acceptable salt, tautomer, prodrug or stereoisomer thereof, wherein $L^{10}$, $L^{20}$, $G^1$, $G^2$, $GR^{35}$, $R^{36}$, and $R^{37}$ are as defined herein. In some embodiments, the cationically ionizable lipid is selected from the following: structures X-1 to X-36 (shown herein); and/or structures A to G (shown herein); and/or N,N-dimethyl-2,3-dioleyloxy-propylamine (DODMA), 1,2-dioleoyl-3-dimethylammonium-propane (DODAP), heptatriaconta-6,9,28,31-tetraen-19-yl-4-(dimethylamino)butanoate (DLin-MC3-DMA), and 4-((di((9Z,12Z)-octadeca-9,12-dien-1-yl)amino)oxy)-N,N-dimethyl-4-oxobutan-1-amine (DPL-14). In some embodiments, the cationically ionizable lipid is the lipid having the structure X-3. In some embodiments, the cationically ionizable lipid is DPL-14 (i.e., the lipid having the structure G). In some embodiments, the cationically ionizable lipid is the lipid having the structure D.

In some embodiments of the second aspect, the cationically ionizable lipid has the structure of Formula (XI):

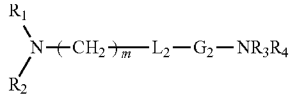

wherein $R_1$, $R_2$ $R_3$, $R_4$, $L_2$, $G_2$, and m are as defined herein. In some embodiments, the cationically ionizable lipid is selected from the structures (XIV-1), (XIV-2), and (XIV-3) (shown herein). In some embodiments, the cationically ionizable lipid is the lipid having the structure XIV-1 In some embodiments, the cationically ionizable lipid is the lipid having the structure XIV-2. In some embodiments, the cationically ionizable lipid is the lipid having the structure XIV-3.

In some embodiments of the second aspect, the cationically ionizable lipid is completely or partially replaced by a cationic lipid. In some embodiments, the cationically ionizable lipid is selected from the structures XV-1 to XV-6 (shown herein). In those embodiments, where the cationically ionizable lipid is completely replaced by a cationic lipid, the molar ratio of the multivalent anion (such as the inorganic polyphosphate) or a salt thereof to the cationically ionizable lipid is replaced by the molar ratio of the multivalent anion (such as the inorganic polyphosphate) or a salt thereof to the cationic lipid. In some embodiments, the molar ratio of the multivalent anion (such as the inorganic polyphosphate) or a salt thereof to the cationic lipid is at least about 1:2 (such as at least about 0.55, at least about 0.60, at least about 0.65, at least about 2:3, at least about 0.7, at least about 0.75, at least about 0.80, at least about 0.85, at least about 0.90, at least about 0.95, at least about 1.00, at least about 1.10, at least about 1.20, at least about 1.30, at least about 4:3, at least about 1.40, at least about 1.50, at least about 1.60, at least about 1.70, at least about 1.80, at least about 1.90, or at least about 2.0, preferably the molar ratio of the multivalent anion (such as the inorganic polyphosphate) or a salt thereof to the cationic lipid is at least about 2:3, such as at least about 4:3). In those embodiments, where the cationically ionizable lipid is partially replaced by a cationic lipid, the molar ratio of the multivalent anion (such as the inorganic polyphosphate) to the cationically ionizable lipid is replaced by the molar ratio of the multivalent anion (such as the inorganic polyphosphate) to the sum of cationic lipid and cationically ionizable lipid. In some embodiments, the molar ratio of the multivalent anion (such as the inorganic polyphosphate) to the sum of cationic lipid and cationically ionizable lipid is at least about 1:2 (such as at least about 0.55, at least about 0.60, at least about 0.65, at least about 2:3, at least about 0.7, at least about 0.75, at least about 0.80, at least about 0.85, at least about 0.90, at least about 0.95, at least about 1.00, at least about 1.10, at least about 1.20, at least about 1.30, at least about 4:3, at least about 1.40, at least about 1.50, at least about 1.60, at least about 1.70, at least about 1.80, at least about 1.90, or at least about 2.0, preferably the molar ratio of the multivalent anion (such as the inorganic polyphosphate) to the sum of cationic lipid and cationically ionizable lipid is at least about 2:3, such as at least about 4:3).

In some embodiments of the second aspect, the cationically ionizable lipid comprises from about 20 mol % to about 75 mol %, such as from about 40 mol % to about 70 mol %, from about 45 mol % to about 65 mol %, or from about 50 mol % to about 60 mol % (in particular for those embodiments having higher relative amounts of ionizable and neutral lipids and a lower relative amount of steroid); or from about 20 mol % to about 40 mol %, from about 25 mol % to about 40 mol %, or from about 25 mol % to about 35 mol % (in particular for those embodiments having lower relative amounts of ionizable and neutral lipids and a higher relative amount of steroid), of the total lipid present in the organic solution. In some embodiments of the second aspect, the cationically ionizable lipid comprises from about 20 mol % to about 75 mol %, such as from about 40 mol % to about 70 mol %, from about 45 mol % to about 65 mol %, or from about 50 mol % to about 60 mol % (in particular for those embodiments having higher relative amounts of ionizable and neutral lipids and a lower relative amount of steroid); or from about 20 mol % to about 40 mol %, from about 25 mol % to about 40 mol %, or from about 25 mol % to about 35 mol % (in particular for those embodiments having lower relative amounts of ionizable and neutral lipids and a higher relative amount of steroid), of the total lipid present in the composition. In those embodiments, where the cationically ionizable lipid is completely or partially replaced by a cationic lipid, it is preferred that the same ranges as specified above for the cationically ionizable lipid (e.g., from about 20 mol % to about 75 mol %, etc.) apply to the sum of cationically ionizable lipid and cationic lipid.

In some embodiments of the second aspect, the steroid comprises a sterol. In some preferred embodiments of the second aspect, the steroid comprises or is cholesterol.

In some embodiments of the second aspect, the steroid comprises from about 15 mol % to about 60 mol %, such as from about 15 mol % to about 40 mol %, from about 20 mol % to about 35 mol %, or from about 20 mol % to about 30 mol % (in particular for those embodiments having higher relative amounts of ionizable and neutral lipids and a lower relative amount of steroid); or from about 35 mol % to about 60 mol %, from about 40 mol % to about 60 mol %, or from about 45 mol % to about 60 mol % (in particular for those embodiments having lower relative amounts of ionizable and neutral lipids and a higher relative amount of steroid), of the total lipid present in the organic solution. In some embodiments of the second aspect, the steroid comprises from about 15 mol % to about 60 mol %, such as from about 15 mol % to about 40 mol %, from about 20 mol % to about 35 mol %, or from about 20 mol % to about 30 mol % (in particular for those embodiments having higher relative amounts of ionizable and neutral lipids and a lower relative amount of steroid); or from about 35 mol % to about 60 mol %, from about 40 mol % to about 60 mol %, or from about 45 mol % to about 60 mol % (in particular for those embodiments having lower relative amounts of ionizable and neutral lipids and a higher relative amount of steroid), of the total lipid present in the composition.

In some embodiments of the second aspect, the neutral lipid is a phospholipid. In some embodiments, the phospholipid is selected from the group consisting of phosphatidylcholines, phosphatidylethanolamines, phosphatidylglycerols, phosphatidic acids, phosphatidylserines and sphingomyelins. In some embodiments, the phospholipid is selected from the group consisting of phospholipids having a $T_g$ value of higher than 30° C. In some embodiments, the phospholipid is selected from the group consisting of distearoylphosphatidylcholine (DSPC), dipalmitoylphosphatidylcholine (DPPC), distearoyl-phosphatidylethanolamine (DSPE), and dipalmitoyl-phosphatidylethanolamine (DPPE). In some embodiments, the neutral lipid is DSPC.

In some embodiments of the second aspect, the neutral lipid comprises from about 5 mol % to about 25 mol %, such as from about 15 mol % to about 25 mol % or from about 17 mol % to about 21 mol % (in particular for those embodiments having higher relative amounts of ionizable and neutral lipids and a lower relative amount of steroid); or from about 5 mol % to about 15 mol % or from about 7 mol % to about 14 mol % (in particular for those embodiments having lower relative amounts of ionizable and neutral lipids and a higher relative amount of steroid), of the total lipid present in the organic solution. In some embodiments of the second aspect, the neutral lipid comprises from about 5 mol % to about 25 mol 00 such as from about 15 mol % to about 25 mol % or from about 17 mol % to about 21 mol % (in particular for those embodiments having higher relative amounts of ionizable and neutral lipids and a lower relative amount of steroid); or from about 5 mol % to about 15 mol % or from about 7 mol % to about 14 mol % (in particular for those embodiments having lower relative amounts of ionizable and neutral lipids and a higher relative amount of steroid), of the total lipid present in the composition.

In some embodiments of the second aspect, the cationically ionizable lipid comprises from about 20 mol % to about 70 mol % of the total lipid present in the organic solution; the steroid comprises from about 15 mol % to about 60 mol % of the total lipid present in the organic solution; and the neutral lipid (e.g., phospholipid) comprises from about 5 mol % to about 25 mol % of the total lipid present in the organic solution.

In some embodiments of the second aspect, the cationically ionizable lipid comprises from about 40 mol % to about 70 mol %, such as from about 45 mol % to about 65 mol % or from about 50 mol % to about 60 mol %, of the total lipid present in the organic solution; the steroid (which preferably is cholesterol) comprises from about 15 mol % to about 40 mol %, such as from about 20 mol % to about 35 mol 00 or from about 20 mol % to about 30 mol %, of the total lipid present in the organic solution; and the neutral lipid (which preferably is a phospholipid) comprises from about 15 mol % to about 25 mol %, such as from about 17 mol % to about 21 mol %, of the total lipid present in the organic solution. In some embodiments of the second aspect, the cationically ionizable lipid comprises from about 40 mol % to about 70 mol %, such as from about 45 mol % to about 65 mol %, or from about 50 mol % to about 60 mol %, of the total lipid present in the composition; the steroid (which preferably is cholesterol) comprises from about 15 mol % to about 40 mol %, such as from about 20 mol % to about 35 mol %, or from about 20 mol % to about 30 mol %, of the total lipid present in the composition; and the neutral lipid (which preferably is a phospholipid) comprises from about 15 mol % to about 25 mol %, such as from about 17 mol % to about 21 mol %, of the total lipid present in the composition. These embodiments of the second aspect, i.e., for preparing nucleic acid compositions containing higher relative amounts of ionizable and neutral lipids and a lower relative amount of steroid, are especially suitable for transfecting cells in the presence of serum. In some of these embodiments, the steroid is cholesterol and the neutral lipid is a phospholipid.

In some embodiments of the second aspect, which contain higher relative amounts of ionizable and neutral lipids and a lower relative amount of steroid, the molar ratio of steroid to neutral lipid is at most 2.5, preferably said ratio is between 1 and 2.5. Thus, in some embodiments of the second aspect, the cationically ionizable lipid comprises from about 40 mol % to about 70 mol % (such as from about 45 mol % to about 65 mol % or from about 50 mol % to about 60 mol %) of the total lipid present in the organic solution (or in the composition); the steroid comprises from about 15 mol % to about 40 mol % (such as from about 20 mol % to about 35 mol % or from about 20 mol % to about 30 mol %) of the total lipid present in the organic solution (or in the composition); the neutral lipid comprises from about 15 mol % to about 25 mol % (such as from about 17 mol % to about 21 mol %) of the total lipid present in the organic solution (or in the composition); and the molar ratio of steroid to neutral lipid is at most 2.5, preferably said ratio is between 1 and 2.5. In some of these embodiments, the steroid is cholesterol and the neutral lipid is a phospholipid.

In some alternative embodiments of the second aspect, the cationically ionizable lipid comprises from about 20 mol % to about 40 mol %, such as from about 25 mol % to about 40 mol % or from about 25 mol % to about 35 mol %, of the total lipid present in the organic solution; the steroid (which preferably is cholesterol) comprises from about 35 mol % to about 60 mol %, such as from about 40 mol % to about 60 mol % or from about 45 mol % to about 60 mol %, of the total lipid present in the organic solution; and the neutral lipid (which preferably is a phospholipid) comprises from about 5 mol % to about 15 mol %, such as from about 7 mol % to about 14 mol %, of the total lipid present in the organic solution. In some embodiments of the second aspect, the cationically ionizable lipid comprises from about 20 mol % to about 40 mol %, such as from about 25 mol % to about 40 mol % or from about 25 mol % to about 35 mol %, of the total lipid present in the composition; the steroid (which preferably is cholesterol) comprises from about 35 mol % to about 60 mol %, such as from about 40 mol % to about 60 mol % or from about 45 mol % to about 60 mol %, of the total lipid present in the composition; and the neutral lipid (which preferably is a phospholipid) comprises from about 5 mol % to about 15 mol %, such as from about 7 mol % to about 14 mol %, of the total lipid present in the composition. These embodiments of the second aspect, i.e., for preparing nucleic acid compositions containing lower relative amounts of ionizable and neutral lipids and a higher relative amount of steroid, are especially suitable for transfecting cells in the absence of serum. In some of these embodiments, the steroid is cholesterol and the neutral lipid is a phospholipid.

In some embodiments of the second aspect, which contain lower relative amounts of ionizable and neutral lipids and a higher relative amount of steroid, the molar ratio of steroid to neutral lipid is at least 3.0, preferably said ratio is between 3.0 and 10.0, such as between 5.0 and 7.0. Thus, in some embodiments of the second aspect, the cationically ionizable lipid comprises from about 20 mol % to about 40 mol % (such as from about 25 mol % to about 40 mol % or from about 25 mol % to about 35 mol %) of the total lipid present in the organic solution (or in the composition); the steroid comprises from about 35 mol % to about 60 mol % (such as from about 40 mol % to about 60 mol % or from about 45 mol % to about 60 mol %) of the total lipid present in the organic solution (or in the composition); the neutral lipid comprises from about 5 mol % to about 15 mol % (such as from about 7 mol % to about 14 mol %) of the total lipid present in the organic solution (or in the composition); and the molar ratio of steroid to neutral lipid is at least 3.0, preferably said ratio is between 3.0 and 10.0, such as between 5.0 and 7.0. In some of these embodiments, the steroid is cholesterol and the neutral lipid is a phospholipid.

In some embodiments of the second aspect, the organic solution/composition further comprises one or more additional lipids. In these embodiments, where a cationic lipid is present, the sum of (1) the amount the cationically ionizable lipid and (2) the amount of cationic lipid is used for calculations. E.g., if the amount of cationically ionizable lipid in an organic solution/composition should be from about 20 mol % to about 70 mol % and the organic solution/composition should also contain a cationic lipid, then the sum of (1) the amount the cationically ionizable lipid and (2) the amount of cationic lipid is to be from about 20 mol % to about 70 mol %.

In some embodiments of the second aspect, the organic solution, the composition, or both is/are substantially free of a lipid comprising polyethyleneglycol (PEG). In some embodiments of the second aspect, the organic solution, the composition, or both is/are substantially free of any compound comprising PEG. In some embodiments of the second aspect, the organic solution, the composition, or both is/are substantially free of PEG. In some of these embodiments, the multivalent anion or a salt thereof is selected from the group consisting of an inorganic polyphosphate, an inorganic phosphate, sulfate, succinate, glutarate, tartrate, malate, citrate, salts and mixtures thereof. In some of these embodiments, the multivalent anion is selected from the group consisting of an inorganic polyphosphate, an inorganic phosphate, citrate, and salts thereof. In some embodiments of these embodiments, the multivalent anion is an inorganic polyphosphate or a salt thereof.

In some embodiments of the second aspect, the organic solution is also substantially free of another polymer-conjugated lipid. In some embodiments, the another polymer-conjugated lipid is a polysarcosine-conjugated lipid. Thus, in some embodiments, the organic solution is substantially free of PEG lipids and substantially free of polysarcosine-conjugated lipids. In some embodiments, the organic solution is substantially free of any polymer-conjugated lipid (including PEG lipids and polysarcosine-conjugated lipids). In some of these embodiments, the multivalent anion or a salt thereof is selected from the group consisting of an inorganic polyphosphate, an inorganic phosphate, sulfate, succinate, glutarate, tartrate, malate, citrate, salts and mixtures thereof. In some of these embodiments, the multivalent anion is selected from the group consisting of an inorganic polyphosphate, an inorganic phosphate, citrate, and salts thereof. In some embodiments of these embodiments, the multivalent anion is an inorganic polyphosphate or a salt thereof.

In some embodiments of the second aspect, the only lipids contained in the organic solution are the cationically ionizable lipid, the steroid and the neutral lipid, in particular the cationically ionizable lipid, the steroid and the phospholipid. In some embodiments of the second aspect, the composition is substantially free of any polymer-conjugated lipid. In some embodiments of the second aspect, the only lipids contained in the composition are the cationically ionizable lipid, the steroid and the neutral lipid, in particular the cationically ionizable lipid, the steroid and the phospholipid. In some of these embodiments, the multivalent anion or a salt thereof is selected from the group consisting of an inorganic polyphosphate, an inorganic phosphate, sulfate, succinate, glutarate, tartrate, malate, citrate, salts and mixtures thereof. In some of these embodiments, the multivalent anion is selected from the group consisting of an inorganic polyphosphate, an inorganic phosphate, citrate, and salts thereof. In some embodiments of these embodiments, the multivalent anion is an inorganic polyphosphate or a salt thereof.

In some embodiments of the second aspect, the particles comprise or are selected from lipid nanoparticles (LNPs), liposomes, lipoplexes (LPXs), and mixtures thereof. In some embodiments, the particles comprise or are LNPs. In some embodiments, the particles comprise or are liposomes. In some embodiments, the particles comprise or are LPXs. In some embodiments, the particles comprise or are mixtures of LNPs and liposomes. In some embodiments, the particles comprise or are mixtures of LNPs and LPXs. In some embodiments, the particles comprise or are mixtures of liposomes and LPXs. In some embodiments, the particles comprise or are mixtures of LNPs, liposomes, and LPXs.

In some embodiments of the second aspect, the particles comprise essentially all of lipids (in particular all of the cationically ionizable lipid, the steroid, and the neutral lipid) present in the composition.

In some embodiments of the second aspect, the aqueous phase is substantially free of the cationically ionizable lipid, the steroid, and the neutral lipid (e.g., substantially free of lipids).

In some embodiments of the second aspect, the particles comprise at least 50% (such as at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%) of the nucleic acid (in particular RNA) present in the composition. In some embodiments, the particles comprise at least 75%, preferably at least 85% of the nucleic acid (in particular RNA) present in the composition.

In some embodiments of the second aspect, the aqueous phase is substantially free of the nucleic acid.

In some embodiments of the second aspect, the nucleic acid (such as RNA) is encapsulated within or associated with the particles.

In some embodiments of the second aspect, at least 10% (such as at least 15%, at least 20%, at least 25%, at least 30%, at least 35%, at least 40%, at least 45%, at least 50%, at least 55%, at least 60%) of the multivalent anion (such as inorganic polyphosphate) present in the composition is associated with the particles. In some embodiments, at least 20%, and more preferably at least 50% of the multivalent anion (such as inorganic polyphosphate) present in the composition is associated with the particles.

In some embodiments of the second aspect, the particles have a size of from about 30 nm to about 500 nm. In some embodiments, the particles have a size from about 50 nm to about 150 nm.

In some embodiments of the second aspect, the nucleic acid is DNA.

In some embodiments of the second aspect, the nucleic acid is RNA (such as mRNA or inhibitory RNA, e.g. siRNA).

In some embodiments of the second aspect, the RNA (such as mRNA) (i) comprises a modified nucleoside in place of uridine; (ii) has a coding sequence which is codon-optimized; and/or (iii) has a coding sequence whose G/C content is increased compared to the wild-type coding sequence. In some embodiments, the modified nucleoside is selected from pseudouridine (ψ), N1-methyl-pseudouridine (m1ψ), and 5-methyl-uridine (m5U).

In some embodiments of the second aspect, the RNA (such as mRNA) comprises one or more of the following (a) a 5' cap, such as a cap1 or cap2 structure; (b) a 5' UTR; (c) a 3' UTR; and (d) a poly-A sequence. In some embodiments, the RNA (such as mRNA) comprises all of the following: a 5' cap; a 5' UTR; a 3' UTR; and a poly-A sequence. In some embodiments, the poly-A sequence comprises at least 100 A nucleotides, wherein the poly-A sequence preferably is an interrupted sequence of A nucleotides.

In some embodiments of the second aspect, the RNA (such as mRNA) encodes one or more polypeptides. In some embodiments, the one or more polypeptides are pharmaceutically active polypeptides and/or comprise an epitope for inducing an immune response against an antigen in a subject.

In some embodiments of the second aspect, the pharmaceutically active polypeptide and/or the antigen or epitope is derived from or is a protein of a pathogen, an immunogenic variant of the protein, or an immunogenic fragment of the protein or the immunogenic variant thereof. In some embodiments, the pathogen is a pathogen causing an infectious disease.

In some embodiments of the second aspect, the pharmaceutically active polypeptide and/or the antigen or epitope is derived from or is a SARS-CoV-2 spike (S) protein, an immunogenic variant thereof, or an immunogenic fragment of the SARS-CoV-2 S protein or the immunogenic variant thereof. In some embodiments, the RNA (such as mRNA) comprises an open reading frame (ORF) encoding an amino acid sequence comprising a SARS-CoV-2 S protein, an immunogenic variant thereof, or an immunogenic fragment of the SARS-CoV-2 S protein or the immunogenic variant thereof.

In some embodiments of the second aspect, the nucleic acid is inhibitory RNA (such as siRNA) and selectively hybridizes to and/or is specific for a target mRNA. In some embodiments, the target mRNA comprises an ORF encoding a pharmaceutically active peptide or polypeptide, in particular a pharmaceutically active peptide or polypeptide whose expression (in particular increased expression, e.g., compared to the expression in a healthy subject) is associated with a disease. In some embodiments, the target mRNA comprises an ORF encoding a pharmaceutically active peptide or polypeptide whose expression (in particular increased expression, e.g., compared to the expression in a healthy subject) is associated with cancer.

It is understood that any embodiment described herein in the context of the first aspect may also apply to any embodiment of the second aspect.

In a third aspect, the present disclosure provides a method of storing a composition, comprising preparing a composition according to the method of the second aspect and storing the composition at a temperature ranging from about −90° C. to about −10° C., such as from about −90° C. to about −40° C. or from about −40° C. to about −25° C. or from about −25° C. to about −10° C., or a temperature of about −20° C. In some embodiments of the third aspect, storing the frozen composition is for at least 1 week, such as at least 2 weeks, at least 3 weeks, at least 4 weeks, at least 1 month, at least 2 months, at least 3 months, at least 6 months, at least 12 months, at least 24 months, or at least 36 months, preferably at least 4 weeks. In some embodiments of the third aspect, storing the frozen composition is for at least 4 weeks, preferably at least 1 month, more preferably at least 2 months, more preferably at least 3 months, more preferably at least 6 months at −20° C. In some embodiments of the third aspect, the composition can be stored at −70° C.

In some embodiments of the third aspect, the composition comprises a cryoprotectant. In some embodiments of the third aspect, the composition is substantially free of a cryoprotectant.

In some embodiments of the third aspect, the method of storing a composition comprises preparing a composition according to the method of the second aspect comprising step (II) (i.e., freezing the formulation to about −10° C. or below); storing the frozen composition at a temperature ranging from about −90° C. to about −10° C. for a certain period of time (e.g., at least one week); and storing the frozen composition a temperature ranging from about 0° C. to about 20° C. for a certain period of time (e.g., at least four weeks).

It is understood that any embodiment described herein in the context of the first or second aspect may also apply to any embodiment of the third aspect.

In a fourth aspect, the present disclosure provides a method of storing a composition, comprising preparing a liquid composition according to the method of the second aspect and storing the liquid composition at a temperature ranging from about 0° C. to about 20° C., such as from about 1° C. to about 15° C., from about 2° C. to about 10° C., or from about 2° C. to about 8° C., or at a temperature of about 5° C. In some embodiments of the fourth aspect, storing the liquid composition is for at least 1 week, such as at least 2 weeks, at least 3 weeks, at least 4 weeks, at least 1 month, at least 2 months, at least 3 months, at least 6 months, at least 12 months, or at least 24 months, preferably at least 4 weeks. In some embodiments of the fourth aspect, storing the liquid composition is for at least 4 weeks, preferably at least 1 month, more preferably at least 2 months, more preferably at least 3 months, more preferably at least 6 months at 5° C.

In some embodiments of the fourth aspect, the composition comprises a cryoprotectant. In some preferred embodiments of the fourth aspect, the composition is substantially free of a cryoprotectant.

It is understood that any embodiment described herein in the context of the first or second aspect may also apply to any embodiment of the fourth aspect.

In a fifth aspect, the present disclosure provides a composition preparable by the method of the second, third, or fourth aspect. In some embodiments of the fifth aspect, the composition can be in frozen form which, preferably, can be stored at a temperature of about −90° C. or higher, such as about −90° C. to about −10° C. For example, the frozen composition of the fifth aspect can be stored at a temperature ranging from about −90° C. to about −40° C. or from about −40° C. to about −25° C. or from about −25° C. to about −10° C., or a temperature to about −20°. In some embodiments of the fifth aspect, the composition can be stored for at least 1 week, such as at least 2 weeks, at least 3 weeks, at least 4 weeks, at least 1 month, at least 2 months, at least 3 months, at least 6 months, at least 12 months, at least 24 months, or at least 36 months, preferably at least 4 weeks. For example, the frozen composition can be stored for at least 4 weeks, preferably at least 1 month, more preferably at least 2 months, more preferably at least 3 months, more preferably at least 6 months at −20° C.

In some embodiments of the fifth aspect, the composition comprises a cryoprotectant. In some embodiments of the fifth aspect, the composition is substantially free of a cryoprotectant.

In some embodiments of the fifth aspect, where the composition is in frozen form, the nucleic acid integrity (in particular the RNA integrity) after thawing the frozen composition is at least 90%, at least 95%, at least 97%, at least 98% or substantially 100%, e.g., after thawing the frozen composition which has been stored at −20° C., compared to the nucleic acid integrity (in particular the RNA integrity) of the composition before the composition has been frozen.

In some embodiments, the initial nucleic acid integrity (in particular the initial RNA integrity) of the composition (i.e., after its preparation but before freezing) is at least 50% and the nucleic acid integrity (in particular the RNA integrity) of the composition after thawing the frozen composition is at least 90%, preferably at least 95%, more preferably at least 97%, more preferably at least 98%, more preferably substantially 100%, of the initial nucleic acid integrity (in particular the initial RNA integrity).

Additionally or alternatively, in some embodiments of the fifth aspect, where the composition is in frozen form, the size ($Z_{average}$) (and/or size distribution and/or polydispersity index (PDI)) of the nucleic acid (such as RNA) particles after thawing the frozen composition is essentially equal to the size ($Z_{average}$) (and/or size distribution and/or PDI) of the nucleic acid (such as RNA) particles before the composition has been frozen. In some embodiments, the size ($Z_{average}$) of the nucleic acid (such as RNA) particles after thawing the frozen composition is between about 50 nm and about 500 nm, preferably between about 40 nm and about 200 nm, more preferably between about 40 nm and about 120 nm. In some embodiments, the PDI of the nucleic acid (such as RNA) particles after thawing the frozen composition is less than 0.3, preferably less than 0.2, more preferably less than 0.1. In some embodiments, the size ($Z_{average}$) of the nucleic acid (such as RNA) particles after thawing the frozen composition is between about 50 nm and about 500 nm, preferably between about 40 nm and about 200 nm, more preferably between about 40 nm and about 120 nm, and the size ($Z_{average}$) (and/or size distribution and/or PDI) of the nucleic acid (such as RNA) particles after thawing the frozen composition is essentially equal to the size ($Z_{average}$) (and/or size distribution and/or PDI) of the nucleic acid (such as RNA) particles before freezing. In some embodiments, the size ($Z_{average}$) of the nucleic acid (such as RNA) particles after thawing the frozen composition is between about 50 nm and about 500 nm, preferably between about 40 nm and about 200 nm, more preferably between about 40 nm and about 120 nm, and the PDI of the nucleic acid (such as RNA) particles after thawing the frozen composition is less than 0.3 (preferably less than 0.2, more preferably less than 0.1).

In some embodiments, the size of the nucleic acid (such as RNA) particles and the nucleic acid integrity (in particular the RNA integrity) of the composition after one freeze/thaw cycle, preferably after two freeze/thaw cycles, more preferably after three freeze/thaw cycles, more preferably after four freeze/thaw cycles, more preferably after five freeze/thaw cycles or more, are essentially equal to the size of the nucleic acid (such as RNA) particles and the nucleic acid integrity (in particular the RNA integrity) of the initial composition (i.e., before the composition has been frozen for the first time).

In an alternative embodiment of the fifth aspect, the composition is in liquid form.

In some embodiments of the fifth aspect, where the composition is in liquid form, the nucleic acid integrity (in particular the RNA integrity) of the liquid composition, when stored, e.g., at 0° C. or higher for at least one week, is such that the desired effect, e.g., to induce an immune response, can be achieved. For example, the nucleic acid integrity (in particular the RNA integrity) of the liquid composition, when stored, e.g., at 0° C. or higher for at least one week (such as for at least 2 weeks, at least three weeks, at least four weeks, at least one month, at least two months, at least three months, at least 4 months, or at least 6 months), may be at least 90%, at least 95%, at least 97% or at least 98%, compared to the nucleic acid integrity (in particular the RNA integrity) before storage. In some embodiments, the nucleic acid integrity (in particular the RNA integrity) of the composition after storage for at least four weeks, preferably at a temperature of 0° C. or higher, such as about 2° C. to about 8° C., is at least 90%, at least 95%, at least 97% or at least 98%, compared to the nucleic acid integrity (in particular the RNA integrity) before storage.

In some embodiments, the initial nucleic acid integrity (in particular the initial RNA integrity) of the liquid composition (i.e., after its preparation but before storage) is at least 50% and the nucleic acid integrity (in particular the RNA integrity) of the liquid composition after storage for at least one week (such as for at least 2 weeks, at least three weeks, at least four weeks, at least one month, at least two months, or at least 3 months), preferably at a temperature of 0° C. or higher, such as about 2° C. to about 8° C., is at least 90% of the initial nucleic acid integrity (in particular the initial RNA integrity).

Additionally or alternatively, in some embodiments of the fifth aspect, where the composition is in liquid form, the size ($Z_{average}$) (and/or size distribution and/or polydispersity index (PDI)) of the nucleic acid (such as RNA) particles of the liquid composition, when stored, e.g., at 0° C. or higher for at least one week, is such that the desired effect, e.g., to induce an immune response, can be achieved. For example, the size ($Z_{average}$) (and/or size distribution and/or polydispersity index (PDI)) of the nucleic acid (such as RNA) particles of the liquid composition, when stored, e.g., at 0° C. or higher for at least one week, is essentially equal to the size ($Z_{average}$) (and/or size distribution and/or PDI) of the nucleic acid (such as RNA) particles of the initial composition, i.e., before storage. In some embodiments, the size ($Z_{average}$) of the nucleic acid (such as RNA) particles after storage of the liquid composition, e.g., at 0° C. or higher for at least one week is between about 50 nm and about 500 nm, preferably between about 40 nm and about 200 nm, more preferably between about 40 nm and about 120 nm. In some embodiments, the PDI of the nucleic acid (such as RNA) particles after storage of the liquid composition, e.g., at 0° C. or higher for at least one week is less than 0.3, preferably less than 0.2, more preferably less than 0.1. In some embodiments, the size ($Z_{average}$) of the nucleic acid (such as RNA) particles after storage of the liquid composition, e.g., at 0° C. or higher for at least one week is between about 50 nm and about 500 nm, preferably between about 40 nm and about 200 nm, more preferably between about 40 nm and about 120 nm, and the size ($Z_{average}$) (and/or size distribution and/or PDI) of the nucleic acid (such as RNA) particles after storage of the liquid composition, e.g., at 0° C. or higher for at least one week is essentially equal to the size ($Z_{average}$) (and/or size distribution and/or PDI) of the nucleic acid (such as RNA) particles before storage. In some embodiments, the size ($Z_{average}$) of the nucleic acid (such as RNA) particles after storage of the liquid composition, e.g., at 0° C. or higher for at least one week is between about 50 nm and about 500 nm, preferably between about 40 nm and about 200 nm, more preferably between about 40 nm and about 120 nm, and the PDI of the nucleic acid (such as RNA) particles after storage of the liquid composition, e.g., at 0° C. or higher for at least one week is less than 0.3 (preferably less than 0.2, more preferably less than 0.1).

It is understood that any embodiment described herein in the context of the first, second, third, or fourth aspect may also apply to any embodiment of the fifth aspect.

In a sixth aspect, the present disclosure provides a method for preparing a ready-to-use pharmaceutical composition, the method comprising the steps of providing a frozen composition prepared by the method of the second, third, or fourth aspect and thawing the frozen composition thereby obtaining the ready-to-use pharmaceutical composition.

It is understood that any embodiment described herein in the context of the first, second, third, fourth, or fifth aspect may also apply to any embodiment of the sixth aspect.

In a seventh aspect, the present disclosure provides a method for preparing a ready-to-use pharmaceutical composition, the method comprising the steps of providing a liquid composition prepared by the method of the second, third, or fourth aspect thereby obtaining the ready-to-use pharmaceutical composition.

It is understood that any embodiment described herein in the context of the first, second, third, fourth, fifth, or sixth aspect may also apply to any embodiment of the seventh aspect.

In an eighth aspect, the present disclosure provides a ready-to-use pharmaceutical composition preparable by the method of the sixth or seventh aspect.

It is understood that any embodiment described herein in the context of the first, second, third, fourth, fifth, sixth, or seventh aspect may also apply to any embodiment of the eighth aspect.

In a ninth aspect, the present disclosure provides a composition of any one of the first, fifth, and eighth aspect for use in therapy.

It is understood that any embodiment described herein in the context of the first, second, third, fourth, fifth, sixth, seventh, or eighth aspect may also apply to any embodiment of the ninth aspect.

In a tenth aspect, the present disclosure provides a composition of any one of the first, fifth, eighth, and ninth aspect for use in inducing an immune response.

It is understood that any embodiment described herein in the context of the first, second, third, fourth, fifth, sixth, seventh, eighth, or ninth aspect may also apply to any embodiment of the tenth aspect.

In an eleventh aspect, the present disclosure provides a method of transfecting cells, comprising adding a composition of any one of the first, fifth or eighth aspect to cells; and incubating the mixture of the composition and cells for a sufficient amount of time. In some embodiments, in particular those, where the nucleic acid is DNA or RNA (such as mRNA) and encodes a pharmaceutically active protein, the mixture of the composition and cells is incubated for a time sufficient to allow the expression of the pharmaceutically active protein. In some embodiments, in particular those, where the nucleic acid is inhibitory RNA (such as siRNA) directed against a target mRNA, the mixture of the composition and cells is incubated for a time sufficient to allow the inhibition of the transcription and/or translation of the target mRNA. In some embodiments, the sufficient amount of time is at least one hour (such at least about 2 hours, at least about 3 hours, at least about 4 hours, at least about 5 hours, at least about 6 hours, at least about 9 hours, at least about 12 hours) and/or up to about 48 hours (such as up to about 36 or up to about 24 hours). In some embodiments of the eleventh aspect, incubating the mixture of the composition and cells is conducted in the presence of serum (such as human serum).

In some embodiments of the eleventh aspect, the cationically ionizable lipid comprises from about 40 mol % to about 70 mol %, such as from about 45 mol % to about 65 mol % or from about 50 mol % to about 60 mol %, of the total lipid present in the composition; the steroid (which preferably is cholesterol) comprises from about 15 mol % to about 40 mol %, such as from about 20 mol % to about 35 mol 00 or from about 20 mol % to about 30 mol %, of the total lipid present in the composition; and the neutral lipid (which preferably is a phospholipid) comprises from about 15 mol % to about 25 mol %, such as from about 17 mol % to about 21 mol %, of the total lipid present in the composition. For these embodiments (i.e., a composition containing higher relative amounts of ionizable and neutral lipids and a lower relative amount of steroid), it is preferred that incubating the mixture of the composition and cells is conducted in the presence of serum (such as human serum). In some of these embodiments, the steroid is cholesterol and the neutral lipid is a phospholipid.

In some embodiments of the eleventh aspect, which relate to compositions containing higher relative amounts of ionizable and neutral lipids and a lower relative amount of steroid, the molar ratio of steroid to neutral lipid is at most 2.5, preferably said ratio is between 1 and 2.5. Thus, in some embodiments of the eleventh aspect, the cationically ionizable lipid comprises from about 40 mol % to about 70 mol % (such as from about 45 mol % to about 65 mol % or from about 50 mol % to about 60 mol %) of the total lipid present in the composition; the steroid comprises from about 15 mol % to about 40 mol % (such as from about 20 mol % to about 35 mol % or from about 20 mol % to about 30 mol %) of the total lipid present in the composition; the neutral lipid comprises from about 15 mol % to about 25 mol % (such as from about 17 mol % to about 21 mol %) of the total lipid present in the composition; and the molar ratio of steroid to neutral lipid is at most 2.5, preferably said ratio is between 1 and 2.5. In some of these embodiments, the steroid is cholesterol and the neutral lipid is a phospholipid.

In some alternative embodiments of the eleventh aspect, the cationically ionizable lipid comprises from about 20 mol % to about 40 mol %, such as from about 25 mol % to about 40 mol % or from about 25 mol % to about 35 mol %, of the total lipid present in the composition; the steroid (which preferably is cholesterol) comprises from about 35 mol % to about 60 mol %, such as from about 40 mol % to about 60 mol % or from about 45 mol % to about 60 mol %, of the total lipid present in the composition; and the neutral lipid (which preferably is a phospholipid) comprises from about 5 mol % to about 15 mol %, such as from about 7 mol % to about 14 mol %, of the total lipid present in the composition. For these embodiments (i.e., a composition containing lower relative amounts of ionizable and neutral lipids and a higher relative amount of steroid), incubating the mixture of the composition and cells may be conducted in the presence or absence of serum, such as in the absence of serum.

In some embodiments of the eleventh aspect, which relate to compositions containing lower relative amounts of ionizable and neutral lipids and a higher relative amount of steroid, the molar ratio of steroid to neutral lipid is at least 3.0, preferably said ratio is between 3.0 and 10.0, such as between 5.0 and 7.0.

Thus, in some embodiments of the eleventh aspect, the cationically ionizable lipid comprises from about 20 mol % to about 40 mol % (such as from about 25 mol % to about 40 mol % or from about 25 mol % to about 35 mol %) of the total lipid present in the composition; the steroid comprises from about 35 mol % to about 60 mol % (such as from about 40 mol % to about 60 mol % or from about 45 mol % to about 60 mol %) of the total lipid present in the composition; the neutral lipid comprises from about 5 mol % to about 15 mol % (such as from about 7 mol % to about 14 mol %) of the total lipid present in the composition; and the molar ratio of steroid to neutral lipid is at least 3.0, preferably said ratio is between 3.0 and 10.0, such as between 5.0 and 7.0. In some of these embodiments, the steroid is cholesterol and the neutral lipid is a phospholipid.

In some embodiments of the eleventh aspect, the method is conducted in vivo (i.e., the cells form part of an organ, a tissue and/or an organism of a subject). In some embodiments of the eleventh aspect, the method is conducted in vitro (i.e., the cells do not form part of an organ, a tissue and/or an organism of a subject, e.g., the cells are an ex vivo cell culture).

It is understood that any embodiment described herein in the context of the first, second, third, fourth, fifth, sixth, seventh, eighth, ninth, or tenth aspect may also apply to any embodiment of the eleventh aspect.

In a twelfth aspect, the present disclosure provides a use of a composition of any one of any one of the first, fifth or eighth aspect for transfecting cells. In some embodiments of the twelfth aspect, the transfection of the cells is conducted in the presence of serum (such as human serum).

In some embodiments of the twelfth aspect, the cationically ionizable lipid comprises from about 40 mol % to about 70 mol %, such as from about 45 mol % to about 65 mol % or from about 50 mol % to about 60 mol %, of the total lipid present in the composition; the steroid (which preferably is cholesterol) comprises from about 20 mol % to about 40 mol % of the total lipid present in the composition; and the neutral lipid (which preferably is a phospholipid) comprises from about 15 mol % to about 25 mol % of the total lipid present in the composition. For these embodiments (i.e., a composition containing higher relative amounts of ionizable and neutral lipids and a lower relative amount of steroid), it is preferred that incubating the mixture of the composition and cells is conducted in the presence of serum (such as human serum). In some of these embodiments, the steroid is cholesterol and the neutral lipid is a phospholipid.

In some embodiments of the twelfth aspect, which relate to compositions containing higher relative amounts of ionizable and neutral lipids and a lower relative amount of steroid, the molar ratio of steroid to neutral lipid is at most 2.5, preferably said ratio is between 1 and 2.5. Thus, in some embodiments of the twelfth aspect, the cationically ionizable lipid comprises from about 40 mol % to about 70 mol % (such as from about 45 mol % to about 65 mol % or from about 50 mol % to about 60 mol %) of the total lipid present in the composition; the steroid comprises from about 15 mol % to about 40 mol % (such as from about 20 mol % to about 35 mol % or from about 20 mol % to about 30 mol %) of the total lipid present in the composition; the neutral lipid comprises from about 15 mol % to about 25 mol % (such as from about 17 mol % to about 21 mol %) of the total lipid present in the composition; and the molar ratio of steroid to neutral lipid is at most 2.5, preferably said ratio is between 1 and 2.5. In some of these embodiments, the steroid is cholesterol and the neutral lipid is a phospholipid.

In some alternative embodiments of the twelfth aspect, the cationically ionizable lipid comprises from about 20 mol % to about 40 mol %, such as from about 25 mol % to about 40 mol % or from about 25 mol % to about 35 mol %, of the total lipid present in the composition; the steroid (which preferably is cholesterol) comprises from about 35 mol % to about 60 mol %, such as from about 40 mol % to about 60 mol % or from about 45 mol % to about 60 mol %, of the total lipid present in the composition; and 30 the neutral lipid (which preferably is a phospholipid) comprises from about 5 mol % to about 15 mol %, such as from about 7 mol % to about 14 mol %, of the total lipid present in the composition. For these embodiments (i.e., a composition containing lower relative amounts of ionizable and neutral lipids and a higher relative amount of steroid), incubating the mixture of the composition and cells may be conducted in the presence or absence of serum, such as in the absence of serum.

In some embodiments of the twelfth aspect, which relate to compositions containing lower relative amounts of ionizable and neutral lipids and a higher relative amount of steroid, the molar ratio of steroid to neutral lipid is at least 3.0, preferably said ratio is between 3.0 and 10.0, such as between 5.0 and 7.0.

Thus, in some embodiments of the twelfth aspect, the cationically ionizable lipid comprises from about 20 mol % to about 40 mol % (such as from about 25 mol % to about 40 mol % or from about 25 mol % to about 35 mol %) of the total lipid present in the composition; the steroid comprises from about 35 mol % to about 60 mol % (such as from about 40 mol % to about 60 mol % or from about 45 mol % to about 60 mol %) of the total lipid present in the composition; the neutral lipid comprises from about 5 mol % to about 15 mol % (such as from about 7 mol % to about 14 mol %) of the total lipid present in the composition; and the molar ratio of steroid to neutral lipid is at least 3.0, preferably said ratio is between 3.0 and 10.0, such as between 5.0 and 7.0. In some of these embodiments, the steroid is cholesterol and the neutral lipid is a phospholipid.

In some embodiments of the twelfth aspect, the use is an in vivo use (i.e., the cells form part of an organ, a tissue and/or an organism of a subject). In some embodiments of the twelfth aspect, the use is an in vitro use (i.e., the cells do not form part of an organ, a tissue and/or an organism of a subject, e.g., the cells are an ex vivo cell culture).

It is understood that any embodiment described herein in the context of the first, second, third, fourth, fifth, sixth, seventh, eighth, ninth, tenth, or eleventh aspect may also apply to any embodiment of the twelfth aspect.

In a further aspect, the present disclosure provides a kit comprising a composition of any one of the first, fifth, eighth, ninth, or tenth aspect or a pharmaceutical composition as described herein. In some embodiments, the kit is for use in therapy, such as for inducing an immune response. In some embodiments, the kit is for use in inducing an immune response against a pathogen, such as for treating or preventing an infectious disease.

Further itemised embodiments are as follows:

1. A composition comprising (i) a nucleic acid; (ii) a cationically ionizable lipid; (iii) a steroid; (iv) a neutral lipid; and (v) a multivalent anion.
2. The composition of item 1, wherein the multivalent anion comprises between 2 and 10 negative charges, optionally between 2 and 5 negative charges.
3. The composition of item 1 or 2, wherein the multivalent anion is selected from the group consisting of: an inorganic polyphosphate, inorganic phosphate, sulfate, succinate, glutarate, tartrate, malate, citrate, or mixtures thereof.
4. The composition of any one of items 1 to 3, wherein the multivalent anion is an inorganic polyphosphate.

4a. The composition of item 4, wherein the inorganic polyphosphate comprises the formula $[P_xO_{(3x+1)}]^y$, wherein x is an integer and is at least 3; and y is the anionic charge.

4b. The composition of item 4 or 4a, wherein the inorganic polyphosphate is selected from the group consisting of triphosphate, tetraphosphate, pentaphosphate, hexaphosphate, heptaphosphate, and mixtures thereof, preferably from the group consisting of triphosphate, tetraphosphate, pentaphosphate, and mixtures thereof, more preferably, the inorganic polyphosphate is triphosphate.

4c. The composition of any one of items 4 to 4b, wherein the inorganic polyphosphate is a linear inorganic polyphosphate, such as a linear inorganic triphosphate.

5. The composition of any one of items 1 to 4c, wherein the molar ratio of (v) the multivalent anion (e.g., the inorganic polyphosphate) to (ii) the cationically ionizable lipid is at least about 1:2, preferably at least about 2:3, such as at least about 4:3.
6. The composition of any one of items 1 to 5, which is substantially free of a lipid comprising polyethyleneglycol (PEG), preferably substantially free of any compound comprising PEG, more preferably substantially free of PEG.

6a. The composition of any one of items 1 to 6, which is substantially free of any polymer-conjugated lipid.

7. The composition of any one of items 1 to 6a, wherein the pH of the composition is between about 4.0 and about 8.0, preferably between about 4.5 and about 8.0, such as between about 5.0 and about 8.0, between about 5.5 and about 8.0, between about 6.0 and about 8.0, between about 6.5 and about 8.0, between about 6.8 and about 7.9, or between about 7.0 and about 7.8.
8. The composition of any one of items 1 to 7, wherein water is the main component in the composition and/or the total amount of solvent(s) other than water contained in the composition is less than about 0.5% (v/v).
9. The composition of any one of items 1 to 8, wherein the osmolality of the composition is at most about $1000\times10^{-3}$ osmol/kg, preferably between about $100\times10^{-3}$ osmol/kg and about $500\times10^{-3}$ osmol/kg, more preferably about $300\times10^{-3}$ osmol/kg.
10. The composition of any one of items 1 to 9, wherein the concentration of the nucleic acid in the composition is about 1 mg/l to about 500 mg/l, such as about 1 mg/l to about 100 mg/l, about 5 mg/l to about 100 mg/l, or about 10 mg/l to about 100 mg/l.
11. The composition of any one of items 1 to 10, wherein the cationically ionizable lipid comprises a head group which includes at least one tertiary amine moiety.
12. The composition of any one of items 1 to 11, wherein the cationically ionizable lipid has the structure of Formula (X)

(X)

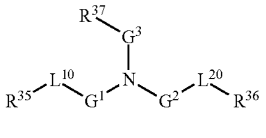

or a pharmaceutically acceptable salt, tautomer, prodrug or stereoisomer thereof, wherein:

one of $L^{10}$ and $L^{20}$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, $NR^aC$(═O)$NR^a$—, —OC(═O)$NR^a$— or —$NR^aC$(═O)O—, and the other of $L^{10}$ and $L^{20}$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, $NR^aC$(═O)$NR^a$—, —OC(═O)$NR^a$— or —$NR^aC$(═O)O— or a direct bond;

$G^1$ and $G^2$ are each independently unsubstituted $C_1$-$C_{12}$ alkylene or $C_{2-12}$ alkenylene;

$G^3$ is $C_{1-24}$ alkylene, $C_{2-24}$ alkenylene, $C_{3-8}$ cycloalkylene, or $C_{3-8}$ cycloalkenylene;

$R^a$ is H or $C_{1-12}$ alkyl;

$R^{35}$ and $R^{36}$ are each independently $C_{6-24}$ alkyl or $C_{6-24}$ alkenyl;

$R^{37}$ is H, $OR^{50}$, CN, —C(═O)$OR^{40}$, —OC(═O)$R^{40}$ or —$NR^{50}C$(═O)$R^{40}$;

$R^{40}$ is $C_{1-12}$ alkyl;

$R^{50}$ is H or $C_{1-6}$ alkyl; and x is 0, 1 or 2.

13. The composition of any one of items 1 to 11, wherein the cationic or cationically ionizable lipid has the structure of Formula (XI):

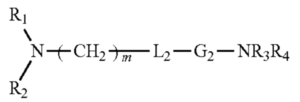

wherein each of $R_1$ and $R_2$ is independently $R_5$ or -$G_1$-$L_1$-$R_6$, wherein at least one of $R_1$ and $R_2$ is -$G_1$-$L_1$-$R_6$;

each of $R_3$ and $R_4$ is independently selected from the group consisting of $C_{1-6}$ alkyl, $C_{2-6}$ alkenyl, aryl, and $C_{3-10}$ cycloalkyl;

each of $R_5$ and $R_6$ is independently a non-cyclic hydrocarbyl group having at least 10 carbon atoms;

each of $G_1$ and $G_2$ is independently unsubstituted $C_{1-12}$ alkylene or $C_{2-12}$ alkenylene;

each of $L_1$ and $L_2$ is independently selected from the group consisting of —O(C═O)—, —(C═O)O—, —C(═O)—, —O—, —$S(O)_x$—, —S—S—, —C(═O)S—, —SC(═O)—, —NRaC(═O)—, —C(═O)$NR^a$—, —NRaC(═O)$NR^a$—, —OC(═O)$NR^a$— and —NRaC(═O)O—;

Ra is H or $C_{1-12}$ alkyl;

m is 0, 1, 2, 3, or 4; and x is 0, 1 or 2.

14. The composition of any one of items 1 to 13, wherein the cationically ionizable lipid comprises from about 20 mol % to about 75 mol %, such as from about 40 mol % to about 70 mol %, from about 45 mol % to about 65 mol %, from about 50 mol % to about 60 mol %, from about 20 mol % to about 40 mol %, from about 25 mol % to about 40 mol %, or from about 25 mol % to about 35 mol %, of the total lipid present in the composition.

15. The composition of any one of items 1 to 14, wherein the steroid comprises a sterol such as cholesterol.

16. The composition of any one of items 1 to 15, wherein the steroid comprises from about 15 mol % to about 60 mol %, such as from about 15 mol % to about 40 mol %, from about 20 mol % to about 35 mol %, from about 20 mol % to about 30 mol %, from about 35 mol % to about 60 mol %, from about 40 mol % to about 60 mol %, or from about 45 mol % to about 60 mol %, of the total lipid present in the composition.

17. The composition of any one of items 1 to 16, wherein the neutral lipid is a phospholipid, preferably selected from the group consisting of phosphatidylcholines, phosphatidylethanolamines, phosphatidylglycerols, phosphatidic acids, phosphatidylserines and sphingomyelins, more preferably selected from the group consisting of distearoylphosphatidylcholine (DSPC), dipalmitoylphosphatidylcholine (DPPC), distearoylphosphatidylethanolamine (DSPE), and dipalmitoylphosphatidylethanolamine (DPPE).

18. The composition of any one of items 1 to 17, wherein the neutral lipid comprises from about 5 mol % to about 25 mol %, such as from about 10 mol % to about 25 mol %, from about 15 mol % to about 25 mol %, from about 17 mol % to about 21 mol %, from about 5 mol % to about 15 mol %, or from about 7 mol % to about 14 mol %, of the total lipid present in the composition.

19. The composition of any one of items 1 to 18, wherein the cationically ionizable lipid comprises from about 20 mol % to about 70 mol % of the total lipid present in the composition; the steroid comprises from about 15 mol % to about 60 mol % of the total lipid present in the composition; and the neutral lipid (e.g., phospholipid) comprises from about 5 mol % to about 25 mol % of the total lipid present in the composition.

20. The composition of any one of items 1 to 19, wherein the cationically ionizable lipid comprises from about 40 mol % to about 70 mol %, such as from about 45 mol % to about 65 mol % or from about 50 mol % to about 60 mol %, of the total lipid present in the composition; the steroid comprises from about 15 mol % to about 40 mol %, such as from about 20 mol % to about 35 mol %, or from about 20 mol % to about 30 mol %, of the total lipid present in the composition; and the neutral lipid comprises from about 15 mol % to about 25 mol %, such as from about 17 mol % to about 21 mol %, of the total lipid present in the composition.

20a. The composition of any one of items 1 to 20, wherein the steroid is cholesterol and the neutral lipid is a phospholipid.

21. The composition of any one of items 1 to 20a, wherein the molar ratio of steroid to neutral lipid is at most 2.5, preferably said ratio is between 1 and 2.5.

22. The composition of any one of items 1 to 19, wherein the cationically ionizable lipid comprises from about 20 mol % to about 40 mol %, such as from about 25 mol % to about 40 mol % or from about 25 mol % to about 35 mol %, of the total lipid present in the composition; the steroid comprises from about 35 mol % to about 60 mol %, such as from about 40 mol % to about 60 mol % or from about 45 mol % to about 60 mol %, of the total lipid present in the composition; and the neutral lipid comprises from about 5 mol % to about 15 mol %, such as from about 7 mol % to about 14 mol %, of the total lipid present in the composition.

22a. The composition of item 22, wherein the steroid is cholesterol and the neutral lipid is a phospholipid.

23. The composition of any one of items 1 to 19, 22, and 22a, wherein the molar ratio of steroid to neutral lipid is at least 3.0, preferably said ratio is between 3.0 and 10.0, such as between 5.0 and 7.0.

24. The composition of any one of items 1 to 23, wherein the composition comprises particles dispersed in an aqueous phase, wherein the particles comprise at least a portion of the nucleic acid, at least a portion of the cationically ionizable lipid, at least a portion of the steroid, and at least a portion of the neutral lipid; and wherein at least a portion of the multivalent anion (e.g., the inorganic polyphosphate) is associated with the particles.
25. The composition of item 24, wherein the particles are selected from lipid nanoparticles (LNPs), liposomes, lipoplexes (LPXs), and mixtures thereof.
25a. The composition of item 24 or 25, wherein the particles comprise essentially all of the cationically ionizable lipid, the steroid, and the neutral lipid present in the composition.
25b. The composition of any one of items 24 to 25a, wherein the aqueous phase is substantially free of the cationically ionizable lipid, the steroid, and the neutral lipid.
26. The composition of any one of items 24 to 25b, wherein the particles comprise at least 50%, preferably at least 75%, more preferably at least 85%, of the nucleic acid present in the composition.
26a. The composition of any one of items 24 to 26, wherein the aqueous phase is substantially free of the nucleic acid.
27. The composition of any one of items 24 to 26a, wherein at least 10%, preferably at least 20%, and more preferably at least 50% of the multivalent anion (e.g., the inorganic polyphosphate) present in the composition is associated with the particles.
28. The composition of any one of items 24 to 27, wherein the particles have a size of from about 30 nm to about 500 nm, such as from about 50 nm to about 150 nm.
29. The composition of any one of items 1 to 28, wherein the nucleic acid is RNA, preferably mRNA.
29a. The composition of any one of items 1 to 28, wherein the nucleic acid is DNA.
29b. The composition of any one of items 1 to 28, wherein the nucleic acid is inhibitory RNA, such as siRNA.
30. The composition of item 29, wherein the RNA (1) comprises a modified nucleoside in place of uridine, wherein the modified nucleoside is preferably selected from pseudouridine (ψ), N1-methyl-pseudouridine (m1ψ), and 5-methyl-uridine (m5U); (2) has a coding sequence which is codon-optimized; and/or (3) has a coding sequence whose G/C content is increased compared to the wild-type coding sequence.
31. The composition of item 29 or 30, wherein the RNA comprises at least one of the following, preferably all of the following: a 5' cap; a 5' UTR; a 3' UTR; and a poly-A sequence.
32. The composition of item 31, wherein the poly-A sequence comprises at least 100 A nucleotides, wherein the poly-A sequence preferably is an interrupted sequence of A nucleotides.
33. The composition of item 31 or 32, wherein the 5' cap is a cap1 or cap2 structure.
34. The composition of any one of items 29 and 30 to 33, wherein the RNA encodes one or more polypeptides, wherein preferably the one or more polypeptides are pharmaceutically active polypeptides and/or comprise an epitope for inducing an immune response against an antigen in a subject.
35. The composition of item 34, wherein the pharmaceutically active polypeptide and/or the antigen or epitope is derived from or is a protein of a pathogen, an immunogenic variant of the protein, or an immunogenic fragment of the protein or the immunogenic variant thereof.
36. The composition of item 34 or 35, wherein the pharmaceutically active polypeptide and/or the antigen or epitope is derived from or is a SARS-CoV-2 spike (S) protein, an immunogenic variant thereof, or an immunogenic fragment of the SARS-CoV-2 S protein or the immunogenic variant thereof.
37. The composition of any one of items 1 to 36, wherein the composition is in liquid form, preferably at a temperature of about 2° C. to about 10° C.
37a. The composition of item 37, wherein the concentration of the nucleic acid in the composition is about 10 mg/l to about 100 mg/l.
38. The composition of any one of items 1 to 37a, wherein the nucleic acid integrity of the composition after storage for at least one week, preferably at a temperature of about 2° C. to about 8° C., is at least 90% compared to the nucleic acid integrity before storage.
38a. The composition of any one of items 1 to 38, wherein the nucleic acid integrity of the composition after storage for at least four weeks, preferably at a temperature of about 2° C. to about 8° C., is at least 90% compared to the nucleic acid integrity before storage.
38b. The composition of any one of items 1 to 38a, wherein the nucleic acid integrity of the composition after storage for at least three months, preferably at a temperature of about 2° C. to about 8° C., is at least 90% compared to the nucleic acid integrity before storage.
39. The composition of any one of items 24 to 38b, wherein the size ($Z_{average}$) and/or size distribution and/or polydispersity index (PDI) of nucleic acid particles after storage of the composition is essentially equal to the size ($Z_{average}$) and/or size distribution and/or PDI of the nucleic acid particles before storage.
40. The composition of any one of items 1 to 36, wherein the composition is in frozen form.
40a. The composition of item 40, wherein the concentration of the nucleic acid in the composition is about 1 mg/l to about 50 mg/l.
40b. The composition of item 40 or 40a, wherein the nucleic acid integrity after thawing the frozen composition is at least 50% compared to the nucleic acid integrity before the composition has been frozen.
41. The composition of item 40, 40a, or 40b, wherein the nucleic acid integrity after thawing the frozen composition is at least 90% or substantially 100% compared to the nucleic acid integrity before the composition has been frozen.
42. The composition of any one of items 40 to 41, wherein the size ($Z_{average}$) and/or size distribution and/or polydispersity index (PDI) of nucleic acid particles after thawing the frozen composition is essentially equal to the size ($Z_{average}$) and/or size distribution and/or PDI of the nucleic acid particles before the composition has been frozen.
42a. The composition of any one of items 40 to 42, wherein the size of the particles and the nucleic acid integrity of the composition after one freeze/thaw cycle, preferably after two freeze/thaw cycles, are essentially equal to the size of the particles and the nucleic acid integrity before the composition has been frozen for the first time.

43. A method of preparing a composition comprising particles dispersed in a final aqueous phase, wherein the composition comprises (i) a nucleic acid; (ii) a cationically ionizable lipid; (iii) a steroid; (iv) a neutral lipid; and (v) a multivalent anion (e.g., an inorganic polyphosphate); wherein the particles comprise at least a portion of the nucleic acid, at least a portion of the cationically ionizable lipid, and at least a portion of the steroid; wherein at least a portion of the multivalent anion (e.g., the inorganic polyphosphate) is associated with the particles; and wherein the final aqueous phase comprises a final buffer system;

wherein the method comprises:

(I) preparing a formulation comprising particles dispersed in the final aqueous phase, wherein the particles comprise at least a portion of the nucleic acid, at least a portion of the cationically ionizable lipid, at least a portion of the steroid, and at least a portion of the neutral lipid, and wherein at least a portion of the multivalent anion (e.g., the inorganic polyphosphate) is associated with the particles; and (II) optionally freezing the formulation to about −10° C. or below, thereby obtaining the composition, wherein step (I) comprises:

(a) providing a nucleic acid solution containing water and a first buffer system;

(b) providing an organic solution comprising the cationically ionizable lipid, the steroid, and the neutral lipid;

(c) mixing the nucleic acid solution provided under (a) with the organic solution provided under (b), thereby preparing a first intermediate formulation comprising the particles dispersed in a first aqueous phase comprising the first buffer system;

(d) mixing the first intermediate formulation prepared under (c) with a multivalent anion (e.g., an inorganic polyphosphate) or a salt thereof, thereby preparing a second intermediate formulation comprising the particles dispersed in a second aqueous phase comprising a second buffer system, wherein at least a portion of the multivalent anion (e.g., the inorganic polyphosphate) is associated with the particles; and (e) filtrating and/or diluting the second intermediate formulation prepared under (d) using a final aqueous buffer solution comprising the final buffer system, thereby preparing the formulation comprising the particles dispersed in the final aqueous phase.

43a. The method of item 43, wherein step (a) comprises (a') providing an aqueous nucleic acid solution; (b') providing a first aqueous buffer solution comprising a first buffer system; and (c') mixing the aqueous nucleic acid solution provided under (a') with the first aqueous buffer solution provided under (b') thereby providing a nucleic acid solution containing water and the first buffer system.

43b. The method of item 43 or 43a, wherein the organic solution comprises an organic solvent selected from the group consisting of alcohols having up to 6 carbon atoms and mixtures of two or more of these alcohols, preferably selected from the group consisting of ethanol, propanol, isopropanol, 1,2-propandiol, and mixtures of two or more of these alcohols.

44. The method of any one of items 43 to 43b, wherein step (I) further comprises one or more steps selected from diluting and filtrating.

45. The method of any one of items 43 to 44, wherein step (I) comprises:

(a') providing an aqueous nucleic acid solution;

(b') providing a first aqueous buffer solution comprising a first buffer system;

(c') mixing the aqueous nucleic acid solution provided under (a') with the first aqueous buffer solution provided under (b') thereby preparing a nucleic acid solution containing water and the first buffer system;

(d') providing (e.g., preparing) an organic solution comprising the cationically ionizable lipid, the steroid, and the neutral lipid;

(e') mixing the nucleic acid solution prepared under (c') with the organic solution provided under (d'), thereby preparing a first intermediate formulation comprising particles dispersed in a first aqueous phase comprising the first buffer system;

(f') optionally diluting the first intermediate formulation prepared under (e') using water or a further aqueous buffer solution comprising a further buffer system, thereby preparing a further intermediate formulation comprising the particles dispersed in a further aqueous phase comprising the first or further buffer system, wherein the further aqueous buffer solution may be identical to or different from the first aqueous buffer solution;

(g') mixing the first intermediate formulation obtained in step (e'), if step (f') is absent, or the further intermediate formulation obtained in step (f'), if step (f') is present, with a multivalent anion (e.g., an inorganic polyphosphate) or a salt thereof, thereby preparing a second intermediate formulation comprising the particles dispersed in a second aqueous phase, wherein at least a portion of the multivalent anion (e.g., the inorganic polyphosphate) is associated with the particles;

(h') optionally filtrating the second first intermediate formulation prepared under (g') using a further aqueous buffer solution comprising a further buffer system, thereby preparing a further intermediate formulation comprising the particles dispersed in a further aqueous phase comprising the further buffer system, wherein the further aqueous buffer solution may be identical to or different from the first and/or second aqueous buffer solution;

(i') optionally repeating step (h') once or two or more times, wherein the further intermediate formulation comprising the particles dispersed in the further aqueous phase comprising the further buffer system obtained after step (h') of one cycle is used as the second intermediate formulation of the next cycle, wherein in each cycle the further aqueous buffer solution may be identical to or different from the first and/or second aqueous buffer solution;

(j') filtrating the second intermediate formulation obtained in step (g'), if step (h') is absent, or the further intermediate formulation obtained in step (h'), if step (h') is present and step (i') is not present, or the further intermediate formulation obtained after step (i'), if steps (h') and (i') are present, using a final aqueous buffer solution comprising the final buffer system; and (k') optionally diluting the formulation obtained in step (j') with a dilution solution;

thereby preparing the formulation comprising the particles dispersed in the final aqueous phase.

45a. The method of item 45, wherein the organic solution comprises an organic solvent selected from the group consisting of alcohols having up to 6 carbon atoms and mixtures of two or more of these alcohols, preferably selected from the group consisting of ethanol, propanol, isopropanol, 1,2-propandiol, and mixtures of two or more of these alcohols.

45b. The method of item 45 or 45a, wherein step (f') is absent.

45c. The method of item 45 or 45a, wherein step (f') is present.

45d. The method of any one of items 45 to 45c, wherein step (g') is conducted at most about 20 min after step (e').

45e. The method of any one of items 43 to 45d, wherein the organic solution provided under (b) or (d'), respectively, additionally comprises an acid.

45f. The method of any one of items 43 to 45e, wherein step (f') comprises changing the pH of the first intermediate formulation to a pH between about 7.0 and about 9.0, optionally to a pH between about 7.5 and about 8.5, preferably to a pH between about 7.5 and about 8.0.

45g. The method of item 45f, wherein step (f') is conducted no later than 12 hours, preferably no later than 4 hours and more preferred no later than 30 minutes after step (e').

45h. The method of item 45f or 45g, wherein step (f') is used to change the pH of the first intermediate formulation to pH between 7 and 9 followed by the addition of the multivalent anion in step (g') and the combined duration of steps (f') and (g') is no longer than 12 hours, preferably no longer than 4 hours and more preferred no longer than 30 minutes after step (e').

46. The method of any one of items 43 to 45h, wherein filtrating is dialyzing, tangential flow filtrating or diafiltrating, preferably dialyzing or tangential flow filtrating.

47. The method of any one of items 43 to 46, wherein the multivalent anion comprises between 2 and 10 negative charges, optionally between 2 and 5 negative charges.

47a. The method of any one of items 43 to 47, wherein the multivalent anion is selected from the group consisting of: an inorganic polyphosphate, inorganic phosphate, sulfate, succinate, glutarate, tartrate, malate, citrate, or mixtures thereof.

47b. The method of any one of items 43 to 46, wherein the multivalent anion is an inorganic polyphosphate or a salt thereof.

47c. The method of item 47b, wherein the inorganic polyphosphate or a salt thereof comprises or has the formula $P_xO_{(3x+1)}M_{y'}$, wherein x is an integer and is at least 3; each M is independently $H^+$ or a cation; and y' is the number of cations needed for charge equalization.

48. The method of item 47c, wherein each M is independently selected from the group consisting of $H^+$, an alkaline cation, ammonium, and a monovalent organic cation, preferably each M is independently selected from the group consisting of $H^+$, $Na^+$, $K^+$, $L_1^+$, and $NH_4^+$.

49. The method of any one of items 47b to 48, wherein the inorganic polyphosphate or a salt thereof is selected from the group consisting of triphosphate, tetraphosphate, pentaphosphate, hexaphosphate, heptaphosphate, salts and mixtures thereof, preferably from the group consisting of triphosphate, tetraphosphate, pentaphosphate, salts and mixtures thereof, more preferably, the inorganic polyphosphate or a salt thereof is triphosphate or a salt thereof.

50. The method of any one of items 47b to 49, wherein the inorganic polyphosphate or a salt thereof is a linear inorganic polyphosphate or a salt thereof, such as a linear triphosphate or a salt thereof.

51. The method of any one of items 43 to 50, wherein the molar ratio of (v) the multivalent anion (e.g., the inorganic polyphosphate) to (ii) the cationically ionizable lipid is at least about 1:2, preferably at least about 2:3, such as at least about 4:3.

52. The method of any one of items 43 to 51, wherein the composition is substantially free of a lipid comprising PEG, preferably substantially free of any compound comprising PEG, more preferably substantially free of PEG.

52a. The method of any one of items 43 to 52, wherein the composition is substantially free of any polymer-conjugated lipid.

53. The method of any one of items 43 to 52a, wherein (1) the nucleic acid solution obtained in step (a) has a pH of below 6.0, preferably at most about 5.0, more preferably at most about 4.5; or (2) the first aqueous buffer solution has a pH of below 6.0, preferably at most about 5.0, more preferably at most about 4.5.

54. The method of any one of items 43 to 53, wherein the pH of the composition is between about 4.0 and about 8.0, preferably between about 4.5 and about 8.0, such as between about 5.0 and about 8.0, between about 5.5 and about 8.0, between about 6.0 and about 8.0, between about 6.5 and about 8.0, between about 6.8 and about 7.9, or between about 7.0 and about 7.8.

55. The method of any one of items 43 to 54, wherein water is the main component in the formulation and/or composition and/or the total amount of solvent(s) other than water contained in the composition is less than about 0.5% (v/v).

56. The method of any one of items 43 to 55, wherein the osmolality of the composition is at most about $1000\times10^{-3}$ osmol/kg, preferably between about $100\times10^{-3}$ osmol/kg and about $500\times10^{-3}$ osmol/kg, more preferably about $300\times10^{-3}$ osmol/kg.

57. The method of any one of items 43 to 56, wherein the concentration of the nucleic acid in the composition is about 1 mg/l to about 500 mg/l, such as about 1 mg/l to about 100 mg/l, about 5 mg/l to about 100 mg/l, or about 10 mg/l to about 100 mg/l.

58. The method of any one of items 43 to 57, wherein the cationically ionizable lipid comprises a head group which includes at least one tertiary amine moiety.

59. The method of any one of items 43 to 58, wherein the cationically ionizable lipid, the steroid, and the neutral lipid are present in the organic solution in a molar ratio of about 20 mol % to about 70 mol % of the cationically ionizable lipid; about 15 mol % to about 60 mol % of the steroid; and from about 5 mol % to about 25 mol % of the neutral lipid (e.g., phospholipid).

60. The method of any one of items 43 to 59, wherein the cationically ionizable lipid, the steroid, and the neutral lipid are present in the organic solution in a molar ratio of about 40 mol % to about 70 mol %, such as from about 45 mol % to about 65 mol % or from about 50 mol % to about 60 mol %, of the cationically ionizable lipid; about 15 mol % to about 40 mol %, such as from about 20 mol % to about 35 mol % or from about 20 mol % to about 30 mol %, of the steroid; and from about 15 mol % to about 25 mol %, such as from about 17 mol % to about 21 mol %, of the neutral lipid.

60a. The method of any one of items 43 to 60, wherein the steroid is cholesterol and the neutral lipid is a phospholipid.

61. The method of any one of items 43 to 60a, wherein the molar ratio of steroid to neutral lipid in the organic solution is at most 2.5, preferably said ratio is between 1 and 2.5.
62. The method of any one of items 43 to 59, wherein the cationically ionizable lipid, the steroid, and the neutral lipid are present in the organic solution in a molar ratio of about 20 mol % to about 40 mol %, such as from about 25 mol % to about 40 mol % or from about 25 mol % to about 35 mol %, of the cationically ionizable lipid; about 35 mol % to about 60 mol %, such as from about 40 mol % to about 60 mol % or from about 45 mol % to about 60 mol %, of the steroid; and from about 5 mol % to about 15 mol %, such as from about 7 mol % to about 14 mol %, of the neutral lipid.
62a. The method of item 62, wherein the steroid is cholesterol and the neutral lipid is a phospholipid.
63. The method of any one of items 43 to 59, 62, and 62a, wherein the molar ratio of steroid to neutral lipid is at least 3.0, preferably said ratio is between 3.0 and 10.0, such as between 5.0 and 7.0.
64. The method of any one of items 43 to 63, wherein the particles have a size of from about 30 nm to about 500 nm, such as from about 50 nm to about 150 nm.
65. The method of any one of items 43 to 64, wherein the particles are selected from the group consisting of lipid nanoparticles (LNPs), liposomes, lipoplexes (LPXs), and mixtures of two or more thereof.
65a. The method of any one of items 43 to 65, wherein the particles comprise essentially all of the cationically ionizable lipid, the steroid, and the neutral lipid present in the composition.
65b. The method of any one of items 43 to 65a, wherein the final aqueous phase is substantially free of the cationically ionizable lipid, the steroid, and the neutral lipid.
65c. The method of any one of items 43 to 65b, wherein the particles comprise at least 50%, preferably at least 75%, more preferably at least 85%, of the nucleic acid present in the composition.
65d. The method of any one of items 43 to 65c, wherein the final aqueous phase is substantially free of the nucleic acid.
65e. The method of any one of items 43 to 65d, wherein at least 10%, preferably at least 20%, and more preferably at least 50% of the multivalent anion (e.g., the inorganic polyphosphate) present in the composition is associated with the particles.
66. The method of any one of items 43 to 65e, wherein the nucleic acid is RNA, preferably mRNA.
66a. The method of any one of items 43 to 65e, wherein the nucleic acid is DNA.
66b. The method of any one of items 43 to 65e, wherein the nucleic acid is inhibitory RNA, such as siRNA.
67. The method of item 66, wherein the RNA (i) comprises a modified nucleoside in place of uridine, wherein the modified nucleoside is preferably selected from pseudouridine (ψ), N1-methyl-pseudouridine (m1ψ), and 5-methyl-uridine (m5U); (ii) has a coding sequence which is codon-optimized; and/or (iii) has a coding sequence whose G/C content is increased compared to the wild-type coding sequence.
68. The method of item 66 or 67, wherein the RNA comprises at least one of the following, preferably all of the following: a 5' cap; a 5' UTR; a 3' UTR; and a poly-A sequence.
69. The method of item 68, wherein the poly-A sequence comprises at least 100 A nucleotides, wherein the poly-A sequence preferably is an interrupted sequence of A nucleotides.
70. The method of item 68 or 69, wherein the 5' cap is a cap1 or cap2 structure.
71. The method of any one of items 66 and 67 to 70, wherein the RNA encodes one or more polypeptides, wherein preferably the one or more polypeptides are pharmaceutically active polypeptides and/or comprise an epitope for inducing an immune response against an antigen in a subject.
72. The method of item 71, wherein the pharmaceutically active polypeptide and/or the antigen or epitope is derived from or is a protein of a pathogen, an immunogenic variant of the protein, or an immunogenic fragment of the protein or the immunogenic variant thereof.
73. The method of item 71 or 72, wherein the pharmaceutically active polypeptide and/or the antigen or epitope is derived from or is a SARS-CoV-2 spike (S) protein, an immunogenic variant thereof, or an immunogenic fragment of the SARS-CoV-2 S protein or the immunogenic variant thereof.
74. The method of any one of items 43 to 73, which comprises (II) freezing the formulation to about −10° C. or below.
74a. The method of item 74, wherein the concentration of the nucleic acid in the composition is about 1 mg/l to about 50 mg/l.
74b. The method of item 74 or 74a, wherein the final aqueous buffer solution comprises the multivalent anion (e.g., the inorganic polyphosphate) or a salt thereof.
75. The method of any one of items 43 to 73, which does not comprise step (II).
75a. The method of item 75, wherein the concentration of the nucleic acid in the composition is about 10 mg/l to about 100 mg/l.
76. A method of storing a composition, comprising preparing a composition according to the method of any one of items 43 to 74b and storing the composition at a temperature ranging from about −90° C. to about −10° C., such as from about −90° C. to about −40° C. or from about −25° C. to about −10° C.
77. The method of item 76, wherein storing the composition is for at least 1 month, such as at least 2 months, at least 3 months, at least 6 months, at least 12 months, at least 24 months, or at least 36 months.
78. A method of storing a composition, comprising preparing a composition according to the method of any one of items 43 to 75a and storing the composition at a temperature ranging from about 0° C. to about 20° C., such as from about 1° C. to about 15° C., from about 2° C. to about 10° C., or from about 2° C. to about 8° C., or at a temperature of about 5° C.
79. The method of item 78, wherein storing the composition is for at least 1 week, such as at least 2 weeks, at least 3 weeks, at least 4 weeks, at least 1 month, at least 2 months, at least 3 months, at least 6 months, at least 12 months, or at least 24 months.
80. A composition preparable by the method of any one of items 43 to 79.
81. The composition of item 80, which is in frozen form.
81a. The composition of item 81, wherein the concentration of the nucleic acid in the composition is about 1 mg/l to about 50 mg/l.

81b. The composition of item 81 or 81a, wherein the nucleic acid integrity after thawing the frozen composition is at least 50% compared to the nucleic acid integrity of the composition before the composition has been frozen.

81c. The composition of any one of items 81, 81a, and 81b, wherein the nucleic acid integrity after thawing the frozen composition is at least 50% compared to the nucleic acid integrity before the composition has been frozen.

82. The composition of item 81, 81a, 81b, and 81c, wherein the nucleic acid integrity after thawing the frozen composition is at least 90% or substantially 100% compared to the nucleic acid integrity before the composition has been frozen.

83. The composition of any one of items 81 to 82, wherein the size ($Z_{average}$) and/or size distribution and/or polydispersity index (PDI) of nucleic acid particles after thawing the frozen composition is essentially equal to the size ($Z_{average}$) and/or size distribution and/or PDI of the nucleic acid particles before the composition has been frozen.

83a. The composition of any one of items 81 to 83, wherein the size of the particles and the nucleic acid integrity of the composition after one freeze/thaw cycle, preferably after two freeze/thaw cycles, are essentially equal to the size of the particles and the nucleic acid integrity before the composition has been frozen for the first time.

84. The composition of item 80, which is in liquid form.

84a. The composition of item 84, wherein the concentration of the nucleic acid in the composition is about 10 mg/l to about 100 mg/l.

85. The composition of item 84 or 84a, wherein the nucleic acid integrity after storage of the composition for at least one week, preferably at a temperature of about 2° C. to about 8° C., is at least 90% compared to the nucleic acid integrity before storage.

85a. The composition of any one of items 84, 84a, and 85, wherein the nucleic acid integrity after storage of the composition for at least four weeks, preferably at a temperature of about 2° C. to about 8° C., is at least 90% compared to the nucleic acid integrity before storage.

85b. The composition of any one of items 84, 84a, 85, and 85a, wherein the nucleic acid integrity after storage of the composition for at least three months, preferably at a temperature of about 2° C. to about 8° C., is at least 90% compared to the nucleic acid integrity before storage.

86. The composition of any one of items 84, 84a, 85, 85a, and 85b, wherein the size ($Z_{average}$) and/or size distribution and/or polydispersity index (PDI) of nucleic acid particles after storage of the composition for at least one week is essentially equal to the size ($Z_{average}$) and/or size distribution and/or PDI of the nucleic acid particles before storage.

87. A method for preparing a ready-to-use pharmaceutical composition, the method comprising the steps of providing a frozen composition prepared by the method of any one of items 43 to 74b, 76, and 77, and thawing the frozen composition thereby obtaining the ready-to-use pharmaceutical composition.

88. A method for preparing a ready-to-use pharmaceutical composition, the method comprising the step of providing a liquid composition prepared by the method of any one of items 43 to 73 and 75 to 77, thereby obtaining the ready-to-use pharmaceutical composition.

89. A ready-to-use pharmaceutical composition preparable by the method of item 87 or 88.

90. A composition of any one of items 1 to 42a, 80 to 86, and 89 for use in therapy.

91. A composition of any one of items 1 to 42a, 80 to 86, and 89 for use in inducing an immune response in a subject.

92. A method of transfecting cells, comprising adding a composition of any one of items 1 to 42a, 80 to 86, and 89 to cells; and incubating the mixture of the composition and cells for a sufficient amount of time.

93. The method of item 92, wherein incubating the mixture of the composition and cells is conducted in the presence of serum.

93a. The method of item 93, wherein the serum is human serum.

94. The method of item 92, 93, or 93a, wherein the cationically ionizable lipid comprises from about 40 mol % to about 70 mol %, such as from about 45 mol % to about 65 mol % or from about 50 mol % to about 60 mol %, of the total lipid present in the composition; the steroid comprises from about 15 mol % to about 40 mol %, such as from about 20 mol % to about 35 mol %, or from about 20 mol % to about 30 mol %, of the total lipid present in the composition; and the neutral lipid comprises from about 15 mol % to about 25 mol %, such as from about 17 mol % to about 21 mol %, of the total lipid present in the composition.

94a. The method of any one of items 92 to 94, wherein the steroid is cholesterol and the neutral lipid is a phospholipid.

95. The method of any one of items 92 to 94a, wherein the molar ratio of steroid to neutral lipid is at most 2.5, preferably said ratio is between 1 and 2.5.

96. The method of item 92, wherein the cationically ionizable lipid comprises from about 20 mol % to about 40 mol %, such as from about 25 mol % to about 40 mol % or from about 25 mol % to about 35 mol %, of the total lipid present in the composition; the steroid comprises from about 35 mol % to about 60 mol %, such as from about 40 mol % to about 60 mol % or from about 45 mol % to about 60 mol %, of the total lipid present in the composition; and the neutral lipid comprises from about 5 mol % to about 15 mol %, such as from about 7 mol % to about 14 mol %, of the total lipid present in the composition.

96a. The method of item 96, wherein the steroid is cholesterol and the neutral lipid is a phospholipid.

97. The method of any one of items 92, 96, and 96a, wherein the molar ratio of steroid to neutral lipid is at least 3.0, preferably said ratio is between 3.0 and 10.0, such as between 5.0 and 7.0.

98. Use of a composition of any one of items 1 to 42a, 80 to 86, and 89 for transfecting cells.

99. The use of item 98, wherein the transfection of the cells is conducted in the presence of serum.

99a. The use of item 99, wherein the serum is human serum.

100. The use of item 98, 99, or 99a, wherein the cationically ionizable lipid comprises from about 40 mol % to about 70 mol %, such as from about 45 mol % to about 65 mol %, or from about 50 mol % to about 60 mol %, of the total lipid present in the composition; the steroid comprises from about 15 mol % to about 40 mol %, such as from about 20 mol % to about 35 mol %, or from about 20 mol % to about 30 mol %, of the total lipid present in the composition; and the neutral lipid comprises from about 15 mol % to about 25 mol %, such as from about 17 mol % to about 21 mol %, of the total lipid present in the composition.

100a. The use of any one of items 98 to 100, wherein the steroid is cholesterol and the neutral lipid is a phospholipid.

101. The use of any one of items 98 to 100a, wherein the molar ratio of steroid to neutral lipid is at most 2.5, preferably said ratio is between 1 and 2.5.

102. The use of item 98, wherein the cationically ionizable lipid comprises from about 20 mol % to about 40 mol %, such as from about 25 mol % to about 40 mol % or from about 25 mol % to about 35 mol %, of the total lipid present in the composition; the steroid comprises from about 35 mol % to about 60 mol %, such as from about 40 mol % to about 60 mol % or from about 45 mol % to about 60 mol %, of the total lipid present in the composition; and the neutral lipid comprises from about 5 mol % to about 15 mol %, such as from about 7 mol % to about 14 mol %, of the total lipid present in the composition.

102a. The use of item 102, wherein the steroid is cholesterol and the neutral lipid is a phospholipid.

103. The use of any one of items 98, 102, and 102a, wherein the molar ratio of steroid to neutral lipid is at least 3.0, preferably said ratio is between 3.0 and 10.0, such as between 5.0 and 7.0.

Further aspects of the present disclosure are disclosed herein.

BRIEF DESCRIPTION OF THE FIGURES

FIG. 2: Aggregation of non-PEG lipid particle compositions vs stable polyphosphate lipid particle compositions. A: Lipid particle compositions comprising a cationically ionizable lipid, a steroid, and a neutral lipid but being free of PEG and inorganic polyphosphate were prepared and their size (diameter ($Z_{ave}$) in nm) was measured over time (up to 30 min). B: Lipid particle compositions comprising a cationically ionizable lipid, a steroid, a neutral lipid, and an inorganic polyphosphate (triphosphate (3P)) in different concentrations (0-10 mM) but being free of PEG were prepared and their size (diameter ($Z_{ave}$) in nm) was measured 16 h after their preparation.

FIG. 3: Polyphosphate lipid particle compositions are stable under various conditions. Lipid particle compositions comprising RNA (in two different concentrations: 10 or 70 mg/l), a cationically ionizable lipid, a steroid, a neutral lipid, an inorganic polyphosphate (triphosphate (3P), added at a concentration of 2.5 mM after formation of the particles, optionally also present in the final filtration (dialysis) step) with a PEG lipid (+PEG) or without PEG lipid (−PEG) were prepared. After storing under various conditions (5° C., −20° C., or −70° C.), the colloidal parameters (diameter in nm and polydispersity index (PDI)) of the particle compositions were measured.

FIG. 4: Influence of different molar ratios of the cationically ionizable lipid, a steroid, and a neutral lipid in the absence or presence of serum on the expression level. Lipid particle compositions comprising RNA (encoding luciferase), a cationically ionizable lipid (A: lipid XIV-3; B: lipid XIV-1; C: lipid XIV-2; D: lipid G (DPL-14)), a steroid (cholesterol), a neutral lipid (DSPC), and an inorganic polyphosphate (triphosphate (3P)) were prepared using compositions having the molar percentage of DSPC as indicated in the figures, the remainder of the lipid composition being the ionizable lipid (ION) and cholesterol (CHOL) in the molar ratio as indicated in the figures. Cells were transfected with either of the compositions in the presence of serum (+Serum (+S)) or in the absence of serum (−Serum (−S)). Luciferase expression was determined and the serum stimulation was calculated based on the ratio of the luciferase expression in the presence of serum (+S) to the luciferase expression in the absence of serum (−S) (ratio+S/−S). FIG. 4 shows the results for the luciferase expression, the serum stimulation (expressed as $\log_{10}$ (ratio+S/−S) values).

DESCRIPTION OF THE SEQUENCES

Figure 1A:
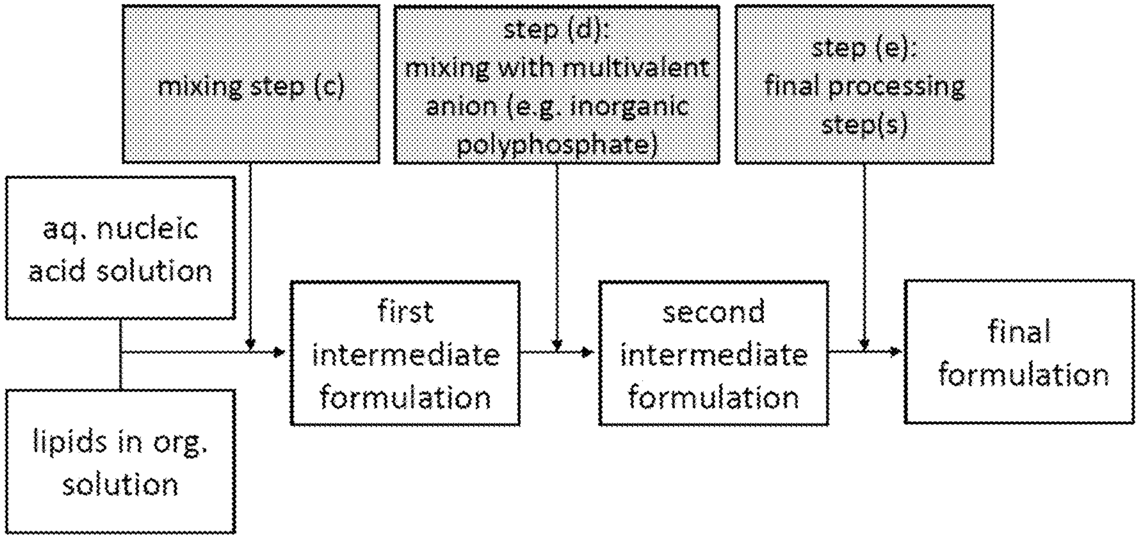
FIG. 1: Exemplary flowcharts illustrating certain steps according to the method of the second aspect.

The following table provides a listing of certain sequences referenced herein. 0

TABLE 1

Description of the sequences

| SEQ ID NO: | Description | Sequence |
|---|---|---|
| | | 5'-UTR (hAg-Kozak) |
| 1 | 5'-UTR | AACUAGUAUUCUUCUGGUCCCCACAGACUCAGAGAGAACCCGCCACC |
| | | 3'-UTR (FI element) |
| 2 | 3'-UTR | CUGGUACUGCAUGCACGCAAUGCUAGCUGCCCCUUUCCCGUCCUGGGUACCCCGAGUCUCCCCCGACCUCG GGUCCCAGGUAUGCUCCCACCUCCACCUGCCCCACUCACCACCUCUGCUAGUUCCAGACACCUCCCAAGCA CGCAGCAAUGCAGCUCAAAACGCUUAGCCUAGCCACACCCCCACGGGAAACAGCAGUGAUUAACCUUUAGC AAUAAACGAAAGUUUAACUAAGCUAUACUAACCCCAGGGUUGGUCAAUUUCGUGCCAGCCACACC |

TABLE 1-continued

| Description of the sequences | | |
|---|---|---|
| SEQ ID NO: | Des-cription | Sequence |
| | | A30L70 |
| 3 | A30L70 | AAAAAAAAAAAAAAAAAAAAAAAAAAAAAAGCAUAUGACUAAAAAAAAAAAAAAAAAAAAAAAAAAAAAAA AAAAAAAAAAAAAAAAAAAAAAAAAAAAAAAAAAAAAAA |
| | | Sec/MITD |
| 4 | Sec | MRVMAPRTLILLLSGALALTETWAGS |
| 5 | MITD | IVGIVAGLAVLAVVVIGAVVATVMCRRKSSGGKGGSYSQAASSDSAQGSDVSLTA |
| | | P2P16 |
| 6 | P2P16 | KKQYIKANSKFIGITELKKLGGGKRGGGKKMTNSVDDALINSTKIYSYFPSVISKVNQGAQGKKL |
| | | GS Linker |
| 7 | GS Linker 1 | GGSGGGGSGG |
| 8 | GS Linker 2 | GSSGGGGSPGGGSS |
| | | Helper epitopes |
| 9 | P2 | QYIKANSKFIGITEL |
| 10 | P16 | MTNSVDDALINSTKIYSYFPSVISKVNQGAQG |

DETAILED DESCRIPTION OF THE INVENTION

Although the present disclosure is further described in more detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

In the following, the elements of the present disclosure will be described in more detail. These elements are listed with specific embodiments, however, it should be understood that they may be combined in any manner and in any number to create additional embodiments. The variously described examples and preferred embodiments should not be construed to limit the present disclosure to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kolbl, Eds., Helvetica Chimica Acta, CH-4010 Basel, Switzerland, (1995).

The practice of the present disclosure will employ, unless otherwise indicated, conventional chemistry, biochemistry, cell biology, immunology, and recombinant DNA techniques which are explained in the literature in the field (cf, e.g., Organikum, Deutscher Verlag der Wissenschaften, Berlin 1990; Streitwieser/Heathcook, "Organische Chemie", VCH, 1990; Beyer/Walter, "Lehrbuch der Organischen Chemie", S. Hirzel Verlag Stuttgart, 1988; Carey/Sundberg, "Organische Chemie", VCH, 1995; March, "Advanced Organic Chemistry", John Wiley & Sons, 1985; Römpp Chemie Lexikon, Falbe/Regitz (Hrsg.), Georg Thieme Verlag Stuttgart, New York, 1989; Molecular Cloning: A Laboratory Manual, 2nd Edition, J. Sambrook et al. eds., Cold Spring Harbor Laboratory Press, Cold Spring Harbor 1989.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The terms "a", "an" and "the" and similar references used in the context of describing the present disclosure (especially in the context of the claims) are to be construed to cover both the singular and the plural, unless otherwise indicated herein or clearly contradicted by the context.

All methods described herein can be performed in any suitable order unless otherwise indicated herein or otherwise clearly contradicted by the context.

The use of any and all examples, or exemplary language (e.g., "such as"), provided herein is intended merely to better illustrate the present disclosure and does not pose a limitation on the scope of the present disclosure otherwise claimed. No language in the specification should be construed as indicating any non-claimed element essential to the practice of the present disclosure.

Where used herein, "and/or" is to be taken as specific disclosure of each of the two specified features or components with or without the other. For example, "X and/or Y" is to be taken as specific disclosure of each of (i) X, (ii) Y, and (iii) X and Y, just as if each is set out individually herein.

In the context of the present disclosure, the term "about" denotes an interval of accuracy that the person of ordinary skill will understand to still ensure the technical effect of the feature in question. The term typically indicates deviation from the indicated numerical value by ±10%, such as ±5%, ±4%, ±3%, 2%, ±1%, ±0.9%, ±0.8%, ±0.7%, ±0.6%, ±0.5%, 0.4%, ±0.3%, ±0.2%, ±0.1%, 0.05%, and for example ±0.010%. In some embodiments, "about" indicates deviation from the indicated numerical value by ±10%. In some embodiments, "about" indicates deviation from the indicated numerical value by ±5%. In some embodiments, "about" indicates deviation from the indicated numerical value by ±4%. In some embodiments, "about" indicates deviation from the indicated numerical value by ±3%. In some embodiments, "about" indicates deviation from the indicated numerical value by ±2%. In some embodiments, "about" indicates deviation from the indicated numerical value by ±1%. In some embodiments, "about" indicates deviation from the indicated numerical value by ±0.9%. In some embodiments, "about" indicates deviation from the indicated numerical value by ±0.8%. In some embodiments, "about" indicates deviation from the indicated numerical value by ±0.7%. In some embodiments, "about" indicates deviation from the indicated numerical value by ±0.6%. In some embodiments, "about" indicates deviation from the indicated numerical value by +0.5%. In some embodiments, "about" indicates deviation from the indicated numerical value by ±0.4%. In some embodiments, "about" indicates deviation from the indicated numerical value by ±0.3%. In some embodiments, "about" indicates deviation from the indicated numerical value by ±0.2%. In some embodiments, "about" indicates deviation from the indicated numerical value by ±0.1%. In some embodiments, "about" indicates deviation from the indicated numerical value by ±0.05%. In some embodiments, "about" indicates deviation from the indicated numerical value by ±0.01%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect.

Recitation of ranges of values herein is merely intended to serve as a shorthand method of referring individually to each separate value falling within the range. Unless otherwise indicated herein, each individual value is incorporated into the specification as if it were individually recited herein.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

In the following, definitions will be provided which apply to all aspects of the present disclosure. The following terms have the following meanings unless otherwise indicated. Any undefined terms have their art recognized meanings.

Terms such as "reduce" or "inhibit" as used herein means the ability to cause an overall decrease, for example, of about 5% or greater, about 10% or greater, about 15% or greater, about 20% or greater, about 25% or greater, about 30% or greater, about 40% or greater, about 50% or greater, or about 75% or greater, in the level. The term "inhibit" or similar phrases includes a complete or essentially complete inhibition, i.e. a reduction to zero or essentially to zero.

Terms such as "enhance" and "increase" as used herein means the ability to cause an overall increase, or enhancement, for example, by at least about 5% or greater, about 10% or greater, about 15% or greater, about 20% or greater, about 25% or greater, about 30% or greater, about 40% or greater, about 50% or greater, about 75% or greater, or about 100% or greater in the level. In some embodiments, these terms relate to an increase or enhancement by at least about 10%, at least about 20%, at least about 30%, at least about 40%, at least about 50%, at least about 80%, or at least about 100%.

"Physiological pH" as used herein refers to a pH of about 7.5 or about 7.4. In some embodiments, physiological pH is from 7.3 to 7.5. In some embodiments, physiological pH is from 7.35 to 7.45. In some embodiments, physiological pH is 7.3, 7.35, 7.4, 7.45, or 7.5.

"Physiological conditions" as used herein refer to the conditions (in particular pH and temperature) in a living subject, in particular a human. Preferably, physiological conditions mean a physiological pH and/or a temperature of about 37° C.

As used in the present disclosure, "% (w/v)" (or "% w/v") refers to weight by volume percent, which is a unit of concentration measuring the amount of solute in grams (g) expressed as a percent of the total volume of solution in milliliters (ml).

As used in the present disclosure, "% by volume" or "% (v/v)" (or "% v/v") refers to volume percent, which is a unit of concentration measuring the amount of a liquid substance in milliliters (ml) expressed as a percent of the total volume of solution in milliliters (ml).

As used in the present disclosure, "% by weight" or "% (w/w)" (or "% w/w") refers to weight percent, which is a unit of concentration measuring the amount of a substance in grams (g) expressed as a percent of the total weight of the total composition in grams (g).

As used in the present disclosure, "mol %" is defined as the ratio of the number of moles of one component to the total number of moles of all components, multiplied by 100.

As used in the present disclosure, "mol % of the total lipid" is defined as the ratio of the number of moles of one lipid component to the total number of moles of all lipids, multiplied by 100. In this context, in some embodiments, the term "total lipid" includes lipids and lipid-like material.

The term "relative amount" as used herein refers to the number of moles of one component (e.g., a lipid component) to the total number of moles of all components (e.g., all lipid components). For example, if a composition comprises 3 lipid components (lipid 1, lipid 2, and lipid 3) in the amount of 45 mol, 45 mol, and 10 mol, respectively, the relative amounts are 45 mol % (for lipid 1), 45 mol % (for lipid 2) and 10 mol % (for lipid 3). Increasing the relative amount of one component requires the decrease of the relative amount of at least one of the other components (such that the absolute amount of lipids stays essentially constant), and vice versa. E.g., increasing the relative amount of lipids 1 and 3 (to, for example, 58 mol % (for lipid 1) and 20 mol %

(for lipid 3)) would require the decrease of the relative amount of lipid 2 (to a lower relative amount of, for example, 22 mol %). Furthermore, decreasing the relative amount of lipids 1 and 3 (to, for example, 39 mol % (for lipid 1) and 5 mol % (for lipid 3)), would require the increase of the relative amount of lipid 2 (to a higher relative amount of, for example, 56 mol %).

The term "ionic strength" refers to the mathematical relationship between the number of different kinds of ionic species in a particular solution and their respective charges. Thus, ionic strength I is represented mathematically by the formula:

$$I = \frac{1}{2} \cdot \sum_i z_i^2 \cdot c_i$$

in which c is the molar concentration of a particular ionic species and z the absolute value of its charge. The sum Σ is taken over all the different kinds of ions (i) in solution.

According to the disclosure, the term "ionic strength" in some embodiments relates to the presence of monovalent ions.

Regarding the presence of divalent inorganic ions, in particular divalent inorganic cations, their concentration or effective concentration (presence of free ions) due to the presence of chelating agents is in one embodiment sufficiently low so as to prevent degradation of the RNA. In one embodiment, the concentration or effective concentration of divalent inorganic ions is below the catalytic level for hydrolysis of the phosphodiester bonds between RNA nucleotides. In one embodiment, the concentration of free divalent inorganic ions is 20 μM or less. In one embodiment, there are no or essentially no free divalent inorganic ions.

"Molar ratio", as used herein, refers to the ratio between the amounts in moles of any two substances. For example, if a first substance is present in a composition in an amount of 1 millimole (mmol) and a second substance is present in the composition in an amount of 2 millimole (mmol), the molar ratio of the first substance to the second substance is 1:2 or 0.5.

"Osmolality" refers to the concentration of a particular solute expressed as the number of osmoles of solute per kilogram of solvent.

The term "lyophilizing" or "lyophilization" refers to the freeze-drying of a substance by freezing it and then reducing the surrounding pressure (e.g., below 15 Pa, such as below 10 Pa, below 5 Pa, or 1 Pa or less) to allow the frozen medium in the substance to sublimate directly from the solid phase to the gas phase. Thus, the terms "lyophilizing" and "freeze-drying" are used herein interchangeably.

The term "spray-drying" refers to spray-drying a substance by mixing (heated) gas with a fluid that is atomized (sprayed) within a vessel (spray dryer), where the solvent from the formed droplets evaporates, leading to a dry powder.

The term "reconstitute" relates to adding a solvent such as water to a dried product to return it to a liquid state such as its original liquid state.

The term "freezing" relates to the solidification of a liquid, usually with the removal of heat. In some embodiments, freezing is reverse action to thawing.

The term "thawing" relates to the liquification of a solid, usually with the addition of heat. In some embodiments, thawing is reverse action to freezing.

The term "aqueous phase" as used herein in relation to a composition/formulation comprising particles, in particular LNPs, liposomes, and/or lipoplexes, means the mobile or liquid phase, i.e., the continuous water phase including all components dissolved therein but (formally) excluding the particles. Thus, if particles, such as LNPs, are dispersed in an aqueous phase and the aqueous phase is to be substantially free of compound X, the aqueous phase is free of X is such manner as it is practically and realistically feasible, e.g., the concentration of compound X in the aqueous composition is less than 1% by weight. However, it is possible that, at the same time, the particles dispersed in the aqueous phase may comprise compound X in an amount of more than 1% by weight.

The term "recombinant" in the context of the present disclosure means "made through genetic engineering". In some embodiments, a "recombinant object" in the context of the present disclosure is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

As used herein, the terms "room temperature" and "ambient temperature" are used interchangeably herein and refer to temperatures from at least about 15° C., preferably from about 15° C. to about 35° C., from about 15° C. to about 30° C., from about 15° C. to about 25° C., or from about 17° C. to about 22° C. Such temperatures will include 15° C., 16° C., 17° C., 18° C., 19° C., 20° C., 21° C. and 22° C.

The term "alkyl" refers to a monoradical of a saturated straight or branched hydrocarbon. Preferably, the alkyl group comprises from 1 to 12 (such as 1 to 10) carbon atoms, i.e., 1, 2, 3, 4, 5, 6, 7, 8, 9, 10, 11, or 12 carbon atoms, abbreviated as $C_{1-12}$ alkyl, (such as 1, 2, 3, 4, 5, 6, 7, 8, 9, or 10 carbon atoms, abbreviated as $C_{1-10}$ alkyl), more preferably 1 to 8 carbon atoms, such as 1 to 6 or 1 to 4 carbon atoms. Exemplary alkyl groups include methyl, ethyl, propyl, iso-propyl (also called 2-propyl or 1-methylethyl), butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethylhexyl, n-nonyl, n-decyl, n-undecyl, n-dodecyl, and the like. A "substituted alkyl" means that one or more (such as 1 to the maximum number of hydrogen atoms bound to an alkyl group, e.g., 1, 2, 3, 4, 5, 6, 7, 8, 9, or up to 10, such as between 1 to 5, 1 to 4, or 1 to 3, or 1 or 2) hydrogen atoms of the alkylene group are replaced with a substituent other than hydrogen (when more than one hydrogen atom is replaced the substituents may be the same or different). Preferably, the substituent other than hydrogen is a $1^{st}$ level substituent, as specified herein. Examples of a substituted alkyl include chloromethyl, dichloromethyl, fluoromethyl, and difluoromethyl.

The term "alkylene" refers to a diradical of a saturated straight or branched hydrocarbon. Preferably, the alkylene comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. Exemplary alkylene groups include methylene, ethylene (i.e., 1,1-ethylene, 1,2-ethylene), propylene (i.e., 1,1-propylene, 1,2-propylene (—$CH(CH_3)CH_2$—), 2,2-propylene (—$C(CH_3)_2$-), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylene isomers (e.g., 1,1-hexylene, 1,2-hexylene, 1,3-hexylene, 1,4-hexylene, 1,5-hexylene, 1,6-hexylene, and 1,1-isohexylene), the heptylene isomers (e.g., 1,1-heptylene, 1,2-heptylene, 1,3-heptylene, 1,4-heptylene, 1,5-heptylene, 1,6-heptylene, 1,7-heptylene, and 1,1-isoheptylene), the octylene isomers (e.g., 1,1-octylene, 1,2-octylene, 1,3-octylene, 1,4-octylene, 1,5-octylene, 1,6-octylene, 1,7-octylene, 1,8-octylene, and 1,1-isooctylene), and the like. The straight alkylene moieties having at least 3 carbon atoms and a free valence at each end can also be designated as a multiple of methylene (e.g., 1,4-butylene can also be called tetramethylene). Generally, instead of using the ending "ylene" for alkylene moieties as specified above, one can also use the ending "diyl" (e.g., 1,2-butylene can also be called butan-1,2-diyl). A "substituted alkylene" means that one or more (such as 1 to the maximum number of hydrogen atoms bound to an alkylene group, e.g., 1, 2, 3, 4, 5, 6, 7, 8, 9, or up to 10, such as between 1 to 5, 1 to 4, or 1 to 3, or 1 or 2) hydrogen atoms of the alkylene group are replaced with a substituent other than hydrogen (when more than one hydrogen atom is replaced the substituents may be the same or different). Preferably, the substituent other than hydrogen is a $1^{st}$ level substituent, as specified herein.

The term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 6 (such as 1 to 4), i.e., 1, 2, 3, 4, 5, or 6, carbon-carbon double bonds. Preferably, the alkenyl group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkenyl group comprises from 2 to 12, abbreviated as $C_{2-12}$ alkenyl, (e.g., 2 to 10) carbon atoms and 1, 2, 3, 4, 5, or 6 (e.g., 1, 2, 3, 4, or 5) carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, and the like. If an alkenyl group is attached to a nitrogen atom, the double bond cannot be alpha to the nitrogen atom. A "substituted alkenyl" means that one or more (such as 1 to the maximum number of hydrogen atoms bound to an alkenyl group, e.g., 1, 2, 3, 4, 5, 6, 7, 8, 9, or up to 10, such as between 1 to 5, 1 to 4, or 1 to 3, or 1 or 2) hydrogen atoms of the alkenyl group are replaced with a substituent other than hydrogen (when more than one hydrogen atom is replaced the substituents may be the same or different). Preferably, the substituent other than hydrogen is a $1^{st}$ level substituent as specified herein.

The term "alkynyl" refers to a linear or branched monovalent hydrocarbon moiety having at least one carbon-carbon triple bond in which the total carbon atoms may be six to thirty, typically six to twenty, often six to eighteen. Alkynyl groups can optionally have one or more carbon carbon double bonds. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 6 (such as 1 to 4), i.e., 1, 2, 3, 4, 5, or 6, more preferably 1 or 2 carbon-carbon triple bonds.

The term "alkenylene" refers to a diradical of an unsaturated straight or branched hydrocarbon having at least one carbon-carbon double bond. Generally, the maximal number of carbon-carbon double bonds in the alkenylene group can be equal to the integer which is calculated by dividing the number of carbon atoms in the alkenylene group by 2 and, if the number of carbon atoms in the alkenylene group is uneven, rounding the result of the division down to the next integer. For example, for an alkenylene group having 9 carbon atoms, the maximum number of carbon-carbon double bonds is 4. Preferably, the alkenylene group has 1 to 6 (such as 1 to 4), i.e., 1, 2, 3, 4, 5, or 6, carbon-carbon double bonds. Preferably, the alkenylene group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkenylene group comprises from 2 to 12 (such as 2 to 10 carbon) atoms and 1, 2, 3, 4, 5, or 6 (such as 1, 2, 3, 4, or 5) carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenylene groups include ethen-1,2-diyl, vinylidene (also called ethenylidene), 1-propen-1,2-diyl, 1-propen-1,3-diyl, 1-propen-2,3-diyl, allylidene, 1-buten-1,2-diyl, 1-buten-1,3-diyl, 1-buten-1,4-diyl, 1-buten-2,3-diyl, 1-buten-2,4-diyl, 1-buten-3,4-diyl, 2-buten-1,2-diyl, 2-buten-1,3-diyl, 2-buten-1,4-diyl, 2-buten-2,3-diyl, 2-buten-2,4-diyl, 2-buten-3,4-diyl, and the like. If an alkenylene group is attached to a nitrogen atom, the double bond cannot be alpha to the nitrogen atom. A "substituted alkenylene" means that one or more (such as 1 to the maximum number of hydrogen atoms bound to an alkenylene group, e.g., 1, 2, 3, 4, 5, 6, 7, 8, 9, or up to 10, such as between 1 to 5, 1 to 4, or 1 to 3, or 1 or 2) hydrogen atoms of the alkenylene group are replaced with a substituent other than hydrogen (when more than one hydrogen atom is replaced the substituents may be the same or different). Preferably, the substituent other than hydrogen is a $1^{st}$ level substituent as specified herein.

The term "cycloalkyl" represents cyclic non-aromatic versions of "alkyl" and "alkenyl" with preferably 3 to 14 carbon atoms, such as 3 to 12 or 3 to 10 carbon atoms, i.e., 3, 4, 5, 6, 7, 8, 9, 10, 11, 12, 13, or 14 carbon atoms (such as 3, 4, 5, 6, 7, 8, 9, or 10 carbon atoms), more preferably 3 to 7 carbon atoms. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The cycloalkyl group may consist of one ring (monocyclic), two rings (bicyclic), or more than two rings (polycyclic).

The term "cycloalkylene" represents cyclic non-aromatic versions of "alkylene" and is a geminal, vicinal or isolated diradical. In certain embodiments, the cycloalkylene (i) is monocyclic or polycyclic (such as bi- or tricyclic) and/or (ii) is 3-to 14-membered (i.e., 3-, 4-, 5-, 6-, 7-, 8-, 9-, 10-, 11-, 12-, 13-, or 14-membered, such as 3-to 12-membered or 3-to 10-membered). In one embodiment the cycloalkylene is a mono-, bi- or tricyclic 3-to 14-membered (i.e., 3-, 4-, 5-, 6-, 7-, 8-, 9-, 10-, 11-, 12-, 13-, or 14-membered, such as 3- to 12-membered or 3- to 10-membered) cycloalkylene. Generally, instead of using the ending "ylene" for cycloalkylene moieties as specified above, one can also use the ending "diyl" (e.g., 1,2-cyclopropylene can also be called cyclopropan-1,2-diyl) Exemplary cycloalkylene groups include cyclohexylene, cycloheptylene, cyclopropylene, cyclobutylene, cyclopentylene, cyclooctylene, bicyclo[3.2.1]octylene, bicyclo[3.2.2]nonylene, and adamantanylene (e.g., tricyclo[$3.3.1.1^{3,7}$]decan-2,2-diyl). A "substituted cycloalkylene" means that one or more (such as 1 to the maximum number of hydrogen atoms bound to an cycloalkylene group, e.g., 1, 2, 3, 4, 5, 6, 7, 8, 9, or up to 10, such as between 1 to 5, 1 to 4, or 1 to 3, or 1 or 2) hydrogen atoms of the alkylene group are replaced with a substituent other than hydrogen (when more than one hydrogen atom is replaced the substituents may be the same or different). Preferably, the substituent other than hydrogen is a $1^{st}$ level substituent as specified herein.

The term "cycloalkenylene" represents cyclic non-aromatic versions of "alkenylene" and is a geminal, vicinal or isolated diradical. Generally, the maximal number of carbon-carbon double bonds in the cycloalkenylene group can be equal to the integer which is calculated by dividing the number of carbon atoms in the cycloalkenylene group by 2 and, if the number of carbon atoms in the cycloalkenylene group is uneven, rounding the result of the division down to the next integer. For example, for an cycloalkenylene group having 9 carbon atoms, the maximum number of carbon-carbon double bonds is 4. Preferably, the cycloalkenylene group has 1 to 6 (such as 1 to 4), i.e., 1, 2, 3, 4, 5, or 6, carbon-carbon double bonds. In certain embodiments, the cycloalkenylene (i) is monocyclic or polycyclic (such as bi- or tricyclic) and/or (ii) is 3- to 14-membered (i.e., 3-, 4-, 5-, 6-, 7-, 8-, 9-, 10-, 11-, 12-, 13-, or 14-membered, such as 3- to 12-membered or 3- to 10-membered). In one embodiment the cycloalkenylene is a mono-, bi- or tricyclic 3- to 14-membered (i.e., 3-, 4-, 5-, 6-, 7-, 8-, 9-, 10-, 11-, 12-, 13-, or 14-membered, such as 3- to 12-membered or 3- to 10-membered) cycloalkenylene. Exemplary cycloalkenylene groups include cyclohexenylene, cycloheptenylene, cyclopropenylene, cyclobutenylene, cyclopentenylene, and cyclooctenylene. A "substituted cycloalkenylene" means that one or more (such as 1 to the maximum number of hydrogen atoms bound to an cycloalkenylene group, e.g., 1, 2, 3, 4, 5, 6, 7, 8, 9, or up to 10, such as between 1 to 5, 1 to 4, or 1 to 3, or 1 or 2) hydrogen atoms of the cycloalkenylene group are replaced with a substituent other than hydrogen (when more than one hydrogen atom is replaced the substituents may be the same or different). Preferably, the substituent other than hydrogen is a $1^{st}$ level substituent as specified herein.

The term "aryl" refers to a monoradical of an aromatic cyclic hydrocarbon. Preferably, the aryl group contains 3 to 14 (e.g., 5, 6, 7, 8, 9, or 10, such as 5, 6, or 10) carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. Aryl does not encompass fullerenes.

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present disclosure. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present disclosure (even if one ring, such as in 1,2-dihydronaphthyl, is still aromatic).

The term "hydrocarbyl" as used herein relates to a monovalent organic group obtained by removing one H atom from a hydrocarbon molecule. In some embodiments, hydrocarbyl groups are non-cyclic, e.g., linear (straight) or branched. Typical examples of hydrocarbyl groups include alkyl, alkenyl, alkynyl, cycloalkyl, aryl groups, and combinations thereof (such as arylalkyl (aralkyl), etc.). Particular examples of hydrocarbyl groups are $C_{1-6}$ alkyl, aryl, and aryl($C_{1-6}$ alkyl). In some embodiments, the hydrocarbyl group is optionally substituted (e.g., with one or more $1^{st}$ level substituents as defined herein), provided that the overall polarity of the hydrocarbon remains relatively nonpolar.

Typical $1^{st}$ level substituents are preferably selected from the group consisting of $C_{1-3}$ alkyl, phenyl, halogen, $—CF_3$, —OH, $—OCH_3$, $—SCH_3$, $—NH_{2-z}(CH_3)_z$, —C(═O)OH, and $—C(═O)OCH_3$, wherein z is 0, 1, or 2 and $C_{1-3}$ alkyl is methyl, ethyl, propyl or isopropyl. Particularly preferred $1^{st}$ level substituents are selected from the group consisting of methyl, ethyl, propyl, isopropyl, halogen (such as F, Cl, or Br), and $—CF_3$, such as halogen (e.g., F, Cl, or Br), and $—CF_3$.

The term "tertiary amine moiety" as used herein relates to a moiety containing a nitrogen atom which is substituted with three organic substituents (wherein the substituents may be the same or different from each other). In some embodiments, the organic substituents are selected from hydrocarbyl groups (such as alkyl groups, in particular $C_{1-6}$ alkyl groups) which are optionally substituted (e.g., with one or more $1^{st}$ level substituents as defined herein).

The term "filtrating" as used herein relates to any process that involves removal or separation of at least one component (such as permeable molecules like salts, small proteins, solvents etc.,) of a liquid composition based on the molecular size of the components contained in the composition. This separation may use micro-molecule permeable filters (e.g., for diafiltration or tangential flow filtration) or semi-permeable membranes (e.g., for dialysis). Thus, examples of filtrating comprise dialyzing, tangential flow filtrating and diafiltrating.

The expression "after thawing the frozen composition", as used herein in context with a frozen composition, means that the frozen composition has to be thawed before the characteristics (such as nucleic acid integrity (such as RNA integrity) and/or size ($Z_{average}$) and/or size distribution and/or the PDI of the particles (such as LNPs) contained in the composition) can be measured.

A "monovalent" compound relates to a compound having only one functional group of interest. For example, a monovalent acid relates to a compound having only one acid group (such as one carboxyl (—COOH) group). A monovalent cation, for example, relates to a compound having only one cationic group, such as an alkaline cation (e.g., $Na^+$, $K^+$, $Li^+$), an ammonium cation ($NH_4^+$) or an organic compound having one primary, secondary or tertiary amine group (like the protonated form of triethylamine, trimethylamine, etc.) an organic compound having one quaternary amine group.

A "divalent" or "dibasic" compound relates to a compound having two functional groups of interest. For example, a dibasic organic acid has two carboxyl groups.

A "polyvalent", "multivalent", "polybasic" or "multibasic" compound relates to a compound having two or more functional groups of interest, preferably three or more functional groups of interest. For example, a polybasic organic acid has two or more, preferably three or more acid carboxyl groups.

A "polyphosphate" relates to a compound containing two or more consecutive phosphate groups, preferably three or more consecutive phosphate groups. Examples of polyphosphates include inorganic polyphosphates as well as esters of polyphosphates (such as triphosphate) with one or more organic alcohols, such as nucleotides, oligonucleotides or polynucleotides having at least three consecutive phosphate groups.

The expression "inorganic polyphosphate", as used herein, means a compound which contains two or more consecutive phosphate groups, preferably three or more consecutive phosphate groups and which does not contain any organic moiety covalently bound thereto (e.g., the inorganic polyphosphate lacks a covalent bond between any oxygen or phosphor atom contained in the anionic moiety of the polyphosphate and a carbon atom). Thus, the expression "inorganic polyphosphate" does not include esters of a polyphosphate with one or more organic alcohols. Consequently, the expression "inorganic polyphosphate" does not encompass nucleotides, oligonucleotides or polynucleotides even if they comprise at least two, preferably at least three consecutive phosphate groups. Inorganic polyphosphates may be linear (i.e., all phosphate moieties of the polyphosphate are arranged in a chain), branched or cyclic. In some embodiments, polyphosphate comprises the formula $[P_xO_{3x+1)}]^{y-}$, wherein x is an integer and is at least 2, preferably at least 3; and y is the anionic charge. Examples of polyphosphates include diphosphate, triphosphate, tetraphosphate, pentaphosphate, hexaphosphate, heptaphosphate, higher homologues, and mixtures thereof (in particular the linear forms of these polyphosphates), in particular triphosphate, tetraphosphate, pentaphosphate, hexaphosphate, heptaphosphate, higher homologues, and mixtures thereof (in particular the linear forms of these polyphosphates). Preferred polyphosphates include diphosphate, triphosphate, tetraphosphate, pentaphosphate, hexaphosphate, heptaphosphate, and mixtures thereof (in particular the linear forms of these polyphosphates), such as triphosphate, tetraphosphate, pentaphosphate, hexaphosphate, heptaphosphate, and mixtures thereof (in particular the linear forms of these polyphosphates), e.g., triphosphate, tetraphosphate, pentaphosphate, and mixtures thereof (in particular the linear forms of these polyphosphates). A particularly preferred polyphosphate is triphosphate.

Similarly, the expression "inorganic phosphate", as used herein, means a compound which contains only one phosphate group and which does not contain any organic moiety covalently bound thereto (e.g., the inorganic phosphate lacks a covalent bond between any oxygen or phosphor atom contained in the anionic moiety of the phosphate and a carbon atom). Thus, the expression "inorganic phosphate" does not include esters of a phosphate with one or more organic alcohols. Consequently, the expression "inorganic phosphate" does not encompass nucleotides, oligonucleotides or polynucleotides even if they comprise one phosphate group. Inorganic phosphates may be linear or cyclic. In some embodiments, inorganic phosphate comprises the formula $[PO_4]^{3-}$.

The expression "substantially free of X", as used herein, means that a mixture (such as an aqueous phase of a composition or formulation described herein) is free of X in such manner as it is practically and realistically feasible. For example, if the mixture is substantially free of X, the amount of X in the mixture may be less than 1% by weight (e.g., less than 0.5% by weight, less than 0.4% by weight, less than 0.3% by weight, less than 0.2% by weight, less than 0.1% by weight, less than 0.09% by weight, less than 0.08% by weight, less than 0.07% by weight, less than 0.06% by weight, less than 0.05% by weight, less than 0.04% by weight, less than 0.03% by weight, less than 0.02% by weight, less than 0.01% by weight, less than 0.005% by weight, less than 0.001% by weight), based on the total weight of the mixture.

For example, "substantially free of a lipid comprising polyethyleneglycol (PEG)" as used herein, means that a mixture (such as an aqueous phase of a composition or formulation described herein) is free of a lipid comprising PEG in such manner as it is practically and realistically feasible. For example, if the mixture is substantially free of a lipid comprising PEG, the amount of a lipid comprising PEG in the mixture may be less than 1% by weight (e.g., less than 0.5% by weight, less than 0.4% by weight, less than 0.3% by weight, less than 0.2% by weight, less than 0.1% by weight, less than 0.09% by weight, less than 0.08% by weight, less than 0.07% by weight, less than 0.06% by weight, less than 0.05% by weight, less than 0.04% by weight, less than 0.03% by weight, less than 0.02% by weight, less than 0.01% by weight, less than 0.005% by weight, less than 0.001% by weight), based on the total weight of the mixture. Similar considerations apply to the expressions "substantially free of any compound comprising PEG", "substantially free of PEG", and "substantially free of the cationically ionizable lipid, the steroid, and the neutral lipid".

The expression "nucleic acid integrity" means the percentage of the full-length (i.e., non-fragmented) nucleic acid to the total amount of nucleic acid (i.e., non-fragmented plus fragmented nucleic acid) contained in a sample. The nucleic acid integrity may be determined by chromatographically separating the nucleic acid (e.g., using capillary electrophoresis), determining the peak area of the main nucleic acid peak (i.e., the peak area of the full-length (i.e., non-fragmented) nucleic acid), determining the peak area of the total nucleic acid, and dividing the peak area of the main nucleic acid peak by the peak area of the total nucleic acid. Likewise, the expression "RNA integrity" means the percentage of the full-length (i.e., non-fragmented) RNA to the total amount of RNA (i.e., non-fragmented plus fragmented RNA) contained in a sample. The RNA integrity may be determined by chromatographically separating the RNA (e.g., using capillary electrophoresis), determining the peak area of the main RNA peak (i.e., the peak area of the full-length (i.e., non-fragmented) RNA), determining the peak area of the total RNA, and dividing the peak area of the main RNA peak by the peak area of the total RNA.

The term "cryoprotectant" relates to a substance that is added to a preparation (e.g., formulation or composition) in order to protect the active ingredients of the preparation during the freezing stages.

The term "lyoprotectant" relates to a substance that is added to a formulation in order to protect the active ingredients during the drying stages.

The expression "glass-transition temperature" (abbreviated: $T_g$) of a substance means the temperature range of over which this glass transition occurs. The expression "glass-transition" means gradual and reversible transition in amorphous materials (or in amorphous regions within semicrystalline materials) from a hard (e.g., relatively brittle "glassy") amorphous state into a viscous (e.g., rubbery) molten state as the temperature is increased. Methods for determining glass-transition temperatures are known to the skilled person and include thermal dilatometric, dielectric, dynamic mechanical (DTMA), calorimetric (DSC) or refractrometric methods or NMR spectroscopy. Suitable standardized methods include DIN 53765: 1994-03 and ISO 11357-2: 1999-03.

According to the present disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "polypeptide" refers to large peptides, in particular peptides having at least about 151 amino acids. "Peptides" and "polypeptides" are both protein molecules, although the terms "protein" and "polypeptide" are used herein usually as synonyms.

A "therapeutic protein" has a positive or advantageous effect on a condition or disease state of a subject when provided to the subject in a therapeutically effective amount. In some embodiments, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides, and can also refer to therapeutically active fragments thereof. It can also include therapeutically active variants of a protein. Examples of therapeutically active proteins include, but are not limited to, antigens for vaccination and immunostimulants such as cytokines. The terms "therapeutic protein" and "pharmaceutically active peptide or protein" are used interchangeable herein.

According to various embodiments of the present disclosure, a nucleic acid such as RNA (e.g., mRNA) encoding a peptide, polypeptide or protein is taken up by or introduced, i.e. transfected or transduced, into a cell which cell may be present in vitro or in a subject, resulting in expression of said peptide, polypeptide or protein. The cell may express the encoded peptide, polypeptide or protein intracellularly (e.g. in the cytoplasm and/or in the nucleus), may secrete the encoded peptide, polypeptide or protein, and/or may express it on the surface.

According to the present disclosure, terms such as "nucleic acid expressing" and "nucleic acid encoding" or similar terms are used interchangeably herein and with respect to a particular peptide, polypeptide or protein mean that the nucleic acid, if present in the appropriate environment, preferably within a cell, can be expressed to produce said peptide, polypeptide or protein.

The term "portion" refers to a fraction. With respect to a particular structure such as an amino acid sequence or protein the term "portion" thereof may designate a continuous or a discontinuous fraction of said structure.

The terms "part" and "fragment" are used interchangeably herein and refer to a continuous element. For example, a part of a structure such as an amino acid sequence or protein refers to a continuous element of said structure. When used in context of a composition, the term "part" means a portion of the composition. For example, a part of a composition may any portion from 0.1% to 99.9% (such as 0.10%, 0.5%, 1%, 5%, 10%, 50%, 90%, or 99%) of said composition.

"Fragment", with reference to an amino acid sequence (peptide, polypeptide or protein), relates to a part of an amino acid sequence, i.e. a sequence which represents the amino acid sequence shortened at the N-terminus and/or C-terminus. A fragment shortened at the C-terminus (N-terminal fragment) is obtainable, e.g., by translation of a truncated open reading frame that lacks the 3'-end of the open reading frame. A fragment shortened at the N-terminus (C-terminal fragment) is obtainable, e.g., by translation of a truncated open reading frame that lacks the 5'-end of the open reading frame, as long as the truncated open reading frame comprises a start codon that serves to initiate translation. A fragment of an amino acid sequence comprises, e.g., at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence. A fragment of an amino acid sequence comprises, e.g., a sequence of up to 8, in particular up to 10, up to 12, up to 15, up to 20, up to 30 or up to 55, consecutive amino acids of the amino acid sequence.

According to the present disclosure, a part or fragment of a peptide, polypeptide or protein preferably has at least one functional property of the peptide, polypeptide or protein from which it has been derived. Such functional properties comprise a pharmacological activity, the interaction with other peptides, polypeptides or proteins, an enzymatic activity, the interaction with antibodies, and the selective binding of nucleic acids. E.g., a pharmacological active fragment of a peptide, polypeptide or protein has at least one of the pharmacological activities of the peptide, polypeptide or protein from which the fragment has been derived. A part or fragment of a peptide, polypeptide or protein preferably comprises a sequence of at least 6, in particular at least 8, at least 10, at least 12, at least 15, at least 20, at least 30 or at least 50, consecutive amino acids of the peptide or protein. A part or fragment of a peptide or protein preferably comprises a sequence of up to 8, in particular up to 10, up to 12, up to 15, up to 20, up to 30 or up to 55, consecutive amino acids of the peptide or protein.

"Variant", as used herein and with reference to an amino acid sequence (peptide, polypeptide, or protein), is meant an amino acid sequence that differs from a parent amino acid sequence by virtue of at least one amino acid (e.g., a different amino acid, or a modification of the same amino acid). The parent amino acid sequence may be a naturally occurring or wild type (WT) amino acid sequence, or may be a modified version of a wild type amino acid sequence. In some embodiments, the variant amino acid sequence has at least one amino acid difference as compared to the parent amino acid sequence, e.g., from 1 to about 20 amino acid differences, and preferably from 1 to about 10 or from 1 to about 5 amino acid differences compared to the parent.

By "wild type" or "WT" or "native" with respect to an amino acid sequence is meant an amino acid sequence that is found in nature, including allelic variations. A wild type amino acid sequence, peptide, polypeptide or protein has an amino acid sequence that has not been intentionally modified. Likewise by "wild type" or "WT" or "native" with respect to a nucleic acid sequence is meant a nucleic acid sequence that is found in nature, including allelic variations. For example, a wild type coding sequence is meant to be a coding sequence that is found in nature and that has not been intentionally modified.

A "coding sequence", as sued herein means the portion of a nucleic acid (e.g., a gene's DNA or RNA) that codes for protein.

The expression "guanosine/cytosine (G/C) content" or "G/C content" means the percentage of bases in a DNA or RNA molecule that are either guanine (G) or cytosine (C). The G/C content may be given for a specific portion of DNA or RNA or for an entire genome. When the G/C content refers to a portion, it may denote the G/C content of an individual gene or portion of a gene (domain), a group of genes or gene clusters, a non-coding region, a coding sequence, or a synthetic oligonucleotide such as a primer.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, post-translationally modified variants, conformations, isoforms, allelic variants, species variants, and species homologs, in particular those which are naturally occurring. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. In some embodiments, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

In some embodiments, the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical" and "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq&LINK_LOC=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, -2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments continuous nucleotides. In some embodiments, the degree of similarity or identity is given for the entire length of the reference sequence.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In some embodiments, a fragment or variant of an amino acid sequence (peptide, polypeptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to antigens or antigenic sequences, one particular function is one or more immunogenic activities displayed by the amino acid sequence from which the fragment or variant is derived. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., inducing an immune response (immunogenic fragment). In one embodiment, the modifications in the amino acid sequence of the parent molecule or sequence do not significantly affect or alter the characteristics of the molecule or sequence. In different embodiments, the function of the functional fragment or functional variant may be reduced but still significantly present, e.g., immunogenicity of the functional variant may be at least 50%, at least 60%, at least 70%, at least 80%, or at least 90% of the parent molecule or sequence. However, in other embodiments, immunogenicity of the functional fragment or functional variant may be enhanced compared to the parent molecule or sequence.

An amino acid sequence (peptide, protein or polypeptide) "derived from" a designated amino acid sequence (peptide, protein or polypeptide) refers to the origin of the first amino acid sequence. In some embodiments, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the antigens suitable for use herein may be altered such that they vary in sequence from the naturally occurring or native sequences from which they were derived, while retaining the desirable activity of the native sequences.

In some embodiments, "isolated" means altered or removed (e.g., purified) from the natural state or from an artificial composition, such as a composition from a production process. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell. In some embodiments, the RNA (such as mRNA) used in the present disclosure is in substantially purified form. In some embodiments, a solution (preferably an aqueous solution) of RNA (such as mRNA) in substantially purified form contains a first buffer system.

The term "genetic modification" or simply "modification" includes the transfection of cells with nucleic acid. The term "transfection" relates to the introduction of nucleic acids, in particular RNA, into a cell. For purposes of the present disclosure, the term "transfection" also includes the introduction of a nucleic acid into a cell or the uptake of a nucleic acid by such cell, wherein the cell may be present in a subject, e.g., a patient. Thus, according to the present disclosure, a cell for transfection of a nucleic acid described herein can be present in vitro (e.g., in cell culture) or in vivo, e.g., the cell can form part of an organ, a tissue and/or an organism of a patient. According to the disclosure, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection. Generally, nucleic acid encoding antigen is transiently transfected into cells. RNA can be transfected into cells to transiently express its coded protein.

The disclosure includes analogs of a peptide, polypeptide or protein. According to the present disclosure, an analog of a peptide, polypeptide or protein is a modified form of said peptide, polypeptide or protein from which it has been derived and has at least one functional property of said peptide, polypeptide or protein. E.g., a pharmacological active analog of a peptide, polypeptide or protein has at least one of the pharmacological activities of the peptide, polypeptide or protein from which the analog has been derived. Such modifications include any chemical modification and comprise single or multiple substitutions, deletions and/or additions of any molecules associated with the protein, polypeptide or peptide, such as carbohydrates, lipids and/or proteins or peptides. In one embodiment, "analogs" of proteins, polypeptides or peptides include those modified forms resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "analog" also extends to all functional chemical equivalents of said proteins, polypeptides and peptides.

"Activation" or "stimulation", as used herein, refers to the state of a cell (e.g., an immune effector cell such as T cell) that has been sufficiently stimulated to induce detectable cellular proliferation. Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In some embodiments, the term is preferably used in the context of an immunological response in which immune effector cells are stimulated by an antigen, proliferate, and the specific immune effector cell recognizing said antigen is amplified. In some embodiments, expansion leads to differentiation of the immune effector cells.

An "antigen" according to the present disclosure covers any substance that will elicit an immune response and/or any substance against which an immune response or an immune mechanism such as a cellular response is directed. This also includes situations wherein the antigen is processed into antigen peptides and an immune response or an immune mechanism is directed against one or more antigen peptides, in particular if presented in the context of MHC molecules. In particular, an "antigen" relates to any substance, preferably a peptide or protein, that reacts specifically with antibodies or T-lymphocytes (T-cells). According to the present disclosure, the term "antigen" comprises any molecule which comprises at least one epitope, such as a T cell epitope. Preferably, an antigen in the context of the present disclosure is a molecule which, optionally after processing, induces an immune reaction, which is preferably specific for the antigen (including cells expressing the antigen). In one embodiment, an antigen is a disease-associated antigen, such as a tumor antigen, a viral antigen, or a bacterial antigen, or an epitope derived from such antigen.

According to the present disclosure, any suitable antigen may be used, which is a candidate for an immune response, wherein the immune response may be a humoral or cellular immune response or both. In the context of some embodiments of the present disclosure, the antigen is presented by a cell, preferably by an antigen presenting cell, in the context of MHC molecules, which results in an immune response against the antigen. An antigen may be a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present disclosure, an antigen may correspond to a naturally occurring product, for example, a viral protein, or a part thereof.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. Disease-associated antigens include pathogen-associated antigens, i.e., antigens which are associated with infection by microbes, typically microbial antigens (such as bacterial or viral antigens), or antigens associated with cancer, typically tumors, such as tumor antigens.

In some embodiments, the antigen is a tumor antigen, i.e., a part of a tumor cell, in particular those which primarily occur intracellularly or as surface antigens of tumor cells. In another embodiment, the antigen is a pathogen-associated antigen, i.e., an antigen derived from a pathogen, e.g., from a virus, bacterium, unicellular organism, or parasite, for example a viral antigen such as viral ribonucleoprotein or coat protein. In particular, the antigen should be presented by MHC molecules which results in modulation, in particular activation of cells of the immune system, preferably CD4+ and CD8+ lymphocytes, in particular via the modulation of the activity of a T-cell receptor.

The term "tumor antigen" or "tumor-associated antigen" refers to a constituent of cancer cells which may be derived from the cytoplasm, the cell surface or the cell nucleus. In particular, it refers to those antigens which are produced intracellularly or as surface antigens on tumor cells. For example, tumor antigens include the carcinoembryonal antigen, $\alpha$1-fetoprotein, isoferritin, and fetal sulphoglycoprotein, $\alpha$2-H-ferroprotein and $\gamma$-fetoprotein, as well as various virus tumor antigens. According to some embodiments of the present disclosure, a tumor antigen comprises any antigen which is characteristic for tumors or cancers as well as for tumor or cancer cells with respect to type and/or expression level.

The term "viral antigen" refers to any viral component having antigenic properties, i.e., being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "epitope" refers to an antigenic determinant in a molecule such as an antigen, i.e., to a part in or fragment of the molecule that is recognized by the immune system, for example, that is recognized by antibodies T cells or B cells, in particular when presented in the context of MHC molecules. An epitope of a protein may comprise a continuous or discontinuous portion of said protein and, e.g., may be between about 5 and about 100, between about 5 and about 50, between about 8 and about 0, between about 10 and about 25 amino acids in length, for example, the epitope may be preferably 9, 10, 11, 12, 13, 14, 15, 16, 17, 18, 19, 20, 21, 22, 23, 24, or 25 amino acids in length. In some embodiments, the epitope in the context of the present disclosure is a T cell epitope.

Terms such as "epitope", "fragment of an antigen", "immunogenic peptide" and "antigen peptide" are used interchangeably herein and, e.g., may relate to an incomplete representation of an antigen which is, e.g., capable of eliciting an immune response against the antigen or a cell expressing or comprising and presenting the antigen. In some embodiments, the terms relate to an immunogenic portion of an antigen. Preferably, it is a portion of an antigen that is recognized (i.e., specifically bound) by a T cell receptor, in particular if presented in the context of MHC molecules. Certain preferred immunogenic portions bind to an MHC class I or class II molecule. The term "epitope" refers to a part or fragment of a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 8 and about 25 amino acids in length, for example, the epitope may be preferably 9, 10, 11, 12, 13, 14, 15, 16, 17, 18, 19, 20, 21, 22, 23, 24, or 25 amino acids in length. In some embodiments, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

The peptide and protein antigen can be 2 to 100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids in length. In some embodiments, a peptide can be greater than 50 amino acids. In some embodiments, the peptide can be greater than 100 amino acids.

The peptide or protein antigen can be any peptide or protein that can induce or increase the ability of the immune system to develop antibodies and T cell responses to the peptide or protein.

In some embodiments, vaccine antigen, i.e., an antigen whose inoculation into a subject induces an immune response, is recognized by an immune effector cell. In some embodiments, the vaccine antigen if recognized by an immune effector cell is able to induce in the presence of appropriate co-stimulatory signals, stimulation, priming and/or expansion of the immune effector cell carrying an antigen receptor recognizing the vaccine antigen. In the context of the embodiments of the present disclosure, the vaccine antigen is preferably presented or present on the surface of a cell, preferably an antigen presenting cell. In some embodiments, an antigen is presented by a diseased cell (such as tumor cell or an infected cell). In some embodiments, an antigen receptor is a TCR which binds to an epitope of an antigen presented in the context of MHC. In some embodiment, binding of a TCR when expressed by T cells and/or present on T cells to an antigen presented by cells such as antigen presenting cells results in stimulation, priming and/or expansion of said T cells. In some embodiments, binding of a TCR when expressed by T cells and/or present on T cells to an antigen presented on diseased cells results in cytolysis and/or apoptosis of the diseased cells, wherein said T cells preferably release cytotoxic factors, e.g., perforins and granzymes.

In some embodiments, an antigen receptor is an antibody or B cell receptor which binds to an epitope in an antigen. In some embodiments, an antibody or B cell receptor binds to native epitopes of an antigen.

The term "expressed on the cell surface" or "associated with the cell surface" means that a molecule such as an antigen is associated with and located at the plasma membrane of a cell, wherein at least a part of the molecule faces the extracellular space of said cell and is accessible from the outside of said cell, e.g., by antibodies located outside the cell. In this context, a part may be, e.g., at least 4, at least 8, at least 12, or at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a molecule associated with the surface of a cell may be a transmembrane protein having an extracellular portion or may be a protein associated with the surface of a cell by interacting with another protein that is a transmembrane protein.

"Cell surface" or "surface of a cell" is used in accordance with its normal meaning in the art, and thus includes the outside of the cell which is accessible to binding by proteins and other molecules. An antigen is expressed on the surface of cells if it is located at the surface of said cells and is accessible to binding by, e.g., antigen-specific antibodies added to the cells. In some embodiments, an antigen expressed on the surface of cells is an integral membrane protein having an extracellular portion which may be recognized by a CAR.

The term "extracellular portion" or "exodomain" in the context of the present disclosure refers to a part of a molecule such as a protein that is facing the extracellular space of a cell and preferably is accessible from the outside of said cell, e.g., by binding molecules such as antibodies located outside the cell. In some embodiments, the term refers to one or more extracellular loops or domains or a fragment thereof.

The terms "T cell" and "T lymphocyte" are used interchangeably herein and include T helper cells (CD4+ T cells) and cytotoxic T cells (CTLs, CD8+ T cells) which comprise cytolytic T cells. The term "antigen-specific T cell" or similar terms relate to a T cell which recognizes the antigen to which the T cell is targeted, in particular when presented on the surface of antigen presenting cells or diseased cells such as cancer cells in the context of MHC molecules and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as interferon-γ) can be measured. In certain embodiments of the present disclosure, the RNA (in particular mRNA) encodes at least one epitope.

The term "target" shall mean an agent such as a cell or tissue which is a target for an immune response such as a cellular immune response. Targets include cells that present an antigen or an antigen epitope, i.e., a peptide fragment derived from an antigen. In one embodiment, the target cell is a cell expressing an antigen and preferably presenting said antigen with class I MHC.

"Antigen processing" refers to the degradation of an antigen into processing products which are fragments of said antigen (e.g., the degradation of a protein into peptides) and the association of one or more of these fragments (e.g., via binding) with MHC molecules for presentation by cells, preferably antigen-presenting cells to specific T-cells. Antigen-presenting cells can be distinguished in professional antigen presenting cells and non-professional antigen presenting cells.

By "antigen-responsive CTL" is meant a CD8+ T-cell that is responsive to an antigen or a peptide derived from said antigen, which is presented with class I MHC on the surface of antigen presenting cells.

According to the disclosure, CTL responsiveness may include sustained calcium flux, cell division, production of cytokines such as IFN-γ and TNF-α, up-regulation of activation markers such as CD44 and CD69, and specific cytolytic killing of tumor antigen expressing target cells. CTL responsiveness may also be determined using an artificial reporter that accurately indicates CTL responsiveness.

The terms "immune response" and "immune reaction" are used herein interchangeably in their conventional meaning and refer to an integrated bodily response to an antigen and may refer to a cellular immune response, a humoral immune response, or both. According to the disclosure, the term "immune response to" or "immune response against" with respect to an agent such as an antigen, cell or tissue, relates to an immune response such as a cellular response directed against the agent. An immune response may comprise one or more reactions selected from the group consisting of developing antibodies against one or more antigens and expansion of antigen-specific T-lymphocytes, such as CD4+ and CD8+ T-lymphocytes, e.g., CD8+T-lymphocytes, which may be detected in various proliferation or cytokine production tests in vitro.

The terms "inducing an immune response" and "eliciting an immune response" and similar terms in the context of the present disclosure refer to the induction of an immune response, such as the induction of a cellular immune response, a humoral immune response, or both. The immune response may be protective/preventive/prophylactic and/or therapeutic. The immune response may be directed against any immunogen or antigen or antigen peptide, preferably against a tumor-associated antigen or a pathogen-associated antigen (e.g., an antigen of a virus (such as influenza virus (A, B, or C), CMV or RSV)). "Inducing" in this context may mean that there was no immune response against a particular antigen or pathogen before induction, but it may also mean that there was a certain level of immune response against a particular antigen or pathogen before induction and after induction said immune response is enhanced. Thus, "inducing the immune response" in this context also includes "enhancing the immune response". In some embodiments, after inducing an immune response in an individual, said individual is protected from developing a disease such as an infectious disease or a cancerous disease or the disease condition is ameliorated by inducing an immune response.

The terms "cellular immune response", "cellular response", "cell-mediated immunity" or similar terms are meant to include a cellular response directed to cells characterized by expression of an antigen and/or presentation of an antigen with class I or class II MHC. The cellular response relates to cells called T cells or T lymphocytes which act as either "helpers" or "killers". The helper T cells (also termed CD4+ T cells) play a central role by regulating the immune response and the killer cells (also termed cytotoxic T cells, cytolytic T cells, CD8+ T cells or CTLs) kill cells such as diseased cells.

The term "humoral immune response" refers to a process in living organisms wherein antibodies are produced in response to agents and organisms, which they ultimately neutralize and/or eliminate. The specificity of the antibody response is mediated by T and/or B cells through membrane-associated receptors that bind antigen of a single specificity. Following binding of an appropriate antigen and receipt of various other activating signals, B lymphocytes divide, which produces memory B cells as well as antibody secreting plasma cell clones, each producing antibodies that recognize the identical antigenic epitope as was recognized by its antigen receptor. Memory B lymphocytes remain dormant until they are subsequently activated by their specific antigen. These lymphocytes provide the cellular basis of memory and the resulting escalation in antibody response when re-exposed to a specific antigen.

The term "antibody" as used herein, refers to an immunoglobulin molecule, which is able to specifically bind to an epitope on an antigen. In particular, the term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies and combinations of any of the foregoing. Each heavy chain is comprised of a heavy chain variable region (VH) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3, the CDRs of a VL are termed LCDR1, LCDR2 and LCDR3. The variable regions of the heavy and light chains contain a binding domain that interacts with an antigen. The constant regions of an antibody comprise the heavy chain constant region (CH) and the light chain constant region (CL), wherein CH can be further subdivided into constant domain CH1, a hinge region, and constant domains CH2 and CH3 (arranged from amino-terminus to carboxy-terminus in the following order: CH1, CH2, CH3). The constant regions of the antibodies may mediate the binding of the immunoglobulin to host tissues or factors, including various cells of the immune system (e.g., effector cells) and the first component (C1q) of the classical complement system. Antibodies can be intact immunoglobulins derived from natural sources or from recombinant sources and can be immunoactive portions of intact immunoglobulins. Antibodies are typically tetramers of immunoglobulin molecules. Antibodies may exist in a variety of forms including, for example, polyclonal antibodies, monoclonal antibodies, Fv, Fab and $F(ab)_2$, as well as single chain antibodies and humanized antibodies.

The term "immunoglobulin" relates to proteins of the immunoglobulin superfamily, such as to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, $V_H$ (variable heavy chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The terms "vaccination" and "immunization" describe the process of treating an individual for therapeutic or prophylactic reasons and relate to the procedure of administering one or more immunogen(s) or antigen(s) or derivatives thereof, in particular in the form of RNA (especially mRNA) coding therefor, as described herein to an individual and stimulating an immune response against said one or more immunogen(s) or antigen(s) or cells characterized by presentation of said one or more immunogen(s) or antigen(s).

By "cell characterized by presentation of an antigen" or "cell presenting an antigen" or "MHC molecules which present an antigen on the surface of an antigen presenting cell" or similar expressions is meant a cell such as a diseased cell, in particular a tumor cell or an infected cell, or an antigen presenting cell presenting the antigen or an antigen peptide, either directly or following processing, in the context of MHC molecules, preferably MHC class I and/or MHC class II molecules, most preferably MHC class I molecules.

In the context of the present disclosure, the term "transcription" relates to a process, wherein the genetic code in a DNA sequence is transcribed into RNA (especially mRNA). Subsequently, the RNA (especially mRNA) may be translated into peptide, polypeptide or protein.

With respect to RNA, the term "expression" or "translation" relates to the process in the ribosomes of a cell by which a strand of mRNA directs the assembly of a sequence of amino acids to make a peptide or protein.

The term "serum" as used herein, in particular with respect to the incubation of cells in the presence of serum, means the fluid resulting from the removal of cells and clotting factors from whole blood, such as whole blood obtained from humans or mice. In some embodiments, serum is human serum or mouse serum.

A medical preparation, in particular kit, described herein may comprise instructional material or instructions. As used herein, "instructional material" or "instructions" includes a publication, a recording, a diagram, or any other medium of expression which can be used to communicate the usefulness of the compositions and methods of the present disclosure. The instructional material of the kit of the present disclosure may, for example, be affixed to a container which contains the compositions of the present disclosure or be shipped together with a container which contains the compositions. Alternatively, the instructional material may be shipped separately from the container with the intention that the instructional material and the compositions be used cooperatively by the recipient.

The term "optional" or "optionally" as used herein means that the subsequently described event, circumstance or condition may or may not occur, and that the description includes instances where said event, circumstance, or condition occurs and instances in which it does not occur.

Prodrugs of a particular compound described herein are those compounds that upon administration to an individual undergo chemical conversion under physiological conditions to provide the particular compound. Additionally, prodrugs can be converted to the particular compound by chemical or biochemical methods in an ex vivo environment. For example, prodrugs can be slowly converted to the particular compound when, for example, placed in a transdermal patch reservoir with a suitable enzyme or chemical reagent. Exemplary prodrugs are esters (using an alcohol or a carboxy group contained in the particular compound) or amides (using an amino or a carboxy group contained in the particular compound) which are hydrolyzable in vivo. Specifically, any amino group which is contained in the particular compound and which bears at least one hydrogen atom can be converted into a prodrug form. Typical N-prodrug forms include carbamates, Mannich bases, enamines, and enaminones.

In the present specification, a structural formula of a compound may represent a certain isomer of said compound. It is to be understood, however, that the present disclosure includes all isomers such as geometrical isomers, optical isomers based on an asymmetrical carbon, stereoisomers, tautomers and the like which occur structurally and isomer mixtures and is not limited to the description of the formula. Furthermore, in the present specification, a structural formula of a compound may represent a specific salt and/or solvate of said compound. It is to be understood, however, that the present disclosure includes all salts (e.g., pharmaceutically acceptable salts) and solvates (e.g., hydrates) and is not limited to the description of the specific salt and/or solvate.

"Isomers" are compounds having the same molecular formula but differ in structure ("structural isomers") or in the geometrical (spatial) positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (±). "Diastereomers" are stereoisomers which are non-superimposable and which are not mirror-images of each other. "Tautomers" are structural isomers of the same chemical substance that spontaneously and reversibly interconvert into each other, even when pure, due to the migration of individual atoms or groups of atoms; i.e., the tautomers are in a dynamic chemical equilibrium with each other. An example of tautomers are the isomers of the keto-enol-tautomerism. "Conformers" are stereoisomers that can be interconverted just by rotations about formally single bonds, and include—in particular—those leading to different 3-dimensional forms of (hetero)cyclic rings, such as chair, half-chair, boat, and twist-boat forms of cyclohexane.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

In isotopically labeled compounds one or more atoms are replaced by a corresponding atom having the same number of protons but differing in the number of neutrons. For example, a hydrogen atom may be replaced by a deuterium or tritium atom. Exemplary isotopes which can be used in the present disclosure include deuterium, tritium, $^{11}C$, $^{13}C$, $^{14}C$, $^{15}N$, $^{18}F$, $^{32}P$, $^{32}S$, $^{35}S$, $^{36}Cl$, and $^{125}I$.

The term "average diameter" refers to the mean hydrodynamic diameter of particles as measured by dynamic light scattering (DLS) with data analysis using the so-called cumulant algorithm, which provides as results the so-called $Z_{average}$ with the dimension of a length, and the polydispersity index (PDI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

In some embodiments, the "polydispersity index" is calculated based on dynamic light scattering measurements by the so-called cumulant analysis as mentioned in the definition of the "average diameter". Under certain prerequisites, it can be taken as a measure of the size distribution of an ensemble of nanoparticles.

The "radius of gyration" (abbreviated herein as $R_g$) of a particle about an axis of rotation is the radial distance of a point from the axis of rotation at which, if the whole mass of the particle is assumed to be concentrated, its moment of inertia about the given axis would be the same as with its actual distribution of mass. Mathematically, $R_g$ is the root mean square distance of the particle's components from either its center of mass or a given axis. For example, for a macromolecule composed of n mass elements, of masses $m_i$ (i=1, 2, 3, . . . , n), located at fixed distances $s_i$ from the center of mass, $R_g$ is the square-root of the mass average of $s_i^2$ over all mass elements and can be calculated as follows:

$$R_g = \left(\sum_{i=1}^{n} m_i \cdot s_i^2 / \sum_{i=1}^{n} m_i\right)^{1/2}$$

The radius of gyration can be determined or calculated experimentally, e.g., by using light scattering. In particular, for small scattering vectors q the structure function S is defined as follows:

$$S(\vec{q}) \approx N \cdot \left(1 - \frac{q^2 \cdot R_g^2}{3}\right)$$

wherein N is the number of components (Guinier's law).

The "D10 value", in particular regarding a quantitative size distribution of particles, is the diameter at which 10% of the particles have a diameter less than this value. The D10 value is a means to describe the proportion of the smallest particles within a population of particles (such as within a particle peak obtained from a field-flow fractionation).

"D50 value", in particular regarding a quantitative size distribution of particles, is the diameter at which 50% of the particles have a diameter less than this value. The D50 value is a means to describe the mean particle size of a population of particles (such as within a particle peak obtained from a field-flow fractionation).

The "D90 value", in particular regarding a quantitative size distribution of particles, is the diameter at which 90% of the particles have a diameter less than this value. The "D95", "D99", and "D100" values have corresponding meanings. The D90, D95, D99, and D100 values are means to describe the proportion of the larger particles within a population of particles (such as within a particle peak obtained from a field-flow fractionation).

The "hydrodynamic radius" (which is sometimes called "Stokes radius" or "Stokes-Einstein radius") of a particle is the radius of a hypothetical hard sphere that diffuses at the same rate as said particle. The hydrodynamic radius is related to the mobility of the particle, taking into account not only size but also solvent effects. For example, a smaller charged particle with stronger hydration may have a greater hydrodynamic radius than a larger charged particle with weaker hydration. This is because the smaller particle drags a greater number of water molecules with it as it moves through the solution. Since the actual dimensions of the particle in a solvent are not directly measurable, the hydrodynamic radius may be defined by the Stokes-Einstein equation:

$$R_h = \frac{k_B \cdot T}{6 \cdot \pi \cdot \eta \cdot D}$$

wherein $k_B$ is the Boltzmann constant; T is the temperature; η is the viscosity of the solvent; and D is the diffusion coefficient. The diffusion coefficient can be determined experimentally, e.g., by using dynamic light scattering (DLS). Thus, one procedure to determine the hydrodynamic radius of a particle or a population of particles (such as the hydrodynamic radius of particles such as LNPs contained in a formulation or composition as disclosed herein or the hydrodynamic radius of a particle peak obtained from subjecting such a formulation or composition to field-flow fractionation) is to measure the DLS signal of said particle or population of particles (such as DLS signal of particles such as LNPs contained in a formulation or composition as disclosed herein or the DLS signal of a particle peak obtained from subjecting such a formulation or composition to field-flow fractionation).

The term "aggregate" as used herein relates to a cluster of particles, wherein the particles are identical or very similar and adhere to each other in a non-covalently manner (e.g., via ionic interactions, H bridge interactions, dipole interactions, and/or van der Waals interactions).

The expression "light scattering" as used herein refers to the physical process where light is forced to deviate from a straight trajectory by one or more paths due to localized non-uniformities in the medium through which the light passes.

The term "UV" means ultraviolet and designates a band of the electromagnetic spectrum with a wavelength from 10 nm to 400 nm, i.e., shorter than that of visible light but longer than X-rays.

The expression "multi-angle light scattering" or "MALS" as used herein relates to a technique for measuring the light scattered by a sample into a plurality of angles. "Multi-angle" means in this respect that scattered light can be detected at different discrete angles as measured, for example, by a single detector moved over a range including the specific angles selected or an array of detectors fixed at specific angular locations. In one preferred embodiment, the light source used in MALS is a laser source (MALLS: multi-angle laser light scattering). Based on the MALS signal of a composition comprising particles and by using an appropriate formalism (e.g., Zimm plot, Berry plot, or Debye plot), it is possible to determine the radius of gyration ($R_g$) and, thus, the size of said particles. Preferably, the Zimm plot is a graphical presentation using the following equation:

$$\frac{R_\theta}{K^*c} = M_w P(\theta) - 2A_2 c M_w^2 P^2(\theta)$$

wherein c is the mass concentration of the particles in the solvent (g/mL); $A_2$ is the second virial coefficient (mol·mL/g$^2$); P(θ) is a form factor relating to the dependence of scattered light intensity on angle; $R_\theta$ is the excess Rayleigh ratio (cm$^{-1}$); and K* is an optical constant that is equal to $4\pi^2\eta_0\,(dn/dc)^2\lambda_0^{-4}N_A^{-1}$, where $\eta_0$ is the refractive index of the solvent at the incident radiation (vacuum) wavelength, $\lambda_0$ is the incident radiation (vacuum) wavelength (nm), $N_A$ is Avogadro's number (mol$^{-1}$), and dn dc is the differential refractive index increment (mL/g) (cf, e.g., Buchholz et al. (Electrophoresis 22 (2001), 4118-4128); B. H. Zimm (J. Chem. Phys. 13 (1945), 141; P. Debye (J. Appl. Phys. 15 (1944): 338; and W. Burchard (Anal. Chem. 75 (2003), 4279-4291). Preferably, the Berry plot is calculated the following term or the reciprocal thereof:

$$\sqrt{\frac{R_\theta}{K^*c}}$$

wherein c, $R_\theta$ and K* are as defined above. Preferably, the Debye plot is calculated the following term or the reciprocal thereof:

$$\frac{K^*c}{R_\theta}$$

wherein c, $R_\theta$ and K* are as defined above.

The expression "dynamic light scattering" or "DLS" as used herein refers to a technique to determine the size and size distribution profile of particles, in particular with respect to the hydrodynamic radius of the particles. A monochromatic light source, usually a laser, is shot through a polarizer and into a sample. The scattered light then goes through a second polarizer where it is detected and the resulting image is projected onto a screen. The particles in the solution are being hit with the light and diffract the light in all directions. The diffracted light from the particles can either interfere constructively (light regions) or destructively (dark regions). This process is repeated at short time intervals and the resulting set of speckle patterns are analyzed by an autocorrelator that compares the intensity of light at each spot over time.

The expression "static light scattering" or "SLS" as used herein refers to a technique to determine the size and size distribution profile of particles, in particular with respect to the radius of gyration of the particles, and/or the molar mass of particles. A high-intensity monochromatic light, usually a laser, is launched in a solution containing the particles. One or many detectors are used to measure the scattering intensity at one or many angles. The angular dependence is needed to obtain accurate measurements of both molar mass and size for all macromolecules of radius. Hence simultaneous measurements at several angles relative to the direction of incident light, known as multi-angle light scattering (MALS) or multi-angle laser light scattering (MALLS), is generally regarded as the standard implementation of static light scattering.

Nucleic Acids

The term "nucleic acid" comprises deoxyribonucleic acid (DNA), ribonucleic acid (RNA), combinations thereof, and modified forms thereof. The term comprises genomic DNA, cDNA, mRNA, recombinantly produced and chemically synthesized molecules. A nucleic acid may be present as a single-stranded or double-stranded and linear or covalently circularly closed molecule. A nucleic acid can be isolated. The term "isolated nucleic acid" means, according to the present disclosure, that the nucleic acid (i) was amplified in vitro, for example via polymerase chain reaction (PCR) for DNA or in vitro transcription (using, e.g., an RNA polymerase) for RNA, (ii) was produced recombinantly by cloning, (iii) was purified, for example, by cleavage and separation by gel electrophoresis, or (iv) was synthesized, for example, by chemical synthesis.

The term "nucleoside" (abbreviated herein as "N") relates to compounds which can be thought of as nucleotides without a phosphate group. While a nucleoside is a nucleobase linked to a sugar (e.g., ribose or deoxyribose), a nucleotide is composed of a nucleoside and one or more phosphate groups. Examples of nucleosides include cytidine, uridine, pseudouridine, adenosine, and guanosine.

The five standard nucleosides which usually make up naturally occurring nucleic acids are uridine, adenosine, thymidine, cytidine and guanosine. The five nucleosides are commonly abbreviated to their one letter codes U, A, T, C and G, respectively. However, thymidine is more commonly written as "dT" ("d" represents "deoxy") as it contains a 2'-deoxyribofuranose moiety rather than the ribofuranose ring found in uridine. This is because thymidine is found in deoxyribonucleic acid (DNA) and not ribonucleic acid (RNA). Conversely, uridine is found in RNA and not DNA. The remaining three nucleosides may be found in both RNA and DNA. In RNA, they would be represented as A, C and G, whereas in DNA they would be represented as dA, dC and dG.

A modified purine (A or G) or pyrimidine (C, T, or U) base moiety is preferably modified by one or more alkyl groups, more preferably one or more $C_{1-4}$ alkyl groups, even more preferably one or more methyl groups. Particular examples of modified purine or pyrimidine base moieties include $N^7$-alkyl-guanine, $N^6$-alkyl-adenine, 5-alkyl-cytosine, 5-alkyl-uracil, and N(1)-alkyl-uracil, such as $N^7$—$C_{1-4}$ alkyl-guanine, $N^6$—$C_{1-4}$ alkyl-adenine, 5-$C_{1-4}$ alkyl-cytosine, 5-$C_{1-4}$ alkyl-uracil, and N(1)-$C_{1-4}$ alkyl-uracil, preferably $N^7$-methyl-guanine, $N^6$-methyl-adenine, 5-methyl-cytosine, 5-methyl-uracil, and N(1)-methyl-uracil.

In some embodiments of all aspects of the disclosure, the nucleic acid is DNA.

Herein, the term "DNA" relates to a nucleic acid molecule which includes deoxyribonucleotide residues. In preferred embodiments, the DNA contains all or a majority of deoxyribonucleotide residues. As used herein, "deoxyribonucleotide" refers to a nucleotide which lacks a hydroxyl group at the 2'-position of a β-D-ribofuranosyl group. DNA encompasses without limitation, double stranded DNA, single stranded DNA, isolated DNA such as partially purified DNA, essentially pure DNA, synthetic DNA, recombinantly produced DNA, as well as modified DNA that differs from naturally occurring DNA by the addition, deletion, substitution and/or alteration of one or more nucleotides. Such alterations may refer to addition of non-nucleotide material to internal DNA nucleotides or to the end(s) of DNA. It is also contemplated herein that nucleotides in DNA may be non-standard nucleotides, such as chemically synthesized nucleotides or ribonucleotides. For the present disclosure, these altered DNAs are considered analogs of naturally-occurring DNA. A molecule contains "a majority of deoxyribonucleotide residues" if the content of deoxyribonucleotide residues in the molecule is more than 50% (such as at least 55%, at least 60%, at least 65%, at least 70%, at least 75%, at least 80%, at least 85%, at least 90%, at least 95%, at least 96%, at least 97%, at least 98%, at least 99%), based on the total number of nucleotide residues in the molecule. The total number of nucleotide residues in a molecule is the sum of all nucleotide residues (irrespective of whether the nucleotide residues are standard (i.e., naturally occurring) nucleotide residues or analogs thereof).

DNA may be recombinant DNA and may be obtained by cloning of a nucleic acid, in particular cDNA. The cDNA may be obtained by reverse transcription of RNA.

RNA

In some embodiments of all aspects of the disclosure, the nucleic acid is RNA.

According to the present disclosure, the term "RNA" means a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered/modified nucleotides (or modified nucleosides) can be referred to as analogs of naturally occurring nucleotides (nucleosides), and the corresponding RNAs containing such altered/modified nucleotides or nucleosides (i.e., altered/modified RNAs) can be referred to as analogs of naturally occurring RNAs. A molecule contains "a majority of ribonucleotide residues" if the content of ribonucleotide residues in the molecule is more than 50% (such as at least 55%, at least 60%, at least 65%, at least 70%, at least 75%, at least 80%, at least 85%, at least 90%, at least 95%, at least 96%, at least 97%, at least 98%, at least 99%), based on the total number of nucleotide residues in the molecule. The total number of nucleotide residues in a molecule is the sum of all nucleotide residues (irrespective of whether the nucleotide residues are standard (i.e., naturally occurring) nucleotide residues or analogs thereof).

"RNA" includes mRNA, tRNA, ribosomal RNA (rRNA), small nuclear RNA (snRNA), self-amplifying RNA (saRNA), single-stranded RNA (ssRNA), dsRNA, inhibitory RNA (such as antisense ssRNA, small interfering RNA (siRNA), or microRNA (miRNA)), activating RNA (such as small activating RNA) and immunostimulatory RNA (isRNA). In some embodiments, "RNA" refers to mRNA.

In a preferred embodiment, the RNA comprises an open reading frame (ORF) encoding a peptide, polypeptide or protein.

The term "in vitro transcription" or "IVT" as used herein means that the transcription (i.e., the generation of RNA) is conducted in a cell-free manner. I.e., IVT does not use living/cultured cells but rather the transcription machinery extracted from cells (e.g., cell lysates or the isolated components thereof, including an RNA polymerase (preferably T7, T3 or SP6 polymerase)).

mRNA

In some embodiments of all aspects of the disclosure, the nucleic acid is mRNA.

According to the present disclosure, the term "mRNA" means "messenger-RNA" and includes a "transcript" which may be generated by using a DNA template. Generally, mRNA encodes a peptide, polypeptide or protein. Typically, an mRNA comprises a 5'-UTR, a peptide/protein coding region, and a 3'-UTR. In the context of the present disclosure, mRNA is preferably generated by in vitro transcription (IVT) from a DNA template. As set forth above, the in vitro transcription methodology is known to the skilled person, and a variety of in vitro transcription kits is commercially available.

mRNA is single-stranded but may contain self-complementary sequences that allow parts of the mRNA to fold and pair with itself to form double helices.

According to the present disclosure, "dsRNA" means double-stranded RNA and is RNA with two partially or completely complementary strands.

In preferred embodiments of the present disclosure, the mRNA relates to an RNA transcript which encodes a peptide, polypeptide or protein.

In some embodiments, the RNA which preferably encodes a peptide, polypeptide or protein has a length of at least 45 nucleotides (such as at least 60, at least 90, at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 6,000, at least 7,000, at least 8,000, at least 9,000 nucleotides), preferably up to 15,000, such as up to 14,000, up to 13,000, up to 12,000 nucleotides, up to 11,000 nucleotides or up to 10,000 nucleotides.

As established in the art, the RNA (such as mRNA) generally contains a 5' untranslated region (5'-UTR), a peptide/polypeptide/protein coding region and a 3' untranslated region (3'-UTR). In some embodiments, the RNA (such as mRNA) is produced by in vitro transcription or chemical synthesis. In one embodiment, the RNA (such as mRNA) is produced by in vitro transcription using a DNA template. The in vitro transcription methodology is known to the skilled person; cf, e.g., Molecular Cloning: A Laboratory Manual, 2nd Edition, J. Sambrook et al. eds., Cold Spring Harbor Laboratory Press, Cold Spring Harbor 1989. Furthermore, a variety of in vitro transcription kits is commercially available, e.g., from Thermo Fisher Scientific (such as TranscriptAid™ T7 kit, MEGAscript® T7 kit, MAXIscript®), New England BioLabs Inc. (such as HiScribe™ T7 kit, HiScribe™ T7 ARCA mRNA kit), Promega (such as RiboMAX™, HeLaScribe®, Riboprobe® systems), Jena Bioscience (such as SP6 or T7 transcription kits), and Epicentre (such as AmpliScribe™). For providing modified RNA (such as mRNA), correspondingly modified nucleotides, such as modified naturally occurring nucleotides, non-naturally occurring nucleotides and/or modified non-naturally occurring nucleotides, can be incorporated during synthesis (preferably in vitro transcription), or modifications can be effected in and/or added to the mRNA after transcription.

In some embodiments, RNA (such as mRNA) is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

In some embodiments of the present disclosure, the RNA (such as mRNA) is "replicon RNA" (such as "replicon mRNA") or simply a "replicon", in particular "self-replicating RNA" (such as "self-replicating mRNA") or "self-amplifying RNA" (or "self-amplifying mRNA"). In one particularly preferred embodiment, the replicon or self-replicating RNA (such as self-replicating mRNA) is derived from or comprises elements derived from an ssRNA virus, in particular a positive-stranded ssRNA virus such as an alphavirus. Alphaviruses are typical representatives of positive-stranded RNA viruses. Alphaviruses replicate in the cytoplasm of infected cells (for review of the alphaviral life cycle see Jose et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1. In cells infected by an alphavirus, only the nucleic acid sequence encoding non-structural proteins is translated from the genomic RNA, while the genetic information encoding structural proteins is translatable from a subgenomic transcript, which is an RNA molecule that resembles eukaryotic messenger RNA (mRNA; Gould et al., 2010, Antiviral Res., vol. 87 pp. 111-124). Following infection, i.e. at early stages of the viral life cycle, the (+) stranded genomic RNA directly acts like a messenger RNA for the translation of the open reading frame encoding the non-structural poly-protein (nsP1234). Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase, and the other nucleic acid molecule is capable of being replicated by said replicase in trans (hence the designation trans-replication system). Trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

In some embodiments of the present disclosure, the RNA (such as mRNA) described herein (e.g., contained in the compositions of the present disclosure and/or used in the methods of the present disclosure) contains one or more modifications, e.g., in order to increase its stability and/or increase translation efficiency and/or decrease immunogenicity and/or decrease cytotoxicity. For example, in order to increase expression of the RNA (such as mRNA), it may be modified within the coding region, i.e., the sequence encoding the expressed peptide or protein, preferably without altering the sequence of the expressed peptide or protein. Such modifications are described, for example, in WO 2007/036366 and PCT/EP2019/056502, and include the following: a 5'-cap structure; an extension or truncation of the naturally occurring poly(A) tail; an alteration of the 5'- and/or 3'-untranslated regions (UTR) such as introduction of a UTR which is not related to the coding region of said RNA; the replacement of one or more naturally occurring nucleotides with synthetic nucleotides; and codon optimization (e.g., to alter, preferably increase, the G/C content of the RNA). The term "modification" in the context of modified mRNA according to the present disclosure preferably relates to any modification of an mRNA which is not naturally present in said RNA (such as mRNA).

In some embodiments, the RNA (such as mRNA) described herein comprises a 5'-cap structure. In one embodiment, the mRNA does not have uncapped 5'-triphosphates. In one embodiment, the RNA (such as mRNA) described herein may comprise a conventional 5'-cap and/or a 5'-cap analog. The term "conventional 5'-cap" refers to a cap structure found on the 5'-end of an mRNA molecule and generally consists of a guanosine 5'-triphosphate (Gppp) which is connected via its triphosphate moiety to the 5'-end of the next nucleotide of the mRNA (i.e., the guanosine is connected via a 5' to 5' triphosphate linkage to the rest of the mRNA). The guanosine may be methylated at position $N^7$ (resulting in the cap structure $m^7$Gppp). The term "5'-cap analog" refers to a 5'-cap which is based on a conventional 5'-cap but which has been modified at either the 2'- or 3'-position of the $m^7$guanosine structure in order to avoid an integration of the 5'-cap analog in the reverse orientation (such 5'-cap analogs are also called anti-reverse cap analogs (ARCAs)). Particularly preferred 5'-cap analogs are those having one or more substitutions at the bridging and non-bridging oxygen in the phosphate bridge, such as phosphorothioate modified 5'-cap analogs at the β-phosphate (such as $m_2^{7,2'O}$G(5')ppSp(5')G (referred to as beta-S-ARCA or β-S-ARCA)), as described in WO 2019/175356 (PCT/EP2019/056502). Providing an RNA (such as mRNA) with a 5'-cap structure as described herein may be achieved by in vitro transcription of a DNA template in presence of a corresponding 5'-cap compound, wherein said 5'-cap structure is co-transcriptionally incorporated into the generated RNA (such as mRNA) strand, or the RNA (such as mRNA) may be generated, for example, by in vitro transcription, and the 5'-cap structure may be attached to the mRNA post-transcriptionally using capping enzymes, for example, capping enzymes of vaccinia virus.

In some embodiments, the RNA (such as mRNA) comprises a 5'-cap structure selected from the group consisting of $m_2^{7,2'O}$G(5')ppSp(5')G (in particular its D1 diastereomer), $m_2^{7,3'O}$G(5')ppp(5')G, and $m_2^{7,3'-O}$Gppp($m_1^{2'-O}$)ApG. In some embodiments, RNA encoding a peptide, polypeptide or protein comprising an antigen or epitope comprises $m_2^{7,2'O}$G(5')ppSp(5')G (in particular its D1 diastereomer) as 5'-cap structure.

In some embodiments, the RNA (such as mRNA) comprises a cap0, cap1, or cap2, preferably cap1 or cap2. According to the present disclosure, the term "cap0" means the structure "$m^7$GpppN", wherein N is any nucleoside bearing an OH moiety at position 2'. According to the present disclosure, the term "cap1" means the structure "$m^7$GpppNm", wherein Nm is any nucleoside bearing an $OCH_3$ moiety at position 2'. According to the present disclosure, the term "cap2" means the structure "$m^7$GpppNmNm", wherein each Nm is independently any nucleoside bearing an $OCH_3$ moiety at position 2'.

The 5'-cap analog beta-S-ARCA (β-S-ARCA) has the following structure:

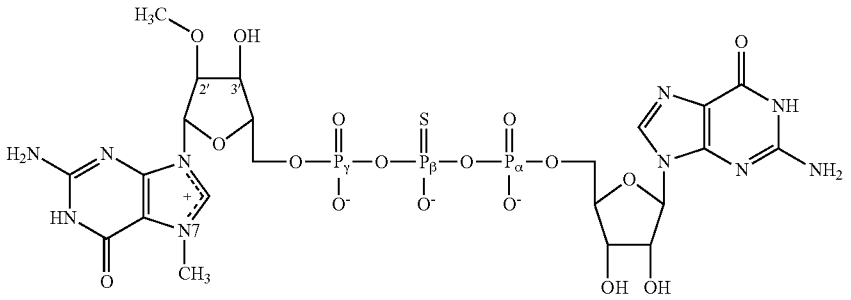

The "D1 diastereomer of beta-S-ARCA" or "beta-S-ARCA(D1)" is the diastereomer of beta-S-ARCA which elutes first on an HPLC column compared to the D2 diastereomer of beta-S-ARCA (beta-S-ARCA(D2)) and thus exhibits a shorter retention time. The HPLC preferably is an analytical HPLC. In one embodiment, a Supelcosil LC-18-T RP column, preferably of the format: 5 m, 4.6×250 mm is used for separation, whereby a flow rate of 1.3 ml/min can be applied. In one embodiment, a gradient of methanol in ammonium acetate, for example, a 0-25% linear gradient of methanol in 0.05 M ammonium acetate, pH=5.9, within 15 min is used. UV-detection (VWD) can be performed at 260 nm and fluorescence detection (FLD) can be performed with excitation at 280 nm and detection at 337 nm. The 5'-cap analog $m_2^{7,3'-O}$Gppp($m_1^{2'-O}$)ApG (also referred to as $m_2^{7,3'O}$ G(5')ppp(5')$m^{2'-O}$ApG) which is a building block of a cap1 has the following structure:

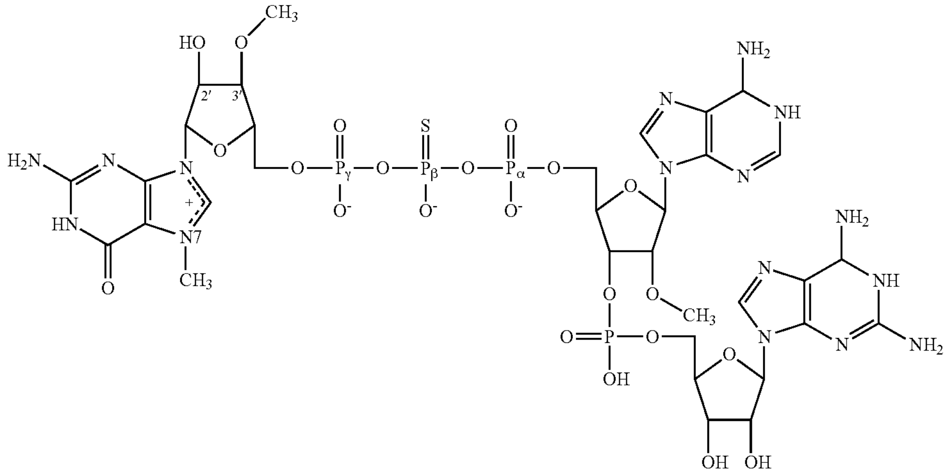

An exemplary cap0 mRNA comprising β-S-ARCA and mRNA has the following structure:

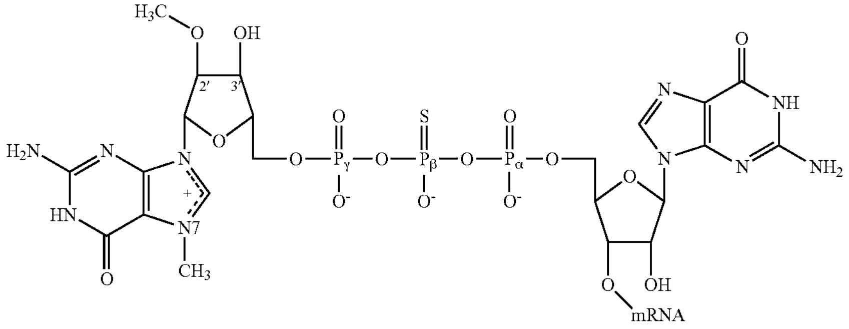

An exemplary cap0 mRNA comprising $m_2^{7,3'O}$ G(5')ppp (5')G and mRNA has the following structure:

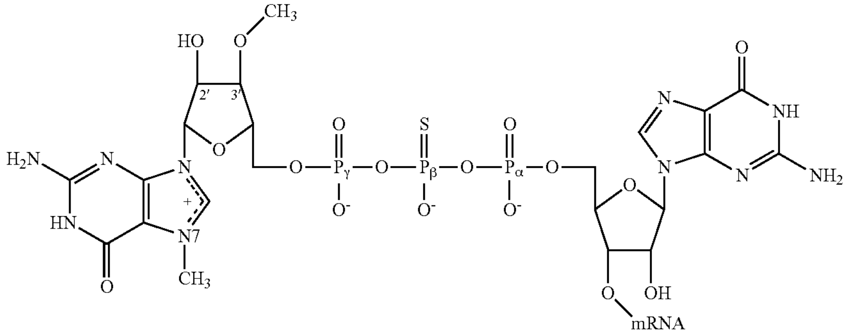

An exemplary cap1 mRNA comprising $m_2^{7,3'-O}$Gppp $(m_1^{2'-O})$ApG and mRNA has the following structure:

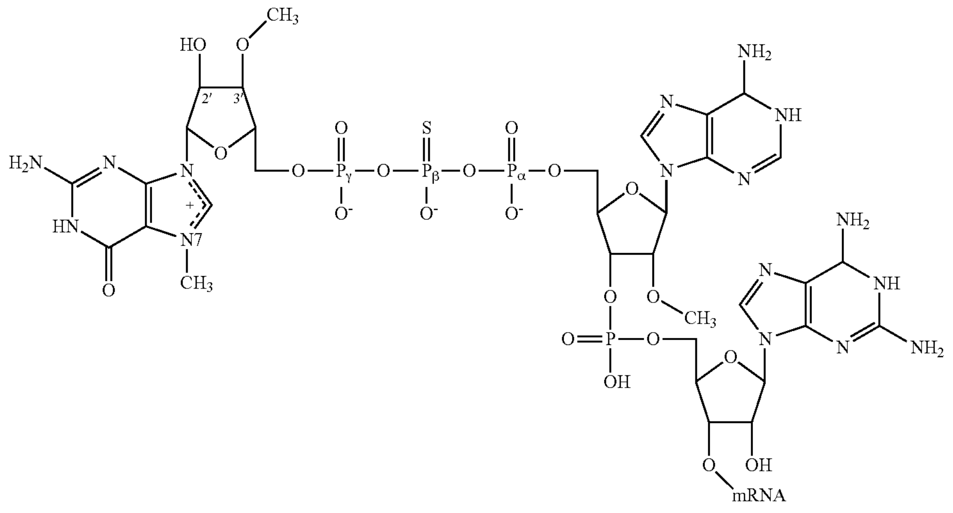

As used herein, the term "poly-A tail" or "poly-A sequence" refers to an uninterrupted or interrupted sequence of adenylate residues which is typically located at the 3'-end of an RNA (such as mRNA) molecule. Poly-A tails or poly-A sequences are known to those of skill in the art and may follow the 3'-UTR in the RNAs (such as mRNAs) described herein. An uninterrupted poly-A tail is characterized by consecutive adenylate residues. In nature, an uninterrupted poly-A tail is typical. RNAs (such as mRNAs) disclosed herein can have a poly-A tail attached to the free 3'-end of the RNA by a template-independent RNA polymerase after transcription or a poly-A tail encoded by DNA and transcribed by a template-dependent RNA polymerase.

It has been demonstrated that a poly-A tail of about 120 A nucleotides has a beneficial influence on the levels of mRNA in transfected eukaryotic cells, as well as on the levels of protein that is translated from an open reading frame that is present upstream (5') of the poly-A tail (Holtkamp et al., 2006, Blood, vol. 108, pp. 4009-4017).

The poly-A tail may be of any length. In some embodiments, a poly-A tail comprises, essentially consists of, or consists of at least 20, at least 30, at least 40, at least 80, or at least 100 and up to 500, up to 400, up to 300, up to 200, or up to 150 A nucleotides, and, in particular, about 120 A nucleotides. In this context, "essentially consists of" means that most nucleotides in the poly-A tail, typically at least 75%, at least 80%, at least 85%, at least 90%, at least 95%, at least 96%, at least 97%, at least 98%, or at least 99% by number of nucleotides in the poly-A tail are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly-A tail, i.e., 100% by number of nucleotides in the poly-A tail, are A nucleotides. The term "A nucleotide" or "A" refers to adenylate.

In some embodiments, a poly-A tail is attached during RNA transcription, e.g., during preparation of in vitro transcribed RNA, based on a DNA template comprising repeated dT nucleotides (deoxythymidylate) in the strand complementary to the coding strand. The DNA sequence encoding a poly-A tail (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present disclosure. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in *E. coli* and is still associated, on RNA level, with the beneficial properties with respect to supporting RNA stability and translational efficiency is encompassed. Consequently, in some embodiments, the poly-A tail contained in an RNA (in particular, mRNA) molecule described herein essentially consists of A nucleotides, but is interrupted by a random sequence of the four nucleotides (A, C, G, U). Such random sequence may be 5 to 50, 10 to 30, or 10 to 20 nucleotides in length.

In some embodiments, no nucleotides other than A nucleotides flank a poly-A tail at its 3'-end, i.e., the poly-A tail is not masked or followed at its 3'-end by a nucleotide other than A.

In some embodiments, a poly-A tail may comprise at least 20, at least 30, at least 40, at least 80, or at least 100 and up to 500, up to 400, up to 300, up to 200, or up to 150 nucleotides. In some embodiments, the poly-A tail may essentially consist of at least 20, at least 30, at least 40, at least 80, or at least 100 and up to 500, up to 400, up to 300, up to 200, or up to 150 nucleotides. In some embodiments, the poly-A tail may consist of at least 20, at least 30, at least 40, at least 80, or at least 100 and up to 500, up to 400, up to 300, up to 200, or up to 150 nucleotides. In some embodiments, the poly-A tail comprises at least 100 nucleotides. In some embodiments, the poly-A tail comprises about 150 nucleotides. In some embodiments, the poly-A tail comprises about 120 nucleotides. In some embodiments, the poly-A tail comprises or consists of the nucleotide sequence of SEQ ID NO: 3. In some embodiments, the poly-A sequence has a nucleotide sequence having at least 99%, 98%, 97%, 96%, 95%, 90%, 85%, or 80% identity to the nucleotide sequence of SEQ ID NO: 3.

In some embodiments, RNA (such as mRNA) used in present disclosure comprises a 5'-UTR and/or a 3'-UTR. The term “untranslated region” or “UTR” relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5'-end, upstream of the start codon of a protein-encoding region. A 5'-UTR is downstream of the 5'-cap (if present), e.g., directly adjacent to the 5'-cap. A 3'-UTR, if present, is located at the 3'-end, downstream of the termination codon of a protein-encoding region, but the term “3'-UTR” does preferably not include the poly-A sequence. Thus, the 3'-UTR is upstream of the poly-A sequence (if present), e.g., directly adjacent to the poly-A sequence. Incorporation of a 3'-UTR into the 3'-non translated region of an RNA (preferably mRNA) molecule can result in an enhancement in translation efficiency. A synergistic effect may be achieved by incorporating two or more of such 3'-UTRs (which are preferably arranged in a head-to-tail orientation; cf., e.g., Holtkamp et al., Blood 108, 4009-4017 (2006)). The 3'-UTRs may be autologous or heterologous to the RNA (preferably mRNA) into which they are introduced. In one particular embodiment the 3'-UTR is derived from a globin gene or mRNA, such as a gene or mRNA of alpha2-globin, alpha1-globin, or beta-globin, preferably beta-globin, more preferably human beta-globin. For example, the RNA (preferably mRNA) may be modified by the replacement of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

In some embodiments, the RNA (such as mRNA) used in present disclosure comprises a 5'-UTR comprising the nucleotide sequence of SEQ ID NO: 1, or a nucleotide sequence having at least 99%, 98%, 97%, 96%, 95%, 90%, 85%, or 80% identity to the nucleotide sequence of SEQ ID NO: 1.

In some embodiments, the RNA (such as mRNA) used in present disclosure comprises a 3'-UTR comprising the nucleotide sequence of SEQ ID NO: 2, or a nucleotide sequence having at least 99%, 98%, 97%, 96%, 95%, 90%, 85%, or 80% identity to the nucleotide sequence of SEQ ID NO: 2.

The RNA (such as mRNA) described herein may have modified ribonucleotides in order to increase its stability and/or decrease immunogenicity and/or decrease cytotoxicity. For example, in some embodiments, uridine in the RNA (such as mRNA) described herein is replaced (partially or completely, preferably completely) by a modified nucleoside. In some embodiments, the modified nucleoside is a modified uridine.

In some embodiments, the modified uridine replacing uridine is selected from the group consisting of pseudouridine (ψ), N1-methyl-pseudouridine (m1ψ), 5-methyl-uridine (m5U), and combinations thereof.

In some embodiments, the modified nucleoside replacing (partially or completely, preferably completely) uridine in the RNA (such as mRNA) may be any one or more of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (im5U), 1-taurinomethyl-pseudouridine, 5-taurinomethyl-2-thio-uridine(zm5s2U), 1-taurinomethyl-4-thio-pseudouridine), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

An RNA (preferably mRNA) which is modified by pseudouridine (replacing partially or completely, preferably completely, uridine) is referred to herein as “ψ-modified”, whereas the term “m1ψ-modified” means that the RNA (preferably mRNA) contains N(1)-methylpseudouridine (replacing partially or completely, preferably completely, uridine). Furthermore, the term “m5U-modified” means that the RNA (preferably mRNA) contains 5-methyluridine (replacing partially or completely, preferably completely, uridine). Such ψ- or m1ψ- or m5U-modified RNAs usually exhibit decreased immunogenicity compared to their unmodified forms and, thus, are preferred in applications where the induction of an immune response is to be avoided or minimized. In some embodiments, the RNA (preferably mRNA) contains N(1)-methylpseudouridine replacing completely uridine.

The codons of the RNA (preferably mRNA) described in the present disclosure may further be optimized, e.g., to increase the G/C content of the RNA and/or to replace codons which are rare in the cell (or subject) in which the peptide or protein of interest is to be expressed by codons which are synonymous frequent codons in said cell (or subject). In some embodiments, the amino acid sequence encoded by the RNA described in the present disclosure is encoded by a coding sequence which is codon-optimized and/or the G/C content of which is increased compared to wild type coding sequence. This also includes embodiments, wherein one or more sequence regions of the coding sequence are codon-optimized and/or increased in the G/C content compared to the corresponding sequence regions of the wild type coding sequence. In one embodiment, the codon-optimization and/or the increase in the G/C content preferably does not change the sequence of the encoded amino acid sequence.

The term "codon-optimized" refers to the alteration of codons in the coding region of a nucleic acid molecule to reflect the typical codon usage of a host organism without preferably altering the amino acid sequence encoded by the nucleic acid molecule. Within the context of the present disclosure, coding regions are preferably codon-optimized for optimal expression in a subject to be treated using the RNA (preferably mRNA) described herein. Codon-optimization is based on the finding that the translation efficiency is also determined by a different frequency in the occurrence of tRNAs in cells. Thus, the sequence of RNA (preferably mRNA) may be modified such that codons for which frequently occurring tRNAs are available are inserted in place of "rare codons".

In some embodiments, the guanosine/cytosine (G/C) content of the coding region of the RNA (preferably mRNA) described herein is increased compared to the G/C content of the corresponding coding sequence of the wild type RNA, wherein the amino acid sequence encoded by the RNA (preferably mRNA) is preferably not modified compared to the amino acid sequence encoded by the wild type RNA. This modification of the RNA sequence is based on the fact that the sequence of any RNA region to be translated is important for efficient translation of that RNA (preferably mRNA). Sequences having an increased G (guanosine)/C (cytosine) content are more stable than sequences having an increased A (adenosine)/U (uracil) content. In respect to the fact that several codons code for one and the same amino acid (so-called degeneration of the genetic code), the most favorable codons for the stability can be determined (so-called alternative codon usage). Depending on the amino acid to be encoded by the RNA (preferably mRNA), there are various possibilities for modification of the RNA sequence, compared to its wild type sequence. In particular, codons which contain A and/or U nucleotides can be modified by substituting these codons by other codons, which code for the same amino acids but contain no A and/or U or contain a lower content of A and/or U nucleotides.

In various embodiments, the G/C content of the coding region of the RNA (in particular, mRNA) described herein is increased by at least 10%, at least 20%, at least 30%, at least 40%, at least 50%, at least 55%, or even more compared to the G/C content of the coding region of the wild type RNA.

A combination of the above described modifications, i.e., incorporation of a 5'-cap structure, incorporation of a poly-A sequence, unmasking of a poly-A sequence, alteration of the 5'- and/or 3'-UTR (such as incorporation of one or more 3'-UTRs), replacing one or more naturally occurring nucleotides with synthetic nucleotides (e.g., 5-methylcytidine for cytidine and/or pseudouridine (ψ) or N(1)-methylpseudouridine (m1ψ) or 5-methyluridine (m5U) for uridine), and codon optimization, has a synergistic influence on the stability of RNA (preferably mRNA) and increase in translation efficiency. Thus, in some embodiments, the RNA (preferably mRNA) described in the present disclosure, in particular an RNA (preferably mRNA) encoding an antigen or epitope for inducing an immune response disclosed herein, contains a combination of at least two, at least three, at least four or all five of the above-mentioned modifications, i.e., (i) incorporation of a 5'-cap structure; (ii) incorporation of a poly-A sequence, unmasking of a poly-A sequence; (iii) alteration of the 5'- and/or 3'-UTR (such as incorporation of one or more 3'-UTRs); (iv) replacing one or more naturally occurring nucleotides with synthetic nucleotides (e.g., 5-methylcytidine for cytidine and/or pseudouridine (ψ) or N(1)-methylpseudouridine (m1ψ) or 5-methyluridine (m5U) for uridine); and (v) codon optimization. In some embodiments, the RNA (preferably mRNA) described in the present disclosure comprises a cap1 or cap2, preferably a cap1 structure. In some embodiments, the poly-A sequence comprises at least 100 nucleotides. In some embodiments, the poly-A sequence comprises or consists of the nucleotide sequence of SEQ ID NO: 3. In some embodiments, the a 5'-UTR comprises the nucleotide sequence of SEQ ID NO: 1, or a nucleotide sequence having at least 99%, 98%, 97%, 96%, 95%, 90%, 85%, or 80% identity to the nucleotide sequence of SEQ ID NO: 1. In some embodiments, the 3'-UTR comprising the nucleotide sequence of SEQ ID NO: 2, or a nucleotide sequence having at least 99%, 98%, 97%, 96%, 95%, 90%, 85%, or 80% identity to the nucleotide sequence of SEQ ID NO: 2.

Some aspects of the disclosure involve the targeted delivery of the RNA (preferably mRNA) disclosed herein to certain cells or tissues. In some embodiments, the disclosure involves targeting the lymphatic system, in particular secondary lymphoid organs, more specifically spleen. Targeting the lymphatic system, in particular secondary lymphoid organs, more specifically spleen is in particular preferred if the RNA (preferably mRNA) administered is RNA (preferably mRNA) encoding an antigen or epitope for inducing an immune response. In some embodiments, the target cell is a spleen cell. In some embodiments, the target cell is an antigen presenting cell such as a professional antigen presenting cell in the spleen. In some embodiments, the target cell is a dendritic cell in the spleen. The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naive lymphocytes and initiate an adaptive immune response. In some embodiments, the target cell is a T cell.

Lipid-based RNA (such as mRNA) delivery systems have an inherent preference to the liver. Liver accumulation is caused by the discontinuous nature of the hepatic vasculature or the lipid metabolism (liposomes and lipid or cholesterol conjugates). In some embodiments, the target organ is liver and the target tissue is liver tissue. The delivery to such target tissue is preferred, in particular, if presence of mRNA or of the encoded peptide or protein in this organ or tissue is desired and/or if it is desired to express large amounts of the encoded peptide or protein and/or if systemic presence of the encoded peptide or protein, in particular in significant amounts, is desired or required.

In some embodiments, after administration of the RNA (in particular, mRNA) compositions described herein, at least a portion of the RNA is delivered to a target cell or target organ. In some embodiments, at least a portion of the RNA is delivered to the cytosol of the target cell. In some embodiments, the RNA is RNA (preferably mRNA) encoding a peptide or protein and the RNA is translated by the target cell to produce the peptide or protein. In some embodiments, the target cell is a cell in the liver. In some embodiments, the target cell is a muscle cell. In some embodiments, the target cell is an endothelial cell. In some embodiments, the target cell is a tumor cell or a cell in the tumor microenvironment. In some embodiments, the target cell is a blood cell. In some embodiments, the target cell is a cell in the lymph nodes. In some embodiments, the target cell is a cell in the lung In some embodiments, the target cell is a cell in the skin. In some embodiments, the target cell is a spleen cell. In some embodiments, the target cell is an antigen presenting cell such as a professional antigen presenting cell in the spleen. In some embodiments, the target cell is a dendritic cell in the spleen. In some embodiments, the target cell is a T cell. In some embodiments, the target cell is a B cell. In some embodiments, the target cell is a NK cell. In some embodiments, the target cell is a monocyte. Thus, nucleic acid (such as RNA) particle (such as RNA LNP) compositions described herein may be used for delivering nucleic acid (such as RNA, preferably mRNA) to such target cell. Accordingly, the present disclosure also relates to a method for delivering nucleic acid (such as RNA, preferably mRNA) to a target cell in a subject comprising the administration of the nucleic acid (such as RNA, preferably mRNA) compositions described herein to the subject. In some embodiments, the RNA is delivered to the cytosol of the target cell. In some embodiments, the RNA is RNA (preferably mRNA) encoding a peptide or protein and the RNA is translated by the target cell to produce the peptide or protein.

Inhibitory RNA

In some embodiments of all aspects of the disclosure, the nucleic acid is an inhibitory RNA.

The term "inhibitory RNA" as used herein means RNA which selectively hybridizes to and/or is specific for a target mRNA, thereby inhibiting (e.g., reducing) transcription and/or translation thereof. Inhibitory RNA includes RNA molecules having sequences in the antisense orientation relative to the target mRNA. Suitable inhibitory oligonucleotides typically vary in length from five to several hundred nucleotides, more typically about 20 to 70 nucleotides in length or shorter, even more typically about 10 to 30 nucleotides in length. Examples of inhibitory RNA include antisense RNA, ribozyme, iRNA, siRNA and miRNA. In some embodiments of all aspects of the disclosure, the inhibitory RNA is siRNA.

The term "antisense RNA" as used herein refers to an RNA which hybridizes under physiological conditions to DNA comprising a particular gene or to mRNA of said gene, thereby inhibiting transcription of said gene and/or translation of said mRNA. An antisense transcript of a nucleic acid or of a part thereof may form a duplex with naturally occurring mRNA and thus prevent accumulation of or translation of the mRNA. Another possibility is the use of ribozymes for inactivating a nucleic acid. The antisense RNA may hybridize with an N-terminal or 5' upstream site such as a translation initiation site, transcription initiation site or promoter site. In some embodiments, the antisense RNA may hybridize with a 3'-untranslated region or mRNA splicing site.

The size of the antisense RNA may vary from 15 nucleotides to 15,000, preferably 20 to 12,000, in particular 100 to 10,000, 150 to 8,000, 200 to 7,000, 250 to 6,000, 300 to 5,000 nucleotides, such as 15 to 2,000, 20 to 1,000, 25 to 800, 30 to 600, 35 to 500, 40 to 400, 45 to 300, 50 to 250, 55 to 200, 60 to 150, or 65 to 100 nucleotides. In one embodiment, the antisense RNA has a length of at least 2,700 nucleotides (such as at least 2,800, at least 2,900, at least 3,000, at least 3,100, at least 3,200, at least 3,300, at least 3,400, at least 3,500, at least 3,600, at least 3,700, at least 3,800, at least 3,900, at least 4,000, at least 4,100, at least 4,200, at least 4,300, at least 4,400, at least 4,500, at least 4,600, at least 4,700, at least 4,800, at least 4,900, at least 5,000 nucleotides).

The stability of antisense RNA may be modified as required. For example, antisense RNA may be stabilized by one or more modifications having a stabilizing effect. Such modifications include modified phosphodiester linkages (such as methylphosphonate, phosphorothioate, phosphorodithioate or phosphoramidate linkages instead of naturally occurring phosphodiester linkages) and 2-substitutions (e.g., 2'-fluoro, 2'-O-alkyl (such as 2-O-methyl, 2-O-propyl, or 2'-O-pentyl) and 2'-O-allyl). For example, in some embodiments of the antisense RNA, phosphorothioate linkages are substituted partially for phosphodiester linkages. Alternatively or additionally, in some embodiments of the antisense RNA, the ribose moiety is substituted partially at the 2'-position with O-alkyl (such as 2'-O-methyl).

An antisense RNA can be targeted to any stretch of approximately 19 to 25 contiguous nucleotides in any of the target mRNA sequences (the "target sequence"). Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

Antisense RNA can be obtained using a number of techniques known to those of skill in the art. For example, antisense RNA can be chemically synthesized or recombinantly produced using methods known in the art. Preferably, antisense RNA is transcribed from recombinant circular or linear DNA plasmids using any suitable promoter.

Selection of plasmids suitable for expressing antisense RNA, methods for inserting nucleic acid sequences for expressing the antisense RNA into the plasmid, and IVT methods of in vitro transcription of said antisense RNA are within the skill in the art.

By "small interfering RNA" or "siRNA" as used herein is meant an RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is capable of binding specifically to a portion of a target mRNA. This binding induces a process, in which said portion of the target mRNA is cut or degraded and thereby the gene expression of said target mRNA inhibited. A range of 19 to 25 nucleotides is the most preferred size for siRNAs. Although, in principle, the sense and antisense strands of siRNAs can comprise two complementary, single-stranded RNA molecules, the siRNAs, according to the present disclosure, comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker, but is preferably a polynucleotide linker. Without wishing to be bound by any theory, it is believed that the hairpin area of the siRNA molecule is cleaved intracellularly by the "Dicer" protein (or its equivalent) to form an siRNA of two individual base-paired RNA molecules.

The siRNA can also comprise a 3'-overhang. As used herein, a "3'-overhang" refers to at least one unpaired nucleotide extending from the 3'-end of an RNA strand. Thus, in some embodiments, the siRNA comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiments in which both strands of the siRNA molecule (i.e., after the siRNA molecule is cleaved intracellularly by the "Dicer" protein) comprise a 3'-overhang, the length of the overhangs can be the same or different for each strand. In some preferred embodiments, the 3'-overhang is present on both strands of the siRNA, and is 2 nucleotides in length. For example, each strand of the siRNA can comprise 3'-overhangs of dideoxythymidylic acid ("TT") or diuridylic acid ("uu").

In order to enhance the stability of the siRNA, the 3'-overhangs can be also stabilized against degradation. In some embodiments, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

As used herein, "target mRNA" refers to an RNA molecule that is a target for downregulation. In some embodiments, the target mRNA comprises an ORF encoding a pharmaceutically active peptide or polypeptide as specified herein. In some embodiments, the pharmaceutically active peptide or polypeptide is one whose expression (in particular increased expression, e.g., compared to the expression in a healthy subject) is associated with a disease. In some embodiments, the target mRNA comprises an ORF encoding a pharmaceutically active peptide or polypeptide whose expression (in particular increased expression, e.g., compared to the expression in a healthy subject) is associated with cancer.

According to the present disclosure, siRNA can be targeted to any stretch of approximately 19 to 25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Further guidance with respect to the selection of target sequences and/or the design of siRNA can be found on the webpages of Protocol Online (www.protocol-online.com) using the keyword "siRNA". Thus, in some embodiments, the sense strand of the siRNA used in the present disclosure comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

siRNA can be obtained using a number of techniques known to those of skill in the art. For example, siRNA can be chemically synthesized or recombinantly produced using methods known in the art, such as the *Drosophila* in vitro system described in U.S. application no. 2002/0086356 of Tuschl et al., the entire disclosure of which is herein incorporated by reference. siRNA can be expressed from pol III expression vectors without a change in targeting site, as expression of RNAs from pol III promoters is only believed to be efficient when the first transcribed nucleotide is a purine.

Preferably, siRNA is transcribed from recombinant circular or linear DNA plasmids using any suitable promoter. Suitable promoters for transcribing siRNA used in the present disclosure from a plasmid include, for example, the U6 or H1 RNA pol III promoter sequences and the cytomegalovirus promoter. Selection of other suitable promoters is within the skill in the art.

Selection of plasmids suitable for transcribing siRNA, methods for inserting nucleic acid sequences for expressing the siRNA into the plasmid, and IVT methods of in vitro transcription of said siRNA are within the skill in the art.

The term "miRNA" (microRNA) as used herein relates to non-coding RNAs which have a length of 21 to 25 (such as 21 to 23, preferably 22) nucleotides and which induce degradation and/or prevent translation of target mRNAs. miRNAs are typically found in plants, animals and some viruses, wherein they are encoded by eukaryotic nuclear DNA in plants and animals and by viral DNA (in viruses whose genome is based on DNA), respectively. miRNAs are post-transcriptional regulators that bind to complementary sequences on target messenger RNA transcripts (mRNAs), usually resulting in translational repression or target degradation and gene silencing.

miRNA can be obtained using a number of techniques known to those of skill in the art. For example, miRNA can be chemically synthesized or recombinantly produced using methods known in the art (e.g., by using commercially available kits such as the miRNA cDNA Synthesis Kit sold by Applied Biological Materials Inc.). Preferably, miRNA is transcribed from recombinant circular or linear DNA plasmids using any suitable promoter.

Pharmaceutically Active Peptides or Polypeptides

"Encoding" refers to the inherent property of specific sequences of nucleotides in a polynucleotide, such as a gene, a cDNA, or an RNA (preferably mRNA), to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of RNA (preferably mRNA) corresponding to that gene produces the protein in a cell or other biological system. Both the coding strand, the nucleotide sequence of which is identical to the RNA sequence and is usually provided in sequence listings, and the non-coding strand, used as the template for transcription of a gene or cDNA, can be referred to as encoding the protein or other product of that gene or cDNA.

In some embodiments, RNA (preferably mRNA) described in the present disclosure comprises a nucleic acid sequence (e.g., an ORF) encoding one or more polypeptides, e.g., a peptide or protein, preferably a pharmaceutically active peptide or protein.

In some embodiments, RNA (preferably mRNA) described in the present disclosure comprises a nucleic acid sequence (e.g., an ORF) encoding a peptide or protein, preferably a pharmaceutically active peptide or protein, and is capable of expressing said peptide or protein, in particular if transferred into a cell or subject. Thus, in some embodiments, the RNA (preferably mRNA) described in the present disclosure contains a coding region (ORF) encoding a peptide or protein, preferably encoding a pharmaceutically active peptide or protein. In this respect, an "open reading frame" or "ORF" is a continuous stretch of codons beginning with a start codon and ending with a stop codon. Such RNA (preferably mRNA) encoding a pharmaceutically active peptide or protein is also referred to herein as "pharmaceutically active RNA" (or "pharmaceutically active mRNA"). In some embodiments, RNA (preferably mRNA) described in the present disclosure comprises a nucleic acid sequence encoding more than one peptide or polypeptide, e.g., two, three, four or more peptides or polypeptides.

According to the present disclosure, the term "pharmaceutically active peptide or protein" means a peptide or protein that can be used in the treatment of an individual where the expression of the peptide or protein would be of benefit, e.g., in ameliorating the symptoms of a disease or disorder. Preferably, a pharmaceutically active peptide or protein has curative or palliative properties and may be administered to ameliorate, relieve, alleviate, reverse, delay onset of or lessen the severity of one or more symptoms of a disease or disorder. In some embodiments, a pharmaceutically active peptide or protein has a positive or advantageous effect on the condition or disease state of an individual when administered to the individual in a therapeutically effective amount. A pharmaceutically active peptide or protein may have prophylactic properties and may be used to delay the onset of a disease or disorder or to lessen the severity of such disease or disorder. The term "pharmaceutically active peptide or protein" includes entire proteins or polypeptides, and can also refer to pharmaceutically active fragments thereof. It can also include pharmaceutically active analogs of a peptide or protein. The terms "pharmaceutically active peptide or protein" and "therapeutic protein" are used interchangeable herein.

Specific examples of pharmaceutically active peptides and proteins include, but are not limited to, immunostimulants, e.g., cytokines, hormones, adhesion molecules, immunoglobulins, immunologically active compounds, growth factors, protease inhibitors, enzymes, receptors, apoptosis regulators, transcription factors, tumor suppressor proteins, structural proteins, reprogramming factors, genomic engineering proteins, and blood proteins. In some embodiments, the pharmaceutically active peptide and polypeptide includes a replacement protein.

An "immunostimulant" is any substance that stimulates the immune system by inducing activation or increasing activity of any of the immune system's components, in particular immune effector cells. The immunostimulant may be pro-inflammatory (e.g., when treating infections or cancer), or anti-inflammatory (e.g., when treating autoimmune diseases).

In some embodiments, the immunostimulant is a cytokine or a variant thereof. Examples of cytokines include interferons, such as interferon-alpha (IFN-α) or interferon-gamma (IFN-γ), interleukins, such as IL2, IL7, IL12, IL15 and IL23, colony stimulating factors, such as M-CSF and GM-CSF, and tumor necrosis factor. According to another aspect, the immunostimulant includes an adjuvant-type immunostimulatory agent such as APC Toll-like Receptor agonists or costimulatory/cell adhesion membrane proteins. Examples of Toll-like Receptor agonists include costimulatory/adhesion proteins such as CD80, CD86, and ICAM-1.

The term "cytokines" relates to proteins which have a molecular weight of about 5 to 60 kDa (such as about 5 to 20 kDa) and which participate in cell signaling (e.g., paracrine, endocrine, and/or autocrine signaling). In particular, when released, cytokines exert an effect on the behavior of cells around the place of their release. Examples of cytokines include lymphokines, interleukins, chemokines, interferons, and tumor necrosis factors (TNFs). According to the present disclosure, cytokines do not include hormones or growth factors. Cytokines differ from hormones in that (i) they usually act at much more variable concentrations than hormones and (ii) generally are made by a broad range of cells (nearly all nucleated cells can produce cytokines). Interferons are usually characterized by antiviral, antiproliferative and immunomodulatory activities. Interferons are proteins that alter and regulate the transcription of genes within a cell by binding to interferon receptors on the regulated cell's surface, thereby preventing viral replication within the cells. The interferons can be grouped into two types. IFN-gamma is the sole type II interferon; all others are type I interferons. Particular examples of cytokines include erythropoietin (EPO), colony stimulating factor (CSF), granulocyte colony stimulating factor (G-CSF), granulocyte-macrophage colony stimulating factor (GM-CSF), tumor necrosis factor (TNF), bone morphogenetic protein (BMP), interferon alfa (IFNα), interferon beta (IFNβ), interferon gamma (INFγ), interleukin 2 (IL-2), interleukin 4 (IL-4), interleukin 10 (IL-10), interleukin 11 (IL-11), interleukin 12 (IL-12), and interleukin 21 (IL-21).

According to the disclosure, a cytokine may be a naturally occurring cytokine or a functional fragment or variant thereof. A cytokine may be human cytokine and may be derived from any vertebrate, especially any mammal. One particularly preferred cytokine is interferon-α.

Immunostimulants may be provided to a subject by administering to the subject RNA encoding an immunostimulant in a formulation for preferential delivery of RNA to liver or liver tissue. The delivery of RNA to such target organ or tissue is preferred, in particular, if it is desired to express large amounts of the immunostimulant and/or if systemic presence of the immunostimulant, in particular in significant amounts, is desired or required. RNA delivery systems have an inherent preference to the liver. This pertains to lipid-based particles, cationic and neutral nanoparticles, in particular lipid nanoparticles.

Examples of suitable immunostimulants for targeting liver are cytokines involved in T cell proliferation and/or maintenance. Examples of suitable cytokines include IL2 or IL7, fragments and variants thereof, and fusion proteins of these cytokines, fragments and variants, such as extended-PK cytokines.

In another embodiment, RNA encoding an immunostimulant may be administered in a formulation for preferential delivery of RNA to the lymphatic system, in particular secondary lymphoid organs, more specifically spleen. The delivery of an immunostimulant to such target tissue is preferred, in particular, if presence of the immunostimulant in this organ or tissue is desired (e.g., for inducing an immune response, in particular in case immunostimulants such as cytokines are required during T-cell priming or for activation of resident immune cells), while it is not desired that the immunostimulant is present systemically, in particular in significant amounts (e.g., because the immunostimulant has systemic toxicity).

Examples of suitable immunostimulants are cytokines involved in T cell priming. Examples of suitable cytokines include IL12, IL15, IFN-α, or IFN-β, fragments and variants thereof, and fusion proteins of these cytokines, fragments and variants, such as extended-PK cytokines.

Interferons (IFNs) are a group of signaling proteins made and released by host cells in response to the presence of several pathogens, such as viruses, bacteria, parasites, and also tumor cells. In a typical scenario, a virus-infected cell will release interferons causing nearby cells to heighten their anti-viral defenses.

Based on the type of receptor through which they signal, interferons are typically divided among three classes: type I interferon, type II interferon, and type III interferon.

All type I interferons bind to a specific cell surface receptor complex known as the IFN-α/β receptor (IFNAR) that consists of IFNAR1 and IFNAR2 chains.

The type I interferons present in humans are IFNα, IFNβ, IFNε, IFNκ and IFNω. In general, type I interferons are produced when the body recognizes a virus that has invaded it. They are produced by fibroblasts and monocytes. Once released, type I interferons bind to specific receptors on target cells, which leads to expression of proteins that will prevent the virus from producing and replicating its RNA and DNA.

The IFNα proteins are produced mainly by plasmacytoid dendritic cells (pDCs). They are mainly involved in innate immunity against viral infection. The genes responsible for their synthesis come in 13 subtypes that are called IFNA1, IFNA2, IFNA4, IFNA5, IFNA6, IFNA7, IFNA8, IFNA10, IFNA13, IFNA14, IFNA16, IFNA17, IFNA21. These genes are found together in a cluster on chromosome 9.

The IFNβ proteins are produced in large quantities by fibroblasts. They have antiviral activity that is involved mainly in innate immune response. Two types of IFNβ have been described, IFNβ 1 and IFNβ3. The natural and recombinant forms of IFNβ1 have antiviral, antibacterial, and anticancer properties.

Type II interferon (IFNγ in humans) is also known as immune interferon and is activated by IL12. Furthermore, type II interferons are released by cytotoxic T cells and T helper cells.

Type III interferons signal through a receptor complex consisting of $IL10R_2$ (also called CRF2-4) and IFNLR1 (also called CRF2-12). Although discovered more recently than type I and type II IFNs, recent information demonstrates the importance of type III IFNs in some types of virus or fungal infections.

In general, type I and II interferons are responsible for regulating and activating the immune response.

According to the disclosure, a type I interferon is preferably IFNα or IFNβ, more preferably IFNα.

According to the disclosure, an interferon may be a naturally occurring interferon or a functional fragment or variant thereof. An interferon may be human interferon and may be derived from any vertebrate, especially any mammal.

Interleukins (ILs) are a group of cytokines (secreted proteins and signal molecules) that can be divided into four major groups based on distinguishing structural features. However, their amino acid sequence similarity is rather weak (typically 15-25% identity). The human genome encodes more than 50 interleukins and related proteins.

According to the disclosure, an interleukin may be a naturally occurring interleukin or a functional fragment or variant thereof. An interleukin may be human interleukin and may be derived from any vertebrate, especially any mammal.

Immunostimulant polypeptides described herein can be prepared as fusion or chimeric polypeptides that include an immunostimulant portion and a heterologous polypeptide (i.e., a polypeptide that is not an immunostimulant). The immunostimulant may be fused to an extended-PK group, which increases circulation half-life. Non-limiting examples of extended-PK groups are described infra. It should be understood that other PK groups that increase the circulation half-life of immunostimulants such as cytokines, or variants thereof, are also applicable to the present disclosure. In certain embodiments, the extended-PK group is a serum albumin domain (e.g., mouse serum albumin, human serum albumin).

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include serum albumin (e.g., HSA), Immunoglobulin Fc or Fc fragments and variants thereof, transferrin and variants thereof, and human serum albumin (HSA) binders (as disclosed in U.S. Publication Nos. 2005/0287153 and 2007/0003549). Other exemplary extended-PK groups are disclosed in Kontermann, Expert Opin Biol Ther, 2016 July; 16(7):903-15 which is herein incorporated by reference in its entirety. As used herein, an "extended-PK" immunostimulant refers to an immunostimulant moiety in combination with an extended-PK group. In some embodiments, the extended-PK immunostimulant is a fusion protein in which an immunostimulant moiety is linked or fused to an extended-PK group.

In certain embodiments, the serum half-life of an extended-PK immunostimulant is increased relative to the immunostimulant alone (i.e., the immunostimulant not fused to an extended-PK group). In certain embodiments, the serum half-life of the extended-PK immunostimulant is at least 20%, at least 40%, at least 60%, at least 80%, at least 100%, at least 120%, at least 150%, at least 180%, at least 200%, at least 400%, at least 600%, at least 800%, or at least 1000% longer relative to the serum half-life of the immunostimulant alone. In certain embodiments, the serum half-life of the extended-PK immunostimulant is at least 1.5-fold, 2-fold, 2.5-fold, 3-fold, 3.5-fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the immunostimulant alone. In certain embodiments, the serum half-life of the extended-PK immunostimulant is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

As used herein, "half-life" refers to the time taken for the serum or plasma concentration of a compound such as a peptide or polypeptide to reduce by 50%, in vivo, for example due to degradation and/or clearance or sequestration by natural mechanisms. An extended-PK immunostimulant suitable for use herein is stabilized in vivo and its half-life increased by, e.g., fusion to serum albumin (e.g., HSA or MSA), which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

In certain embodiments, the extended-PK group includes serum albumin, or fragments thereof or variants of the serum albumin or fragments thereof (all of which for the purpose of the present disclosure are comprised by the term "albumin"). Polypeptides described herein may be fused to albumin (or a fragment or variant thereof) to form albumin fusion proteins. Such albumin fusion proteins are described in U.S. Publication No. 20070048282.

As used herein, "albumin fusion protein" refers to a protein formed by the fusion of at least one molecule of albumin (or a fragment or variant thereof) to at least one molecule of a protein such as a therapeutic protein, in particular an immunostimulant. The albumin fusion protein may be generated by translation of a nucleic acid in which a polynucleotide encoding a therapeutic protein is joined in-frame with a polynucleotide encoding an albumin. The therapeutic protein and albumin, once part of the albumin fusion protein, may each be referred to as a "portion", "region" or "moiety" of the albumin fusion protein (e.g., a "therapeutic protein portion" or an "albumin protein portion"). In a highly preferred embodiment, an albumin fusion protein comprises at least one molecule of a therapeutic protein (including, but not limited to a mature form of the therapeutic protein) and at least one molecule of albumin (including but not limited to a mature form of albumin). In some embodiments, an albumin fusion protein is processed by a host cell such as a cell of the target organ for administered RNA, e.g. a liver cell, and secreted into the circulation. Processing of the nascent albumin fusion protein that occurs in the secretory pathways of the host cell used for expression of the RNA may include, but is not limited to signal peptide cleavage; formation of disulfide bonds; proper folding; addition and processing of carbohydrates (such as for example, N- and O-linked glycosylation); specific proteolytic cleavages; and/or assembly into multimeric proteins. An albumin fusion protein is preferably encoded by RNA in a non-processed form which in particular has a signal peptide at its N-terminus and following secretion by a cell is preferably present in the processed form wherein in particular the signal peptide has been cleaved off In a most preferred embodiment, the "processed form of an albumin fusion protein" refers to an albumin fusion protein product which has undergone N-terminal signal peptide cleavage, herein also referred to as a "mature albumin fusion protein".

In preferred embodiments, albumin fusion proteins comprising a therapeutic protein have a higher plasma stability compared to the plasma stability of the same therapeutic protein when not fused to albumin. Plasma stability typically refers to the time period between when the therapeutic protein is administered in vivo and carried into the bloodstream and when the therapeutic protein is degraded and cleared from the bloodstream, into an organ, such as the kidney or liver, that ultimately clears the therapeutic protein from the body. Plasma stability is calculated in terms of the half-life of the therapeutic protein in the bloodstream. The half-life of the therapeutic protein in the bloodstream can be readily determined by common assays known in the art.

As used herein, "albumin" refers collectively to albumin protein or amino acid sequence, or an albumin fragment or variant, having one or more functional activities (e.g., biological activities) of albumin. In particular, "albumin" refers to human albumin or fragments or variants thereof especially the mature form of human albumin, or albumin from other vertebrates or fragments thereof, or variants of these molecules. The albumin may be derived from any vertebrate, especially any mammal, for example human, cow, sheep, or pig. Non-mammalian albumins include, but are not limited to, hen and salmon. The albumin portion of the albumin fusion protein may be from a different animal than the therapeutic protein portion.

In certain embodiments, the albumin is human serum albumin (HSA), or fragments or variants thereof, such as those disclosed in U.S. Pat. No. 5,876,969, WO 2011/124718, WO 2013/075066, and WO 2011/0514789. The terms, human serum albumin (HSA) and human albumin (HA) are used interchangeably herein. The terms "albumin" and "serum albumin" are broader, and encompass human serum albumin (and fragments and variants thereof) as well as albumin from other species (and fragments and variants thereof).

As used herein, a fragment of albumin sufficient to prolong the therapeutic activity or plasma stability of the therapeutic protein refers to a fragment of albumin sufficient in length or structure to stabilize or prolong the therapeutic activity or plasma stability of the protein so that the plasma stability of the therapeutic protein portion of the albumin fusion protein is prolonged or extended compared to the plasma stability in the non-fusion state.

The albumin portion of the albumin fusion proteins may comprise the full length of the albumin sequence, or may include one or more fragments thereof that are capable of stabilizing or prolonging the therapeutic activity or plasma stability. Such fragments may be of 10 or more amino acids in length or may include about 15, 20, 25, 30, 50, or more contiguous amino acids from the albumin sequence or may include part or all of specific domains of albumin. For instance, one or more fragments of HSA spanning the first two immunoglobulin-like domains may be used. In a preferred embodiment, the HSA fragment is the mature form of HSA.

Generally speaking, an albumin fragment or variant will be at least 100 amino acids long, preferably at least 150 amino acids long.

According to the disclosure, albumin may be naturally occurring albumin or a fragment or variant thereof. Albumin may be human albumin and may be derived from any vertebrate, especially any mammal.

In some embodiments, the albumin fusion protein comprises albumin as the N-terminal portion, and a therapeutic protein as the C-terminal portion. Alternatively, an albumin fusion protein comprising albumin as the C-terminal portion, and a therapeutic protein as the N-terminal portion may also be used. In other embodiments, the albumin fusion protein has a therapeutic protein fused to both the N-terminus and the C-terminus of albumin. In a preferred embodiment, the therapeutic proteins fused at the N- and C-termini are the same therapeutic proteins. In another preferred embodiment, the therapeutic proteins fused at the N- and C-termini are different therapeutic proteins. In some embodiments, the different therapeutic proteins are both cytokines.

In some embodiments, the therapeutic protein(s) is (are) joined to the albumin through (a) peptide linker(s). A peptide linker between the fused portions may provide greater physical separation between the moieties and thus maximize the accessibility of the therapeutic protein portion, for instance, for binding to its cognate receptor. The peptide linker may consist of amino acids such that it is flexible or more rigid. The linker sequence may be cleavable by a protease or chemically.

As used herein, the term "Fe region" refers to the portion of a native immunoglobulin formed by the respective Fc domains (or Fc moieties) of its two heavy chains. As used herein, the term "Fc domain" refers to a portion or fragment of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide described herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

In certain embodiments, an extended-PK group includes an Fc domain or fragments thereof or variants of the Fc domain or fragments thereof (all of which for the purpose of the present disclosure are comprised by the term "Fc domain"). The Fc domain does not contain a variable region that binds to antigen. Fc domains suitable for use in the present disclosure may be obtained from a number of different sources. In certain embodiments, an Fc domain is derived from a human immunoglobulin. In certain embodiments, the Fc domain is from a human IgG1 constant region. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species.

Moreover, the Fc domain (or a fragment or variant thereof) may be derived from any immunoglobulin class, including IgM, IgG, IgD, IgA, and IgE, and any immunoglobulin isotype, including IgG1, IgG2, IgG3, and IgG4.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or fragments or variants thereof) can be derived from these sequences using art recognized techniques.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety. In certain embodiments, the extended-PK group is transferrin, as disclosed in U.S. Pat. Nos. 7,176,278 and 8,158,579, which are herein incorporated by reference in their entirety. In certain embodiments, the extended-PK group is a serum immunoglobulin binding protein such as those disclosed in US2007/0178082, US2014/0220017, and US2017/0145062, which are herein incorporated by reference in their entirety. In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In certain embodiments, the extended-PK immunostimulant, suitable for use according to the disclosure, can employ one or more peptide linkers. As used herein, the term "peptide linker" refers to a peptide or polypeptide sequence which connects two or more domains (e.g., the extended-PK moiety and an immunostimulant moiety) in a linear amino acid sequence of a polypeptide chain. For example, peptide linkers may be used to connect an immunostimulant moiety to a HSA domain.

Linkers suitable for fusing the extended-PK group to, e.g., an immunostimulant are well known in the art. Exemplary linkers include glycine-serine-polypeptide linkers, glycine-proline-polypeptide linkers, and proline-alanine polypeptide linkers. In certain embodiments, the linker is a glycine-serine-polypeptide linker, i.e., a peptide that consists of glycine and serine residues.

In some embodiments, a pharmaceutically active peptide or protein comprises a replacement protein. In these embodiments, the present disclosure provides a method for treatment of a subject having a disorder requiring protein replacement (e.g., protein deficiency disorders) comprising administering to the subject RNA as described herein encoding a replacement protein. The term "protein replacement" refers to the introduction of a protein (including functional variants thereof) into a subject having a deficiency in such protein. The term also refers to the introduction of a protein into a subject otherwise requiring or benefiting from providing a protein, e.g., suffering from protein insufficiency. The term "disorder characterized by a protein deficiency" refers to any disorder that presents with a pathology caused by absent or insufficient amounts of a protein. This term encompasses protein folding disorders, i.e., conformational disorders, that result in a biologically inactive protein product. Protein insufficiency can be involved in infectious diseases, immunosuppression, organ failure, glandular problems, radiation illness, nutritional deficiency, poisoning, or other environmental or external insults.

The term "hormones" relates to a class of signaling molecules produced by glands, wherein signaling usually includes the following steps: (i) synthesis of a hormone in a particular tissue; (ii) storage and secretion; (iii) transport of the hormone to its target; (iv) binding of the hormone by a receptor; (v) relay and amplification of the signal; and (vi) breakdown of the hormone. Hormones differ from cytokines in that (1) hormones usually act in less variable concentrations and (2) generally are made by specific kinds of cells. In some embodiments, a "hormone" is a peptide or protein hormone, such as insulin, vasopressin, prolactin, adrenocorticotropic hormone (ACTH), thyroid hormone, growth hormones (such as human grown hormone or bovine somatotropin), oxytocin, atrial-natriuretic peptide (ANP), glucagon, somatostatin, cholecystokinin, gastrin, and leptins.

The term "adhesion molecules" relates to proteins which are located on the surface of a cell and which are involved in binding of the cell with other cells or with the extracellular matrix (ECM). Adhesion molecules are typically transmembrane receptors and can be classified as calcium-independent (e.g., integrins, immunoglobulin superfamily, lymphocyte homing receptors) and calcium-dependent (cadherins and selectins). Particular examples of adhesion molecules are integrins, lymphocyte homing receptors, selectins (e.g., P-selectin), and addressins.

Integrins are also involved in signal transduction. In particular, upon ligand binding, integrins modulate cell signaling pathways, e.g., pathways of transmembrane protein kinases such as receptor tyrosine kinases (RTK). Such regulation can lead to cellular growth, division, survival, or differentiation or to apoptosis. Particular examples of integrins include: $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_L\beta_2$, $\alpha_M\beta_2$, $\alpha_{IIb}\beta_3$, $\alpha_v\beta_1$, $\alpha_v\beta_3$, $\alpha_v\beta_5$, $\alpha_v\beta_6$, $\alpha_v\beta_8$, and $\alpha_6\beta_4$.

The term "immunoglobulins" or "immunoglobulin superfamily" refers to molecules which are involved in the recognition, binding, and/or adhesion processes of cells. Molecules belonging to this superfamily share the feature that they contain a region known as immunoglobulin domain or fold. Members of the immunoglobulin superfamily include antibodies (e.g., IgG), T cell receptors (TCRs), major histocompatibility complex (MHC) molecules, co-receptors (e.g., CD4, CD8, CD19), antigen receptor accessory molecules (e.g., CD-3γ, CD3-δ, CD-3ε, CD79a, CD79b), co-stimulatory or inhibitory molecules (e.g., CD28, CD80, CD86), and other.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also down-regulate other aspects of the immune response, for example shifting the immune response away from a TH2 immune response, which is useful for treating a wide range of TH2 mediated diseases. Immunologically active compounds can be useful as vaccine adjuvants. Particular examples of immunologically active compounds include interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, selectins, homing receptors, and antigens, in particular tumor-associated antigens, pathogen-associated antigens (such as bacterial, parasitic, or viral antigens), allergens, and autoantigens. A preferred immunologically active compound is a vaccine antigen, i.e., an antigen whose inoculation into a subject induces an immune response.

In some embodiments, RNA (in particular, mRNA) described in the present disclosure comprises a nucleic acid sequence encoding a peptide or polypeptide comprising an epitope for inducing an immune response against an antigen in a subject. The "peptide or polypeptide comprising an epitope for inducing an immune response against an antigen in a subject" is also designated herein as "vaccine antigen", "peptide and protein antigen" or simply "antigen".

In some embodiments, the RNA (in particular, mRNA) encoding vaccine antigen is a single-stranded, 5' capped mRNA that is translated into the respective protein upon entering cells of a subject being administered the RNA, e.g., antigen-presenting cells (APCs). Preferably, the RNA (i) contains structural elements optimized for maximal efficacy of the RNA with respect to stability and translational efficiency (5' cap, 5' UTR, 3' UTR, poly(A) sequence); (ii) is modified for optimized efficacy of the RNA (e.g., increased translation efficacy, decreased immunogenicity, and/or decreased cytotoxicity) (e.g., by replacing (partially or completely, preferably completely) naturally occurring nucleosides (in particular cytidine) with synthetic nucleosides (e.g., modified nucleosides selected from the group consisting of pseudouridine (ψ), N1-methyl-pseudouridine (m1ψ), and 5-methyl-uridine); and/or codon-optimization), or (iii) both (i) and (ii).

In some embodiments, beta-S-ARCA(D1) is utilized as specific capping structure at the 5'-end of the RNA. In some embodiments, the 5'-UTR comprises the nucleotide sequence of SEQ ID NO: 1, or a nucleotide sequence having at least 99%, 98%, 97%, 96%, 95%, 90%, 85%, or 80% identity to the nucleotide sequence of SEQ ID NO: 1. In some embodiments, the 3'-UTR comprises the nucleotide sequence of SEQ ID NO: 2, or a nucleotide sequence having at least 99%, 98%, 97%, 96%, 95%, 90%, 85%, or 80% identity to the nucleotide sequence of SEQ ID NO: 2. In some embodiments, the poly(A) sequence is 110 nucleotides in length and consists of a stretch of 30 adenosine residues, followed by a 10 nucleotide linker sequence and another 70 adenosine residues. This poly(A) sequence was designed to enhance RNA stability and translational efficiency in dendritic cells. In some embodiments, the poly(A) sequence comprises the nucleotide sequence of SEQ ID NO: 3, or a nucleotide sequence having at least 99%, 98%, 97%, 96%, 95%, 90%, 85%, or 80% identity to the nucleotide sequence of SEQ ID NO: 3. In some embodiments, the RNA comprises a modified nucleoside in place of uridine. In some embodiments, the modified nucleoside replacing (partially or completely, preferably completely) uridine is selected from the group consisting of pseudouridine (ψ), N1-methyl-pseudouridine (m1ψ), and 5-methyl-uridine. In some embodiments, the RNA encoding the vaccine antigen has a coding sequence (a) which is codon-optimized, (b) the G/C content of which is increased compared to the wild type coding sequence, or (c) both (a) and (b).

In some embodiments, the RNA encoding the vaccine antigen is expressed in cells of the subject to provide the vaccine antigen. In some embodiments, expression of the vaccine antigen is at the cell surface. In some embodiments, the vaccine antigen is presented in the context of MHC. In some embodiments, the RNA encoding the vaccine antigen is transiently expressed in cells of the subject. In some embodiments, the RNA encoding the vaccine antigen is administered systemically. In some embodiments, after systemic administration of the RNA encoding the vaccine antigen, expression of the RNA encoding the vaccine antigen in spleen occurs. In some embodiments, after systemic administration of the RNA encoding the vaccine antigen, expression of the RNA encoding the vaccine antigen in antigen presenting cells, preferably professional antigen presenting cells occurs. In some embodiments, the antigen presenting cells are selected from the group consisting of dendritic cells, macrophages and B cells. In some embodiments, after systemic administration of the RNA encoding the vaccine antigen, no or essentially no expression of the RNA encoding the vaccine antigen in lung and/or liver occurs. In some embodiments, after systemic administration of the RNA encoding the vaccine antigen, expression of the RNA encoding the vaccine antigen in spleen is at least 5-fold the amount of expression in lung.

The vaccine antigen comprises an epitope for inducing an immune response against an antigen in a subject. Accordingly, the vaccine antigen comprises an antigenic sequence for inducing an immune response against an antigen in a subject. Such antigenic sequence may correspond to a target antigen or disease-associated antigen, e.g., a protein of an infectious agent (e.g., viral or bacterial antigen) or tumor antigen, or may correspond to an immunogenic variant thereof, or an immunogenic fragment of the target antigen or disease-associated antigen or the immunogenic variant thereof. Thus, the antigenic sequence may comprise at least an epitope of a target antigen or disease-associated antigen or an immunogenic variant thereof.

The antigenic sequences, e.g., epitopes, suitable for use according to the disclosure typically may be derived from a target antigen, i.e. the antigen against which an immune response is to be elicited. For example, the antigenic sequences contained within the vaccine antigen may be a target antigen or a fragment or variant of a target antigen.

The antigenic sequence or a procession product thereof, e.g., a fragment thereof, may bind to the antigen receptor such as TCR or CAR carried by immune effector cells. In some embodiments, the antigenic sequence is selected from the group consisting of the antigen expressed by a target cell to which the immune effector cells are targeted or a fragment thereof, or a variant of the antigenic sequence or the fragment.

A vaccine antigen which may be provided to a subject according to the present disclosure by administering RNA encoding the vaccine antigen, preferably results in the induction of an immune response, e.g., in the stimulation, priming and/or expansion of immune effector cells, in the subject being provided the vaccine antigen. Said immune response, e.g., stimulated, primed and/or expanded immune effector cells, is preferably directed against a target antigen, in particular a target antigen expressed by diseased cells, tissues and/or organs, i.e., a disease-associated antigen. Thus, a vaccine antigen may comprise the disease-associated antigen, or a fragment or variant thereof. In some embodiments, such fragment or variant is immunologically equivalent to the disease-associated antigen.

In the context of the present disclosure, the term "fragment of an antigen" or "variant of an antigen" means an agent which results in the induction of an immune response, e.g., in the stimulation, priming and/or expansion of immune effector cells, which immune response, e.g., stimulated, primed and/or expanded immune effector cells, targets the antigen, i.e. a disease-associated antigen, in particular when presented by diseased cells, tissues and/or organs. Thus, the vaccine antigen may correspond to or may comprise the disease-associated antigen, may correspond to or may comprise a fragment of the disease-associated antigen or may correspond to or may comprise an antigen which is homologous to the disease-associated antigen or a fragment thereof. If the vaccine antigen comprises a fragment of the disease-associated antigen or an amino acid sequence which is homologous to a fragment of the disease-associated antigen said fragment or amino acid sequence may comprise an epitope of the disease-associated antigen to which the antigen receptor of the immune effector cells is targeted or a sequence which is homologous to an epitope of the disease-associated antigen. Thus, according to the disclosure, a vaccine antigen may comprise an immunogenic fragment of a disease-associated antigen or an amino acid sequence being homologous to an immunogenic fragment of a disease-associated antigen. An "immunogenic fragment of an antigen" according to the disclosure preferably relates to a fragment of an antigen which is capable of inducing an immune response against, e.g., stimulating, priming and/or expanding immune effector cells carrying an antigen receptor binding to, the antigen or cells expressing the antigen. It is preferred that the vaccine antigen (similar to the disease-associated antigen) provides the relevant epitope for binding by the antigen receptor present on the immune effector cells. In some embodiments, the vaccine antigen or a fragment thereof (similar to the disease-associated antigen) is expressed on the surface of a cell such as an antigen-presenting cell (optionally in the context of MHC) so as to provide the relevant epitope for binding by immune effector cells. The vaccine antigen may be a recombinant antigen.

In some embodiments of all aspects of the invention, the RNA encoding the vaccine antigen is expressed in cells of a subject to provide the antigen or a procession product thereof for binding by the antigen receptor expressed by immune effector cells, said binding resulting in stimulation, priming and/or expansion of the immune effector cells. An "antigen" according to the present disclosure covers any substance that will elicit an immune response and/or any substance against which an immune response or an immune mechanism such as a cellular response and/or humoral response is directed. This also includes situations wherein the antigen is processed into antigen peptides and an immune response or an immune mechanism is directed against one or more antigen peptides, in particular if presented in the context of MHC molecules. In particular, an "antigen" relates to any substance, such as a peptide or polypeptide, that reacts specifically with antibodies or T-lymphocytes (T-cells). The term "antigen" may comprise a molecule that comprises at least one epitope, such as a T cell epitope. In some embodiments, an antigen is a molecule which, optionally after processing, induces an immune reaction, which may be specific for the antigen (including cells expressing the antigen). In some embodiments, an antigen is a disease-associated antigen, such as a tumor antigen, a viral antigen, or a bacterial antigen, or an epitope derived from such antigen.

In some embodiments, an antigen is presented or present on the surface of cells of the immune system such as antigen presenting cells like dendritic cells or macrophages. An antigen or a procession product thereof such as a T cell epitope is in some embodiments bound by an antigen receptor. Accordingly, an antigen or a procession product thereof may react specifically with immune effector cells such as T-lymphocytes (T cells).

The term "autoantigen" or "self-antigen" refers to an antigen which originates from within the body of a subject (i.e., the autoantigen can also be called "autologous antigen") and which produces an abnormally vigorous immune response against this normal part of the body. Such vigorous immune reactions against autoantigens may be the cause of "autoimmune diseases".

In some embodiments, an antigen is expressed on the surface of a diseased cell (such as tumor cell or an infected cell). In some embodiments, an antigen receptor is a CAR which binds to an extracellular domain or to an epitope in an extracellular domain of an antigen. In some embodiments, a CAR binds to native epitopes of an antigen present on the surface of living cells. In some embodiments, binding of a CAR when expressed by T cells and/or present on T cells to an antigen present on cells such as antigen presenting cells results in stimulation, priming and/or expansion of said T cells. In some embodiments, binding of a CAR when expressed by T cells and/or present on T cells to an antigen present on diseased cells results in cytolysis and/or apoptosis of the diseased cells, wherein said T cells preferably release cytotoxic factors, e.g., perforins and granzymes.

According to some embodiments, an amino acid sequence enhancing antigen processing and/or presentation is fused, either directly or through a linker, to an antigenic peptide or polypeptide (antigenic sequence). Accordingly, in some embodiments, the RNA described herein comprises at least one coding region encoding an antigenic peptide or polypeptide and an amino acid sequence enhancing antigen processing and/or presentation.

In some embodiments, antigen for vaccination which may be administered in the form of RNA coding therefor comprises a naturally occurring antigen or a fragment such as an epitope thereof.

Such amino acid sequences enhancing antigen processing and/or presentation are preferably located at the C-terminus of the antigenic peptide or polypeptide (and optionally at the C-terminus of an amino acid sequence which breaks immunological tolerance), without being limited thereto. Amino acid sequences enhancing antigen processing and/or presentation as defined herein preferably improve antigen processing and presentation. In some embodiments, the amino acid sequence enhancing antigen processing and/or presentation as defined herein includes, without being limited thereto, sequences derived from the human MHC class I complex (HLA-B51, haplotype A2, B27/B51, Cw2/Cw3), in particular a sequence comprising the amino acid sequence of SEQ ID NO: 5 or a functional variant thereof.

In some embodiments, a secretory sequence, e.g., a sequence comprising the amino acid sequence of SEQ ID NO: 4, may be fused to the N-terminus of the antigenic peptide or polypeptide.

In some embodiments, an amino acid sequence enhancing antigen processing and/or presentation comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or a functional fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In some embodiments, an amino acid sequence enhancing antigen processing and/or presentation comprises the amino acid sequence of SEQ ID NO: 5.

Accordingly, in some embodiments, the RNA described herein comprises at least one coding region encoding an antigenic peptide or polypeptide and an amino acid sequence enhancing antigen processing and/or presentation, said amino acid sequence enhancing antigen processing and/or presentation preferably being fused to the antigenic peptide or polypeptide, more preferably to the C-terminus of the antigenic peptide or polypeptide as described herein.

Furthermore, a secretory sequence, e.g., a sequence comprising the amino acid sequence of SEQ ID NO: 4, may be fused to the N-terminus of the antigenic peptide or polypeptide.

Amino acid sequences derived from tetanus toxoid of *Clostridium tetani* may be employed to overcome self-tolerance mechanisms in order to efficiently mount an immune response to self-antigens by providing T-cell help during priming.

It is known that tetanus toxoid heavy chain includes epitopes that can bind promiscuously to MHC class II alleles and induce $CD4^+$ memory T cells in almost all tetanus vaccinated individuals. In addition, the combination of tetanus toxoid (TT) helper epitopes with tumor-associated antigens is known to improve the immune stimulation compared to application of tumor-associated antigen alone by providing $CD4^+$-mediated T-cell help during priming. To reduce the risk of stimulating $CD8^+$ T cells with the tetanus sequences which might compete with the intended induction of tumor antigen-specific T-cell response, not the whole fragment C of tetanus toxoid is used as it is known to contain $CD8^+$ T-cell epitopes. Two peptide sequences containing promiscuously binding helper epitopes were selected alternatively to ensure binding to as many MHC class II alleles as possible. Based on the data of the ex vivo studies the well-known epitopes p2 (QYIKANSKFIGITEL; $TT_{830-844}$; SEQ ID NO: 9) and p16 (MTNSVDDALINSTKIYSYFPSVISKVNQGAQG; $TT_{578-609}$; SEQ ID NO: 10) were selected. The p2 epitope was already used for peptide vaccination in clinical trials to boost anti-melanoma activity.

Non-clinical data showed that RNA vaccines encoding both a tumor antigen plus promiscuously binding tetanus toxoid sequences lead to enhanced CD8+ T-cell responses directed against the tumor antigen and improved break of tolerance. Immunomonitoring data from patients vaccinated with vaccines including those sequences fused in frame with the tumor antigen-specific sequences reveal that the tetanus sequences chosen are able to induce tetanus-specific T-cell responses in almost all patients.

According to some embodiments, an amino acid sequence which breaks immunological tolerance is fused, either directly or through a linker, e.g., a linker having the amino acid sequence according to SEQ ID NO: 7, to the antigenic peptide or polypeptide.

Such amino acid sequences which break immunological tolerance are preferably located at the C-terminus of the antigenic peptide or polypeptide (and optionally at the N-terminus of the amino acid sequence enhancing antigen processing and/or presentation, wherein the amino acid sequence which breaks immunological tolerance and the amino acid sequence enhancing antigen processing and/or presentation may be fused either directly or through a linker, e.g., a linker having the amino acid sequence according to SEQ ID NO: 8), without being limited thereto. Amino acid sequences which break immunological tolerance as defined herein preferably improve T cell responses. In some embodiments, the amino acid sequence which breaks immunological tolerance as defined herein includes, without being limited thereto, sequences derived from tetanus toxoid-derived helper sequences p2 and p16 (P2P16), in particular a sequence comprising the amino acid sequence of SEQ ID NO: 6 or a functional variant thereof.

In some embodiments, an amino acid sequence which breaks immunological tolerance comprises the amino acid sequence of SEQ ID NO: 6, an amino acid sequence having at least 99%, 98%, 97%, 96%, 95%, 90%, 85%, or 80% identity to the amino acid sequence of SEQ ID NO: 6, or a functional fragment of the amino acid sequence of SEQ ID NO: 6, or the amino acid sequence having at least 99%, 98%, 97%, 96%, 95%, 90%, 85%, or 80% identity to the amino acid sequence of SEQ ID NO: 6. In some embodiments, an amino acid sequence which breaks immunological tolerance comprises the amino acid sequence of SEQ ID NO: 6.

In the following, embodiments of vaccine RNAs are described, wherein certain terms used when describing elements thereof have the following meanings:

cap: 5'-cap structure selected from the group consisting of $m_2^{7,2'O}$G(5')ppSp(5')G (in particular its D1 diastereomer), $m_2^{7,3'O}$G(5')ppp(5')G, and $m_2^{7,3'-O}$Gppp($m_1^{2'-O}$)ApG.

hAg-Kozak: 5'-UTR sequence of the human alpha-globin mRNA with an optimized 'Kozak sequence' to increase translational efficiency.

see/MITD: Fusion-protein tags derived from the sequence encoding the human MHC class I complex (HLA-B51, haplotype A2, B27/B51, Cw2/Cw3), which have been shown to improve antigen processing and presentation. See corresponds to the 78 bp fragment coding for the secretory signal peptide, which guides translocation of the nascent polypeptide chain into the endoplasmatic reticulum. MITD corresponds to the transmembrane and cytoplasmic domain of the MHC class I molecule, also called MHC class I trafficking domain.

Antigen: Sequences encoding the respective vaccine antigen/epitope.

Glycine-serine linker (GS): Sequences coding for short peptide linkers predominantly consisting of the amino acids glycine (G) and serine (S), as commonly used for fusion proteins.

P2P16: Sequence coding for tetanus toxoid-derived helper epitopes to break immunological tolerance.

FI element: The 3'-UTR is a combination of two sequence elements derived from the "amino terminal enhancer of split" (AES) mRNA (called F) and the mitochondrial encoded 12S ribosomal RNA (called I). These were identified by an ex vivo selection process for sequences that confer RNA stability and augment total protein expression.

A30L70: A poly(A)-tail measuring 110 nucleotides in length, consisting of a stretch of 30 adenosine residues, followed by a 10 nucleotide linker sequence and another 70 adenosine residues designed to enhance RNA stability and translational efficiency in dendritic cells.

In some embodiments, vaccine RNA described herein has one of the following structures:

cap-hAg-Kozak-sec-GS(1)-Antigen-GS(2)-P2P16-GS(3)-MITD-FI-A30L70 beta-S-ARCA(D1)-hAg-Kozak-sec-GS(1)-Antigen-GS(2)-P2P16-GS(3)-MITD-FI-A30L70

In some embodiments, vaccine antigen described herein has the structure:

sec-GS(1)-Antigen-GS(2)-P2P16-GS(3)-MITD

In some embodiments, hAg-Kozak comprises the nucleotide sequence of SEQ ID NO: 1. In some embodiments, see comprises the amino acid sequence of SEQ ID NO: 4. In some embodiments, P2P16 comprises the amino acid sequence of SEQ ID NO: 6. In some embodiments, MITD comprises the amino acid sequence of SEQ ID NO: 5. In some embodiments, GS(1) comprises the amino acid sequence of SEQ ID NO: 7. In some embodiments, GS(2) comprises the amino acid sequence of SEQ ID NO: 8. In some embodiments, GS(3) comprises the amino acid sequence of SEQ ID NO: 8. In some embodiments, FI comprises the nucleotide sequence of SEQ ID NO: 2. In some embodiments, A30L70 comprises the nucleotide sequence of SEQ ID NO: 3.

In some embodiments, the sequence encoding the vaccine antigen/epitope comprises a modified nucleoside replacing (partially or completely, preferably completely) uridine, wherein the modified nucleoside is selected from the group consisting of pseudouridine (ψ), N1-methyl-pseudouridine (m1ψ), and 5-methyl-uridine.

In some embodiments, the sequence encoding the vaccine antigen/epitope is codon-optimized.

In some embodiments, the G/C content of the sequence encoding the vaccine antigen/epitope is increased compared to the wild type coding sequence.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

The term "dendritic cell" (DC) refers to a subtype of phagocytic cells belonging to the class of antigen presenting cells. In some embodiments, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In some embodiments, the dendritic cells are splenic dendritic cells.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In some embodiments, the macrophages are splenic macrophages.

The term "allergen" refers to a kind of antigen which originates from outside the body of a subject (i.e., the allergen can also be called "heterologous antigen") and which produces an abnormally vigorous immune response in which the immune system of the subject fights off a perceived threat that would otherwise be harmless to the subject. "Allergies" are the diseases caused by such vigorous immune reactions against allergens. An allergen usually is an antigen which is able to stimulate a type-I hypersensitivity reaction in atopic individuals through immunoglobulin E (IgE) responses. Particular examples of allergens include allergens derived from peanut proteins (e.g., Ara h 2.02), ovalbumin, grass pollen proteins (e.g., Phl p 5), and proteins of dust mites (e.g., Der p 2).

The term "growth factors" refers to molecules which are able to stimulate cellular growth, proliferation, healing, and/or cellular differentiation. Typically, growth factors act as signaling molecules between cells. The term "growth factors" include particular cytokines and hormones which bind to specific receptors on the surface of their target cells. Examples of growth factors include bone morphogenetic proteins (BMPs), fibroblast growth factors (FGFs), vascular endothelial growth factors (VEGFs), such as VEGFA, epidermal growth factor (EGF), insulin-like growth factor, ephrins, macrophage colony-stimulating factor, granulocyte colony-stimulating factor, granulocyte macrophage colony-stimulating factor, neuregulins, neurotrophins (e.g., brain-derived neurotrophic factor (BDNF), nerve growth factor (NGF)), placental growth factor (PGF), platelet-derived growth factor (PDGF), renalase (RNLS) (anti-apoptotic survival factor), T-cell growth factor (TCGF), thrombopoietin (TPO), transforming growth factors (transforming growth factor alpha (TGF-$\alpha$), transforming growth factor beta (TGF-$\beta$)), and tumor necrosis factor-alpha (TNF-$\alpha$). In one embodiment, a "growth factor" is a peptide or protein growth factor.

The term "protease inhibitors" refers to molecules, in particular peptides or proteins, which inhibit the function of proteases. Protease inhibitors can be classified by the protease which is inhibited (e.g., aspartic protease inhibitors) or by their mechanism of action (e.g., suicide inhibitors, such as serpins). Particular examples of protease inhibitors include serpins, such as alpha 1-antitrypsin, aprotinin, and bestatin.

The term "enzymes" refers to macromolecular biological catalysts which accelerate chemical reactions. Like any catalyst, enzymes are not consumed in the reaction they catalyze and do not alter the equilibrium of said reaction. Unlike many other catalysts, enzymes are much more specific. In one embodiment, an enzyme is essential for homeostasis of a subject, e.g., any malfunction (in particular, decreased activity which may be caused by any of mutation, deletion or decreased production) of the enzyme results in a disease. Examples of enzymes include herpes simplex virus type 1 thymidine kinase (HSV1-TK), hexosaminidase, phenylalanine hydroxylase, pseudocholinesterase, and lactase.

The term "receptors" refers to protein molecules which receive signals (in particular chemical signals called ligands) from outside a cell. The binding of a signal (e.g., ligand) to a receptor causes some kind of response of the cell, e.g., the intracellular activation of a kinase. Receptors include transmembrane receptors (such as ion channel-linked (ionotropic) receptors, G protein-linked (metabotropic) receptors, and enzyme-linked receptors) and intracellular receptors (such as cytoplasmic receptors and nuclear receptors). Particular examples of receptors include steroid hormone receptors, growth factor receptors, and peptide receptors (i.e., receptors whose ligands are peptides), such as P-selectin glycoprotein ligand-1 (PSGL-1). The term "growth factor receptors" refers to receptors which bind to growth factors.

The term "apoptosis regulators" refers to molecules, in particular peptides or proteins, which modulate apoptosis, i.e., which either activate or inhibit apoptosis. Apoptosis regulators can be grouped into two broad classes: those which modulate mitochondrial function and those which regulate caspases. The first class includes proteins (e.g., BCL-2, BCL-xL) which act to preserve mitochondrial integrity by preventing loss of mitochondrial membrane potential and/or release of pro-apoptotic proteins such as cytochrome C into the cytosol. Also to this first class belong proapoptotic proteins (e.g., BAX, BAK, BIM) which promote release of cytochrome C. The second class includes proteins such as the inhibitors of apoptosis proteins (e.g., XIAP) or FLIP which block the activation of caspases.

The term "transcription factors" relates to proteins which regulate the rate of transcription of genetic information from DNA to messenger RNA, in particular by binding to a specific DNA sequence. Transcription factors may regulate cell division, cell growth, and cell death throughout life; cell migration and organization during embryonic development; and/or in response to signals from outside the cell, such as a hormone. Transcription factors contain at least one DNA-binding domain which binds to a specific DNA sequence, usually adjacent to the genes which are regulated by the transcription factors. Particular examples of transcription factors include MECP2, FOXP2, FOXP3, the STAT protein family, and the HOX protein family.

The term "tumor suppressor proteins" relates to molecules, in particular peptides or proteins, which protect a cell from one step on the path to cancer. Tumor-suppressor proteins (usually encoded by corresponding tumor-suppressor genes) exhibit a weakening or repressive effect on the regulation of the cell cycle and/or promote apoptosis. Their functions may be one or more of the following: repression of genes essential for the continuing of the cell cycle;

coupling the cell cycle to DNA damage (as long as damaged DNA is present in a cell, no cell division should take place); initiation of apoptosis, if the damaged DNA cannot be repaired; metastasis suppression (e.g., preventing tumor cells from dispersing, blocking loss of contact inhibition, and inhibiting metastasis); and DNA repair. Particular examples of tumor-suppressor proteins include p53, phosphatase and tensin homolog (PTEN), SWI/SNF (SWItch/Sucrose Non-Fermentable), von Hippel-Lindau tumor suppressor (pVHL), adenomatous polyposis *coli* (APC), CD95, suppression of tumorigenicity 5 (ST5), suppression of tumorigenicity 5 (ST5), suppression of tumorigenicity 14 (ST14), and Yippee-like 3 (YPEL3).

The term “structural proteins” refers to proteins which confer stiffness and rigidity to otherwise-fluid biological components. Structural proteins are mostly fibrous (such as collagen and elastin) but may also be globular (such as actin and tubulin). Usually, globular proteins are soluble as monomers, but polymerize to form long, fibers which, for example, may make up the cytoskeleton. Other structural proteins are motor proteins (such as myosin, kinesin, and dynein) which are capable of generating mechanical forces, and surfactant proteins. Particular examples of structural proteins include collagen, surfactant protein A, surfactant protein B, surfactant protein C, surfactant protein D, elastin, tubulin, actin, and myosin.

The term “reprogramming factors” or “reprogramming transcription factors” relates to molecules, in particular peptides or proteins, which, when expressed in somatic cells optionally together with further agents such as further reprogramming factors, lead to reprogramming or de-differentiation of said somatic cells to cells having stem cell characteristics, in particular pluripotency. Particular examples of reprogramming factors include OCT4, SOX2, c-MYC, KLF4, LIN28, and NANOG.

The term “genomic engineering proteins” relates to proteins which are able to insert, delete or replace DNA in the genome of a subject. Particular examples of genomic engineering proteins include meganucleases, zinc finger nucleases (ZFNs), transcription activator-like effector nucleases (TALENs), and clustered regularly spaced short palindromic repeat-CRISPR-associated protein 9 (CRISPR-Cas9).

The term “blood proteins” relates to peptides or proteins which are present in blood plasma of a subject, in particular blood plasma of a healthy subject. Blood proteins have diverse functions such as transport (e.g., albumin, transferrin), enzymatic activity (e.g., thrombin or ceruloplasmin), blood clotting (e.g., fibrinogen), defense against pathogens (e.g., complement components and immunoglobulins), protease inhibitors (e.g., alpha 1-antitrypsin), etc. Particular examples of blood proteins include thrombin, serum albumin, Factor VII, Factor VIII, insulin, Factor IX, Factor X, tissue plasminogen activator, protein C, von Willebrand factor, antithrombin III, glucocerebrosidase, erythropoietin, granulocyte colony stimulating factor (G-CSF), modified Factor VIII, and anticoagulants.

Thus, in some embodiments, the pharmaceutically active peptide or protein is (i) a cytokine, preferably selected from the group consisting of erythropoietin (EPO), interleukin 4 (IL-2), and interleukin 10 (IL-11), more preferably EPO; (ii) an adhesion molecule, in particular an integrin; (iii) an immunoglobulin, in particular an antibody; (iv) an immunologically active compound, in particular an antigen, such as a viral or bacterial antigen, e.g., an antigen of SARS-CoV-2; (v) a hormone, in particular vasopressin, insulin or growth hormone; (vi) a growth factor, in particular VEGFA; (vii) a protease inhibitor, in particular alpha 1-antitrypsin; (viii) an enzyme, preferably selected from the group consisting of herpes simplex virus type 1 thymidine kinase (HSV1-TK), hexosaminidase, phenylalanine hydroxylase, pseudocholinesterase, pancreatic enzymes, and lactase; (ix) a receptor, in particular growth factor receptors; (x) an apoptosis regulator, in particular BAX; (xi) a transcription factor, in particular FOXP3; (xii) a tumor suppressor protein, in particular p53; (xiii) a structural protein, in particular surfactant protein B; (xiv) a reprogramming factor, e.g., selected from the group consisting of OCT4, SOX2, c-MYC, KLF4, LIN28 and NANOG; (xv) a genomic engineering protein, in particular clustered regularly spaced short palindromic repeat-CRISPR-associated protein 9 (CRISPR-Cas9); and (xvi) a blood protein, in particular fibrinogen.

In some embodiments, a pharmaceutically active peptide or protein comprises one or more antigens or one or more epitopes, i.e., administration of the peptide or protein to a subject elicits an immune response against the one or more antigens or one or more epitopes in a subject which may be therapeutic or partially or fully protective.

In certain embodiments, the RNA (preferably mRNA) encodes at least one epitope, e.g., at least two epitopes, at least three epitopes, at least four epitopes, at least five epitopes, at least six epitopes, at least seven epitopes, at least eight epitopes, at least nine epitopes, or at least ten epitopes.

In certain embodiments, the target antigen is a tumor antigen and the antigenic sequence (e.g., an epitope) is derived from the tumor antigen. The tumor antigen may be a “standard” antigen, which is generally known to be expressed in various cancers. The tumor antigen may also be a “neo-antigen”, which is specific to an individual’s tumor and has not been previously recognized by the immune system. A neo-antigen or neo-epitope may result from one or more cancer-specific mutations in the genome of cancer cells resulting in amino acid changes. If the tumor antigen is a neo-antigen, the vaccine antigen preferably comprises an epitope or a fragment of said neo-antigen comprising one or more amino acid changes.

Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A 10, MAGE-A 11, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes. The use of multiple epitopes has been shown to promote therapeutic efficacy in tumor vaccine compositions. Rapid sequencing of the tumor mutanome may provide multiple epitopes for individualized vaccines which can be encoded by RNA (in particular mRNA) described herein, e.g., as a single polypeptide wherein the epitopes are optionally separated by linkers. In certain embodiments of the present disclosure, the RNA (in particular mRNA) encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA (in particular, mRNA) that encodes at least five epitopes (termed a "pentatope") and RNA (in particular, mRNA) that encodes at least ten epitopes (termed a "decatope").

In certain embodiments, the epitope is derived from a pathogen-associated antigen. In some embodiments, the pharmaceutically active polypeptide and/or the antigen or epitope is derived from or is a protein of a pathogen, an immunogenic variant of the protein, or an immunogenic fragment of the protein or the immunogenic variant thereof.

In some embodiments, the pathogen is selected from viruses, bacteria, fungi, parasites, and other microorganisms.

Exemplary viruses include, but are not limited to, are severe acute respiratory syndrome coronavirus (SARS-CoV), such as SARS-CoV2, human immunodeficiency virus (HIV), Epstein-Barr virus (EBV), cytomegalovirus (CMV) (e.g., CMV5), human herpesviruses (HHV) (e.g., HHV6, 7 or 8), herpes simplex viruses (HSV), bovine herpes virus (BHV) (e.g., BHV4), equine herpes virus (EHV) (e.g., EHV2), human T-Cell leukemia viruses (HTLV)5, Varicella-Zoster virus (VZV), measles virus, papovaviruses (JC and BK), hepatitis viruses (e.g., HBV or HCV), myxoma virus, adenoviruses, rhinoviruses, enteroviruses, parvoviruses, polyoma virus, influenza viruses, papillomaviruses (such as human papillomavirus (HPV)), poxviruses such as vaccinia virus, and molluscum contagiosum virus (MCV), lyssaviruses, rotaviruses, noroviruses, rubella viruses, and mumps viruses. Exemplary diseases caused by viral infection include, but are not limited to, SARS, acquired immune deficiency syndrome (AIDS), measles, chicken pox, cytomegalovirus infections, genital herpes, hepatitis (such as hepatitis B or C), influenza (flu, such as human flu, swine flu, dog flu, horse flu, and avian flu), HPV infection, shingles, rabies, common cold, gastroenteritis, rubella, and mumps.

Exemplary bacteria include, but are not limited to, *Campylobacter* (such as *Campylobacter jejuni*), *Enterobacter* species, *Enterococcus faecium, Enterococcus faecalis, Escherichia coli* (e.g., *E. coli* O157:H7), Group A streptococci, *Haemophilus influenzae, Helicobacter pylori, listeria, Mycobacterium tuberculosis, Pseudomonas aeruginosa, S. pneumoniae, Salmonella, Shigella, Staphylococcus aureus, Staphylococcus epidermidis, Borrelia* and *Rickettsia*, Chlamydiaceae, *Neisseria gonorrhoeae, Bordetella pertussis, Clostridium tetani, Neisseria meningitidis, Streptococcus* (such as *Streptococcus pneumoniae* or *Streptococcus pyogenes*), and *Treponema pallidum*. Exemplary diseases caused by bacterial infection include, but are not limited to, anthrax, cholera, diphtheria, foodborne illnesses, leprosy, meningitis, peptic ulcer disease, pneumonia, sepsis, septic shock, tetanus, tuberculosis, typhoid fever, urinary tract infection, Lyme disease, Rocky Mountain spotted fever, *chlamydia*, gonorrhea, pertussis, tetanus, meningitis, scarlet fever, and syphilis.

Exemplary parasites include, but are not limited to, *Plasmodium, Trypanosoma, Leishmania, Trichomonas, Dientamoeba, Giardia, Entamoeba histolytica, Naegleria, Isospora, Toxoplasma, Sarcocystis, Rhinosporidium seeberi*, and *Balantidium*. Exemplary diseases caused by parasite infection include, but are not limited to, malaria, trypanosomiasis, Chagas disease, leishmaniasis, trichomoniasis, dientamoebiasis, giardiasis, amebic dysentery, coccidiosis, toxoplasmosis, sarcocystosis, rhinosporidiosis, and balantidiasis.

In some embodiments, the pathogen is an infectious pathogen, in particular a pathogen causing an infectious disease, such as a viral disease, a bacterial disease, or a parasitic disease. In some embodiments, the pathogen is a virus, bacterium, or parasite. Thus, in these embodiments, the RNA (in particular mRNA) and/or compositions described herein can be used to prevent and/or treat an infectious disease caused by said pathogen.

In certain embodiments, the epitope is derived from a viral antigen.

In some embodiments, the antigen or epitope is derived from a coronavirus protein, an immunogenic variant thereof, or an immunogenic fragment of the coronavirus protein or the immunogenic variant thereof. Thus, in some embodiments, the mRNA used in the present disclosure encodes an amino acid sequence comprising a coronavirus protein, an immunogenic variant thereof, or an immunogenic fragment of the coronavirus protein or the immunogenic variant thereof.

In some embodiments, the antigen or epitope is derived from a coronavirus S protein, an immunogenic variant thereof, or an immunogenic fragment of the coronavirus S protein or the immunogenic variant thereof. Thus, in some embodiments, the RNA (in particular, mRNA) described in the present disclosure encodes an amino acid sequence comprising a coronavirus S protein, an immunogenic variant thereof, or an immunogenic fragment of the coronavirus S protein or the immunogenic variant thereof. In some embodiments, the coronavirus is MERS-CoV. In some embodiments, the coronavirus is SARS-CoV. In some embodiments, the coronavirus is SARS-CoV-2.

Coronaviruses are enveloped, positive-sense, single-stranded RNA ((+) ssRNA) viruses. They have the largest genomes (26-32 kb) among known RNA viruses and are phylogenetically divided into four genera (α, β, γ, and δ), with betacoronaviruses further subdivided into four lineages (A, B, C, and D). Coronaviruses infect a wide range of avian and mammalian species, including humans. Some human coronaviruses generally cause mild respiratory diseases, although severity can be greater in infants, the elderly, and the immunocompromised. Middle East respiratory syndrome coronavirus (MERS-CoV) and severe acute respiratory syndrome coronavirus (SARS-CoV), belonging to betacoronavirus lineages C and B, respectively, are highly pathogenic. Both viruses emerged into the human population from animal reservoirs within the last 15 years and caused outbreaks with high case-fatality rates. The outbreak of severe acute respiratory syndrome coronavirus-2 (SARS-CoV-2) that causes atypical pneumonia (coronavirus disease 2019; COVID-19) has raged in China since mid-December 2019, and has developed to be a public health emergency of international concern. SARS-CoV-2 (MN908947.3) belongs to betacoronavirus lineage B. It has at least 70% sequence similarity to SARS-CoV.

In general, coronaviruses have four structural proteins, namely, envelope (E), membrane (M), nucleocapsid (N), and spike (S). The E and M proteins have important functions in the viral assembly, and the N protein is necessary for viral RNA synthesis. The critical glycoprotein S is responsible for virus binding and entry into target cells. The S protein is synthesized as a single-chain inactive precursor that is cleaved by furin-like host proteases in the producing cell into two noncovalently associated subunits, S1 and S2. The S1 subunit contains the receptor-binding domain (RBD), which recognizes the host-cell receptor. The S2 subunit contains the fusion peptide, two heptad repeats, and a transmembrane domain, all of which are required to mediate fusion of the viral and host-cell membranes by undergoing a large conformational rearrangement. The S1 and S2 subunits trimerize to form a large prefusion spike.

The S precursor protein of SARS-CoV-2 can be proteolytically cleaved into Si (685 aa) and S2 (588 aa) subunits. The Si subunit comprises the receptor-binding domain (RBD), which mediates virus entry into sensitive cells through the host angiotensin-converting enzyme 2 (ACE2) receptor.

In some embodiments, the antigen or epitope is derived from a SARS-CoV-2 S protein, an immunogenic variant thereof, or an immunogenic fragment of the SARS-CoV-2 S protein or the immunogenic variant thereof. Thus, in some embodiments, the RNA (preferably mRNA) described in the present disclosure encodes an amino acid sequence comprising a SARS-CoV-2 S protein, an immunogenic variant thereof, or an immunogenic fragment of the SARS-CoV-2 S protein or the immunogenic variant thereof. Thus, in some embodiments, the encoded amino acid sequence comprises an epitope of SARS-CoV-2 S protein or an immunogenic variant thereof for inducing an immune response against coronavirus S protein, in particular SARS-CoV-2 S protein in a subject.

In some embodiments, RNA (in particular, mRNA) is administered to provide (following expression by appropriate target cells) antigen for induction of an immune response, e.g., antibodies and/or immune effector cells, which is targeted to target antigen (coronavirus S protein, in particular SARS-CoV-2 S protein) or a procession product thereof. In some embodiments, the immune response which is to be induced according to the present disclosure is a B cell-mediated immune response, i.e., an antibody-mediated immune response. Additionally or alternatively, in some embodiments, the immune response which is to be induced according to the present disclosure is a T cell-mediated immune response. In some embodiments, the immune response is an anti-coronavirus, in particular anti-SARS-CoV-2 immune response.

In some embodiments, an immunogenic fragment of the SARS-CoV-2 S protein comprises the S1 subunit of the SARS-CoV-2 S protein, or the receptor binding domain (RBD) of the S1 subunit of the SARS-CoV-2 S protein. In some embodiments, the RNA (e.g., mRNA) described in the present disclosure comprises an open reading frame encoding a polypeptide that comprises a receptor-binding portion of a SARS-CoV-2 S protein, which RNA is suitable for intracellular expression of the polypeptide. In some embodiments, such an encoded polypeptide does not comprise the complete S protein. In some embodiments, the encoded polypeptide comprises the receptor binding domain (RBD).

Those skilled in the art are aware of various spike variants, and/or resources that document them.

In some embodiments, RNA (in particular, mRNA) described herein (e.g., contained in the compositions of the present disclosure and/or used in the methods of the present disclosure) encodes an amino acid sequence which comprises, consists essentially of or consists of a spike (S) protein of SARS-CoV-2, a variant thereof, or a fragment thereof.

In some embodiments, the amino acid sequence comprising a SARS-CoV-2 S protein, an immunogenic variant thereof, or an immunogenic fragment of the SARS-CoV-2 S protein or the immunogenic variant thereof is able to form a multimeric complex, in particular a trimeric complex. To this end, the amino acid sequence comprising a SARS-CoV-2 S protein, an immunogenic variant thereof, or an immunogenic fragment of the SARS-CoV-2 S protein or the immunogenic variant thereof may comprise a domain allowing the formation of a multimeric complex, in particular a trimeric complex of the amino acid sequence comprising a SARS-CoV-2 S protein, an immunogenic variant thereof, or an immunogenic fragment of the SARS-CoV-2 S protein or the immunogenic variant thereof. In some embodiments, the domain allowing the formation of a multimeric complex comprises a trimerization domain, for example, a trimerization domain as described herein.

In some embodiments, the trimerization domain is fused, either directly or through a linker, e.g., a glycine/serine linker, to a SARS-CoV-2 S protein, a variant thereof, or a fragment thereof, i.e., the antigenic peptide or protein. Accordingly, in some embodiments, a trimerization domain is fused to the above described amino acid sequences derived from SARS-CoV-2 S protein or immunogenic fragments thereof (antigenic peptides or proteins) comprised by the encoded amino acid sequences described above (which may optionally be fused to a signal peptide as described above).

Such trimerization domains are preferably located at the C-terminus of the antigenic peptide or protein, without being limited thereto. Trimerization domains as defined herein preferably allow the trimerization of the antigenic peptide or protein as encoded by the RNA. Examples of trimerization domains as defined herein include, without being limited thereto, foldon, the natural trimerization domain of T4 fibritin. The C-terminal domain of T4 fibritin (foldon) is obligatory for the formation of the fibritin trimer structure and can be used as an artificial trimerization domain.

In some embodiments, the RBD antigen expressed by an RNA encoding a SARS-CoV-2 S protein, an immunogenic variant thereof, or an immunogenic fragment of the SARS-CoV-2 S protein or the immunogenic variant thereof (e.g., as described herein) can be modified by addition of a T4-fibritin-derived "foldon" trimerization domain, for example, to increase its immunogenicity.

In some embodiments, the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In some embodiments of the RNA encoding a SARS-CoV-2 S protein, an immunogenic variant thereof, or an immunogenic fragment of the SARS-CoV-2 S protein or the immunogenic variant thereof, said RNA contains one or more of the above described RNA modifications, i.e., incorporation of a 5'-cap structure, incorporation of a poly-A sequence, unmasking of a poly-A sequence, alteration of the 5'- and/or 3'-UTR (such as incorporation of one or more 3'-UTRs), replacing one or more naturally occurring nucleotides with synthetic nucleotides (e.g., 5-methylcytidine for cytidine and/or pseudouridine (Ψ) or N(1)-methylpseudouridine (m1Ψ) or 5-methyluridine (m5U) for uridine), and codon optimization. In one embodiment, said RNA contains a combination of the above described modifications, preferably a combination of at least two, at least three, at least four or all five of the above-mentioned modifications, i.e., (i) incorporation of a 5'-cap structure, (ii) incorporation of a poly-A sequence, unmasking of a poly-A sequence; (iii) alteration of the 5'- and/or 3'-UTR (such as incorporation of one or more 3'-UTRs); (iv) replacing one or more naturally occurring nucleotides with synthetic nucleotides (e.g., 5-methylcytidine for cytidine and/or pseudouridine (Ψ) or N(1)-methylpseudouridine (m1Ψ) or 5-methyluridine (m5U) for uridine), and (v) codon optimization.

In some embodiments of the RNA encoding a SARS-CoV-2 S protein, an immunogenic variant thereof, or an immunogenic fragment of the SARS-CoV-2 S protein or the immunogenic variant thereof, said RNA is a modified RNA, in particular a stabilized mRNA. In some embodiments, said RNA comprises a modified nucleoside in place of at least one uridine. In some embodiments, said RNA comprises a modified nucleoside in place of uridine, such as in place of each uridine. In some embodiments, the modified nucleoside is independently selected from pseudouridine (ψ), N1-methyl-pseudouridine (m1ψ), and 5-methyl-uridine (m5U). In some embodiments, said RNA comprises a 5' cap, preferably a cap1 or cap2 structure, more preferably a cap1 structure. In some embodiments, said RNA comprises a 5'-UTR comprising the nucleotide sequence of SEQ ID NO: 1, or a nucleotide sequence having at least 99%, 98%, 97%, 96%, 95%, 90%, 85%, or 80% identity to the nucleotide sequence of SEQ ID NO: 1.

In some embodiments, said RNA comprises a 3'-UTR comprising the nucleotide sequence of SEQ ID NO: 2, or a nucleotide sequence having at least 99%, 98%, 97%, 96%, 95%, 90%, 85%, or 80% identity to the nucleotide sequence of SEQ ID NO: 2. In some embodiments, said RNA comprises a poly-A sequence. In some embodiments, the poly-A sequence comprises at least 100 nucleotides. In some embodiments, the poly-A sequence comprises or consists of the nucleotide sequence of SEQ ID NO: 3.

In some embodiments of the RNA encoding a SARS-CoV-2 S protein, an immunogenic variant thereof, or an immunogenic fragment of the SARS-CoV-2 S protein or the immunogenic variant thereof, said variants include mutations in RBD and/or mutations in spike protein. Those skilled in the art are aware of various spike variants, and/or resources that document them (e.g., the Table of mutating sites in Spike maintained by the COVID-19 Viral Genome Analysis Pipeline and found at https://cov.lanl.gov/components/sequence/COV/int_sites_tbls.comp) (last accessed 24 Aug. 2020), and, reading the present specification, will appreciate that RNA compositions and/or methods described herein can be characterized for their ability to induce sera in vaccinated subject that display neutralizing activity with respect to any or all of such variants and/or combinations thereof.

In some embodiments of the RNA encoding a SARS-CoV-2 S protein, an immunogenic variant thereof, or an immunogenic fragment of the SARS-CoV-2 S protein or the immunogenic variant thereof, said variants include "Variant of Concern 202012/01" (VOC-202012/01; also known as lineage B.1.1.7). The variant had previously been named the first Variant Under Investigation in December 2020 (VUI-202012/01) by Public Health England, but was reclassified to a Variant of Concern (VOC-202012/01). VOC-202012/01 is a variant of SARS-CoV-2 which was first detected in October 2020 during the COVID-19 pandemic in the United Kingdom from a sample taken the previous month, and it quickly began to spread by mid-December. It is correlated with a significant increase in the rate of COVID-19 infection in United Kingdom; this increase is thought to be at least partly because of change N501Y inside the spike glycoprotein's receptor-binding domain, which is needed for binding to ACE2 in human cells. The VOC-202012/01 variant is defined by 23 mutations: 13 non-synonymous mutations, 4 deletions, and 6 synonymous mutations (i.e., there are 17 mutations that change proteins and six that do not). The spike protein changes in VOC 202012/01 include deletion 69-70, deletion 144, N501Y, A570D, D614G, P681H, T716I, S982A, and D1118H. One of the most important changes in VOC-202012/01 seems to be N501Y, a change from asparagine (N) to tyrosine (Y) at amino-acid site 501. This mutation alone or in combination with the deletion at positions 69/70 in the N terminal domain (NTD) may enhance the transmissibility of the virus.

In some embodiments of the RNA encoding a SARS-CoV-2 S protein, an immunogenic variant thereof, or an immunogenic fragment of the SARS-CoV-2 S protein or the immunogenic variant thereof, said variants include variant "501.V2". This variant was first observed in samples from October 2020, and since then more than 300 cases with the 501.V2 variant have been confirmed by whole genome sequencing (WGS) in South Africa, where in December 2020 it was the dominant form of the virus. Preliminary results indicate that this variant may have an increased transmissibility. The 501.V2 variant is defined by multiple spike protein changes including: D80A, D215G, E484K, N501Y and A701V, and more recently collected viruses have additional changes: L18F, R246I, K417N, and deletion 242-244.

In some embodiments of the RNA encoding a SARS-CoV-2 S protein, an immunogenic variant thereof, or an immunogenic fragment of the SARS-CoV-2 S protein or the immunogenic variant thereof, said variants include variant "Cluster 5", also referred to as ΔFVI-spike by the Danish State Serum Institute (SSI). It was discovered in North Jutland, Denmark, and is believed to have been spread from minks to humans via mink farms. In cluster 5, several different mutations in the spike protein of the virus have been confirmed. The specific mutations include 69-70deltaHV (a deletion of the histidine and valine residues at the 69th and 70th position in the protein), Y453F (a change from tyrosine to phenylalanine at position 453), 1692V (isoleucine to valine at position 692), M12291 (methionine to isoleucine at position 1229), and optionally S1147L (serine to leucine at position 1147).

In some embodiments of the RNA encoding a SARS-CoV-2 S protein, an immunogenic variant thereof, or an immunogenic fragment of the SARS-CoV-2 S protein or the immunogenic variant thereof, said variants include variant lineage B.1.1.248, known as the Brazil(ian) variant. This variant of SARS-CoV-2 has been named P.1 lineage and has 17 unique amino acid changes, 10 of which in its spike protein, including N501Y and E484K. B.1.1.248 originated from B.1.1.28. E484K is present in both B.1.1.28 and B.1.1.248. B.1.1.248 has a number of S-protein polymorphisms [L18F, T20N, P26S, D138Y, R190S, K417T, E484K, N501Y, H655Y, T1027I, V1176F] and is similar in certain key RBD positions (K417, E484, N501) to variant described from South Africa.

In some embodiments of the RNA encoding a SARS-CoV-2 S protein, an immunogenic variant thereof, or an immunogenic fragment of the SARS-CoV-2 S protein or the immunogenic variant thereof, said variants include variant lineage B.1.1.529, known as the Omicron variant. This variant has a large number of mutations, including A67V, A69-70, T95I, G142D, Δ143-145, Δ211, L212I, ins214EPE (insertion of EPE following amino acid 214), G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F.

In some embodiments of the present disclosure, the antigen (such as a tumor antigen or vaccine antigen) is preferably administered as single-stranded, 5' capped RNA (preferably mRNA) that is translated into the respective protein upon entering cells of a subject being administered the RNA. Preferably, the RNA contains structural elements optimized for maximal efficacy of the RNA with respect to stability and translational efficiency (5' cap, 5' UTR, 3' UTR, poly(A) sequence).

In some embodiments, beta-S-ARCA(D1) is utilized as specific capping structure at the 5'-end of the RNA. In one embodiment, $m_2^{7,3'O}$-Gppp($m_1^{2'-O}$)ApG is utilized as specific capping structure at the 5'-end of the RNA. In some embodiments, the 5'-UTR sequence is derived from the human alpha-globin mRNA and optionally has an optimized 'Kozak sequence' to increase translational efficiency. In some embodiments, a combination of two sequence elements (FI element) derived from the "amino terminal enhancer of split" (AES) mRNA (called F) and the mitochondrial encoded 12S ribosomal RNA (called I) are placed between the coding sequence and the poly(A) sequence to assure higher maximum protein levels and prolonged persistence of the mRNA. In some embodiments, two re-iterated 3'-UTRs derived from the human beta-globin mRNA are placed between the coding sequence and the poly(A) sequence to assure higher maximum protein levels and prolonged persistence of the mRNA. In some embodiments, a poly(A) sequence measuring 110 nucleotides in length, consisting of a stretch of 30 adenosine residues, followed by a 10 nucleotide linker sequence and another 70 adenosine residues is used. This poly(A) sequence was designed to enhance RNA stability and translational efficiency.

In general, vaccine RNA described herein may comprise, from 5' to 3', one of the following structures:

Cap-5'-UTR-Vaccine Antigen-Encoding Sequence-3'-UTR-Poly(A)

or beta-S-ARCA(D1)-hAg-Kozak-Vaccine Antigen-Encoding Sequence-FI-A30L70.

The above described RNA or RNA encoding the above described vaccine antigen may be non-modified uridine containing mRNA (uRNA), nucleoside modified mRNA (modRNA) or self-amplifying RNA (saRNA). In some embodiments, the above described RNA or RNA encoding the above described vaccine antigen is nucleoside modified mRNA (modRNA).

Non-Modified Uridine Messenger RNA (uRNA)

The active principle of the non-modified messenger RNA (uRNA) is a single-stranded mRNA that is translated upon entering a cell. In addition to the sequence encoding the vaccine antigen (i.e. open reading frame), each uRNA preferably contains common structural elements optimized for maximal efficacy of the RNA with respect to stability and translational efficiency (5'-cap, 5'-UTR, 3'-UTR, poly(A)-tail). The preferred 5' cap structure is beta-S-ARCA(D1) ($m_2^{7,2'-O}$ GppSpG). The preferred 5'-UTR and 3'-UTR comprise the nucleotide sequence of SEQ ID NO: 1 and the nucleotide sequence of SEQ ID NO: 2, respectively. The preferred poly(A)-tail comprises the sequence of SEQ ID NO: 3.

In this respect, "hAg-Kozak" mean the 5'-UTR sequence of the human alpha-globin mRNA with an optimized 'Kozak sequence' to increase translational efficiency; "FI element" means that the 3'-UTR is a combination of two sequence elements derived from the "amino terminal enhancer of split" (AES) mRNA (called F) and the mitochondrial encoded 12S ribosomal RNA (called I). These were identified by an ex vivo selection process for sequences that confer RNA stability and augment total protein expression; "A30L70" means a poly(A)-tail measuring 110 nucleotides in length, consisting of a stretch of 30 adenosine residues, followed by a 10 nucleotide linker sequence and another 70 adenosine residues designed to enhance RNA stability and translational efficiency in dendritic cells; "GS" means a glycine-seine linker, i.e., sequences coding for short linker peptides predominantly consisting of the amino acids glycine (G) and serine (S), as commonly used for fusion proteins.

Nucleoside Modified Messenger RNA (modRNA)

The active principle of the nucleoside modified messenger RNA (modRNA) drug substance is as well a single-stranded mRNA that is translated upon entering a cell. In addition to the sequence encoding the vaccine antigen (i.e., open reading frame), each modRNA contains common structural elements optimized for maximal efficacy of the RNA as the uRNA (5'-cap, 5'-UTR, 3'-UTR, poly(A)-tail). Compared to the uRNA, modRNA contains 1-methyl-pseudouridine instead of uridine. The preferred 5' cap structure is $m_2$7'3 Gppp($m_{12}$-O)ApG. The preferred 5'-UTR and 3'-UTR comprise the nucleotide sequence of SEQ ID NO: 1 and the nucleotide sequence of SEQ ID NO: 2, respectively. The preferred poly(A)-tail comprises the sequence of SEQ ID NO: 3. An additional purification step is applied for modRNA to reduce dsRNA contaminants generated during the in vitro transcription reaction.

Self-Amplifying RNA (saRNA)

The active principle of the self-amplifying mRNA (saRNA) drug substance is a single-stranded RNA, which self-amplifies upon entering a cell, and the vaccine antigen is translated thereafter. In contrast to uRNA and modRNA that preferably code for a single protein, the coding region of saRNA contains two open reading frames (ORFs). The 5'-ORF encodes the RNA-dependent RNA polymerase such as Venezuelan equine encephalitis virus (VEEV) RNA-dependent RNA polymerase (replicase). The replicase ORF is followed 3' by a subgenomic promoter and a second ORF encoding the antigen. Furthermore, saRNA UTRs contain 5' and 3' conserved sequence elements (CSEs) required for self-amplification. The saRNA contains common structural elements optimized for maximal efficacy of the RNA as the uRNA (5'-cap, 5'-UTR, 3'-UTR, poly(A)-tail). The saRNA preferably contains uridine. The preferred 5' cap structure is beta-S-ARCA(D1) ($m_2^{7,2'-O}$ GppSpG).

Cytoplasmic delivery of saRNA initiates an alphavirus-like life cycle. However, the saRNA does not encode for alphaviral structural proteins that are required for genome packaging or cell entry, therefore generation of replication competent viral particles is very unlikely to not possible. Replication does not involve any intermediate steps that generate DNA. The use/uptake of saRNA therefore poses no risk of genomic integration or other permanent genetic modification within the target cell. Furthermore, the saRNA itself prevents its persistent replication by effectively activating innate immune response via recognition of dsRNA intermediates.

Furthermore, a secretory signal peptide (sec) may be fused to the antigen-encoding regions preferably in a way that the see is translated as N terminal tag. In some embodiments, see corresponds to the secretory signal peptide of the S protein. Sequences coding for short linker peptides predominantly consisting of the amino acids glycine (G) and serine (S), as commonly used for fusion proteins may be used as GS/Linkers.

In some embodiments, RNA (preferably mRNA) encoding an antigen (such as a tumor antigen or a vaccine antigen) is expressed in cells of the subject treated to provide the antigen. In some embodiments, the RNA is transiently expressed in cells of the subject. In some embodiments, the RNA is in vitro transcribed. In some embodiments, expression of the antigen is at the cell surface. In some embodiments, the antigen is expressed and presented in the context of MHC. In some embodiments, expression of the antigen is into the extracellular space, i.e., the antigen is secreted.

The antigen molecule or a procession product thereof, e.g., a fragment thereof, may bind to an antigen receptor such as a BCR or TCR carried by immune effector cells, or to antibodies.

A peptide and protein antigen which is provided to a subject according to the present disclosure by administering RNA (such as mRNA) encoding a peptide and protein antigen, wherein the antigen is a vaccine antigen, preferably results in the induction of an immune response, e.g., a humoral and/or cellular immune response in the subject being provided the peptide or protein antigen. Said immune response is preferably directed against a target antigen. Thus, a vaccine antigen may comprise the target antigen, a variant thereof, or a fragment thereof. In one embodiment, such fragment or variant is immunologically equivalent to the target antigen. In the context of the present disclosure, the term “fragment of an antigen” or “variant of an antigen” means an agent which results in the induction of an immune response which immune response targets the antigen, i.e. a target antigen. Thus, the vaccine antigen may correspond to or may comprise the target antigen, may correspond to or may comprise a fragment of the target antigen or may correspond to or may comprise an antigen which is homologous to the target antigen or a fragment thereof. Thus, according to the present disclosure, a vaccine antigen may comprise an immunogenic fragment of a target antigen or an amino acid sequence being homologous to an immunogenic fragment of a target antigen. An “immunogenic fragment of an antigen” according to the disclosure preferably relates to a fragment of an antigen which is capable of inducing an immune response against the target antigen. The vaccine antigen may be a recombinant antigen.

The term “immunologically equivalent” means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term “immunologically equivalent” is preferably used with respect to the immunological effects or properties of antigens or antigen variants used for immunization. For example, an amino acid sequence is immunologically equivalent to a reference amino acid sequence if said amino acid sequence when exposed to the immune system of a subject induces an immune reaction having a specificity of reacting with the reference amino acid sequence. Thus, in some embodiments, a molecule which is immunologically equivalent to an antigen exhibits the same or essentially the same properties and/or exerts the same or essentially the same effects regarding the stimulation, priming and/or expansion of T cells as the antigen to which the T cells are targeted.

In one embodiment, the RNA (preferably mRNA) used in the present disclosure is non-immunogenic. RNA encoding an immunostimulant may be administered according to the present disclosure to provide an adjuvant effect. The RNA encoding an immunostimulant may be standard RNA or non-immunogenic RNA.

The term “non-immunogenic RNA” (such as “non-immunogenic mRNA”) as used herein refers to RNA that does not induce a response by the immune system upon administration, e.g., to a mammal, or induces a weaker response than would have been induced by the same RNA that differs only in that it has not been subjected to the modifications and treatments that render the non-immunogenic RNA non-immunogenic, i.e., than would have been induced by standard RNA (stdRNA). In certain embodiments, non-immunogenic RNA, which is also termed modified RNA (modRNA) herein, is rendered non-immunogenic by incorporating modified nucleosides suppressing RNA-mediated activation of innate immune receptors into the RNA and/or limiting the amount of double-stranded RNA (dsRNA), e.g., by limiting the formation of double-stranded RNA (dsRNA), e.g., during in vitro transcription, and/or by removing double-stranded RNA (dsRNA), e.g., following in vitro transcription. In certain embodiments, non-immunogenic RNA is rendered non-immunogenic by incorporating modified nucleosides suppressing RNA-mediated activation of innate immune receptors into the RNA and/or by removing double-stranded RNA (dsRNA), e.g., following in vitro transcription.

For rendering the non-immunogenic RNA (especially mRNA) non-immunogenic by the incorporation of modified nucleosides, any modified nucleoside may be used as long as it lowers or suppresses immunogenicity of the RNA. Particularly preferred are modified nucleosides that suppress RNA-mediated activation of innate immune receptors. In some embodiments, the modified nucleosides comprise a replacement of one or more uridines with a nucleoside comprising a modified nucleobase. In one embodiment, the modified nucleobase is a modified uracil. In some embodiments, the nucleoside comprising a modified nucleobase is selected from the group consisting of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($nCm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine(τm5s2U), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3$ $\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($nCm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one particularly preferred embodiment, the nucleoside comprising a modified nucleobase is pseudouridine (ψ), N1-methyl-pseudouridine (m1ψ) or 5-methyl-uridine (m5U), in particular N1-methyl-pseudouridine.

In some embodiments, the replacement of one or more uridines with a nucleoside comprising a modified nucleobase comprises a replacement of at least 1%, at least 2%, at least 3%, at least 4%, at least 5%, at least 10%, at least 25%, at least 50%, at least 75%, at least 90%, at least 95%, at least 96%, at least 97%, at least 98%, at least 99% or 100% of the uridines.

During synthesis of RNA (preferably mRNA) by in vitro transcription (IVT) using T7 RNA polymerase significant amounts of aberrant products, including double-stranded RNA (dsRNA) are produced due to unconventional activity of the enzyme. dsRNA induces inflammatory cytokines and activates effector enzymes leading to protein synthesis inhibition. Formation of dsRNA can be limited during synthesis of mRNA by in vitro transcription (IVT), for example, by limiting the amount of uridine triphosphate (UTP) during synthesis. Optionally, UTP may be added once or several times during synthesis of mRNA. Also, dsRNA can be removed from RNA such as IVT RNA, for example, by ion-pair reversed phase HPLC using a non-porous or porous C-18 polystyrene-divinylbenzene (PS-DVB) matrix. Alternatively, an enzymatic based method using *E. coli* RNaseIII that specifically hydrolyzes dsRNA but not ssRNA, thereby eliminating dsRNA contaminants from IVT RNA preparations can be used. Furthermore, dsRNA can be separated from ssRNA by using a cellulose material. In one embodiment, an RNA preparation is contacted with a cellulose material and the ssRNA is separated from the cellulose material under conditions which allow binding of dsRNA to the cellulose material and do not allow binding of ssRNA to the cellulose material. Suitable methods for providing ssRNA are disclosed, for example, in WO 2017/182524.

As the term is used herein, "remove" or "removal" refers to the characteristic of a population of first substances, such as non-immunogenic RNA, being separated from the proximity of a population of second substances, such as dsRNA, wherein the population of first substances is not necessarily devoid of the second substance, and the population of second substances is not necessarily devoid of the first substance. However, a population of first substances characterized by the removal of a population of second substances has a measurably lower content of second substances as compared to the non-separated mixture of first and second substances.

In some embodiments, the removal of dsRNA (especially dsmRNA) from non-immunogenic RNA comprises a removal of dsRNA such that less than 10%, less than 5%, less than 4%, less than 3%, less than 2%, less than 1%, less than 0.5%, less than 0.3%, or less than 0.1% of the RNA in the non-immunogenic RNA composition is dsRNA. In one embodiment, the non-immunogenic RNA (especially mRNA) is free or essentially free of dsRNA. In some embodiments, the non-immunogenic RNA (especially mRNA) composition comprises a purified preparation of single-stranded nucleoside modified RNA. For example, in some embodiments, the purified preparation of single-stranded nucleoside modified RNA (especially mRNA) is substantially free of double stranded RNA (dsRNA). In some embodiments, the purified preparation is at least 90%, at least 91%, at least 92%, at least 93%, at least 94%, at least 95%, at least 96%, at least 97%, at least 98%, at least 99%, at least 99.5%, or at least 99.9% single stranded nucleoside modified RNA, relative to all other nucleic acid molecules (DNA, dsRNA, etc.).

Various methods can be used to determine the amount of dsRNA. For example, a sample may be contacted with dsRNA-specific antibody and the amount of antibody binding to RNA may be taken as a measure for the amount of dsRNA in the sample. A sample containing a known amount of dsRNA may be used as a reference.

For example, RNA may be spotted onto a membrane, e.g., nylon blotting membrane. The membrane may be blocked, e.g., in TBS-T buffer (20 mM TRIS pH 7.4, 137 mM NaCl, 0.1% (v/v) TWEEN-20) containing 5% (w/v) skim milk powder. For detection of dsRNA, the membrane may be incubated with dsRNA-specific antibody, e.g., dsRNA-specific mouse mAb (English & Scientific Consulting, Szirik, Hungary). After washing, e.g., with TBS-T, the membrane may be incubated with a secondary antibody, e.g., HRP-conjugated donkey anti-mouse IgG (Jackson ImmunoResearch, Cat #715-035-150), and the signal provided by the secondary antibody may be detected.

In some embodiments, the non-immunogenic RNA (especially mRNA) is translated in a cell more efficiently than standard RNA with the same sequence. In some embodiments, translation is enhanced by a factor of 2-fold relative to its unmodified counterpart. In some embodiments, translation is enhanced by a 3-fold factor. In some embodiments, translation is enhanced by a 4-fold factor. In some embodiments, translation is enhanced by a 5-fold factor. In some embodiments, translation is enhanced by a 6-fold factor. In some embodiments, translation is enhanced by a 7-fold factor. In some embodiments, translation is enhanced by an 8-fold factor. In some embodiments, translation is enhanced by a 9-fold factor. In some embodiments, translation is enhanced by a 10-fold factor. In some embodiments, translation is enhanced by a 15-fold factor. In some embodiments, translation is enhanced by a 20-fold factor. In some embodiments, translation is enhanced by a 50-fold factor. In some embodiments, translation is enhanced by a 100-fold factor. In some embodiments, translation is enhanced by a 200-fold factor. In one embodiment, translation is enhanced by a 500-fold factor. In some embodiments, translation is enhanced by a 1000-fold factor. In some embodiments, translation is enhanced by a 2000-fold factor. In some embodiments, the factor is 10-1000-fold. In some embodiments, the factor is 10-100-fold. In some embodiments, the factor is 10-200-fold. In some embodiments, the factor is 10-300-fold. In some embodiments, the factor is 10-500-fold. In some embodiments, the factor is 20-1000-fold. In some embodiments, the factor is 30-1000-fold. In some embodiments, the factor is 50-1000-fold. In some embodiments, the factor is 100-1000-fold. In some embodiments, the factor is 200-1000-fold. In some embodiments, translation is enhanced by any other significant amount or range of amounts.

In some embodiments, the non-immunogenic RNA (especially mRNA) exhibits significantly less innate immunogenicity than standard RNA with the same sequence. In some embodiments, the non-immunogenic RNA (especially mRNA) exhibits an innate immune response that is 2-fold less than its unmodified counterpart. In some embodiments, innate immunogenicity is reduced by a 3-fold factor. In some embodiments, innate immunogenicity is reduced by a 4-fold factor. In some embodiments, innate immunogenicity is reduced by a 5-fold factor. In some embodiments, innate immunogenicity is reduced by a 6-fold factor. In some embodiments, innate immunogenicity is reduced by a 7-fold factor. In some embodiments, innate immunogenicity is reduced by a 8-fold factor. In some embodiments, innate immunogenicity is reduced by a 9-fold factor. In some embodiments, innate immunogenicity is reduced by a 10-fold factor. In some embodiments, innate immunogenicity is reduced by a 15-fold factor. In some embodiments, innate immunogenicity is reduced by a 20-fold factor. In some embodiments, innate immunogenicity is reduced by a 50-fold factor. In some embodiments, innate immunogenicity is reduced by a 100-fold factor. In some embodiments, innate immunogenicity is reduced by a 200-fold factor. In some embodiments, innate immunogenicity is reduced by a 500-fold factor. In some embodiments, innate immunogenicity is reduced by a 1000-fold factor. In some embodiments, innate immunogenicity is reduced by a 2000-fold factor.

The term "exhibits significantly less innate immunogenicity" refers to a detectable decrease in innate immunogenicity. In some embodiments, the term refers to a decrease such that an effective amount of the non-immunogenic RNA (especially mRNA) can be administered without triggering a detectable innate immune response. In some embodiments, the term refers to a decrease such that the non-immunogenic RNA (especially mRNA) can be repeatedly administered without eliciting an innate immune response sufficient to detectably reduce production of the protein encoded by the non-immunogenic RNA. In some embodiments, the decrease is such that the non-immunogenic RNA (especially mRNA) can be repeatedly administered without eliciting an innate immune response sufficient to eliminate detectable production of the protein encoded by the non-immunogenic RNA.

"Immunogenicity" is the ability of a foreign substance, such as RNA, to provoke an immune response in the body of a human or other animal. The innate immune system is the component of the immune system that is relatively unspecific and immediate. It is one of two main components of the vertebrate immune system, along with the adaptive immune system.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

As used herein, the terms "linked", "fused", or "fusion" are used interchangeably. These terms refer to the joining together of two or more elements or components or domains.

Particles

Nucleic acids such as RNA, in particular mRNA, described herein may be present in particles comprising (i) the nucleic acid, (ii) at least one cationic or cationically ionizable compound; and (v) a multivalent anion, such as an inorganic polyphosphate. In some embodiments, the particles comprise (i) the nucleic acid (such as RNA, in particular mRNA); (ii) at least one cationic or cationically ionizable compound as disclosed herein; (iii) a steroid as disclosed herein; (iv) a neutral lipid as disclosed herein; and (v) a multivalent anion (such as an inorganic polyphosphate) as disclosed herein. In some of these embodiments, the multivalent anion is selected from the group consisting of an inorganic polyphosphate, an inorganic phosphate, sulfate, succinate, glutarate, tartrate, malate, citrate, and mixtures thereof. In some of these embodiments, the multivalent anion is selected from the group consisting of an inorganic polyphosphate, an inorganic phosphate and citrate. In some of these embodiments, the multivalent anion is an inorganic polyphosphate.

Different types of RNA containing particles have been described previously to be suitable for delivery of RNA in particulate form (cf, e.g., Kaczmarek, J. C. et al., 2017, Genome Medicine 9, 60). For non-viral RNA delivery vehicles, nanoparticle encapsulation of RNA physically protects RNA from degradation and, depending on the specific chemistry, can aid in cellular uptake and endosomal escape.

Electrostatic interactions between positively charged molecules such as polymers and lipids and negatively charged nucleic acid are involved in particle formation. This results in complexation and spontaneous formation of nucleic acid particles.

During the manufacturing process, introduction of an aqueous solution of nucleic acid (such as RNA) to an organic (e.g., ethanolic) solution comprising a lipid mixture containing a cationically ionizable lipid at pH of, e.g., 5 leads to an electrostatic interaction between the negatively charged nucleic acid (drug substance) and the positively charged cationically ionizable lipid. This electrostatic interaction leads to particle formation coincident with efficient encapsulation of the nucleic acid (drug substance). After nucleic acid encapsulation, adjustment of the medium surrounding the resulting nucleic acid particle (such as RNA-LNP) to, e.g., pH 8 or addition of a multivalent anion (such as an inorganic polyphosphate) results in neutralization of the surface charge on the particle or—in the case of adding a multivalent anion (such as an inorganic polyphosphate)—even in the formation of stable anionic particles. It is known in the art that when all other variables are held constant, charge-neutral particles display longer in vivo circulation lifetimes and better delivery to hepatocytes compared to charged particles, which are cleared rapidly by the reticuloendothelial system. Upon endosomal uptake, the low pH of the endosome renders the particle (such as LNP) fusogenic and allows for release of the RNA into the cytosol of the target cell.

In the context of the present disclosure, the term "particle" relates to a structured entity formed by molecules or molecule complexes, in particular particle forming compounds. In some embodiments, the particle contains an envelope (e.g., one or more layers or lamellas) made of one or more types of amphiphilic substances (e.g., amphiphilic lipids, amphiphilic polymers, and/or amphiphilic proteins/polypeptides). In this context, the expression "amphiphilic substance" means that the substance possesses both hydrophilic and lipophilic properties. The envelope may also comprise additional substances (e.g., additional lipids and/or additional polymers) which do not have to be amphiphilic. Thus, the particle may be a monolamellar or multilamellar structure, wherein the substances constituting the one or more layers or lamellas comprise one or more types of amphiphilic substances (in particular selected from the group consisting of amphiphilic lipids, amphiphilic polymers, and/or amphiphilic proteins/polypeptides) optionally in combination with additional substances (e.g., additional lipids and/or additional polymers) which do not have to be amphiphilic. In some embodiments, the term "particle" relates to a micro- or nano-sized structure, such as a micro- or nano-sized compact structure. In this respect, the term "micro-sized" means that all three external dimensions of the particle are in the microscale, i.e., between 1 and 5 μm. According to the present disclosure, the term "particle" includes lipoplex particles (LPXs), lipid nanoparticles (LNPs), polyplex particles, lipopolyplex particles, virus-like particles (VLPs), and mixtures thereof (e.g., a mixture of two or more of particle types, such as a mixture of LPXs and VLPs or a mixture of LNPs and VLPs).

A "nucleic acid particle" can be used to deliver nucleic acid (such as RNA, in particular mRNA) to a target site of interest (e.g., cell, tissue, organ, and the like). A nucleic acid particle may be formed from at least one cationic or cationically ionizable lipid or lipid-like material, at least one cationic polymer such as protamine, or a mixture thereof and nucleic acid. Nucleic acid particles include lipid nanoparticle (LNP)-based, lipoplex (LPX)-based, and/or liposome-based formulations.

Without intending to be bound by any theory, it is believed that the cationic or cationically ionizable lipid or lipid-like material and/or the cationic polymer combined together with the nucleic acid to form aggregates, and this aggregation results in colloidally stable particles. In some embodiments, particles comprise an amphiphilic lipid, in particular cationic or cationically ionizable amphiphilic lipid, and nucleic acid (such as RNA, especially mRNA) as described herein. In some embodiments, particles comprise or consist of a cationic/cationically ionizable lipid (in particular, a cationically ionizable lipid of formula (X) disclosed herein; a cationically ionizable lipid having one of the structures A to G disclosed herein; or a cationically ionizable lipid of formula (XI) disclosed herein); helper lipids such as a neutral lipid (such as a phospholipid), and a steroid (such as cholesterol), and combinations thereof, and a multivalent anion (such as an inorganic polyphosphate, e.g., a linear inorganic polyphosphate, such as triphosphate).

In some embodiments, the nucleic acid (such as RNA) particles disclosed herein comprise (i) nucleic acid (such as RNA, especially mRNA) as described herein; (ii) an amphiphilic lipid, in particular cationic or cationically ionizable amphiphilic lipid, (such as a cationically ionizable lipid of formula (X) disclosed herein; a cationically ionizable lipid having one of the structures A to G disclosed herein; a cationically ionizable lipid of formula (XI) disclosed herein; or a cationic lipid as disclosed herein); (iii) a steroid (such as cholesterol), a neutral lipid (such as a phospholipid); and (v) a multivalent anion (such as an inorganic polyphosphate, e.g., a linear inorganic polyphosphate, such as triphosphate). In some embodiments, the steroid is cholesterol; and the neutral lipid is selected from the group consisting of DSPC, DPPC, DSPE, and DPPE. In some embodiments, the multivalent anion is selected from the group consisting of an inorganic polyphosphate, an inorganic phosphate, sulfate, succinate, glutarate, tartrate, malate, citrate, and mixtures thereof. In some embodiments, the multivalent anion is selected from the group consisting of an inorganic polyphosphate, an inorganic phosphate and citrate. In some embodiments, the multivalent anion is an inorganic polyphosphate, in particular a linear inorganic polyphosphate (such as a linear inorganic triphosphate). In some embodiments, the inorganic polyphosphate comprises the formula $[P_xO_{(3x+1)}]$, wherein x is an integer and is at least 3; and y is the anionic charge. In some embodiments, the inorganic polyphosphate is selected from the group consisting of diphosphate, triphosphate, tetraphosphate, pentaphosphate, hexaphosphate, heptaphosphate, and mixtures thereof, such as from the group consisting of triphosphate, tetraphosphate, pentaphosphate, hexaphosphate, heptaphosphate, and mixtures thereof. Preferably, the inorganic polyphosphate is selected from the group consisting of triphosphate, tetraphosphate, pentaphosphate, and mixtures thereof. In some preferred embodiments, the inorganic polyphosphate is triphosphate. In some embodiments, the steroid is cholesterol; the neutral lipid is selected from the group consisting of DSPC, DPPC, DSPE, and DPPE; and the inorganic polyphosphate is selected from the group consisting of diphosphate, triphosphate, tetraphosphate, pentaphosphate, hexaphosphate, heptaphosphate, and mixtures thereof, such as from the group consisting of triphosphate, tetraphosphate, pentaphosphate, hexaphosphate, heptaphosphate, and mixtures thereof preferably the inorganic polyphosphate is triphosphate.

In some embodiments, in the nucleic acid particles (such as RNA particles) described herein the nucleic acid (such as RNA, in particular, mRNA) is bound by cationically ionizable lipid (in particular a cationically ionizable lipid of formula (X) disclosed herein; a cationically ionizable lipid having one of the structures A to G disclosed herein; or a cationically ionizable lipid of formula (XI) disclosed herein) that, in the case of LNPs, occupies the central core of the LNPs. In some embodiments, the multivalent anion (such as inorganic polyphosphate, e.g., a linear inorganic polyphosphate, such as triphosphate) forms the surface of the particles (such as LNPs), along with phospholipids. In some embodiments, the particles are substantially free of a PEG lipid. In some embodiments, the particles are substantially free of PEG lipids and substantially free of polysarcosine-conjugated lipids. In some embodiments, the particles are substantially free of polymer-conjugated lipids. In some embodiments, the surface comprises a bilayer. In some embodiments, cholesterol and cationically ionizable lipid (in particular a cationically ionizable lipid of formula (X) disclosed herein; a cationically ionizable lipid having one of the structures A to G disclosed herein; or a cationically ionizable lipid of formula (XI) disclosed herein) in charged and uncharged forms can be distributed throughout the particles such as LNPs.

In general, a lipoplex (LPX) is obtainable from mixing two aqueous phases, namely a phase comprising nucleic acid (in particular RNA) and a phase comprising a dispersion of lipids. In some embodiments, the lipid phase comprises liposomes.

In some embodiments, liposomes are self-closed unilamellar or multilamellar vesicular particles wherein the lamellae comprise lipid bilayers and the encapsulated lumen comprises an aqueous phase. A prerequisite for using liposomes for nanoparticle formation is that the lipids in the mixture as required are able to form lamellar (bilayer) phases in the applied aqueous environment.

In some embodiments, liposomes comprise unilamellar or multilamellar phospholipid bilayers enclosing an aqueous core (also referred to herein as an aqueous lumen). They may be prepared from materials possessing polar head (hydrophilic) groups and nonpolar tail (hydrophobic) groups. In some embodiments, cationic lipids employed in formulating liposomes designed for the delivery of nucleic acids are amphiphilic in nature and consist of a positively charged (cationic) amine head group linked to a hydrocarbon chain or cholesterol derivative via glycerol.

In some embodiments, lipoplexes are multilamellar liposome-based formulations that form upon electrostatic interaction of cationic liposomes with RNAs. In some embodiments, formed lipoplexes possess distinct internal arrangements of molecules that arise due to the transformation from liposomal structure into compact RNA-lipoplexes. In some embodiments, these formulations are characterized by their poor encapsulation of the RNA and incomplete entrapment of the RNA.

In some embodiments, an LPX particle comprises an amphiphilic lipid, in particular cationic or cationically ionizable amphiphilic lipid, and nucleic acid (such as RNA, especially mRNA) as described herein. In some embodiments, electrostatic interactions between positively charged liposomes (made from one or more amphiphilic lipids, in particular cationic or cationically ionizable amphiphilic lipids) and negatively charged nucleic acid (such as RNA, especially mRNA) results in complexation and spontaneous formation of nucleic acid lipoplex particles. Positively charged liposomes may be generally synthesized using a cationic or cationically ionizable amphiphilic lipid, such as a cationically ionizable lipid of formula (I), DOTMA and/or DODMA, and additional lipids, such as DSPC. In some embodiments, a nucleic acid (such as RNA, especially mRNA) lipoplex particle is a nanoparticle.

In general, a lipid nanoparticle (LNP) is obtainable from direct mixing of nucleic acid (such as RNA) in an aqueous phase with lipids in a phase comprising an organic solvent, such as ethanol. In that case, lipids or lipid mixtures can be used for particle formation, which do not form lamellar (bilayer) phases in water. In some embodiments, the lipids comprise a cationically ionizable lipid (in particular a cationically ionizable lipid of formula (X) disclosed herein; a cationically ionizable lipid having one of the structures A to G disclosed herein; or a cationically ionizable lipid of formula (XI) disclosed herein), a steroid as disclosed herein (such as cholesterol), and a neutral lipid as disclosed herein (such as a phospholipid). After formation of the particles, a multivalent anion (such as an inorganic polyphosphate) as disclosed herein (such as an inorganic polyphosphate, an inorganic phosphate, sulfate, succinate, glutarate, tartrate, malate, citrate, and mixtures thereof, in particular a linear inorganic polyphosphate, e.g., triphosphate) is added to the particles resulting in the association of the multivalent anion (such as inorganic polyphosphate) to the surface of the particles due to electrostatic attraction between the positively charged surface of the particles and the anionic multivalent anion (such as anionic inorganic polyphosphate). This association (or decoration) leads to neutralization of the surface charge on the particle or even to the formation of stable anionic particles.

In some embodiments, particles described herein comprise a cationically ionizable lipid as disclosed herein (in particular a cationically ionizable lipid of formula (X) disclosed herein; a cationically ionizable lipid having one of the structures A to G disclosed herein; or a cationically ionizable lipid of formula (XI) disclosed herein), a steroid as disclosed herein (such as cholesterol), a neutral lipid as disclosed herein (such as a phospholipid), and a multivalent anion (such as an inorganic polyphosphate) as disclosed herein (such as an inorganic polyphosphate, an inorganic phosphate, sulfate, succinate, glutarate, tartrate, malate, citrate, and mixtures thereof, in particular a linear inorganic polyphosphate, e.g., triphosphate).

In some embodiments, nucleic acid particles (especially RNA particles such as RNA LNPs (e.g., mRNA particles such as mRNA LNPs)) comprise more than one type of nucleic acid molecules, where the molecular parameters of the nucleic acid molecules may be similar or different from each other, like with respect to molar mass or fundamental structural elements such as molecular architecture, capping, coding regions or other features, In some embodiments, nucleic acid (such as RNA, e.g., mRNA) described herein may be noncovalently associated with a particle as described herein. In some embodiments, the nucleic acid (such as RNA, especially mRNA) may be adhered to the outer surface of the particle (surface nucleic acid (such as surface RNA, especially surface mRNA)) and/or may be contained in the particle (encapsulated nucleic acid (such as encapsulated RNA, especially encapsulated mRNA)).

As used in the present disclosure, "nanoparticle" refers to a particle comprising nucleic acid (especially RNA such as mRNA) as described herein and at least one cationic lipid, wherein all three external dimensions of the particle are in the nanoscale, i.e., at least about 1 nm and below about 1000 nm (preferably, between 10 and 990 nm, such as between 15 and 900 nm, between 20 and 800 nm, between 30 and 700 nm, between 40 and 600 nm, or between 50 and 500 nm). Preferably, the longest and shortest axes do not differ significantly. Preferably, the size of a particle is its diameter.

Nucleic acid particles described herein (especially RNA particles, such as mRNA particles) may exhibit a polydispersity index (PDI) less than about 0.5, less than about 0.4, less than about 0.3, less than about 0.2, less than about 0.1, or less than about 0.05. By way of example, the nucleic acid particles can exhibit a polydispersity index in a range of about 0.01 to about 0.4 or about 0.1 to about 0.3.

In the context of the present disclosure, the term "lipoplex particle" relates to a particle that contains an amphiphilic lipid, in particular cationic amphiphilic lipid, and nucleic acid (especially RNA such as mRNA) as described herein. Electrostatic interactions between positively charged liposomes (made from one or more amphiphilic lipids, in particular cationic amphiphilic lipids) and negatively charged nucleic acid (especially RNA such as mRNA) results in complexation and spontaneous formation of nucleic acid lipoplex particles. Positively charged liposomes may be generally synthesized using a cationic amphiphilic lipid, such as DOTMA, and additional lipids, such as DSPC. In one embodiment, a nucleic acid (especially RNA such as mRNA) lipoplex particle is a nanoparticle.

The term "lipid nanoparticle" relates to a nano-sized lipid containing particle.

In the context of the present disclosure, the term "polyplex particle" relates to a particle that contains an amphiphilic polymer, in particular a cationic amphiphilic polymer, and nucleic acid (especially RNA such as mRNA) as described herein. Electrostatic interactions between positively charged cationic amphiphilic polymers and negatively charged nucleic acid (especially RNA such as mRNA) results in complexation and spontaneous formation of nucleic acid polyplex particles. Positively charged amphiphilic polymers suitable for the preparation of polyplex particle include protamine, polyethyleneimine, poly-L-lysine, poly-L-arginine and histone. In one embodiment, a nucleic acid (especially RNA such as mRNA) polyplex particle is a nanoparticle.

The term "lipopolyplex particle" relates to particle that contains amphiphilic lipid (in particular cationic amphiphilic lipid) as described herein, amphiphilic polymer (in particular cationic amphiphilic polymer) as described herein, and nucleic acid (especially RNA such as mRNA) as described herein. In one embodiment, a nucleic acid (especially RNA such as mRNA) lipopolyplex particle is a nanoparticle.

The term "virus-like particle" (abbreviated herein as VLP) refers to a molecule that closely resembles a virus, but which does not contain any genetic material of said virus and, thus, is non-infectious. Preferably, VLPs contain nucleic acid (preferably RNA) as described herein, said nucleic acid (preferably RNA) being heterologous to the virus(es) from which the VLPs are derived. VLPs can be synthesized through the individual expression of viral structural proteins, which can then self-assemble into the virus-like structure. In one embodiment, combinations of structural capsid proteins from different viruses can be used to create recombinant VLPs. VLPs can be produced from components of a wide variety of virus families including Hepatitis B virus (HBV) (small HBV derived surface antigen (HbsAg)), Parvoviridae (e.g., adeno-associated virus), Papillomaviridae (e.g., HPV), Retroviridae (e.g., HIV), Flaviviridae (e.g., Hepatitis C virus) and bacteriophages (e.g. Qβ, AP205).

The term "nucleic acid containing particle" relates to a particle as described herein to which nucleic acid (especially RNA such as mRNA) is bound. In this respect, the nucleic acid (especially RNA such as mRNA) may be adhered to the outer surface of the particle (surface nucleic acid (especially surface RNA such as surface mRNA)) and/or may be contained in the particle (encapsulated nucleic acid (especially encapsulated RNA such as encapsulated mRNA)).

In one embodiment, the particles utilized in the methods and uses of the present disclosure have a size (preferably a diameter, i.e., double the radius such as double the radius of gyration ($R_g$) value or double the hydrodynamic radius) in the range of about 10 to about 2000 nm, such as at least about 15 nm (preferably at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, or at least about 100 nm) and/or at most 1900 nm (preferably at most about 1900 nm, at most about 1800 nm, at most about 1700 nm, at most about 1600 nm, at most about 1500 nm, at most about 1400 nm, at most about 1300 nm, at most about 1200 nm, at most about 1100 nm, at most about 1000 nm, at most about 950 nm, at most about 900 nm, at most about 850 nm, at most about 800 nm, at most about 750 nm, at most about 700 nm, at most about 650 nm, at most about 600 nm, at most about 550 nm, or at most about 500 nm), preferably in the range of about 20 to about 1500 nm, such as about 30 to about 1200 nm, about 40 to about 1100 nm, about 50 to about 1000 nm, about 60 to about 900 nm, about 70 to 800 nm, about 80 to 700 nm, about 90 to 600 nm, or about 50 to 500 nm or about 100 to 500 nm, such as in the range of 10 to 1000 nm, 15 to 500 nm, 20 to 450 nm, 25 to 400 nm, 30 to 350 nm, 40 to 300 nm, 50 to 250 nm, 60 to 200 nm, or 70 to 150 nm.

In some embodiments, the particles (e.g., LNPs and LPXs) described herein have an average diameter that in some embodiments ranges from about 50 nm to about 1000 nm, from about 50 nm to about 800 nm, from about 50 nm to about 700 nm, from about 50 nm to about 600 nm, from about 50 nm to about 500 nm, from about 50 nm to about 450 nm, from about 50 nm to about 400 nm, from about 50 nm to about 350 nm, from about 50 nm to about 300 nm, from about 50 nm to about 250 nm, from about 50 nm to about 200 nm, from about 100 nm to about 1000 nm, from about 100 nm to about 800 nm, from about 100 nm to about 700 nm, from about 100 nm to about 600 nm, from about 100 nm to about 500 nm, from about 100 nm to about 450 nm, from about 100 nm to about 400 nm, from about 100 nm to about 350 nm, from about 100 nm to about 300 nm, from about 100 nm to about 250 nm, from about 100 nm to about 200 nm, from about 150 nm to about 1000 nm, from about 150 nm to about 800 nm, from about 150 nm to about 700 nm, from about 150 nm to about 600 nm, from about 150 nm to about 500 nm, from about 150 nm to about 450 nm, from about 150 nm to about 400 nm, from about 150 nm to about 350 nm, from about 150 nm to about 300 nm, from about 150 nm to about 250 nm, from about 150 nm to about 200 nm, from about 200 nm to about 1000 nm, from about 200 nm to about 800 nm, from about 200 nm to about 700 nm, from about 200 nm to about 600 nm, from about 200 nm to about 500 nm, from about 200 nm to about 450 nm, from about 200 nm to about 400 nm, from about 200 nm to about 350 nm, from about 200 nm to about 300 nm, or from about 200 nm to about 250 nm.

With respect to nucleic acid particles (such as RNA lipid particles, especially RNA LNPs such as mRNA LNPs), the N/P ratio or N/P value gives the ratio of the nitrogen groups (in particular positively-chargeable polymer amine (N=nitrogen) groups) in the lipid to the number of negatively-charged phosphate (P) groups in the nucleic acid. It is correlated to the charge ratio, as the nitrogen atoms (depending on the pH) are usually positively charged and the phosphate groups are negatively charged. The N/P ratio, where a charge equilibrium exists, depends on the pH. Lipid formulations are frequently formed at N/P ratios larger than four up to twelve, because positively charged nanoparticles are considered favorable for transfection. In that case, RNA is considered to be completely bound to nanoparticles.

Nucleic acid particles (especially RNA particles such as mRNA particles) described herein can be prepared using a wide range of methods that may involve obtaining a colloid from at least one cationic or cationically ionizable lipid and/or at least one cationic polymer and mixing the colloid with nucleic acid to obtain nucleic acid particles.

The term "colloid" as used herein relates to a type of homogeneous mixture in which dispersed particles do not settle out. The insoluble particles in the mixture are microscopic, with particle sizes between 1 and 1000 nanometers. The mixture may be termed a colloid or a colloidal suspension. Sometimes the term "colloid" only refers to the particles in the mixture and not the entire suspension.

For the preparation of colloids comprising at least one cationic or cationically ionizable lipid and/or at least one cationic polymer methods are applicable herein that are conventionally used for preparing liposomal vesicles and are appropriately adapted. The most commonly used methods for preparing liposomal vesicles share the following fundamental stages: (i) lipids dissolution in organic solvents, (ii)

drying of the resultant solution, and (iii) hydration of dried lipid (using various aqueous media).

In the film hydration method, lipids are firstly dissolved in a suitable organic solvent, and dried down to yield a thin film at the bottom of the flask. The obtained lipid film is hydrated using an appropriate aqueous medium to produce a liposomal dispersion. Furthermore, an additional downsizing step may be included.

Reverse phase evaporation is an alternative method to the film hydration for preparing liposomal vesicles that involves formation of a water-in-oil emulsion between an aqueous phase and an organic phase containing lipids. A brief sonication of this mixture is required for system homogenization. The removal of the organic phase under reduced pressure yields a milky gel that turns subsequently into a liposomal suspension.

The term "ethanol injection technique" refers to a process, in which an ethanol solution comprising lipids is rapidly injected into an aqueous solution through a needle. This action disperses the lipids throughout the solution and promotes lipid structure formation, for example lipid vesicle formation such as liposome formation. Generally, the nucleic acid (especially RNA such as mRNA) lipoplex particles described herein are obtainable by adding nucleic acid (especially RNA such as mRNA) to a colloidal liposome dispersion. Using the ethanol injection technique, such colloidal liposome dispersion is, in one embodiment, formed as follows: an ethanol solution comprising lipids, such as cationically ionizable lipids (like a cationically ionizable lipid of formula (X) disclosed herein; a cationically ionizable lipid having one of the structures A to G disclosed herein; a cationically ionizable lipid of formula (XI) disclosed herein; DOTMA and/or DODMA) and additional lipids (such as a polymer-conjugated lipid (e.g., a polyethylene glycol (PEG) lipid; or a polysarcosine-lipid conjugate or a conjugate of polysarcosine and a lipid-like material); a neutral lipid (such as a phospholipid); a steroid (such as cholesterol); and combinations), is injected into an aqueous solution under stirring. In some embodiments, the nucleic acid (especially RNA such as mRNA) lipoplex particles described herein are obtainable without a step of extrusion.

The term "extruding" or "extrusion" refers to the creation of particles having a fixed, cross-sectional profile. In particular, it refers to the downsizing of a particle, whereby the particle is forced through filters with defined pores.

Other methods having organic solvent free characteristics may also be used according to the present disclosure for preparing a colloid.

LNPs typically comprise four components: cationically ionizable or cationic lipids; neutral lipids such as phospholipids; a steroid such as cholesterol; and a polymer-conjugated lipid (which is sometimes called "stealth lipid" or "sterically stabilizing lipid"), such as a PEG lipid or a polysarcosine-conjugated lipid. Each component is responsible for payload protection, and enables effective intracellular delivery. However, due to the disadvantages of PEG lipids (which are the most common polymer-conjugated lipids), LNPs of the present disclosure have a slightly different composition: cationically ionizable or cationic lipids; neutral lipids such as phospholipids; a steroid such as cholesterol; and a multivalent anion (such as an inorganic polyphosphate). In some embodiments, LNPs of the present disclosure are substantially free of a PEG lipid. In some embodiments, LNPs of the present disclosure are substantially free of a polysarcosine-conjugated lipid. In some embodiments, LNPs of the present disclosure are substantially free of a PEG lipid and substantially free of a polysarcosine-conjugated lipid. In some embodiments, LNPs of the present disclosure are substantially free of polymer-conjugated lipids. In some embodiments, where LNPs of the present disclosure are substantially free of a lipid comprising PEG (such as substantially free of any compound comprising PEG or substantially free of PEG)), LNPs may have the following composition: cationically ionizable or cationic lipids; neutral lipids such as phospholipids; a steroid such as cholesterol; and a multivalent anion (such as inorganic phosphate, sulfate, succinate, glutarate, tartrate, malate, citrate, or mixtures thereof).

Figure 1B:
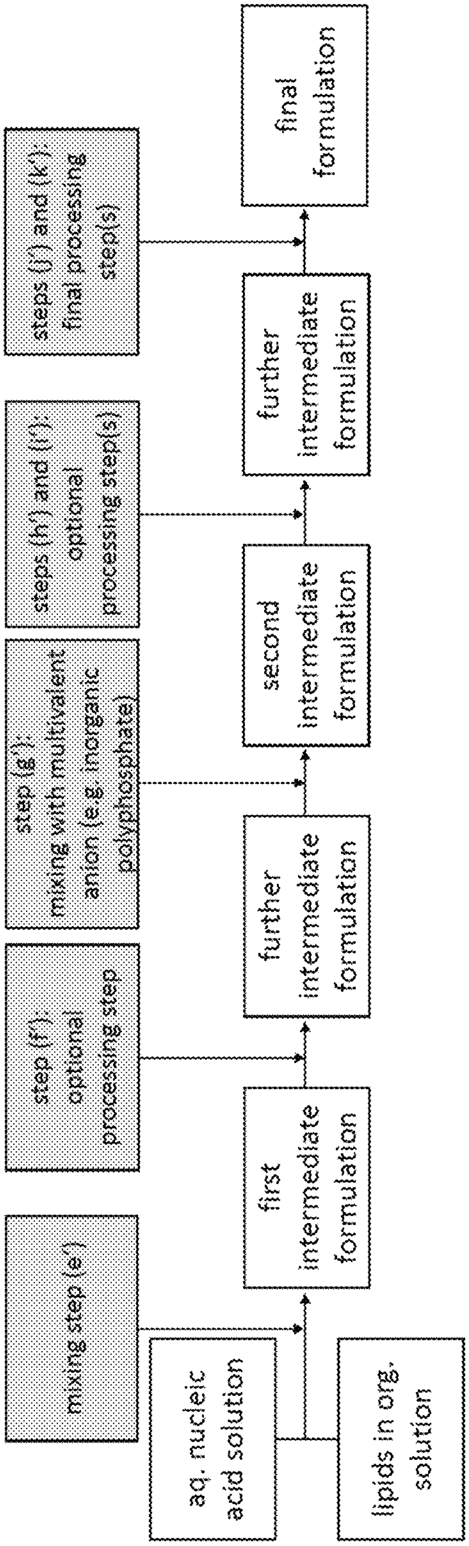
Figure 1C:
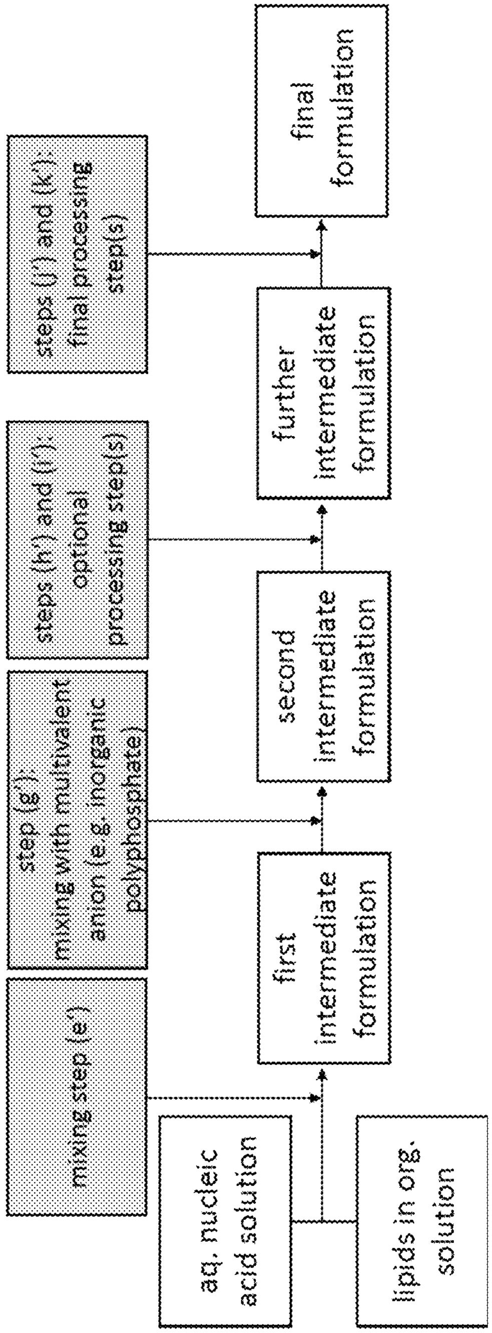

LNPs may be prepared by first mixing lipids dissolved in an organic (e.g., ethanolic) solution rapidly with nucleic acid in an aqueous buffer, and then mixing the obtained formulation with a multivalent anion (such as an inorganic polyphosphate). For example, the method of the second aspect can be used to prepare the LNPs (cf., also FIGS. 1A to C for details).

Different types of nucleic acid containing particles have been described previously to be suitable for delivery of nucleic acid in particulate form (cf., e.g., Kaczmarek, J. C. et al., 2017, Genome Medicine 9, 60). For non-viral nucleic acid delivery vehicles, nanoparticle encapsulation of nucleic acid physically protects nucleic acid from degradation and, depending on the specific chemistry, can aid in cellular uptake and endosomal escape.

In some embodiments, the LNPs comprising nucleic acid (such as RNA) and at least one cationically ionizable lipid described herein are prepared by (a) providing (e.g., preparing) a nucleic acid solution containing water and a first buffer system; (b) providing (e.g., preparing) an organic (e.g. ethanolic) solution comprising the cationically ionizable lipid, the steroid, and the neutral lipid, and optionally one or more additional lipids; (c) mixing the nucleic acid solution provided (e.g., prepared) under (a) with the organic (e.g., ethanolic) solution provided (e.g., prepared) under (b), thereby preparing a first intermediate formulation comprising the LNPs dispersed in a first aqueous phase comprising the first buffer system; and (d) mixing the first intermediate formulation prepared under (c) with a multivalent anion (such as an inorganic polyphosphate) or a salt thereof as disclosed herein, thereby preparing a second intermediate formulation comprising the particles dispersed in a second aqueous phase comprising a second buffer system, wherein at least a portion of the multivalent anion (such as the inorganic polyphosphate) is associated with the particles; and (e) filtrating (e.g., dialyzing, tangential flow filtrating, or diafiltrating) and/or diluting the second intermediate formulation prepared under (d) using a final aqueous buffer solution comprising the final buffer system, thereby preparing the formulation comprising LNPs dispersed in a final aqueous phase comprising the final buffer system. After step (e) one or more steps selected from diluting and filtrating, such as dialyzing, tangential flow filtrating or diafiltrating, can follow. In some embodiments, the first buffer system differs from the final buffer system. In alternative embodiments, the first buffer system and the final buffer system are the same. In some embodiments, in particular those where the second aqueous phase is highly similar to or substantially corresponds to the final aqueous phase or where the second aqueous phase can be transformed into the final aqueous phase simply by diluting the second aqueous phase with a suitable dilution solution (e.g., the final aqueous buffer solution), the filtrating the second intermediate formulation prepared under (d) using a final aqueous buffer solution comprising the final buffer system may be replaced by diluting the second intermediate formulation prepared under (d) using a dilution solution (e.g., the final aqueous buffer solution comprising the final buffer system).

In some embodiments, the LNPs comprising nucleic acid (such as RNA) and at least one cationically ionizable lipid described herein are prepared by (a') providing (e.g., preparing) liposomes or a colloidal preparation of the cationically ionizable lipid and, if present, one or more additional lipids in an aqueous phase; (b') providing (e.g., preparing) a nucleic acid (such as RNA) solution containing water and a buffering system; (c') mixing the liposomes or colloidal preparation provided (e.g., prepared) under (a') with the nucleic acid (such as RNA) solution provided (e.g., prepared) under (b'); and (d') mixing the formulation prepared under (c') with a multivalent anion (such as an inorganic polyphosphate) or a salt thereof. After step (d') one or more steps selected from diluting and filtrating, such as dialyzing, tangential flow filtrating, or diafiltrating, can follow. In case the LNPs comprise a multivalent anion (e.g., inorganic phosphate, sulfate, succinate, glutarate, tartrate, malate, citrate, or mixtures thereof) instead of a multivalent anion (such as an inorganic polyphosphate), step (d') is mixing the formulation prepared under (c') with the multivalent anion (e.g., inorganic phosphate, sulfate, succinate, glutarate, tartrate, malate, citrate, or mixtures thereof), or a salt thereof.

The present disclosure describes compositions which comprise nucleic acid (such as RNA, especially mRNA), and at least one cationically ionizable lipid which associates with the nucleic acid (such as RNA) to form nucleic acid particles. The nucleic acid particles may comprise nucleic acid (such as RNA) which is complexed in different forms by non-covalent interactions to the particle. The particles described herein are not viral particles, in particular infectious viral particles, i.e., they are not able to virally infect cells.

Suitable cationically ionizable lipids are those that form nucleic acid particles and are included by the term “particle forming components” or “particle forming agents”. The term “particle forming components” or “particle forming agents” relates to any components which associate with nucleic acid to form nucleic acid particles. Such components include any component which can be part of nucleic acid particles.

In some embodiments, nucleic acid (such as RNA) particles (especially mRNA particles) comprise more than one type of nucleic acid (such as RNA) molecules, where the molecular parameters of the nucleic acid molecules may be similar or different from each other, like with respect to molar mass or fundamental structural elements such as molecular architecture, capping, coding regions or other features.

In particulate formulation, it is possible that each nucleic acid (such as RNA) species is separately formulated as an individual particulate formulation. In that case, each individual particulate formulation will comprise one nucleic acid (such as RNA) species. The individual particulate formulations may be present as separate entities, e.g. in separate containers. Such formulations are obtainable by providing each nucleic acid (such as RNA) species separately (typically each in the form of a nucleic acid-containing solution) together with a particle-forming agent, thereby allowing the formation of particles. Respective particles will contain exclusively the specific nucleic acid (such as RNA) species that is being provided when the particles are formed (individual particulate formulations). In some embodiments, a composition such as a pharmaceutical composition comprises more than one individual particle formulation. Respective pharmaceutical compositions are referred to as mixed particulate formulations. Mixed particulate formulations according to the present disclosure are obtainable by forming, separately, individual particulate formulations, followed by a step of mixing of the individual particulate formulations. By the step of mixing, a formulation comprising a mixed population of nucleic acid-containing particles is obtainable. Individual particulate populations may be together in one container, comprising a mixed population of individual particulate formulations. Alternatively, it is possible that all nucleic acid (such as RNA) species of the pharmaceutical composition are formulated together as a combined particulate formulation. Such formulations are obtainable by providing a combined formulation (typically combined solution) of all nucleic acid (such as RNA) species together with a particle-forming agent, thereby allowing the formation of particles. As opposed to a mixed particulate formulation, a combined particulate formulation will typically comprise particles which comprise more than one nucleic acid (such as RNA) species. In a combined particulate composition different nucleic acid (such as RNA) species are typically present together in a single particle.

Lipids

The terms “lipid” and “lipid-like material” are broadly defined herein as molecules which comprise one or more hydrophobic moieties or groups and optionally also one or more hydrophilic moieties or groups. Molecules comprising hydrophobic moieties and hydrophilic moieties are also frequently denoted as amphiphiles. Lipids are usually insoluble or poorly soluble in water, but soluble in many organic solvents. In an aqueous environment, the amphiphilic nature allows the molecules to self-assemble into organized structures and different phases. One of those phases consists of lipid bilayers, as they are present in vesicles, multilamellar/unilamellar liposomes, or membranes in an aqueous environment. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). The hydrophilic groups may comprise polar and/or charged groups and include carbohydrates, phosphate, carboxylic, sulfate, amino (e.g., tertiary amino), sulfhydryl, nitro, hydroxyl, and other like groups.

As used herein, the term “hydrophobic” refers to any a molecule, moiety or group which is substantially immiscible or insoluble in aqueous solution. The term hydrophobic group includes hydrocarbons having at least 6 carbon atoms. The monovalent radical of a hydrocarbon is referred to as hydrocarbyl herein. The hydrophobic group can have functional groups (e.g., ether, ester, halide, etc.) and atoms other than carbon and hydrogen as long as the group satisfies the condition of being substantially immiscible or insoluble in aqueous solution.

The term “hydrocarbon” includes non-cyclic, e.g., linear (straight) or branched, hydrocarbyl groups, such as alkyl, alkenyl, or alkynyl as defined herein. It should be appreciated that one or more of the hydrogen atoms in alkyl, alkenyl, or alkynyl may be substituted with other atoms, e.g., halogen, oxygen or sulfur. Unless stated otherwise, hydrocarbon groups can also include a cyclic (alkyl, alkenyl or alkynyl) group or an aryl group, provided that the overall polarity of the hydrocarbon remains relatively nonpolar.

As used herein, the term “amphiphilic” refers to a molecule having both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the disclosure, the amphiphilic compound can be, but is not limited to, one or a plurality of natural or non-natural lipids and lipid-like compounds.

The term "lipid-like material", "lipid-like compound" or "lipid-like molecule" relates to substances that structurally and/or functionally relate to lipids but may not be considered as lipids in a strict sense. For example, the term includes compounds that are able to form amphiphilic layers as they are present in vesicles, multilamellar/unilamellar liposomes, or membranes in an aqueous environment and includes surfactants, or synthesized compounds with both hydrophilic and hydrophobic moieties. Generally speaking, the term refers to molecules, which comprise hydrophilic and hydrophobic moieties with different structural organization, which may or may not be similar to that of lipids. Examples of lipid-like compounds capable of spontaneous integration into cell membranes include functional lipid constructs such as synthetic function-spacer-lipid constructs (FSL), synthetic function-spacer-sterol constructs (FSS) as well as artificial amphipathic molecules. Lipids comprising two long alkyl chains and a polar head group are generally cylindrical. The area occupied by the two alkyl chains is similar to the area occupied by the polar head group. Such lipids have low solubility as monomers and tend to aggregate into planar bilayers that are water insoluble. Traditional surfactant monomers comprising only one linear alkyl chain and a hydrophilic head group are generally cone shaped. The hydrophilic head group tends to occupy more molecular space than the linear alkyl chain. In some embodiments, surfactants tend to aggregate into spherical or elliptoid micelles that are water soluble. While lipids also have the same general structure as surfactants—a polar hydrophilic head group and a nonpolar hydrophobic tail—lipids differ from surfactants in the shape of the monomers, in the type of aggregates formed in solution, and in the concentration range required for aggregation. As used herein, the term "lipid" is to be construed to cover both lipids and lipid-like materials unless otherwise indicated herein or clearly contradicted by context.

Specific examples of amphiphilic compounds that may be included in an amphiphilic layer include, but are not limited to, phospholipids, aminolipids and sphingolipids.

In certain embodiments, the amphiphilic compound is a lipid. The term "lipid" refers to a group of organic compounds that are characterized by being insoluble in water, but soluble in many organic solvents. Generally, lipids may be divided into eight categories: fatty acids, glycerolipids, glycerophospholipids, sphingolipids, saccharolipids, polyketides (derived from condensation of ketoacyl subunits), sterol lipids and prenol lipids (derived from condensation of isoprene subunits). Although the term "lipid" is sometimes used as a synonym for fats, fats are a subgroup of lipids called triglycerides. Lipids also encompass molecules such as fatty acids and their derivatives (including tri-, di-, monoglycerides, and phospholipids), as well as steroids, i.e., sterol-containing metabolites such as cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, tocopherol and derivatives thereof, and mixtures thereof.

Fatty acids, or fatty acid residues are a diverse group of molecules made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. If a fatty acid contains a double bond, there is the possibility of either a cis or trans geometric isomerism, which significantly affects the molecule's configuration. Cis-double bonds cause the fatty acid chain to bend, an effect that is compounded with more double bonds in the chain. Other major lipid classes in the fatty acid category are the fatty esters and fatty amides.

Glycerolipids are composed of mono-, di-, and tri-substituted glycerols, the best-known being the fatty acid triesters of glycerol, called triglycerides. The word "triacylglycerol" is sometimes used synonymously with "triglyceride". In these compounds, the three hydroxyl groups of glycerol are each esterified, typically by different fatty acids. Additional subclasses of glycerolipids are represented by glycosylglycerols, which are characterized by the presence of one or more sugar residues attached to glycerol via a glycosidic linkage.

Glycerophospholipids are amphipathic molecules (containing both hydrophobic and hydrophilic regions) that contain a glycerol core linked to two fatty acid-derived "tails" by ester linkages and to one "head" group by a phosphate ester linkage. Examples of glycerophospholipids, usually referred to as phospholipids (though sphingomyelins are also classified as phospholipids) are phosphatidylcholine (also known as PC, GPCho or lecithin), phosphatidylethanolamine (PE or GPEtn) and phosphatidylserine (PS or GPSer).

Sphingolipids are a complex family of compounds that share a common structural feature, a sphingoid base backbone. The major sphingoid base in mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms. The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

Sterol lipids, such as cholesterol and its derivatives, or tocopherol and its derivatives, are an important component of membrane lipids, along with the glycerophospholipids and sphingomyelins.

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains. The minimal lipopolysaccharide required for growth in *E. coli* is Kdo2-Lipid A, a hexa-acylated disaccharide of glucosamine that is glycosylated with two 3-deoxy-D-manno-octulosonic acid (Kdo) residues.

Polyketides are synthesized by polymerization of acetyl and propionyl subunits by classic enzymes as well as iterative and multimodular enzymes that share mechanistic features with the fatty acid synthases. They comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, or other processes.

Cationically Ionizable Lipids

The nucleic acid (such as RNA) compositions described herein and the nucleic acid particles (especially RNA LNPs) described herein comprise at least one cationically ionizable lipid as particle forming agent. Cationically ionizable lipids contemplated for use herein include any cationically ionizable lipids or lipid-like materials which are able to electrostatically bind nucleic acid. In one embodiment, cationically ionizable lipids contemplated for use herein can be associated with nucleic acid, e.g. by forming complexes with the nucleic acid or forming vesicles in which the nucleic acid is enclosed or encapsulated.

As used herein, a "cationic lipid" or "cationic lipid-like material" refers to a lipid or lipid-like material having a net positive charge. Cationic lipids or lipid-like materials bind negatively charged nucleic acid by electrostatic interaction. Generally, cationic lipids possess a lipophilic moiety, such as a sterol, an acyl chain, a diacyl or more acyl chains, and the head group of the lipid typically carries the positive charge.

In certain embodiments, a cationic lipid or lipid-like material has a net positive charge only at certain pH, in particular acidic pH, while it has preferably no net positive charge, preferably has no charge, i.e., it is neutral, at a different, preferably higher pH such as physiological pH. This ionizable behavior is thought to enhance efficacy through helping with endosomal escape and reducing toxicity as compared with particles that remain cationic at physiological pH.

As used herein, a "cationically ionizable lipid" refers to a lipid or lipid-like material which has a net positive charge or is neutral, i.e., a lipid which is not permanently cationic. Thus, depending on the pH of the composition in which the cationically ionizable lipid is solved, the cationically ionizable lipid is either positively charged or neutral. For purposes of the present disclosure, such "cationically ionizable" lipids are comprised by the term "cationic lipid" unless contradicted by the circumstances.

In one embodiment, the cationically ionizable lipid comprises a head group which includes at least one nitrogen atom (N) which is positive charged or capable of being protonated, preferably under physiological conditions.

Examples of cationic lipids include, but are not limited to N,N-dimethyl-2,3-dioleyloxypropylamine (DODMA), 1,2-di-O-octadecenyl-3-trimethylammonium propane (DOTMA), 3-(N—(N',N'-dimethylaminoethane)-carbamoyl)cholesterol (DC-Chol), dimethyldioctadecylammonium (DDAB); 1,2-dioleoyl-3-trimethylammonium propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-distearyloxy-N,N-dimethyl-3-aminopropane (DSDMA), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-l-propanamium trifluoroacetate (DOSPA), 1,2-dilinoleyloxy-N,N-dimethylaminopropane (DLinDMA), 1,2-dilinolenyloxy-N,N-dimethylaminopropane (DLenDMA), dioctadecylamidoglycyl spermine (DOGS), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-dilinoleoyloxy-N,N-dimethylpropylamine (DLinDAP), 1,2-N,N'-Dilinoleylcarbamyl-3-dimethylaminopropane (DLincarbDAP), 1,2-dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), N-(2-Hydroxyethyl)-N,N-dimethyl-2,3-bis (tetradecyloxy)-1-propanaminium bromide (DMRIE), (±)-N-(3-aminopropyl)-N,N-dimethyl-2,3-bis(cis-9-tetradecenyloxy)-1-propanaminium bromide (GAP-DMORIE), (±)-N-(3-aminopropyl)-N,N-dimethyl-2,3-bis (dodecyloxy)-1-propanaminium bromide (GAP-DLRIE), (±)-N-(3-aminopropyl)-N,N-dimethyl-2,3-bis(tetradecyloxy)-1-propanaminium bromide (GAP-DMRIE), N-(2-aminoethyl)-N,N-dimethyl-2,3-bis(tetradecyloxy)-1-propanaminium bromide (pAE-DMRIE), N-(4-carboxybenzyl)-N,N-dimethyl-2,3-bis(oleoyloxy)propan-1-aminium (DOBAQ), 2-({8-[(3p)-cholest-5-en-3-yloxy] octyl}oxy)-N,N-dimethyl-3-[(9Z,12Z)-octadeca-9,12-dien-1-yloxy]propan-1-amine (octyl-CLinDMA), 1,2-dimyristoyl-3-dimethylammonium-propane (DMDAP), 1,2-dipalmitoyl-3-dimethylammonium-propane (DPDAP), N1-[2-((1S)-1-[(3-aminopropyl)amino]-4-[di(3-amino-propyl) amino]butylcarboxamido)ethyl]-3,4-di[oleyloxy]-benzamide (MVL5), 1,2-dioleoyl-sn-glycero-3-ethylphosphocholine (DOEPC), 2,3-bis(dodecyloxy)-N-(2-hydroxyethyl)-N,N-dimethylpropan-1-amonium bromide (DLRIE), N-(2-aminoethyl)-N,N-dimethyl-2,3-bis(tetradecyloxy)propan-1-aminium bromide (DMORIE), di((Z)-non-2-en-1-yl) 8,8'-((((2(dimethylamino)ethyl)thio)carbonyl)azanediyl)-dioctanoate (ATX), N,N-dimethyl-2,3-bis (dodecyloxy)propan-1-amine (DLDMA), N,N-dimethyl-2,3-bis(tetradecyloxy)propan-1-amine (DMDMA), Di((Z)-non-2-en-1-yl)-9-((4-(dimethylaminobutanoyl)-oxy) heptadecanedioate (L319), N-dodecyl-3-((2-dodecylcarbamoyl-ethyl)-{2-[(2-dodecylcarbamoyl-ethyl)-2-{(2-dodecylcarbamoyl-ethyl)-[2-(2-dodecylcarbamoyl-ethylamino)-ethyl]-amino}-ethyl-amino)propionamide (lipidoid $98N_{12}$-5), 1-[2-[bis(2-hydroxydodecyl)amino] ethyl-[2-[4-[2-[bis(2 hydroxydodecyl)amino]ethyl]piperazin-1-yl]ethyl]amino]dodecan-2-ol (lipidoid C12-200), and the following structures (XV-1) to (XV-6):

(XV-1)

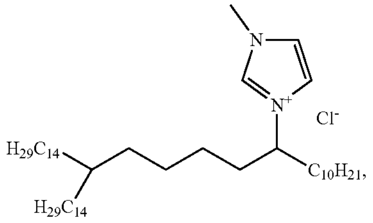

-continued (XV-2)

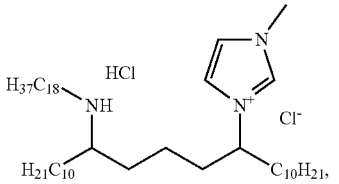

(XV-3)

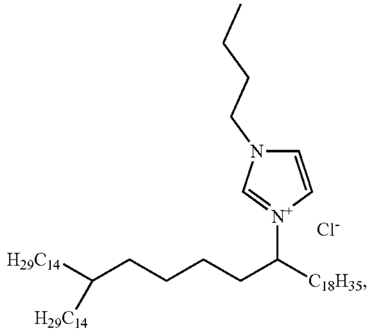

(XV-4)

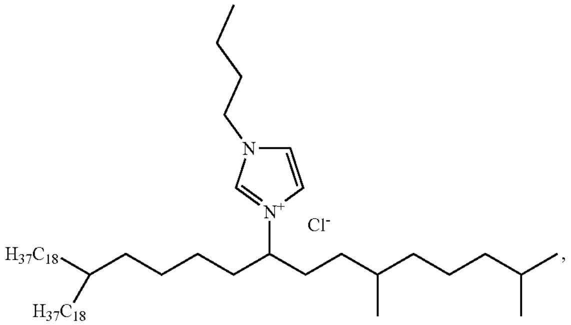

-continued (XV-5)

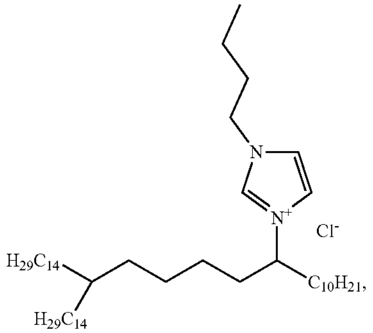

(XV-6)

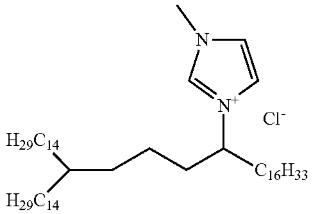

Preferred are DODMA, DOTMA, DOTAP, DODAC, and DOSPA. In specific embodiments, the cationic or cationically ionizable lipid is DODMA.

DOTMA is a cationic lipid with a quaternary amine headgroup. The structure of DOTMA may be represented as follows:

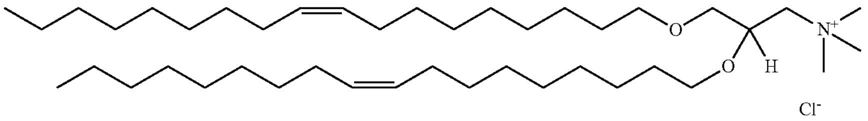 [SMILES: CCCCCCCC/C=C\CCCCCCCCOCC(C[N+](C)(C)C)OCCCCCCCC/C=C\CCCCCCCC ; [Cl-]]

DODMA is an ionizable cationic lipid with a tertiary amine headgroup. The structure of DODMA may be represented as follows:

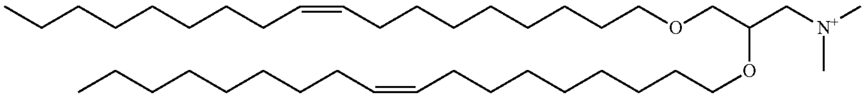 [SMILES: CCCCCCCC/C=C\CCCCCCCCOCC(C[NH+](C)C)OCCCCCCCC/C=C\CCCCCCCC]

In certain embodiments, the composition comprises a cationically ionizable lipid.

In some embodiments, the cationically ionizable lipid comprises a head group which includes at least one nitrogen atom (N) which is positive charged or capable of being protonated, preferably under physiological conditions. In some embodiments, the cationically ionizable lipid comprises a head group which includes at least one tertiary amine moiety.

Examples of cationically ionizable lipids are disclosed, for example, in WO 2016/176330 and WO 2018/078053. In some embodiments, the cationically ionizable lipid has the structure of Formula (X):

(X)

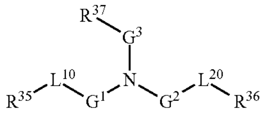

or a pharmaceutically acceptable salt, tautomer, prodrug or stereoisomer thereof, wherein:

one of $L^{10}$ and $L^{20}$ is —O(C═O)—, —(C═O)O—, —C(═O)—, —O—, —$S(O)_x$—, —S—S—, —C(═O)S—, SC(═O)—, —$NR^a$C(═O)—, —C(═O)$NR^a$—, $NR^a$C(═O)$NR^a$—, —OC(═O)$NR^a$— or —$NR^a$C(═O)O—, and the other of $L^{10}$ and $L^{20}$ is —O(C═O)—, —(C═O)O—, —C(═O)—, —O—, —$S(O)_x$—, —S—S—, —C(═O)S—, SC(═O)—, —$NR^a$C(═O)—, —C(═O)$NR^a$—, $NR^a$C(═O)$NR^a$—, —OC(═O)$NR^a$— or —$NR^a$C(═O)O— or a direct bond;

$G^1$ and $G^2$ are each independently unsubstituted $C_1$-$C_{12}$ alkylene or $C_{2-12}$ alkenylene;

$G^3$ is $C_{1-24}$ alkylene, $C_{2-24}$ alkenylene, $C_{3-8}$ cycloalkylene, or $C_{3-8}$ cycloalkenylene;

$R^a$ is H or $C_{1-12}$ alkyl;

$R^{35}$ and $R^{36}$ are each independently $C_{6-24}$ alkyl or $C_{6-24}$ alkenyl;

$R^{37}$ is H, $OR^{50}$, CN, —C(═O)$OR^{40}$, —OC(═O)$R^{40}$ or —$NR^{50}$C(═O)$R_{40}$;

$R^{40}$ is $C_{1-12}$ alkyl;

$R^{50}$ is H or $C_{1-6}$ alkyl; and x is 0, 1 or 2.

In some of the foregoing embodiments of Formula (X), the lipid has one of the following structures (XA) or (XB):

(XA)

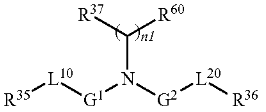

(XB)

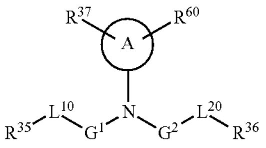

wherein:

A is a 3 to 8-membered cycloalkyl or cycloalkylene group;

$R^{60}$ is, at each occurrence, independently H, OH or $C_1$-$C_{24}$ alkyl;

n1 is an integer ranging from 1 to 15.

In some of the foregoing embodiments of Formula (X), the lipid has structure (XA), and in other embodiments, the lipid has structure (XB).

In other embodiments of Formula (X), the lipid has one of the following structures (XC) or (XD):

(XC)

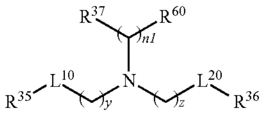

or (XD)

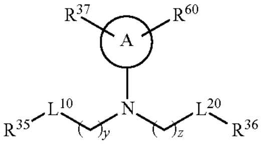

wherein y and z are each independently integers ranging from 1 to 12.

In any of the foregoing embodiments of Formula (X), one of $L^{10}$ and $L^{20}$ is —O(C═O)—. For example, in some embodiments each of $L^{10}$ and $L^{20}$ are —O(C═O)—. In some different embodiments of any of the foregoing, $L^{10}$ and $L^{20}$ are each independently —(C═O)O— or —O(C═O)—. For example, in some embodiments each of $L^{10}$ and $L^{20}$ is —(C═O)O—.

In some different embodiments of Formula (X), the lipid has one of the following structures (XE) or (XF):

(XE)

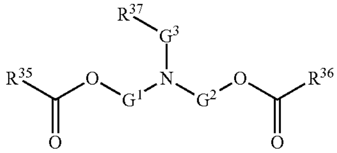

or (XF)

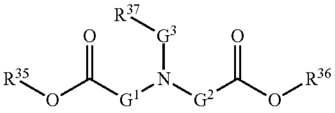

In some of the foregoing embodiments of Formula (X), the lipid has one of the following structures (XG), (XH), (XJ), or (XK):

(XG)

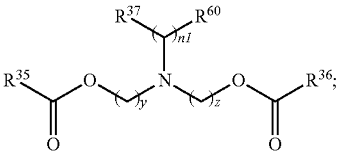

;

(XH)

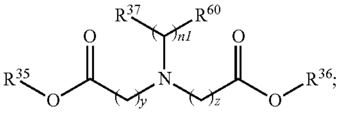

;

-continued (XJ)

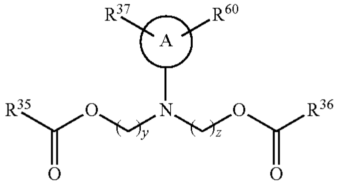

or (XK)

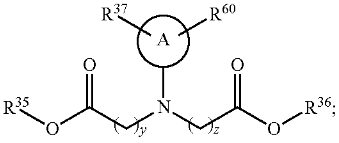

;

In some of the foregoing embodiments of Formula (X), n1 is an integer ranging from 2 to 12, for example from 2 to 8 or from 2 to 4. For example, in some embodiments, n1 is 3, 4, 5 or 6. In some embodiments, n1 is 3. In some embodiments, n1 is 4. In some embodiments, n1 is 5. In some embodiments, n1 is 6.

In some other of the foregoing embodiments of Formula (X), y and z are each independently an integer ranging from 2 to 10. For example, in some embodiments, y and z are each independently an integer ranging from 4 to 9 or from 4 to 6.

In some of the foregoing embodiments of Formula (X), $R^{60}$ is H. In other of the foregoing embodiments, $R^{60}$ is $C_1$-$C_{24}$ alkyl. In other embodiments, $R^{60}$ is OH.

In some embodiments of Formula (X), $G^3$ is unsubstituted. In other embodiments, $G^3$ is substituted. In various different embodiments, $G^3$ is linear $C_1$-$C_{24}$ alkylene or linear $C_2$-$C_{24}$ alkenylene.

In some other foregoing embodiments of Formula (X), $R^{35}$ or $R^{36}$, or both, is $C_6$-$C_{24}$ alkenyl. For example, in some embodiments, $R^{35}$ and $R^{36}$ each, independently have the following structure:

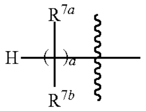

, wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^{35}$ and $R^{36}$ each independently comprise from 6 to 20 carbon atoms. For example, in some embodiments a is an integer ranging from 5 to 9 or from 8 to 12.

In some of the foregoing embodiments of Formula (X), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_5$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (X), $R^{35}$ or $R^{36}$, or both, has one of the following structures:

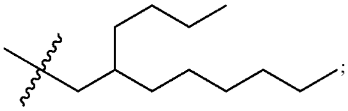

;

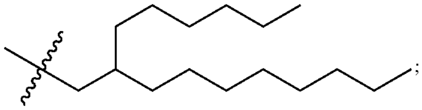

;

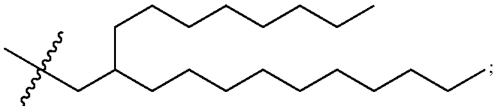

;

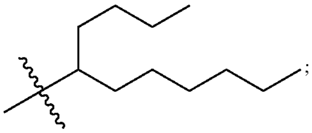

;

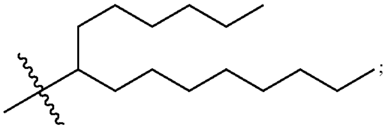

;

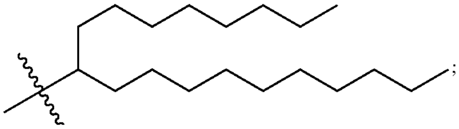

;

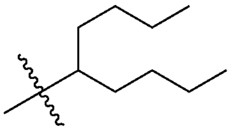

;

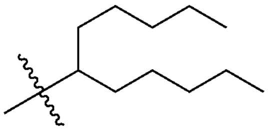

;

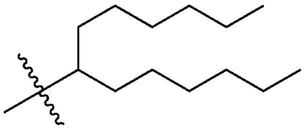

;

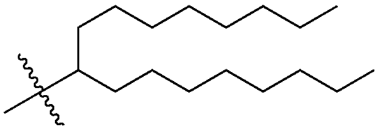

.

In some of the foregoing embodiments of Formula (X), $R^{37}$ is OH, CN, —C(═O)OR$^{40}$, —OC(═O)R$^{40}$ or —NHC(═O)R$^{40}$. In some embodiments, $R^{40}$ is methyl or ethyl.

In various different embodiments, the cationic lipid of Formula (X) has one of the structures set forth below.

Representative Compounds of Formula (X)
X-1
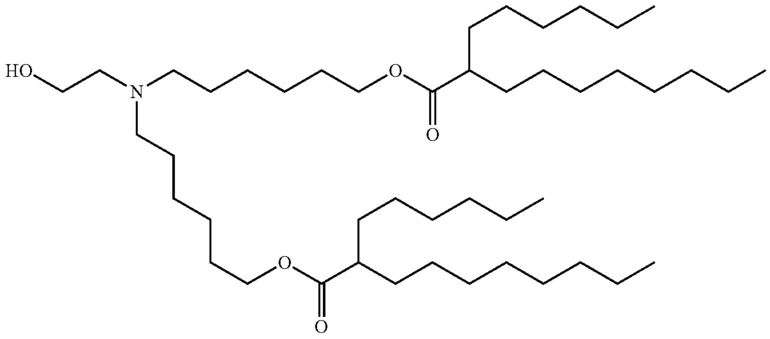 [SMILES: CCCCCCCCC(CCCCCC)C(=O)OCCCCCCN(CCO)CCCCCCOC(=O)C(CCCCCC)CCCCCCCC]
X-2
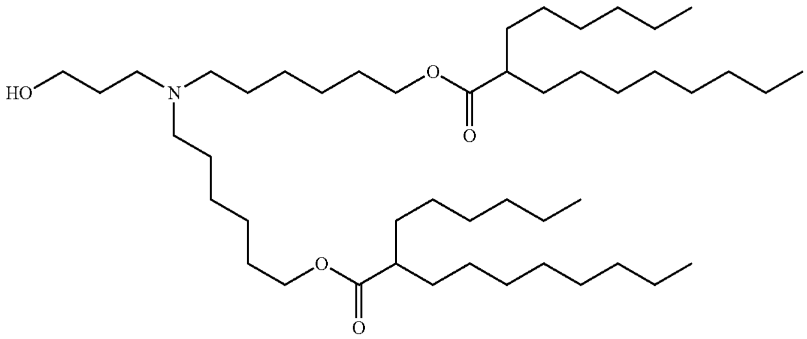 [SMILES: CCCCCCCCC(CCCCCC)C(=O)OCCCCCCN(CCCO)CCCCCCOC(=O)C(CCCCCC)CCCCCCCC]
X-3
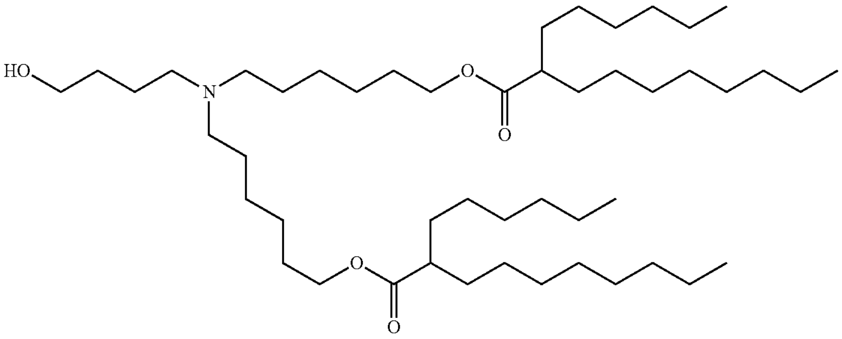 [SMILES: CCCCCCCCC(CCCCCC)C(=O)OCCCCCCN(CCCCO)CCCCCCOC(=O)C(CCCCCC)CCCCCCCC]
X-4
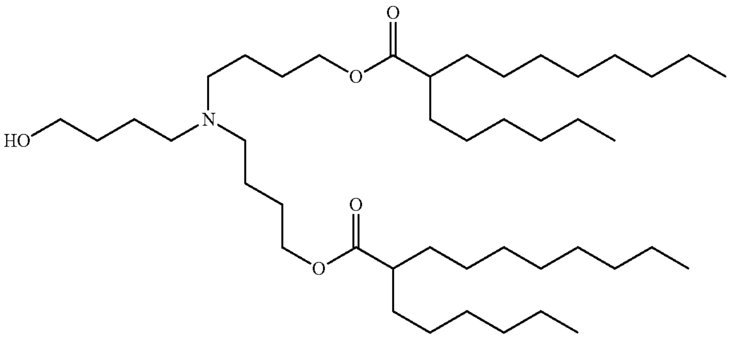 [SMILES: CCCCCCCCC(CCCCCC)C(=O)OCCCCN(CCCCO)CCCCOC(=O)C(CCCCCC)CCCCCCCC]

-continued
Representative Compounds of Formula (X)
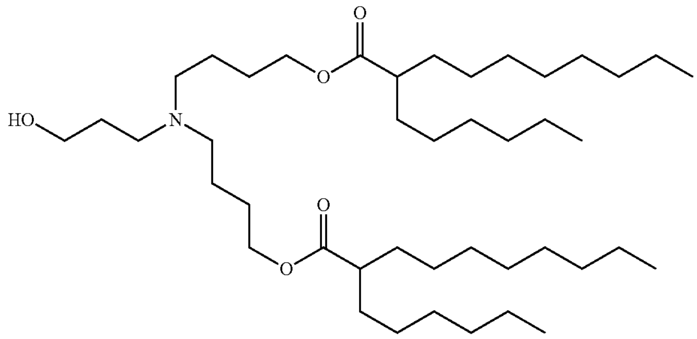 [SMILES: CCCCCCCCC(CCCCCC)C(=O)OCCCCN(CCCO)CCCCOC(=O)C(CCCCCC)CCCCCCCC]
X-5
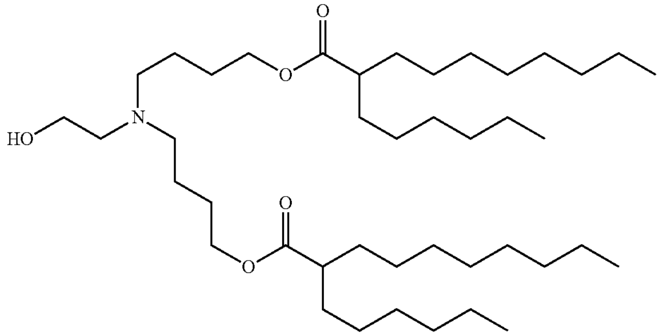 [SMILES: CCCCCCCCC(CCCCCC)C(=O)OCCCCN(CCO)CCCCOC(=O)C(CCCCCC)CCCCCCCC]
X-6
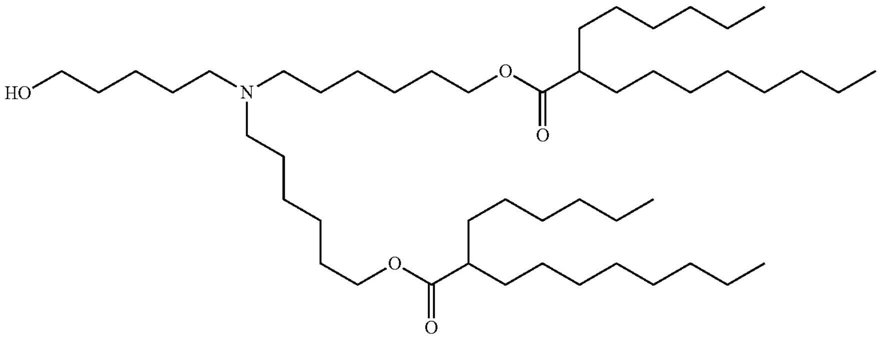 [SMILES: CCCCCCCCC(CCCCCC)C(=O)OCCCCCCN(CCCCCO)CCCCCCOC(=O)C(CCCCCC)CCCCCCCC]
X-7
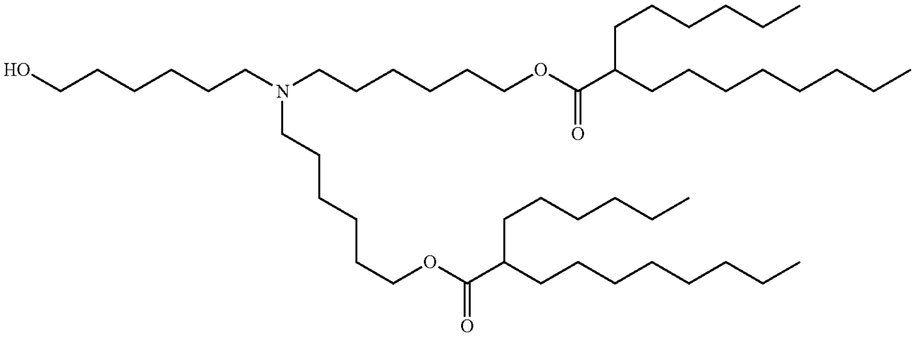 [SMILES: CCCCCCCCC(CCCCCC)C(=O)OCCCCCCN(CCCCCCO)CCCCCCOC(=O)C(CCCCCC)CCCCCCCC]
X-8

-continued
| Representative Compounds of Formula (X) |
| --- |
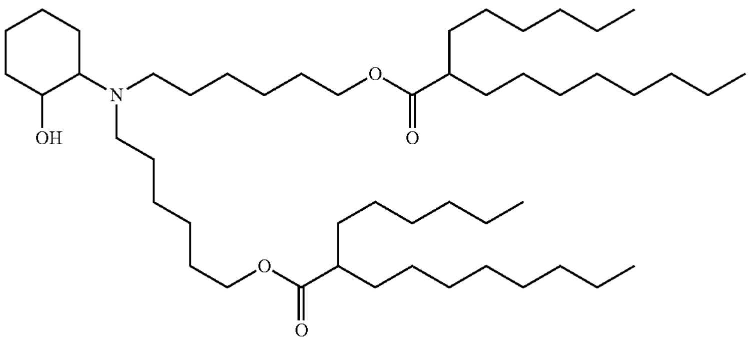 [SMILES: CCCCCCCCC(CCCCCC)C(=O)OCCCCCCN(CCCCCCOC(=O)C(CCCCCC)CCCCCCCC)C1CCCCC1O]
X-9
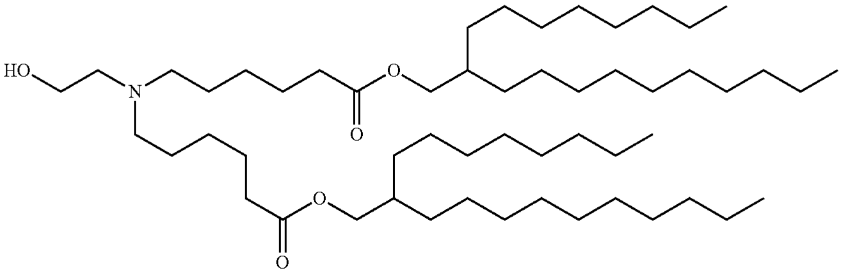 [SMILES: CCCCCCCCCCC(CCCCCCCC)COC(=O)CCCCCN(CCO)CCCCCC(=O)OCC(CCCCCCCC)CCCCCCCCCC]
X-10
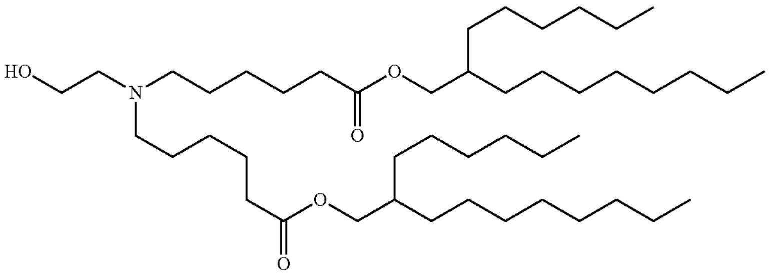 [SMILES: CCCCCCCCC(CCCCCC)COC(=O)CCCCCN(CCO)CCCCCC(=O)OCC(CCCCCC)CCCCCCCC]
X-11
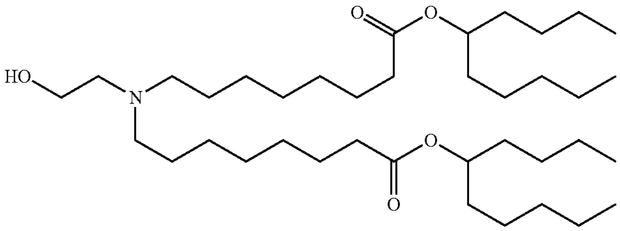 [SMILES: CCCCCC(CCCC)OC(=O)CCCCCCCN(CCO)CCCCCCCC(=O)OC(CCCC)CCCCC]
X-12
X-13
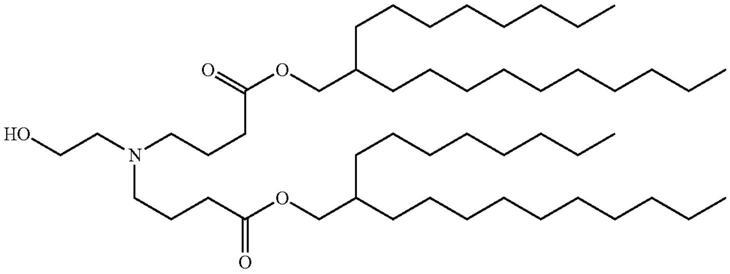 [SMILES: CCCCCCCCCCC(CCCCCCCC)COC(=O)CCCN(CCO)CCCC(=O)OCC(CCCCCCCC)CCCCCCCCCC]

-continued
Representative Compounds of Formula (X)
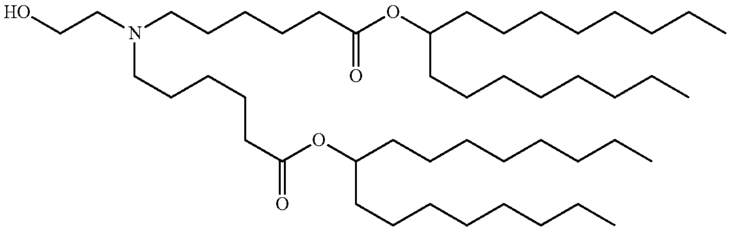 [SMILES: CCCCCCCCC(CCCCCCCC)OC(=O)CCCCCN(CCO)CCCCCC(=O)OC(CCCCCCCC)CCCCCCCC]
X-14
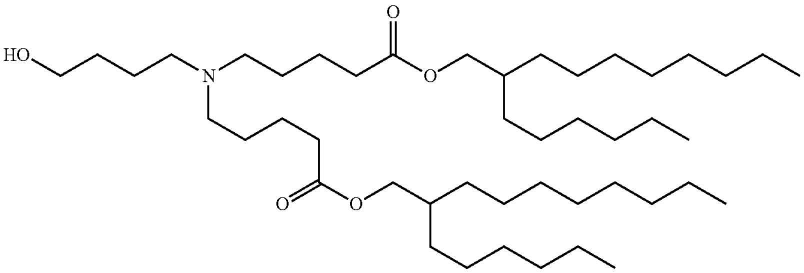 [SMILES: CCCCCCCCC(CCCCCC)COC(=O)CCCCN(CCCCO)CCCCC(=O)OCC(CCCCCC)CCCCCCCC]
X-15
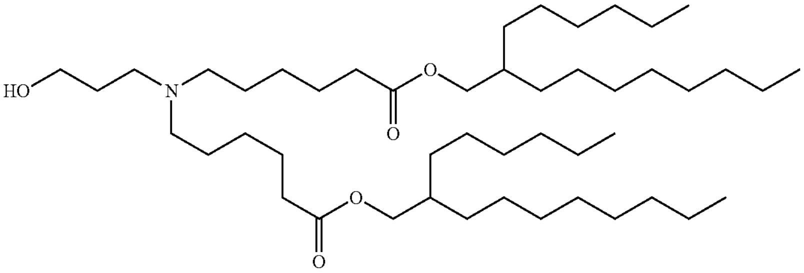 [SMILES: CCCCCCCCC(CCCCCC)COC(=O)CCCCCN(CCCO)CCCCCC(=O)OCC(CCCCCC)CCCCCCCC]
X-16
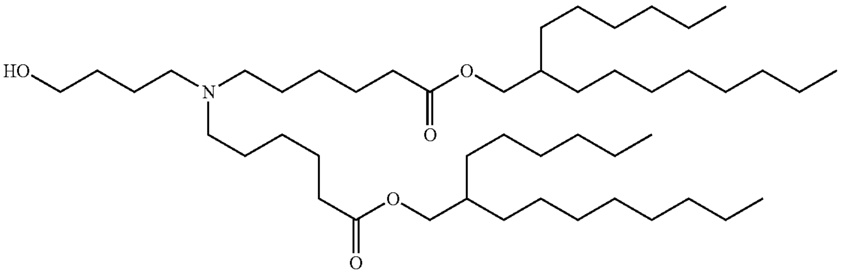 [SMILES: CCCCCCCCC(CCCCCC)COC(=O)CCCCCN(CCCCO)CCCCCC(=O)OCC(CCCCCC)CCCCCCCC]
X-17
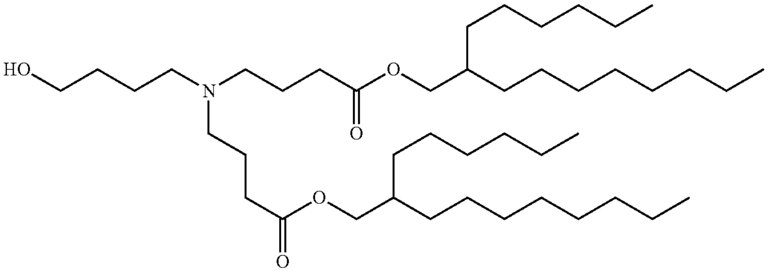 [SMILES: CCCCCCCCC(CCCCCC)COC(=O)CCCN(CCCCO)CCCC(=O)OCC(CCCCCC)CCCCCCCC]
X-18

-continued
| Representative Compounds of Formula (X) |
| --- |
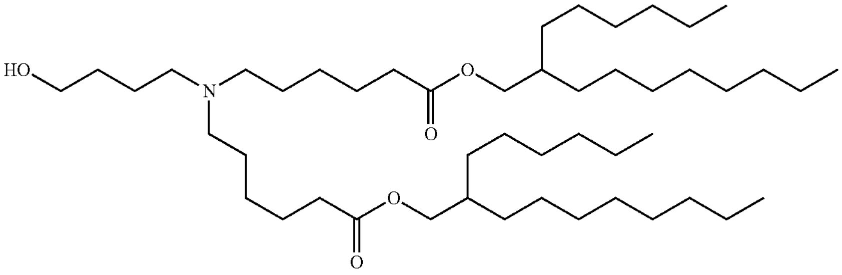 [SMILES: CCCCCCCCC(CCCCCC)COC(=O)CCCCCN(CCCCO)CCCCCC(=O)OCC(CCCCCC)CCCCCCCC]
X-19
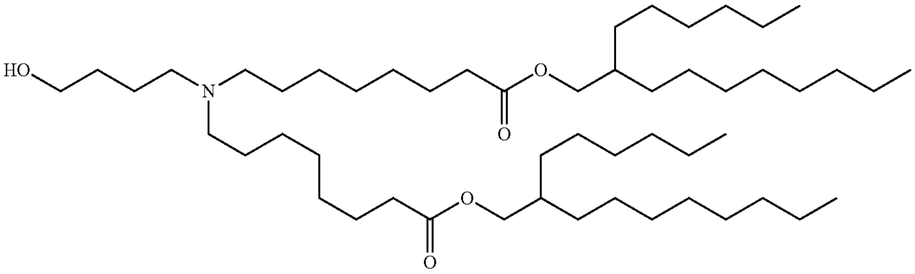 [SMILES: CCCCCCCCC(CCCCCC)COC(=O)CCCCCCCN(CCCCO)CCCCCCCC(=O)OCC(CCCCCC)CCCCCCCC]
X-20
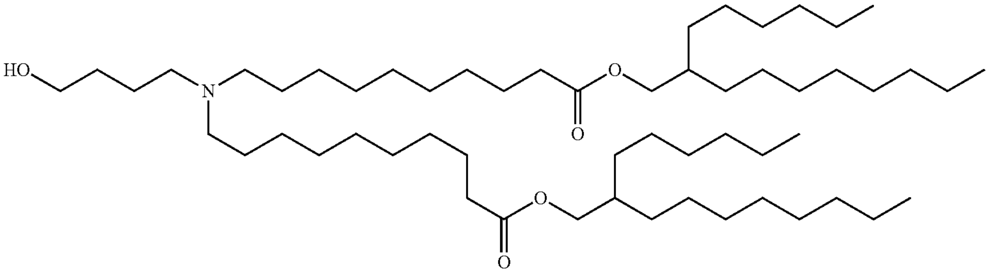 [SMILES: CCCCCCCCC(CCCCCC)COC(=O)CCCCCCCCCN(CCCCO)CCCCCCCCCC(=O)OCC(CCCCCC)CCCCCCCC]
X-21
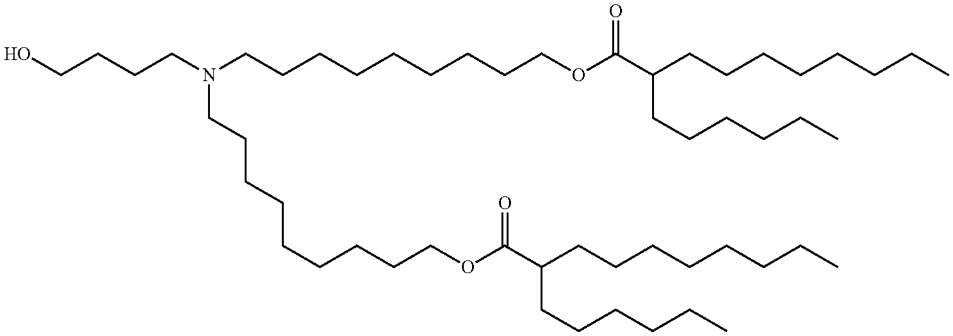 [SMILES: CCCCCCCCC(CCCCCC)C(=O)OCCCCCCCCCN(CCCCO)CCCCCCCCCOC(=O)C(CCCCCC)CCCCCCCC]
X-22
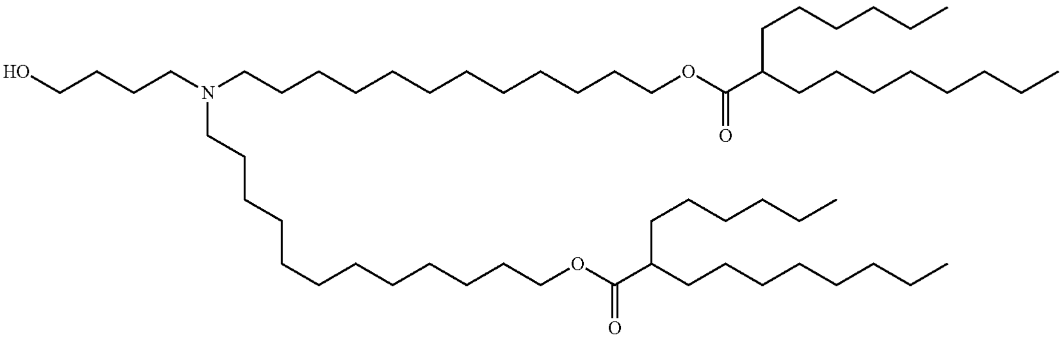 [SMILES: CCCCCCCCC(CCCCCC)C(=O)OCCCCCCCCCCCCN(CCCCO)CCCCCCCCCCCCOC(=O)C(CCCCCC)CCCCCCCC]
X-23

-continued
| Representative Compounds of Formula (X) |
|---|
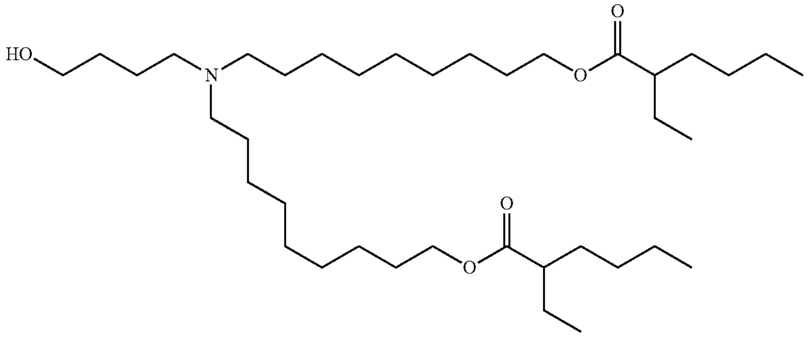 [SMILES: CCCCC(CC)C(=O)OCCCCCCCCCN(CCCCO)CCCCCCCCCOC(=O)C(CC)CCCC]
X-24
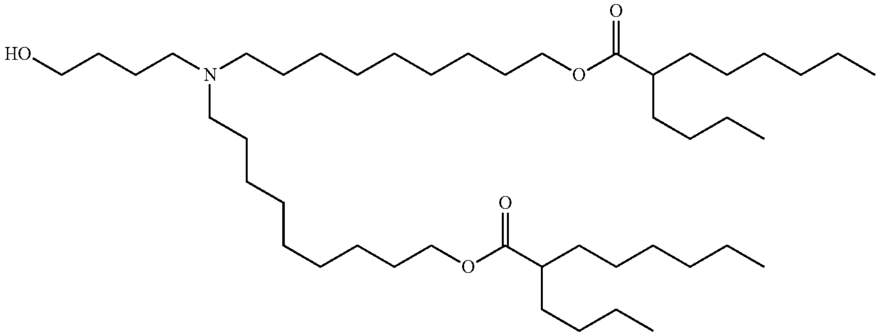 [SMILES: CCCCCCC(CCCC)C(=O)OCCCCCCCCCN(CCCCO)CCCCCCCCCOC(=O)C(CCCC)CCCCCC]
X-25
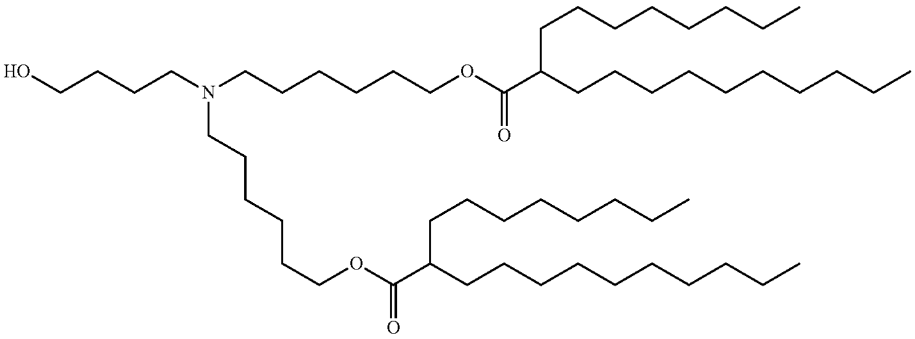 [SMILES: CCCCCCCCCCC(CCCCCCCC)C(=O)OCCCCCCN(CCCCO)CCCCCCOC(=O)C(CCCCCCCC)CCCCCCCCCC]
X-26
X-27
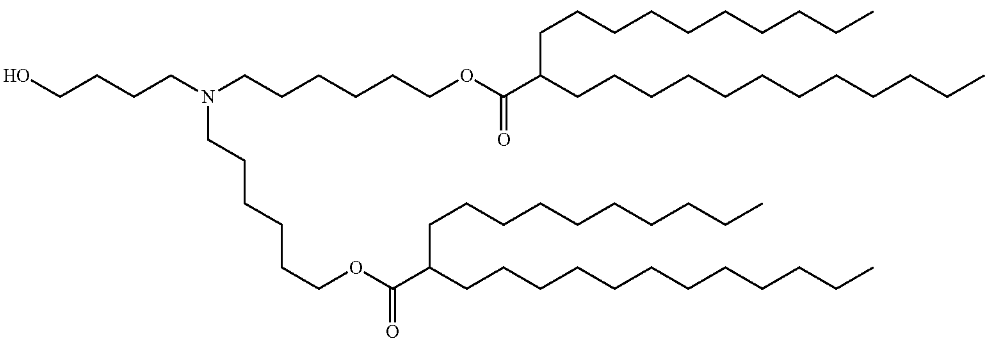 [SMILES: CCCCCCCCCCCCC(CCCCCCCCCC)C(=O)OCCCCCCN(CCCCO)CCCCCCOC(=O)C(CCCCCCCCCC)CCCCCCCCCCCC]

-continued
| Representative Compounds of Formula (X) |
| --- |
X-28
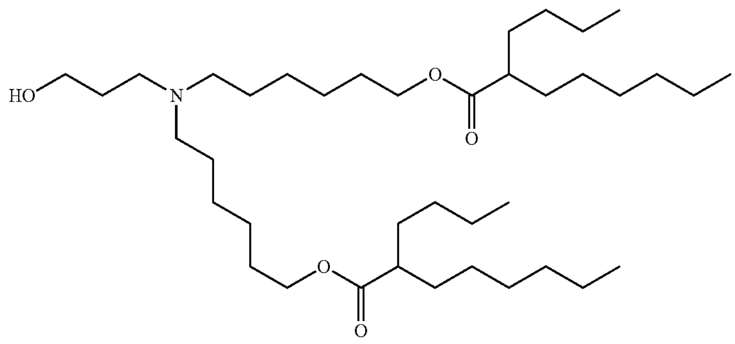 [SMILES: CCCCCCC(CCCC)C(=O)OCCCCCCN(CCCO)CCCCCCOC(=O)C(CCCC)CCCCCC]
X-29
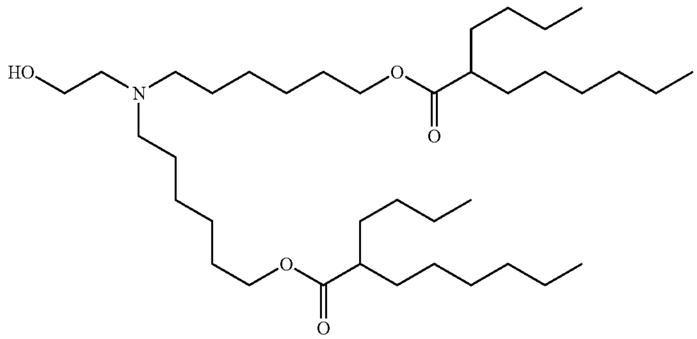 [SMILES: CCCCCCC(CCCC)C(=O)OCCCCCCN(CCO)CCCCCCOC(=O)C(CCCC)CCCCCC]
X-30
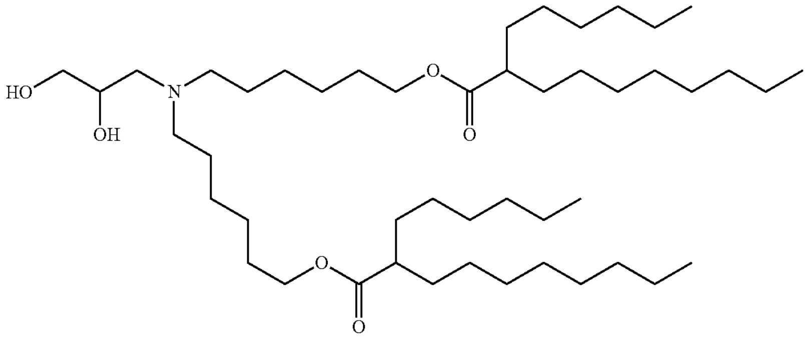 [SMILES: CCCCCCCCC(CCCCCC)C(=O)OCCCCCCN(CCCCCCOC(=O)C(CCCCCC)CCCCCCCC)CC(O)CO]
X-31
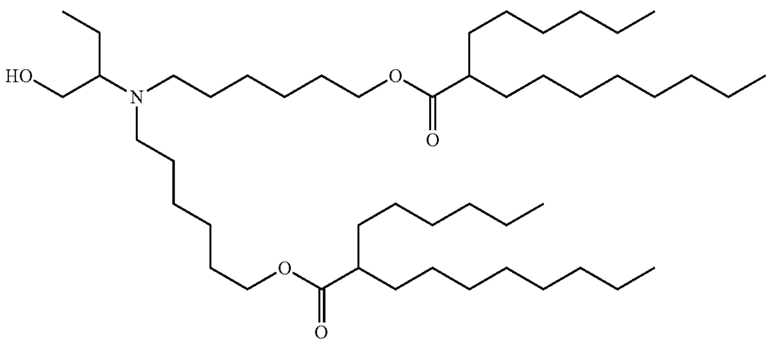 [SMILES: CCCCCCCCC(CCCCCC)C(=O)OCCCCCCN(CCCCCCOC(=O)C(CCCCCC)CCCCCCCC)C(CC)CO]

-continued
Representative Compounds of Formula (X)
X-32
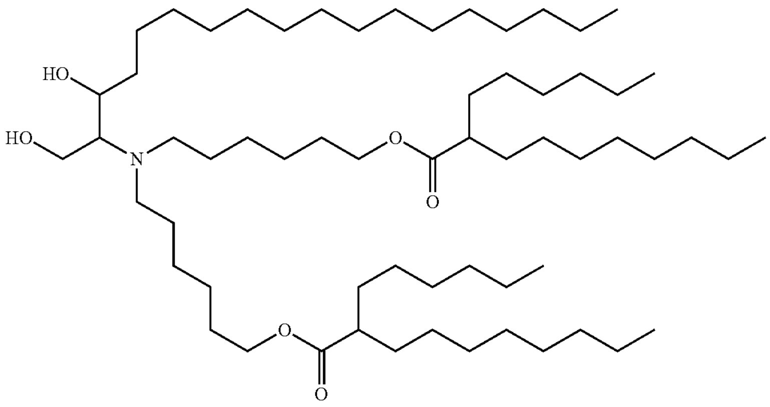 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC]
X-33
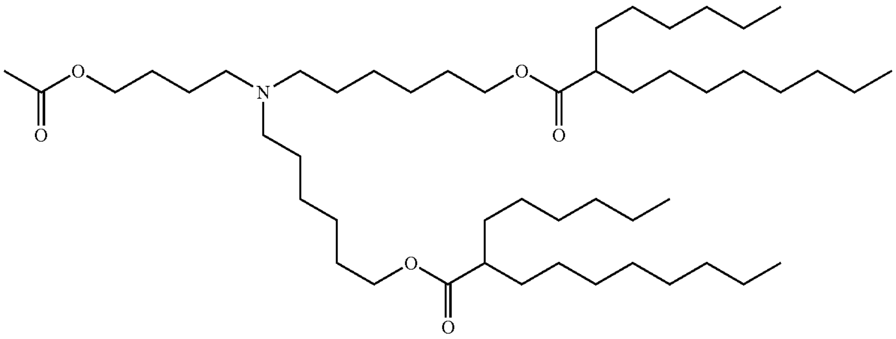 [SMILES: CCCCCCCCC(CCCCCC)C(=O)OCCCCCCN(CCCCCCOC(=O)C(CCCCCC)CCCCCCCC)CCCCOC(C)=O]
X-34
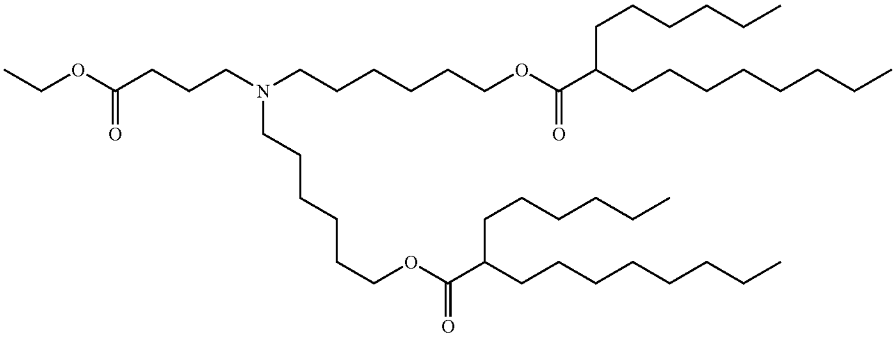 [SMILES: CCCCCCCCC(CCCCCC)C(=O)OCCCCCCN(CCCCCCOC(=O)C(CCCCCC)CCCCCCCC)CCCC(=O)OCC]
X-35
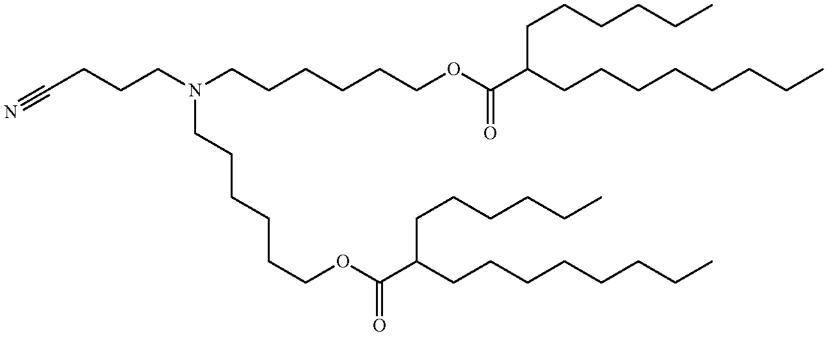 [SMILES: CCCCCCCCC(CCCCCC)C(=O)OCCCCCCN(CCCC#N)CCCCCCOC(=O)C(CCCCCC)CCCCCCCC]

-continued
| Representative Compounds of Formula (X) | |
|---|---|
| 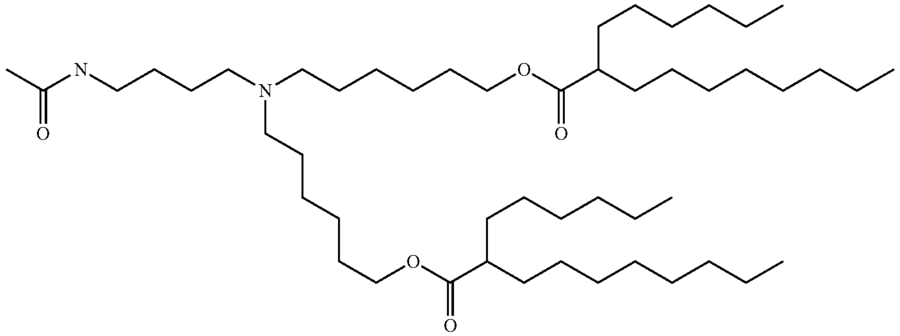 [SMILES: CCCCCCCCC(CCCCCC)C(=O)OCCCCCCN(CCCCCCOC(=O)C(CCCCCC)CCCCCCCC)CCCCNC(C)=O] | X-36 |
In various different embodiments, the cationically ionizable lipid has one of the structures set forth in the table below.
| No. | Structure |
|---|---|
| A | 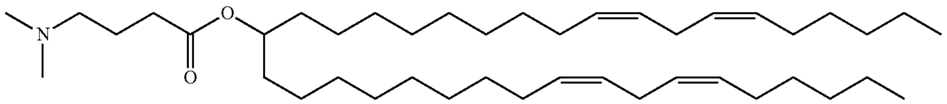 [SMILES: CCCCC/C=C\C/C=C\CCCCCCCCC(CCCCCCCC/C=C\C/C=C\CCCCC)OC(=O)CCCN(C)C] |
| B | 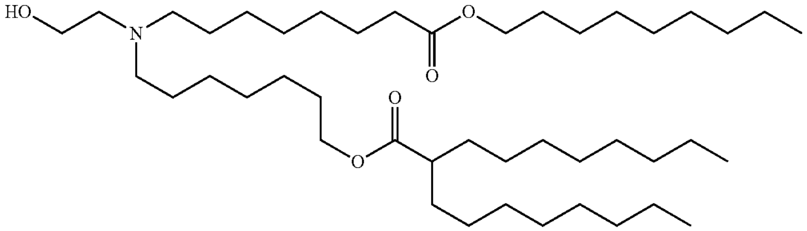 [SMILES: CCCCCCCCCOC(=O)CCCCCCCN(CCO)CCCCCCCOC(=O)C(CCCCCCCC)CCCCCCCC] |
| C | 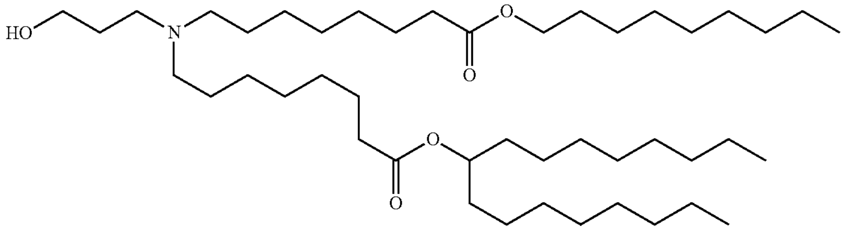 [SMILES: CCCCCCCCCOC(=O)CCCCCCCN(CCCO)CCCCCCCC(=O)OC(CCCCCCCC)CCCCCCCC] |
| D | 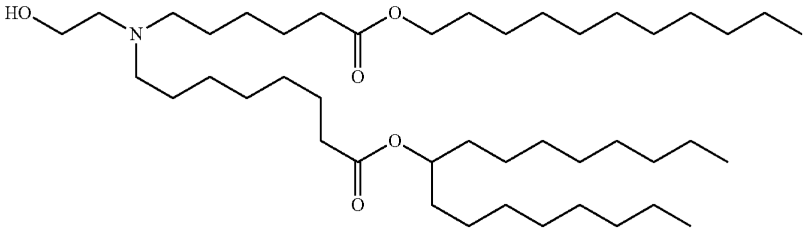 [SMILES: CCCCCCCCCCCOC(=O)CCCCCN(CCO)CCCCCCCC(=O)OC(CCCCCCCC)CCCCCCCC] |
| E | 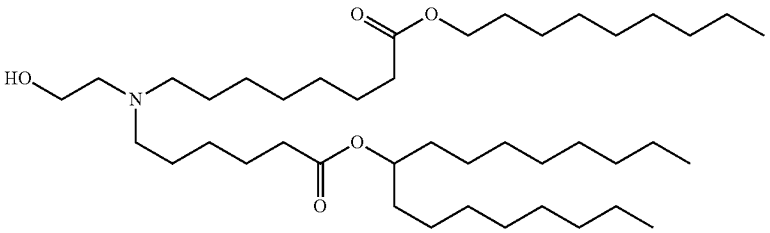 [SMILES: CCCCCCCCCOC(=O)CCCCCCCN(CCO)CCCCCC(=O)OC(CCCCCCCC)CCCCCCCC] |

-continued

| No. | Structure |
| --- | --- |
| F | 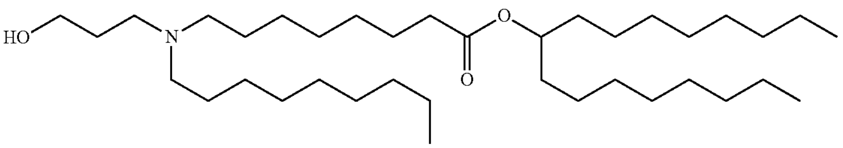 [SMILES: CCCCCCCCCN(CCCO)CCCCCCCC(=O)OC(CCCCCCCC)CCCCCCCC] |
| G | 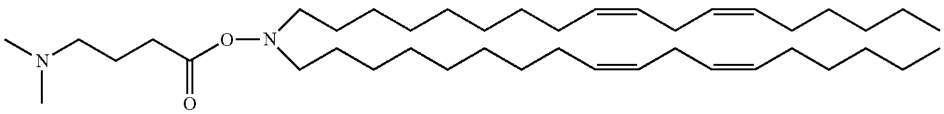 [SMILES: CCCCC/C=C\C/C=C\CCCCCCCCN(CCCCCCCC/C=C\C/C=C\CCCCC)OC(=O)CCCN(C)C] |

In some embodiments, the cationically ionizable lipid has the structure D.

In some embodiments, the cationically ionizable lipid has the structure of Formula (XI):

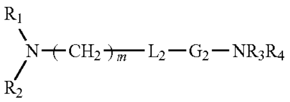

wherein each of $R_1$ and $R_2$ is independently $R_5$ or $-G_1-L_1-R_6$, wherein at least one of $R_1$ and $R_2$ is $-G_i-L_1-R_6$;

each of $R_3$ and $R_4$ is independently selected from the group consisting of $C_{1-6}$ alkyl, $C_{2-6}$ alkenyl, aryl, and $C_{3-10}$ cycloalkyl;

each of $R_5$ and $R_6$ is independently a non-cyclic hydrocarbyl group having at least 10 carbon atoms;

each of $G_1$ and $G_2$ is independently unsubstituted $C_{1-12}$ alkylene or $C_{2-12}$ alkenylene;

each of $L_1$ and $L_2$ is independently selected from the group consisting of —O(C═O)—, —(C═O)O—, —C(═O)—, —O—, $—S(O)_x$, —S—S—, —C(═O)S—, —SC(═O)—, —NRaC(═O)—, $—C(═O)NR^a—$, $—NRac(═O)NR^a—$, $—Oc(═O)NR^a—$ and —NRaC(═O)O—;

Ra is H or $C_{1-12}$ alkyl;

m is 0, 1, 2, 3, or 4; and x is 0, 1 or 2.

In some of the foregoing embodiments of Formula (XI), $G_1$ is independently unsubstituted $C_1$-$C_{12}$ alkylene or unsubstituted $C_{2-12}$ alkenylene, e.g., unsubstituted, straight $C_{1-12}$ alkylene or unsubstituted, straight $C_{2-12}$ alkenylene. In some embodiments, each $G_1$ is independently unsubstituted $C_{6-12}$ alkylene or unsubstituted $C_{6-12}$ alkenylene, e.g., unsubstituted, straight $C_{6-12}$ alkylene or unsubstituted, straight $C_{6-12}$ alkenylene. In some embodiments, each $G_1$ is independently unsubstituted $C_{8-12}$ alkylene or unsubstituted $C_{8-12}$ alkenylene, e.g., unsubstituted, straight $C_{8-12}$ alkylene or unsubstituted, straight $C_{8-12}$ alkenylene. In some embodiments, each $G_1$ is independently unsubstituted $C_{6-10}$ alkylene or unsubstituted $C_{6-10}$ alkenylene, e.g., unsubstituted, straight $C_6$-10 alkylene or unsubstituted, straight $C_{6-10}$ alkenylene. In some embodiments, each $G_1$ is independently unsubstituted alkylene having 8, 9 or 10 carbon atoms, e.g., unsubstituted, straight alkylene having 8, 9 or 10 carbon atoms. In some embodiments, where $R_1$ and $R_2$ are both independently $-G_1-L_1-R_6$, $G_1$ for $R_1$ may be different from $G_1$ for $R_2$. In some of these embodiments, for example, $G_1$ for $R_1$ is unsubstituted, straight $C_{1-12}$ alkylene and $G_1$ for $R_2$ is unsubstituted, straight $C_{2-12}$ alkenylene; or $G_1$ for $R_1$ is an unsubstituted, straight $C_{1-12}$ alkylene group and $G_1$ for $R_2$ is a different unsubstituted, straight $C_{1-12}$ alkylene group. In some embodiments, where $R_1$ and $R_2$ are both independently $-G_1-L_1-R_6$, $G_1$ for $R_1$ may be identical to $G_1$ for $R_2$. In some of these embodiments, for example, each $G_1$ is the same unsubstituted, straight $C_{8-12}$ alkylene, such as unsubstituted, straight $C_{8-10}$ alkylene, or each $G_1$ is the same unsubstituted, straight $C_{6-12}$ alkenylene.

In some of the foregoing embodiments of Formula (XI), each $L_1$ is independently selected from the group consisting of —O(C═O)—, —(C═O)O—, —C(═O)S—, —SC(═O)—, —NRaC(═O)—, and $-C(═O)NR^a—$. In some embodiments, Ra of $L_1$ is H or $C_{1-12}$ alkyl. In some embodiments, Ra of $L_1$ is H or $C_{1-6}$ alkyl, e.g., H or $C_{1-3}$ alkyl. In some embodiments, Ra of $L_1$ is H, methyl, or ethyl. In some embodiments, each $L_1$ is independently selected from the group consisting of —O(C═O)—, —(C═O)O—, —C(═O)S—, and —SC(═O)—. In some embodiments, each $L_1$ is independently —O(C═O)— or —(C═O)O—. In some embodiments, where $R_1$ and $R_2$ are both independently $-G_1-L_1-R_6$, $L_1$ for $R_1$ may be different from $L_1$ for $R_2$. In some of these embodiments, for example, $L_1$ for $R_1$ is one moiety selected from the group consisting of —O(C═O)—, —(C═O)O—, —C(═O)S—, —SC(═O)—, —NRaC(═O)—, and $-c(═O)NR^a—$ (e.g., $L_1$ for $R_1$ is —O(C═O)—), and $L_1$ for $R_2$ is a different moiety selected from the group consisting of —O(C═O)—, —(C═O)O—, —C(═O)S—, —SC(═O)—, —NRaC(═O)—, and $-c(═O)NR^a—$ (e.g., $L_1$ for $R_2$ is —(C═O)O—). In some embodiments, where $R_1$ and $R_2$ are both independently $-G_1-L_1-R_6$, $L_1$ for $R_1$ may be identical to $L_1$ for $R_2$. In some of these embodiments, for example, each $L_1$ is the same moiety selected from the group consisting of —O(C═O)—, —(C═O)O—, —C(═O)S—, —SC(═O)—, —NRaC(═O)—, and $-c(═O)NR^a—$, e.g., each $L_1$ is —O(C═O)— or each $L_1$ is —(C═O)O—.

In some of the foregoing embodiments of Formula (XI), each $R_6$ is independently a non-cyclic hydrocarbyl group having at least 10 carbon atoms, e.g., a straight hydrocarbyl group having at least 10 carbon atoms. In some embodiments, each $R_6$ has independently at most 30 carbon atoms, such as at most 28, at most 26, at most 24, at most 22, or at most 20 carbon atoms. In some embodiments, each $R_6$ is independently a non-cyclic hydrocarbyl group having 10 to 30 carbon atoms (such as 10 to 28, 10 to 26, 10 to 24, 10 to 22, or 10 to 20 carbon atoms), e.g., a straight hydrocarbyl group having 10 to 30 carbon atoms (such as 10 to 28, 10 to 26, 10 to 24, 10 to 22, or 10 to 20 carbon atoms). In some embodiments, each $R_6$ is attached to $L_1$ via an internal carbon atom of $R_6$. In some embodiments, each $R_6$ has independently at most 30 carbon atoms (such as at most 28, at most 26, at most 24, at most 22, or at most 20 carbon atoms), and each $R_6$ is attached to $L_1$ via an internal carbon atom of $R_6$. In some embodiments, each $R_6$ is independently a non-cyclic hydrocarbyl group having at least 10 carbon atoms, e.g., a straight hydrocarbyl group having at least 10 carbon atoms, and each $R_6$ is attached to $L_1$ via an internal carbon atom of $R_6$. In some embodiments, each $R_6$ is independently a non-cyclic hydrocarbyl group having 10 to 30 carbon atoms (such as 10 to 28, 10 to 26, 10 to 24, 10 to 22, or 10 to 20 carbon atoms), e.g., a straight hydrocarbyl group having 10 to 30 carbon atoms (such as 10 to 28, 10 to 26, 10 to 24, 10 to 22, or 10 to 20 carbon atoms), and each $R_6$ is attached to $L_1$ via an internal carbon atom of $R_6$. In some embodiments, the hydrocarbyl group of $R_6$ is an alkyl or alkenyl group, e.g., a $C_{10-30}$ alkyl or alkenyl group. Thus, in some embodiments, each $R_6$ is independently a non-cyclic alkyl group having at least 10 carbon atoms or a non-cyclic alkenyl group having at least 10 carbon atoms, e.g., a straight alkyl group having at least 10 carbon atoms or a straight alkenyl group having at least 10 carbon atoms. In some embodiments, each $R_6$ is independently a non-cyclic alkyl group having 10 to 30 carbon atoms (such as 10 to 28, 10 to 26, 10 to 24, 10 to 22, or 10 to 20 carbon atoms) or a non-cyclic alkenyl group having 10 to 30 carbon atoms (such as 10 to 28, 10 to 26, 10 to 24, 10 to 22, or 10 to 20 carbon atoms), e.g., a straight alkyl group having 10 to 30 carbon atoms (such as 10 to 28, 10 to 26, 10 to 24, 10 to 22, or 10 to 20 carbon atoms) or a straight alkenyl group having 10 to 30 carbon atoms (such as 10 to 28, 10 to 26, 10 to 24, 10 to 22, or 10 to 20 carbon atoms). In some embodiments, each $R_6$ is independently a non-cyclic alkyl group having 11 to 19 carbon atoms (such as 11, 13, 15, 17, or 17 carbon atoms), e.g., a straight alkyl group having 11 to 19 carbon atoms (such as 11, 13, 15, 17, or 17 carbon atoms). In some embodiments, each $R_6$ is independently a non-cyclic alkyl group having 10 to 30 carbon atoms (such as 10 to 28, 10 to 26, 10 to 24, 10 to 22, or 10 to 20 carbon atoms) or a non-cyclic alkenyl group having 10 to 30 carbon atoms (such as 10 to 28, 10 to 26, 10 to 24, 10 to 22, or 10 to 20 carbon atoms), e.g., a straight alkyl group having 10 to 30 carbon atoms (such as 10 to 28, 10 to 26, 10 to 24, 10 to 22, or 10 to 20 carbon atoms) or a straight alkenyl group having 10 to 30 carbon atoms (such as 10 to 28, 10 to 26, 10 to 24, 10 to 22, or 10 to 20 carbon atoms), and each $R_6$ is attached to $L_1$ via an internal carbon atom of $R_6$. In some embodiments, each $R_6$ is independently a non-cyclic alkyl group having 11 to 19 carbon atoms (such as 11, 13, 15, 17, or 17 carbon atoms), e.g., a straight alkyl group having 11 to 19 carbon atoms (such as 11, 13, 15, 17, or 17 carbon atoms), and each $R_6$ is attached to $L_i$ via an internal carbon atom of $R_6$. The expression "internal carbon atom" means that the carbon atom of $R_6$ by which $R_6$ is attached to $L_1$ is directly bonded to at least 2 other carbon atoms of $R_6$. For example, for the following $C_{11}$ alkyl group, each carbon atom at any one of positions 2, 3, 4, 5, and 7 qualifies as "internal carbon atom" according to the present disclosure, whereas the carbon atoms at positions 1, 6, 8, 9, 10, and 11 do not.

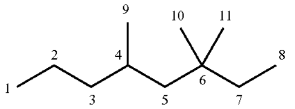

Consequently, $R_6$ being a $C_{11}$ alkyl group attached to $L_1$ via an internal carbon of $R_6$ includes the following groups:

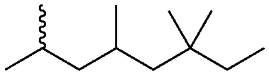

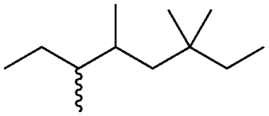

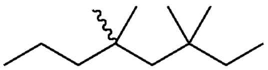

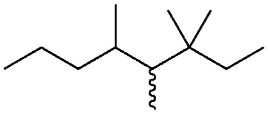

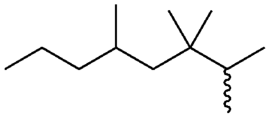

wherein  represents the bond by which $R_6$ is bound to $L_1$. Furthermore, for a straight alkyl group, e.g., a straight $C_{11}$ alkyl group, each carbon atom except for the first and last carbon atoms of the straight alkyl group (i.e., except the carbon atoms at positions 1 and 11 of the straight $C_{11}$ alkyl group) qualifies as "internal carbon atom". Thus, in some embodiments, $R_6$ being a straight alkyl group having p carbon atoms and being attached to $L_1$ via an internal carbon atom of $R_6$ means that $R_6$ is attached to $L_1$ via a carbon atom of $R_6$ at any one of positions 2 to (p-1) (thereby excluding the terminal C atoms at positions 1 and p). In some embodiments, where $R_6$ is a straight alkyl group having p' carbon atoms (wherein p' is an even number) and being attached to $L_1$ via an internal carbon atom of $R_6$, $R_6$ is attached to $L_1$ via a carbon at any one of positions (p'/2-1), (p'/2), and (p'/2+1) of $R_6$ (e.g., if p' is 10, $R_6$ is attached to $L_1$ via a carbon atom at any one of positions 4, 5, and 6 of $R_6$). In some embodiments, where $R_6$ is a straight alkyl group having p" carbon atoms (wherein p" is an uneven number) and being attached to $L_i$ via an internal carbon atom of $R_6$, $R_6$ is attached to $L_i$ via a carbon atom at any one of positions (p"−1)/2 and (p"+1)/2 of $R_6$ (e.g., if p" is 11, $R_6$ is attached to $L_i$ via a carbon at any one of positions 5 and 6 of $R_6$). Generally, it is to be understood that if both $R_1$ and $R_2$ are $-G_1-L_1-R_6$ and each $R_6$ is attached to $L_1$ via an internal carbon atom of $R_6$, $R_6$ of $R_1$ is attached to $L_i$ of $R_1$ (and not to $L_i$ of $R_2$) via an internal carbon atom of $R_6$ of $R_1$ and $R_6$ of $R_2$ is attached to $L_1$ of $R_2$ (and not to $L_i$ of $R_1$) via an internal carbon atom of $R_6$ of $R_2$. In some embodiments, each $R_6$ is independently selected from the group consisting of:

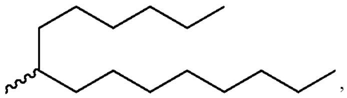
,

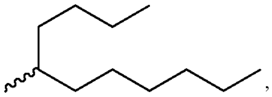
,

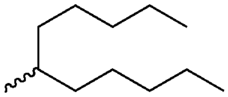
,

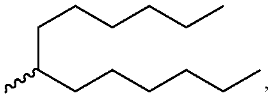
,

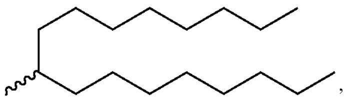
, and

-continued

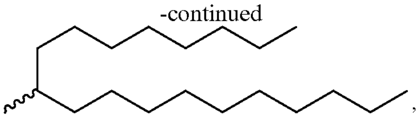

, wherein represents the bond by which $R_6$ is bound to $L_1$. In some embodiments, where $R_1$ and $R_2$ are both independently $-G_1-L_1-R_6$, $R_6$ for $R_1$ is different from $R_6$ for $R_2$. In some of these embodiments, for example, $R_6$ for $R_1$ may be a non-cyclic, preferably straight, hydrocarbyl group having at least 10 carbon atoms (e.g., $R_6$ for $R_1$ is

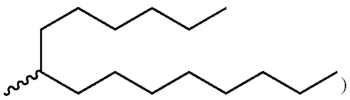 [SMILES: CCCCCCCCC(C)CCCCCC]

)

and $R_6$ for $R_2$ may be a different non-cyclic, preferably straight, hydrocarbyl group having at least 10 carbon atoms (e.g., $R_6$ for $R_2$ is

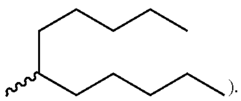

).

In some embodiments, where $R_1$ and $R_2$ are both independently $-G_1-L_1-R_6$, $R_6$ for $R_1$ is identical to $R_6$ for $R_2$. In some of these embodiments, for example, each $R_6$ is the same non-cyclic, preferably straight, hydrocarbyl group having at least 10 carbon atoms (e.g., each $R_6$ is

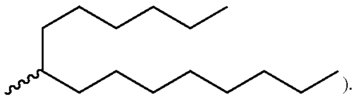 [SMILES: CCCCCCCCC(C)CCCCCC]

).

In some of the foregoing embodiments of Formula (XI), $R_5$ is a non-cyclic hydrocarbyl group having at least 10 carbon atoms, e.g., a straight hydrocarbyl group having at least 10 carbon atoms. In some embodiments, $R_5$ is a non-cyclic hydrocarbyl group having at least 12 carbon atoms, such as at least 14, at least 16, or at least 18 carbon atoms, e.g., a straight hydrocarbyl group having at least 12, at least 14, at least 16, or at least 18 carbon atoms. In some embodiments, $R_5$ has at most 30 carbon atoms, such as at most 28, at most 26, at most 24, at most 22, or at most 20 carbon atoms. In some embodiments, $R_5$ is a non-cyclic hydrocarbyl group, e.g., a straight hydrocarbyl group, wherein each hydrocarbyl group has 10 to 30 carbon atoms (such as 10 to 28, 10 to 26, 10 to 24, 10 to 22, 10 to 20 carbon atoms, or 12 to 30, 12 to 28, 12 to 26, 12 to 24, 12 to 22, 12 to 20 carbon atoms, or 14 to 30, 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms). In some embodiments, the hydrocarbyl group of $R_5$ is an alkyl or alkenyl group, e.g., a $C_{10-30}$ alkyl or alkenyl group. Thus, in some embodiments, $R_5$ is a non-cyclic alkyl group having at least 10 carbon atoms (such as at least 12, at least 14, at least 16, or at least 18 carbon atoms) or a non-cyclic alkenyl group having at least 10 carbon atoms (such as at least 12, at least 14, at least 16, or at least 18 carbon atoms), e.g., a straight alkyl group having at least 10 carbon atoms (such as at least 12, at least 14, at least 16, or at least 18 carbon atoms) or a straight alkenyl group having at least 10 carbon atoms (such as at least 12, at least 14, at least 16, or at least 18 carbon atoms). In some embodiments, $R_5$ is a non-cyclic alkyl group or a non-cyclic alkenyl group, e.g., a straight alkyl group or a straight alkenyl group, wherein each of the alkyl and alkenyl groups has independently 10 to 30 carbon atoms (such as 10 to 28, 10 to 26, 10 to 24, 10 to 22, 10 to 20 carbon atoms, or 12 to 30, 12 to 28, 12 to 26, 12 to 24, 12 to 22, 12 to 20 carbon atoms, or 14 to 30, 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms). In some embodiments, the alkenyl group has at least 2 carbon-carbon double bonds, e.g., 2 or 3 carbon-carbon double bonds, such as 2 carbon-carbon double bonds. In some embodiments, the alkenyl group has at least 1 carbon-carbon double bond in cis configuration, e.g., 1, 2 or 3, such as 2, carbon-carbon double bonds in cis configuration. Thus, in some embodiments, $R_5$ is a non-cyclic alkyl group or a non-cyclic alkenyl group, e.g., a straight alkyl group or a straight alkenyl group, wherein each of the alkyl and alkenyl groups has independently 10 to 30 carbon atoms (such as 10 to 28, 10 to 26, 10 to 24, 10 to 22, 10 to 20 carbon atoms, or 12 to 30, 12 to 28, 12 to 26, 12 to 24, 12 to 22, 12 to 20 carbon atoms, or 14 to 30, 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has at least 2 carbon-carbon double bonds, e.g., 2 or 3 carbon-carbon double bonds. In some embodiments, $R_5$ is a non-cyclic alkyl group or a non-cyclic alkenyl group, e.g., a straight alkyl group or a straight alkenyl group, wherein each of the alkyl and alkenyl groups has independently 10 to 30 carbon atoms (such as 10 to 28, 10 to 26, 10 to 24, 10 to 22, 10 to 20 carbon atoms, or 12 to 30, 12 to 28, 12 to 26, 12 to 24, 12 to 22, 12 to 20 carbon atoms, or 14 to 30, 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has at least 1 carbon-carbon double bond, such as 1, 2, or 3 carbon-carbon double bonds, in cis configuration. In some embodiments, $R_5$ has the following structure:

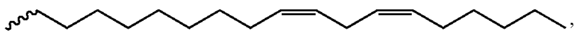

, wherein represents the bond by which $R_5$ is bound to the remainder of the compound. In some of the foregoing embodiments of Formula (XI), $L_2$ is selected from the group consisting of —O(C═O)—, —(C═O)O—, —C(═O)—, —S—S—, —C(═O)S—, —SC(═O)—, —NRaC(═O)—, -c(═O)NR$^a$—, -NRac(═O)NR$^a$—, -Oc(═O)NR$^a$— and —NRaC(═O)O—. In some embodiments, $L_2$ is selected from the group consisting of —O(C═O)—, —(C═O)O—, —C(═O)—, —C(═O)S—, —SC(═O)—, —NRaC(═O)—, and -c(═O)NR$^a$—. In some embodiments, Ra of $L_2$ is H or $C_{1-12}$ alkyl. In some embodiments, Ra of $L_2$ is H or $C_{1-6}$ alkyl, e.g., H or $C_{1-3}$ alkyl. In some embodiments, Ra of $L_2$ is H, methyl, or ethyl. In some embodiments, $L_2$ is selected from the group consisting of —O(C═O)—, —(C═O)O—, —C(═O)S—, and —SC(═O)—. In some embodiments, $L_2$ is —O(C═O)— or —(C═O)O—.

In some of the foregoing embodiments of Formula (XI), $G_2$ is unsubstituted $C_{1-12}$ alkylene or unsubstituted $C_{2-12}$ alkenylene, e.g., unsubstituted, straight $C_{1-12}$ alkylene or unsubstituted, straight $C_{2-12}$ alkenylene. In some embodiments, $G_2$ is unsubstituted $C_{2-10}$ alkylene or unsubstituted $C_{2-10}$ alkenylene, e.g., unsubstituted, straight $C_{2-10}$ alkylene or unsubstituted, straight $C_{2-10}$ alkenylene. In some embodiments, $G_2$ is unsubstituted $C_{2-6}$ alkylene or unsubstituted $C_{2-6}$ alkenylene, e.g., unsubstituted, straight $C_{2-6}$ alkylene or unsubstituted, straight $C_{2-6}$ alkenylene. In some embodiments, $G_2$ is unsubstituted $C_{2-4}$ alkylene or unsubstituted $C_{2-4}$ alkenylene, e.g., unsubstituted, straight $C_{2-4}$ alkylene or unsubstituted, straight $C_{2-4}$ alkenylene. In some embodiments, $G_2$ is ethylene or trimethylene.

In some of the foregoing embodiments of Formula (XI), each of $R_3$ and $R_4$ is independently $C_{1-6}$ alkyl or $C_{2-6}$ alkenyl. In some embodiments, each of $R_3$ and $R_4$ is independently $C_{1-4}$ alkyl or $C_{2-4}$ alkenyl. In some embodiments, each of $R_3$ and $R_4$ is independently $C_{1-3}$ alkyl. In some embodiments, each of $R_3$ and $R_4$ is independently methyl or ethyl. In some embodiments, each of $R_3$ and $R_4$ is methyl.

In some of the foregoing embodiments of Formula (XI), m is 0, 1, 2 or 3. In some embodiments, m is 0 or 2. In some embodiments, m is 0. In some embodiments, m is 2.

In some of the foregoing embodiments of Formula (XI), the cationically ionizable lipid has the structure of Formula (XIIa) or (XIIb):

(XIIa)

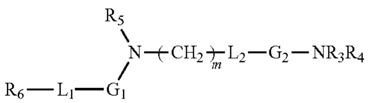

(XIIb)

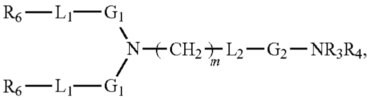

wherein each of $R_3$ and $R_4$ is independently $C_1$-$C_6$ alkyl or $C_{2-6}$ alkenyl;

$R_5$ is a straight hydrocarbyl group having at least 14 carbon atoms (such as at least 16 carbon atoms), wherein the hydrocarbyl group preferably has at least 2 carbon-carbon double bonds;

each $R_6$ is independently a straight hydrocarbyl group (e.g., a straight alkyl group) having at least 10 carbon atoms and/or each $R_6$ is attached to $L_1$ via an internal carbon atom of $R_6$, preferably each $R_6$ is independently a straight hydrocarbyl group (e.g., a straight alkyl group) having at least 10 carbon atoms and each $R_6$ is attached to $L_1$ via an internal carbon atom of $R_6$;

each $G_1$ is independently unsubstituted, straight $C_{4-12}$ alkylene or $C_{4-12}$ alkenylene, e.g., unsubstituted, straight $C_{6-12}$ alkylene or $C_{6-12}$ alkenylene, such as unsubstituted, straight $C_{8-12}$ alkylene or unsubstituted, straight $C_{8-12}$ alkenylene;

$G_2$ is unsubstituted $C_2$-$C_{10}$ alkylene or $C_{2-10}$ alkenylene, preferably unsubstituted $C_2$-$C_6$ alkylene or $C_{2-6}$ alkenylene;

each of $L_1$ and $L_2$ is independently —O(C═O)— or —(C═O)O—; and m is 0, 1, 2 or 3, preferably 0 or 2.

In some of the foregoing embodiments of Formula (XIIa), $R_5$ has at most 30 carbon atoms, such as at most 28, at most 26, at most 24, at most 22, or at most 20 carbon atoms. In some embodiments of formulas (XIIa), $R_5$ is a straight hydrocarbyl group having 14 to 30 carbon atoms (such as 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms). In some embodiments of formula (XIIa), $R_5$ is a straight alkyl or alkenyl group having 14 to 30 carbon atoms (such as 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms). In some embodiments of formula (XIIa), the alkenyl group has at least 2 carbon-carbon double bonds, e.g., 2 or 3 carbon-carbon double bonds, such as 2 carbon-carbon double bonds. In some embodiments, the alkenyl group has at least 1 carbon-carbon double bond in cis configuration, e.g., 1, 2 or 3, such as 2, carbon-carbon double bonds in cis configuration. Thus, in some embodiments of formula (XIIa), $R_5$ is a straight alkyl group or a straight alkenyl group, wherein each of the alkyl and alkenyl groups has independently 14 to 30 carbon atoms (such as 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has at least 2 carbon-carbon double bonds, e.g., 2 or 3 carbon-carbon double bonds. In some embodiments of formula (XIIa), $R_5$ is a straight alkyl group or a straight alkenyl group, wherein each of the alkyl and alkenyl groups has independently 14 to 30 carbon atoms (such as 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has at least 1 carbon-carbon double bond, such as 1, 2, or 3 carbon-carbon double bonds, in cis configuration. In some embodiments of formula (XIIa), $R_5$ is a straight alkyl group or a straight alkenyl group, wherein each of the alkyl and alkenyl groups has independently 14 to 30 carbon atoms (such as 14 to 28, 14 to 26, 14 to 24, 14 to 22, 14 to 20 carbon atoms, or 16 to 30, 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has 2 or 3 carbon-carbon double bonds, wherein at least 1 carbon-carbon double bond, such as 1, 2, or 3 carbon-carbon double bonds, is in cis configuration. In some embodiments of formula (XIIa), $R_5$ has the following structure:

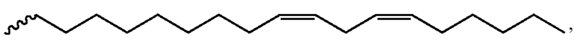, wherein  represents the bond by which $R_5$ is bound to the remainder of the compound. In some embodiments of formula (XIIa), $R_6$ has at most 30 carbon atoms, such as at most 28, at most 26, at most 24, at most 22, or at most 20 carbon atoms. In some embodiments of formula (XIIa), $R_6$ is a non-cyclic hydrocarbyl group (e.g., a non-cyclic alkyl group) having 10 to 30 carbon atoms (such as 10 to 28, 10 to 26, 10 to 24, 10 to 22, or 10 to 20 carbon atoms), e.g., a straight hydrocarbyl group (e.g., a straight alkyl group) having 10 to 30 carbon atoms (such as 10 to 28, 10 to 26, 10 to 24, 10 to 22, or 10 to 20 carbon atoms). In some embodiments of formula (XIIa), $R_6$ is a straight hydrocarbyl group (e.g., a straight alkyl group) having at least 10 carbon atoms and $R_6$ is attached to $L_1$ via an internal carbon atom of $R_6$. In some embodiments of formula (XIIa), $R_6$ is a non-cyclic hydrocarbyl group (e.g., a non-cyclic alkyl group) having 10 to 30 carbon atoms (such as 10 to 28, 10 to 26, 10 to 24, 10 to 22, or 10 to 20 carbon atoms), e.g., a straight hydrocarbyl group (e.g., a straight alkyl group) having 10 to 30 carbon atoms (such as 10 to 28, 10 to 26, 10 to 24, 10 to 22, or 10 to 20 carbon atoms), and $R_6$ is attached to $L_1$ via an internal carbon atom of $R_6$. In some embodiments of formula (XIIa), $G_1$ is independently unsubstituted, straight $C_{4-12}$ alkylene or $C_{4-12}$ alkenylene, e.g., unsubstituted, straight $C_{6-12}$ alkylene or $C_{6-12}$ alkenylene. In some embodiments of formula (XIIa), $R_5$ is a straight hydrocarbyl group, e.g., a straight alkenyl group, having at least 14 carbon atoms (such as 14 to 30 carbon atoms) and 2 or 3 carbon-carbon double bonds; $R_6$ is a straight hydrocarbyl group (e.g., a straight alkyl group) having at least 10 carbon atoms (e.g., having 10 to 30 carbon atoms) and $R_6$ is attached to $L_1$ via an internal carbon atom of $R_6$; and $G_1$ is independently unsubstituted, straight $C_{4-12}$ alkylene or $C_{4-12}$ alkenylene, e.g., unsubstituted, straight $C_{6-12}$ alkylene or $C_{6-12}$ alkenylene.

In some of the foregoing embodiments of Formula (XIIb), each $R_6$ has independently at most 30 carbon atoms, such as at most 28, at most 26, at most 24, at most 22, or at most 20 carbon atoms. In some embodiments of formula (XIIb), each $R_6$ is independently a straight hydrocarbyl group (e.g., a straight alkyl group) having 10 to 30 carbon atoms (such as 10 to 28, 10 to 26, 10 to 24, 10 to 22, or 10 to 20 carbon atoms, or 11 to 19 carbon atoms, such as 11, 13, 15, 17, or 17 carbon atoms). In some embodiments of formula (XIIb), each $R_6$ is independently a straight hydrocarbyl group (e.g., a straight alkyl group) having 10 to 30 carbon atoms (such as 10 to 28, 10 to 26, 10 to 24, 10 to 22, or 10 to 20 carbon atoms, or 11 to 19 carbon atoms, such as 11, 13, 15, 17, or 17 carbon atoms) and each $R_6$ is attached to $L_i$ via an internal carbon atom of $R_6$. In some embodiments of formula (XIIb), each $R_6$ is independently selected from the group consisting of:

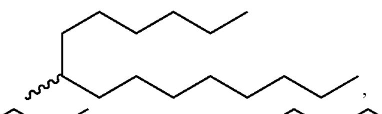
,
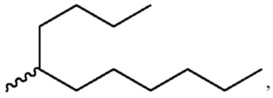
,
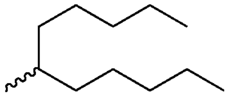
,
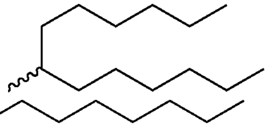
,
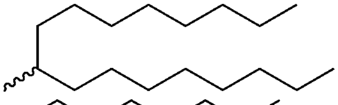
, and
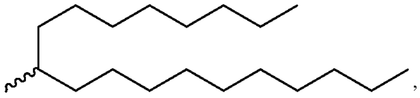
, wherein  resents the bond by which $R_6$ is bound to $L_1$. In some embodiments of formula (XIIb), each $G_1$ is independently unsubstituted, straight $C_{6-12}$ alkylene or $C_{6-12}$ alkenylene. In some embodiments of formula (XIIb), each $G_1$ is independently unsubstituted, straight $C_{8-12}$ alkylene or $C_{8-12}$ alkenylene. In some embodiments of formula (XIIb), each $R_6$ is independently a straight hydrocarbyl group (e.g., a straight alkyl group) having at least 10 carbon atoms (such as 10 to 28, 10 to 26, 10 to 24, 10 to 22, or 10 to 20 carbon atoms, or 11 to 19 carbon atoms, such as 11, 13, 15, 17, or 17 carbon atoms) and is attached to $L_1$ via an internal carbon atom of $R_6$; and each $G_1$ is independently unsubstituted, straight $C_{8-12}$ alkylene or $C_{8-12}$ alkenylene.

In some of the foregoing embodiments of Formula (XI), the cationically ionizable lipid has the structure of Formula (XIIIa) or (XIIIb):

(XIIIa)

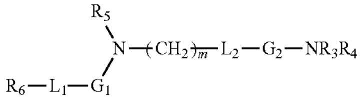

(XIIIb)

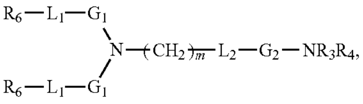

wherein each of $R_3$ and $R_4$ is independently $C_{1-4}$ alkyl or $C_{2-4}$ alkenyl, more preferably $C_{1-3}$ alkyl, such as methyl or ethyl;

$R_5$ is a straight alkyl or alkenyl group having at least 16 carbon atoms, wherein the alkenyl group preferably has at least 2 carbon-carbon double bonds;

each $R_6$ is independently a straight hydrocarbyl group having at least 10 carbon atoms, wherein $R_6$ is attached to $L_1$ via an internal carbon atom of $R_6$;

each $G_1$ is independently unsubstituted, straight $C_{6-12}$ alkylene or unsubstituted, straight $C_{6-12}$ alkenylene, e.g., unsubstituted, straight $C_{8-12}$ alkylene or unsubstituted, straight $C_{8-12}$ alkenylene, such as unsubstituted, straight $C_{8-10}$ alkylene or unsubstituted, straight $C_{8-10}$ alkenylene, such as unsubstituted, straight $C_s$ alkylene;

$G_2$ is unsubstituted $C_{2-6}$ alkylene or $C_{2-6}$ alkenylene, preferably unsubstituted $C_{2-4}$ alkylene or $C_{2-4}$ alkenylene, such as ethylene or trimethylene;

each of $L_1$ and $L_2$ is independently —O(C═O)— or —(C═O)O—; and m is 0, 1, 2 or 3, preferably 0 or 2.

In some of the foregoing embodiments of Formula (XIIIa), $R_5$ has at most 30 carbon atoms, such as at most 28, at most 26, at most 24, at most 22, or at most 20 carbon atoms. In some embodiments of formulas (XIIIa), $R_5$ is a straight alkyl or alkenyl group having 16 to 30 carbon atoms (such as 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms). In some embodiments of formula (XIIIa), the alkenyl group has at least 2 carbon-carbon double bonds, e.g., 2 or 3 carbon-carbon double bonds, such as 2 carbon-carbon double bonds.

In some embodiments, the alkenyl group has at least 1 carbon-carbon double bond in cis configuration, e.g., 1, 2 or 3, such as 2, carbon-carbon double bonds in cis configuration. Thus, in some embodiments of formula (XIIIa), $R_5$ is a straight alkyl group or a straight alkenyl group, wherein each of the alkyl and alkenyl groups has independently 16 to 30 carbon atoms (such as 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has at least 2 carbon-carbon double bonds, e.g., 2 or 3 carbon-carbon double bonds. In some embodiments of formula (XIIIa), $R_5$ is a straight alkyl group or a straight alkenyl group, wherein each of the alkyl and alkenyl groups has independently 16 to 30 carbon atoms (such as 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has at least 1 carbon-carbon double bond, such as 1, 2, or 3 carbon-carbon double bonds, in cis configuration. In some embodiments of formula (XIIIa), $R_5$ is a straight alkyl group or a straight alkenyl group, wherein each of the alkyl and alkenyl groups has independently 16 to 30 carbon atoms (such as 16 to 28, 16 to 26, 16 to 24, 16 to 22, 16 to 20 carbon atoms, or 18 to 30, 18 to 28, 18 to 26, 18 to 24, 18 to 22, or 18 to 20 carbon atoms) and the alkenyl group has 2 or 3 carbon-carbon double bonds, wherein at least 1 carbon-carbon double bond, such as 1, 2, or 3 carbon-carbon double bonds, is in cis configuration. In some embodiments of formula (XIIIa), $R_5$ has the following structure:

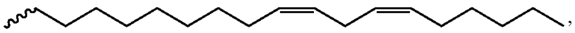, wherein  represents the bond by which $R_5$ is bound to the remainder of the compound. In some embodiments of formula (XIIIa), $R_6$ has at most 30 carbon atoms, such as at most 28, at most 26, at most 24, at most 22, or at most 20 carbon atoms. In some embodiments of formula (XIIIa), $R_6$ is a straight hydrocarbyl group (e.g., a straight alkyl group) having 10 to 30 carbon atoms (such as 10 to 28, 10 to 26, 10 to 24, 10 to 22, or 10 to 20 carbon atoms) and $R_6$ is attached to $L_1$ via an internal carbon atom of $R_6$. In some embodiments of formula (XIIIa), $R_6$ is a straight alkyl group having 10 to 30 carbon atoms (such as 10 to 28, 10 to 26, 10 to 24, 10 to 22, or 10 to 20 carbon atoms) and $R_6$ is attached to $L_1$ via an internal carbon atom of $R_6$. In some embodiments of formula (XIIIa), $G_1$ is independently unsubstituted, straight $C_{4-12}$ alkylene or $C_{4-12}$ alkenylene, e.g., unsubstituted, straight $C_{6-12}$ alkylene or $C_{6-12}$ alkenylene. In some embodiments of formula (XIIIa), $R_5$ is a straight hydrocarbyl group, e.g., a straight alkenyl group, having at least 16 carbon atoms (such as 16 to 30 carbon atoms) and 2 or 3 carbon-carbon double bonds; $R_6$ is a straight hydrocarbyl group (e.g., a straight alkyl group) having at least 10 carbon atoms (e.g., having 10 to 30 carbon atoms) and $R_6$ is attached to $L_1$ via an internal carbon atom of $R_6$; and $G_1$ is independently unsubstituted, straight $C_{4-12}$ alkylene or $C_{4-12}$ alkenylene, e.g., unsubstituted, straight $C_{6-12}$ alkylene or $C_{6-12}$ alkenylene.

In some of the foregoing embodiments of Formula (XIIIb), each $R_6$ has independently at most 30 carbon atoms, such as at most 28, at most 26, at most 24, at most 22, or at most 20 carbon atoms. In some embodiments of formula (XIIIb), each $R_6$ is independently a straight hydrocarbyl group (e.g., a straight alkyl group) having 10 to 30 carbon atoms (such as 10 to 28, 10 to 26, 10 to 24, 10 to 22, or 10 to 20 carbon atoms, or 11 to 19 carbon atoms, such as 11, 13, 15, 17, or 17 carbon atoms) and each $R_6$ is attached to $L_1$ via an internal carbon atom of $R_6$. In some embodiments of formula (XIIIb), each $R_6$ is attached to $L_1$ via an internal carbon atom of $R_6$ and is independently selected from the group consisting of:

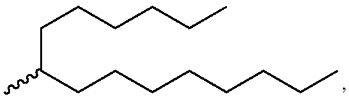,

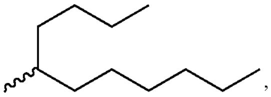, 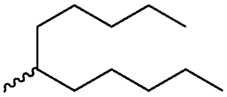,

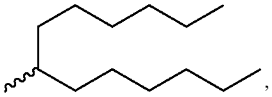,

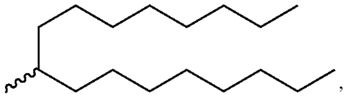, and

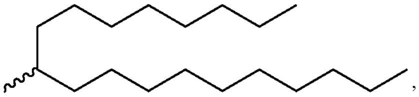, wherein  represents the bond by which $R_6$ is bound to $L_1$. In some embodiments of formula (XIIIb), each $G_1$ is independently unsubstituted, straight $C_{8-12}$ alkylene or $C_{8-12}$ alkenylene, e.g., unsubstituted, straight $C_{8-10}$ alkylene or $C_{8-10}$ alkenylene. In some embodiments of formula (XIIIb), each $R_6$ is independently a straight hydrocarbyl group (e.g., a straight alkyl group) having at least 10 carbon atoms (such as 10 to 28, 10 to 26, 10 to 24, 10 to 22, or 10 to 20 carbon atoms, or 11 to 19 carbon atoms, such as 11, 13, 15, 17, or 17 carbon atoms) and is attached to $L_1$ via an internal carbon atom of $R_6$; and each $G_1$ is independently unsubstituted, straight $C_{8-12}$ alkylene or $C_{8-12}$ alkenylene, e.g., unsubstituted, straight $C_{8-10}$ alkylene or $C_{8-10}$ alkenylene.

In some of the foregoing embodiments of Formula (XI), the cationically ionizable lipid has one of the following formulas (XIV-1), (XIV-2), and (XIV-3):

(XIV-1)

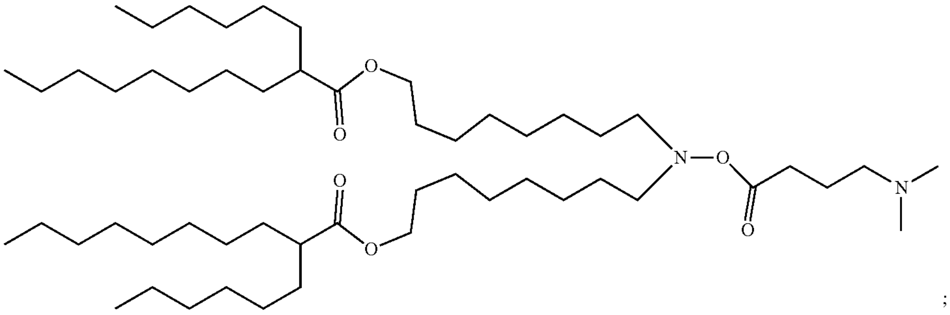

;

(XIV-2)

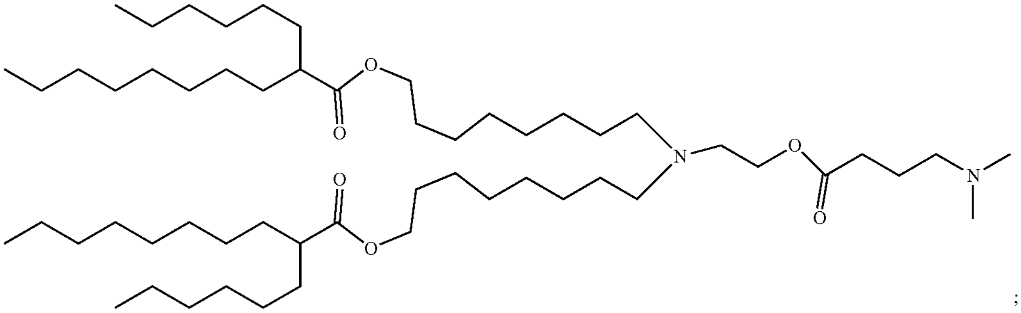

;

(XIV-3)

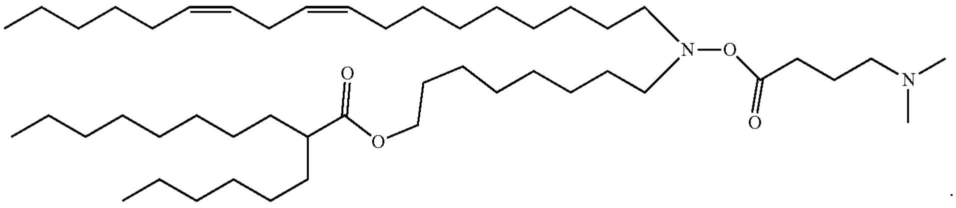

.

Thus, in certain embodiments, the cationically ionizable lipid has the structure XIV-2 or XIV-3.

In some embodiments, the cationically ionizable lipid is (6Z,16Z)-12-((Z)-dec-4-en-1-yl)docosa-6,16-dien-11-yl 5-(dimethylamino)pentanoate (3D-P-DMA). The structure of 3D-P-DMA may be represented as follows:

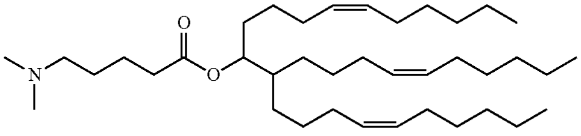 [SMILES: CCCCC/C=C\CCCC(CCC/C=C\CCCCC)C(CCC/C=C\CCCCC)OC(=O)CCCCN(C)C]

In various different embodiments, the cationically ionizable lipid is selected from the group consisting of N,N-dimethyl-2,3-dioleyloxypropylamine (DODMA), 1,2-dioleoyl-3-dimethylammonium-propane (DODAP), heptatriaconta-6,9,28,31-tetraen-19-yl-4-(dimethylamino) butanoate (DLin-MC3-DMA), and 4-((di((9Z,12Z)-octadeca-9,12-dien-1-yl)amino)oxy)-N,N-dimethyl-4-oxobutan-1-amine (DPL-14).

Further examples of cationically ionizable lipids include, but are not limited to, 3-(N—(N',N'-dimethylaminoethane)-carbamoyl)cholesterol (DC-Chol), 1,2-dioleoyl-3-dimethyl-ammonium-propane (DODAP); 1,2-diacyloxy-3-dimethyl-ammonium propanes; 1,2-dialkyloxy-3-dimethylammonium propanes, 1,2-distearyloxy-N,N-dimethyl-3-aminopropane (DSDMA), 1,2-dilinoleyloxy-N,N-dimethylaminopropane (DLinDMA), 1,2-dilinolenyloxy-N,N-dimethylaminopropane (DLenDMA), dioctadecylamidoglycyl spermine (DOGS), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), 2-({8-[(3p)-cholest-5-en-3-yloxy]octyl}oxy)-N,N-dimethyl-3-[(9Z,12Z)-octadeca-9,12-dien-1-yloxy]propan-1-amine (Octyl-CLinDMA), 1,2-dimyristoyl-3-dimethylammonium-propane (DMDAP), 1,2-dipalmitoyl-3-dimethylammonium-propane (DPDAP), N1-[2-((1S)-1-[(3-aminopropyl)amino]-4-[di(3-amino-propyl)amino]butylcarboxamido)ethyl]-3,4-di[oleyloxy]-benzamide (MVL5), di((Z)-non-2-en-1-yl) 8,8'-((((2(dimethylamino)ethyl)thio)carbonyl)azanediyl)dioctanoate (ATX), N,N-dimethyl-2,3-bis(dodecyloxy)propan-1-amine (DLDMA), N,N-dimethyl-2,3-bis(tetradecyloxy)propan-1-amine (DMDMA), di((Z)-non-2-en-1-yl)-9-((4-(dimethylaminobutanoyl)oxy)heptadecanedioate (L319), N-dodecyl-3-((2-dodecylcarbamoyl-ethyl)-{2-[(2-dodecylcarbamoyl-ethyl)-2-{(2-dodecylcarbamoyl-ethyl)-[2-(2-dodecylcarbamoyl-ethylamino)-ethyl]-amino}-ethyl-amino)propionamide (lipidoid 98N12-5), 1-[2-[bis(2-hydroxydodecyl)amino]ethyl-[2-[4-[2-[bis(2 hydroxydodecyl)amino]ethyl]piperazin-1-yl]ethyl]amino] dodecan-2-ol (lipidoid C12-200).

In certain embodiments, the cationically ionizable lipid has the structure X-3.

In some embodiments, the cationic lipid for use herein is or comprises DPL-14. As used herein, "DPL-14" is a lipid comprising the following general formula:

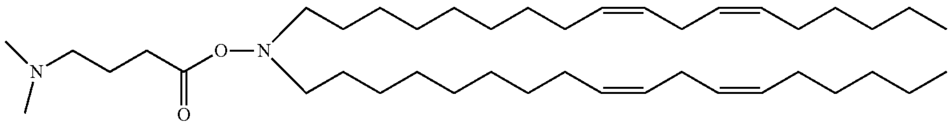

It is to be understood that any reference to a cationically ionizable lipid disclosed herein also includes the salts (in particular pharmaceutically acceptable salts), tautomers, stereoisomers, solvates (e.g., hydrates), and isotopically labeled forms thereof.

In some embodiments, the cationically ionizable lipid may comprise from about 10 mol % to about 100 mol %, about 20 mol % to about 100 mol %, about 30 mol % to about 100 mol %, about 40 mol % to about 100 mol %, or about 50 mol % to about 100 mol % of the total lipid present in the composition/particle. In some embodiments, the cationically ionizable lipid comprises from about 40 mol % to about 75 mol %, preferably from about 40 mol % to about 70 mol %, more preferably from about 45 mol % to about 65 mol %, of the total lipid present in the composition/particles.

In some embodiments, wherein the nucleic acid compositions/particles (in particular the RNA compositions/particles) described herein comprise a cationically ionizable lipid and one or more additional lipids, the cationically ionizable lipid comprises from about 10 mol % to about 80 mol %, from about 20 mol % to about 75 mol %, from about 20 mol % to about 70 mol %, from about 20 mol % to about 60 mol %, from about 25 mol % to about 55 mol %, from about 30 mol % to about 50 mol 00 from about 35 mol % to about 45 mol %, or about 40 mol % of the total lipid present in the composition/particles. In some embodiments, the cationically ionizable lipid comprises from about 40 mol % to about 70 mol %, such as from about 45 mol % to about 65 mol %, or from about 50 mol % to about 60 mol %, of the total lipid present in the composition/particles (in particular for those embodiments having higher relative amounts of ionizable and neutral lipids and a lower relative amount of steroid). In some alternative embodiments, the cationically ionizable lipid comprises from about 20 mol % to about 40 mol %, such as from about 25 mol % to about 40 mol % or from about 25 mol % to about 35 mol %, of the total lipid present in the composition/particles (in particular for those embodiments having lower relative amounts of ionizable and neutral lipids and a higher relative amount of steroid).

In one embodiment, the particles (in particular the RNA LNPs) described herein comprise from about 40 mol % to about 70 mol %, such as from about 45 mol % to about 65 mol %, or from about 50 mol % to about 60 mol %, of the cationically ionizable lipid (in particular for those embodiments having higher relative amounts of ionizable and neutral lipids and a lower relative amount of steroid). In some alternative embodiments, the particles (in particular the RNA LNPs) described herein comprise comprises from about 20 mol % to about 40 mol %, such as from about 25 mol % to about 40 mol % or from about 25 mol % to about 35 mol %, of the cationically ionizable lipid (in particular for those embodiments having lower relative amounts of ionizable and neutral lipids and a higher relative amount of steroid).

In some embodiments, where at least a portion of the cationically ionizable lipid described herein is associated with at least a portion of the nucleic acid (such as RNA) to form particles (e.g., LNPs), the cationically ionizable lipid may comprise from about 40 mol % to about 70 mol %, such as from about 45 mol % to about 65 mol %, or from about 50 mol % to about 60 mol %, of the total lipid present in the composition or particles (in particular for those embodiments having higher relative amounts of ionizable and neutral lipids and a lower relative amount of steroid). In some alternative embodiments, the cationically ionizable lipid comprises from about 20 mol % to about 40 mol %, such as from about 25 mol % to about 40 mol % or from about 25 mol % to about 35 mol %, of the total lipid present in the composition or particles (in particular for those embodiments having lower relative amounts of ionizable and neutral lipids and a higher relative amount of steroid).

In some embodiments, the N/P value is at least about 4. In some embodiments, the N/P value ranges from 4 to 20, 4 to 12, 4 to 10, 4 to 8, or 5 to 7. In some embodiments, the N/P value is about 6.

Additional Lipids

In some embodiments, the nucleic acid (such as RNA) compositions described herein may also comprise lipids or lipid-like materials other than cationically ionizable lipids, i.e., non-cationic lipids or lipid-like materials (including non-cationically ionizable lipids or lipid-like materials). Collectively, anionic and neutral lipids or lipid-like materials are referred to herein as non-cationic lipids or lipid-like materials. In some embodiments, optimizing the formulation of nucleic acid particles by addition of other hydrophobic moieties, such as cholesterol and lipids, in addition to a cationically ionizable lipid may enhance composition and/or particle stability and efficacy of nucleic acid (such as RNA) delivery.

One or more additional lipids may be incorporated which may or may not affect the overall charge of the nucleic acid particles. In certain embodiments, the one or more additional lipids are a non-cationic lipid or lipid-like material. The non-cationic lipid may comprise, e.g., one or more anionic lipids and/or neutral lipids. As used herein, an "anionic lipid" refers to any lipid that is negatively charged at a selected pH. As used herein, a "neutral lipid" refers to any of a number of lipid species that exist either in an uncharged or neutral zwitterionic form at a selected pH.

In certain embodiments, the nucleic acid (such as RNA) compositions (especially the mRNA compositions)

described herein comprise a cationically ionizable lipid and one or more additional lipids.

Without wishing to be bound by theory, the amount of the cationically ionizable lipid compared to the amount of the one or more additional lipids may affect important nucleic acid particle characteristics, such as charge, particle size, stability, tissue selectivity, and bioactivity of the nucleic acid. Accordingly, in some embodiments, the molar ratio of the cationically ionizable lipid to the one or more additional lipids is from about 0.25:1 to about 2.5:1, such as from about 0.6:1 to about 2.4:1, from about 0.8:1 to about 1.9:1, or from about 1.1 to about 1.5:1 (in particular for those embodiments having higher relative amounts of ionizable and neutral lipids and a lower relative amount of steroid); or from about 0.25: 1 to about 0.7:1, from about 0.3:1 to about 0.7:1, or from about 0.3:1 to about 0.54:1 (in particular for those embodiments having lower relative amounts of ionizable and neutral lipids and a higher relative amount of steroid).

In some embodiments, the one or more additional lipids comprised in the nucleic acid (such as RNA) compositions (especially in the mRNA compositions) described herein comprise one or more of the following: neutral lipids, steroids, and combinations thereof.

Neutral Lipids

In some embodiments, the one or more additional lipids comprise a neutral lipid which is preferably a phospholipid. In some embodiments, the phospholipid is selected from the group consisting of phosphatidylcholines, phosphatidylethanolamines, phosphatidylglycerols, phosphatidic acids, phosphatidylserines and sphingomyelins. Specific phospholipids that can be used include, but are not limited to, phosphatidylcholines, phosphatidylethanolamines, phosphatidylglycerols, phosphatidic acids, phosphatidylserines or sphingomyelin. Such phospholipids include in particular diacylphosphatidylcholines, such as distearoylphosphatidylcholine (DSPC), dioleoylphosphatidylcholine (DOPC), dimyristoylphosphatidylcholine (DMPC), dipentadecanoylphosphatidylcholine, dilauroylphosphatidylcholine, dipalmitoylphosphatidylcholine (DPPC), diarachidoylphosphatidylcholine (DAPC), dibehenoylphosphatidylcholine (DBPC), ditricosanoylphosphatidylcholine (DTPC), dilignoceroylphatidylcholine (DLPC), palmitoyloleoyl-phosphatidylcholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC) and phosphatidylethanolamines, in particular diacylphosphatidylethanolamines, such as dioleoylphosphatidylethanolamine (DOPE), distearoyl-phosphatidylethanolamine (DSPE), dipalmitoyl-phosphatidylethanolamine (DPPE), dimyristoyl-phosphatidylethanolamine (DMPE), dilauroyl-phosphatidylethanolamine (DLPE), diphytanoyl-phosphatidylethanolamine (DPyPE), 1,2-di-(9Z-octadecenoyl)-sn-glycero-3-phosphocholine (DOPG), 1,2-dipalmitoyl-sn-glycero-3-phospho-(1'-rac-glycerol) (DPPG), 1-palmitoyl-2-oleoyl-sn-glycero-3-phosphoethanolamine (POPE), N-palmitoyl-D-erythro-sphingosylphosphorylcholine (SM), and further phosphatidylethanolamine lipids with different hydrophobic chains. In some embodiments, the neutral lipid is selected from the group consisting of DSPC, DOPC, DMPC, DPPC, POPC, DOPE, DOPG, DPPG, POPE, DPPE, DMPE, DSPE, and SM. In some embodiments, the neutral lipid is selected from the group consisting of DSPC, DPPC, DMPC, DOPC, POPC, DOPE and SM. In some embodiments, the neutral lipid is DSPC.

In some embodiments, the phospholipid is selected from the group consisting of phospholipids having a $T_g$ value of higher than 30° C. Thus, in some embodiments, the phospholipid is selected from the group consisting of DSPC, DPPC, DSPE, and DPPE. In some embodiments, the neutral lipid is DSPC.

Thus, in some embodiments, the nucleic acid (such as RNA) compositions (especially the mRNA compositions) described herein comprise a cationically ionizable lipid and a phospholipid having a $T_g$ value of higher than 30° C. In some embodiments, the nucleic acid (such as RNA) compositions (especially the mRNA compositions) described herein comprise a cationically ionizable lipid and a phospholipid selected from the group consisting of DSPC, DPPC, DSPE, and DPPE. In some embodiments, the nucleic acid (such as RNA) compositions (especially the mRNA compositions) described herein comprise a cationically ionizable lipid and DSPC.

In some embodiments, the neutral lipid is present in the nucleic acid (such as RNA) compositions (in particular the mRNA compositions) described herein in a concentration ranging from 5 to 25 mol percent. In some embodiments, the neutral lipid is present in a concentration of from about 15 mol % to about 25 mol %, such as from about 17 mol % to about 21 mol %, of the total lipids present in the nucleic acid (such as RNA) composition (especially the mRNA composition) described herein (in particular for those embodiments having higher relative amounts of ionizable and neutral lipids and a lower relative amount of steroid). In some embodiments, the neutral lipid is present in a concentration of from about 5 mol % to about 15 mol %, such as from about 7 mol % to about 14 mol %, of the total lipids present in the nucleic acid (such as RNA) composition (especially the mRNA composition) described herein (in particular for those embodiments having lower relative amounts of ionizable and neutral lipids and a higher relative amount of steroid).

Steroid

In some embodiments, the steroid is cholesterol. Thus, in some embodiments, the nucleic acid (such as RNA) compositions (especially the mRNA compositions) described herein comprise a cationically ionizable lipid and cholesterol.

In some embodiments, the steroid is present in the nucleic acid (such as RNA) compositions (in particular the mRNA compositions) described herein in a concentration ranging from 15 to 60 mol percent. In some embodiments, the steroid is present in a concentration from about 15 mol % to about 40 mol %, such as from about 20 mol % to about 35 mol %, or from about 20 mol % to about 30 mol %, of the total lipids present in the compositions (especially the mRNA compositions) described herein (in particular for those embodiments having higher relative amounts of ionizable and neutral lipids and a lower relative amount of steroid). In some embodiments, the steroid is present in the nucleic acid (such as RNA) compositions (in particular the mRNA compositions) described herein in a concentration ranging from about 35 mol % to about 60 mol %, such as from about 40 mol % to about 60 mol % or from about 45 mol % to about 60 mol %, of the total lipids present in the compositions (in particular for those embodiments having lower relative amounts of ionizable and neutral lipids and a higher relative amount of steroid).

In certain preferred embodiments, the nucleic acid (such as RNA) compositions (especially the mRNA compositions) described herein comprise a phospholipid having a $T_g$ value of higher than 30° C. and cholesterol, preferably in the concentrations given above. In some embodiments, the nucleic acid (such as RNA) compositions (especially the mRNA compositions) described herein comprise a phospholipid selected from the group consisting of DSPC, DPPC, DSPE, and DPPE, and cholesterol, preferably in the concentrations given above. In some embodiments, the nucleic acid (such as RNA) compositions (especially the mRNA compositions) described herein comprise DSPC and cholesterol, preferably in the concentrations given above.

In some embodiments, the combined concentration of the neutral lipid (in particular, one or more phospholipids) and steroid (in particular, cholesterol) may comprise from about 0 mol % to about 80 mol %, such as from about 30 mol % to about 65 mol %, from about 30 mol % to about 60 mol %, from about 32 mol % to about 60 mol %, from about 35 mol % to about 60 mol %, from about 37 mol % to about 55 mol %, or from about 37 mol % to about 51 mol % (in particular for those embodiments having higher relative amounts of ionizable and neutral lipids and a lower relative amount of steroid); or from about 40 mol % to about 75 mol %, from about 42 mol % to about 74 mol %, from about 45 mol % to about 74 mol %, from about 47 mol % to about 70 mol %, from about 50 mol % to about 67 mol %, or from about 52 mol % to about 65 mol % (in particular for those embodiments having lower relative amounts of ionizable and neutral lipids and a higher relative amount of steroid), of the total lipids present in the nucleic acid (such as RNA) compositions (especially the mRNA compositions) described herein.

In some embodiments of the nucleic acid (such as RNA) compositions (especially the mRNA compositions) described herein, where at least a portion of (i) the nucleic acid (such as RNA), (ii) the cationically ionizable lipid, and (iii) the one or more additional lipids (e.g., one or more phospholipids and/or steroids) form particles (e.g., LNPs), at least a portion of the multivalent anion (such as the inorganic polyphosphate or citrate or inorganic phosphate) is associated with the particles and the additional lipid (e.g., one or more phospholipids and/or steroids) may comprise from about 0 mol % to about 60 mol %, from about 2 mol % to about 55 mol %, from about 5 mol % to about 50 mol %, from about 5 mol % to about 45 mol %, from about 10 mol % to about 45 mol %, from about 15 mol % to about 40 mol %, or from about 20 mol % to about 40 mol % of the total lipid present in the particles.

In some embodiments, the phospholipid may comprise from about 5 mol % to about 25 mol %, such as from about 15 mol % to about 25 mol % or from about 17 mol % to about 21 mol % of the total lipid present in the particles (in particular for those embodiments having higher relative amounts of ionizable and neutral lipids and a lower relative amount of steroid). In alternative some embodiments, the phospholipid comprises from about 5 mol % to about 15 mol %, such as from about 7 mol % to about 14 mol %, of the total lipid present in the particles (in particular for those embodiments having lower relative amounts of ionizable and neutral lipids and a higher relative amount of steroid).

In some embodiments, the steroid (in particular, cholesterol) comprises from about 15 mol % to about 40 mol %, such as from about 20 mol % to about 35 mol %, or from about 20 mol % to about 30 mol %, of the total lipid present in the particles (in particular for those embodiments having higher relative amounts of ionizable and neutral lipids and a lower relative amount of steroid). In some embodiments, the steroid (in particular, cholesterol) comprises from about 35 mol % to about 60 mol %, such as from about 40 mol % to about 60 mol % or from about 45 mol % to about 60 mol %, of the total lipid present in the particles (in particular for those embodiments having lower relative amounts of ionizable and neutral lipids and a higher relative amount of steroid).

Polymer-Conjugated Lipids

A polymer-conjugated lipid is typically a molecule comprising a lipid portion and a polymer portion conjugated thereto.

An example of a polymer-conjugated lipid is a PEG-conjugated lipid, also referred to herein as pegylated lipid or PEG-lipid. The term "pegylated lipid" refers to a molecule comprising both a lipid portion and a polyethylene glycol portion. Pegylated lipids are known in the art.

Another example of a polymer-conjugated lipid is a polysarcosine-conjugated lipid, also referred to herein as sarcosinylated lipid or pSar-lipid. The term "sarcosinylated lipid" refers to a molecule comprising both a lipid portion and a polysarcosine (poly(N-methylglycine) portion.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer such as a protein. In some cases, additional moieties can also be present in the polymer, for example targeting moieties. If more than one type of repeat unit is present within the polymer, then the polymer is said to be a "copolymer." The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In some embodiments, a polymer-conjugated lipid is designed to sterically stabilize a lipid particle by forming a protective hydrophilic layer that shields the hydrophobic lipid layer. In some embodiments, a polymer-conjugated lipid can reduce its association with serum proteins and/or the resulting uptake by the reticuloendothelial system when such lipid particles are administered in vivo.

In some embodiments, the nucleic acid (such as RNA) compositions described herein are substantially free of a sarcosinylated lipid.

In some embodiments, the nucleic acid (such as RNA) compositions described herein are is substantially free of a pegylated lipid.

In some embodiments, the nucleic acid (such as RNA) compositions described herein are substantially free of pegylated lipid and substantially free of sarcosinylated lipid (or do not include a pegylated lipid or a sarcosinylated lipid).

In some embodiments, the nucleic acid (such as RNA) compositions described herein are substantially free of any polymer-conjugated lipid (or do not include any polymer-conjugated lipid).

Embodiments of Nucleic Acid (Such as RNA) Compositions

In some embodiments, the one or more additional lipids comprise one of the following components: (1) a neutral lipid; (2) a steroid; or (3) a mixture of a neutral lipid and a steroid; preferably each in the concentration given above. In some embodiments, the one or more additional lipids comprise (3) a mixture of a neutral lipid and a steroid (and preferably do not comprise a PEG-lipid, more preferably do not comprise any polymer-conjugated lipid). In some embodiments, the one or more additional lipids comprise one of the following components: (1) a phospholipid; (2) cholesterol; (3) a mixture of a phospholipid and cholesterol; preferably each in the concentration given above. In some embodiments, the one or more additional lipids comprise (3) a mixture a phospholipid and cholesterol (and preferably do not comprise a PEG-lipid, more preferably do not comprise any polymer-conjugated lipid).

Thus, in preferred embodiments, the nucleic acid (such as RNA) compositions (especially the mRNA compositions) described herein comprise (ii) a cationic or cationically ionizable lipid; (iii) a steroid; (iv) a neutral lipid (in particular, a phospholipid); and (v) a multivalent anion (such as an inorganic polyphosphate), preferably each in the concentration given above. In specific embodiments (in particular those having higher relative amounts of ionizable and neutral lipids and a lower relative amount of steroid), the cationic or cationically ionizable lipid is present in a concentration of from about 40 mol % to about 70 mol % (such as from about 45 mol % to about 65 mol %, or from about 50 mol % to about 60 mol %; the steroid is present in a concentration of from about 15 to about 40 mol percent (such as from about 20 mol % to about 35 mol %, or from about 20 mol % to about 30 mol %); the neutral lipid (in particular, a phospholipid) is present in a concentration of from about 15 to about 25 mol percent (such as from about 17 mol % to about 21 mol %); and the molar ratio of multivalent anion (such as inorganic polyphosphate) to the cationic or cationically ionizable lipid is at least about 1:2, preferably at least about 2:3, such as at least about 4:3. In some embodiments, the steroid is cholesterol; and the neutral lipid is selected from the group consisting of DSPC, DPPC, DSPE, and DPPE. In some embodiments, the molar ratio of steroid to neutral lipid is at most 2.5, preferably said ratio is between 1 and 2.5. In some embodiments, the inorganic polyphosphate is a linear inorganic polyphosphate (such as a linear inorganic triphosphate). In some embodiments, the inorganic polyphosphate comprises the formula $[P_xO_{(3x+1)}]^{y\prime}$, wherein x is an integer and is at least 2, preferably at least 3; and y is the anionic charge. In some embodiments, the inorganic polyphosphate is selected from the group consisting of diphosphate, triphosphate, tetraphosphate, pentaphosphate, hexaphosphate, heptaphosphate, and mixtures thereof, such as from the group consisting of triphosphate, tetraphosphate, pentaphosphate, hexaphosphate, heptaphosphate, and mixtures thereof. Preferably, the inorganic polyphosphate is selected from the group consisting of triphosphate, tetraphosphate, pentaphosphate, and mixtures thereof. In some preferred embodiments, the inorganic polyphosphate is triphosphate. In some embodiments, the steroid is cholesterol; the neutral lipid is selected from the group consisting of DSPC, DPPC, DSPE, and DPPE; and the inorganic polyphosphate is selected from the group consisting of triphosphate, tetraphosphate, pentaphosphate, hexaphosphate, heptaphosphate, and mixtures thereof, preferably the inorganic polyphosphate is triphosphate. In some embodiments, the molar ratio of steroid to neutral lipid is at most 2.5, preferably said ratio is between 1 and 2.5.

In some other specific embodiments (in particular those having lower relative amounts of ionizable and neutral lipids and a higher relative amount of steroid), the nucleic acid (such as RNA) compositions (especially the mRNA compositions) described herein comprise (ii) a cationic or cationically ionizable lipid; (iii) a steroid; (iv) a neutral lipid (in particular, a phospholipid); and (v) a multivalent anion (such as an inorganic polyphosphate), wherein the cationic or cationically ionizable lipid is present in a concentration of from about 20 mol % to about 40 mol % (such as from about 25 mol % to about 40 mol % or from about 25 mol % to about 35 mol %); the steroid is present in a concentration of from about 35 mol % to about 60 mol % (such as from about 40 mol % to about 60 mol % or from about 45 mol % to about 60 mol %); the neutral lipid (in particular, a phospholipid) is present in a concentration of from about 5 to about 15 mol percent (such as from about 7 mol % to about 14 mol %); and the molar ratio of multivalent anion (such as inorganic polyphosphate) to the cationic or cationically ionizable lipid is at least about 1:2, preferably at least about 2:3, such as at least about 4:3. In some embodiments, the steroid is cholesterol; and the neutral lipid is selected from the group consisting of DSPC, DPPC, DSPE, and DPPE. In some embodiments, the molar ratio of steroid to neutral lipid is at least 3.0, preferably said ratio is between 3.0 and 10.0, such as between 5.0 and 7.0. In some embodiments, the inorganic polyphosphate is a linear inorganic polyphosphate (such as a linear inorganic triphosphate). In some embodiments, the inorganic polyphosphate comprises the formula $[P_xO_{(3x+1)}]^{y\prime}$, wherein x is an integer and is at least 2, preferably at least 3; and y is the anionic charge. In some embodiments, the inorganic polyphosphate is selected from the group consisting of diphosphate, triphosphate, tetraphosphate, pentaphosphate, hexaphosphate, heptaphosphate, and mixtures thereof, such as from the group consisting of triphosphate, tetraphosphate, pentaphosphate, hexaphosphate, heptaphosphate, and mixtures thereof. Preferably, the inorganic polyphosphate is selected from the group consisting of triphosphate, tetraphosphate, pentaphosphate, and mixtures thereof. In some preferred embodiments, the inorganic polyphosphate is triphosphate. In some embodiments, the steroid is cholesterol; the neutral lipid is selected from the group consisting of DSPC, DPPC, DSPE, and DPPE; and the inorganic polyphosphate is selected from the group consisting of triphosphate, tetraphosphate, pentaphosphate, hexaphosphate, heptaphosphate, and mixtures thereof, preferably the inorganic polyphosphate is triphosphate. In some embodiments, the molar ratio of steroid to neutral lipid is at least 3.0, preferably said ratio is between 3.0 and 10.0, such as between 5.0 and 7.0.

In some of the above described embodiments of the nucleic acid (such as RNA) compositions (in particular those having higher relative amounts of ionizable and neutral lipids and a lower relative amount of steroid or those having lower relative amounts of ionizable and neutral lipids and a higher relative amount of steroid), these nucleic acid compositions are substantially free of a lipid comprising PEG (such as substantially free of any compound comprising PEG, substantially free of PEG, or substantially free of any polymer-conjugated lipid). In these embodiments, the multivalent anion may be as defined herein, (e.g., selected from the group consisting of an inorganic polyphosphate, inorganic phosphate, sulfate, succinate, glutarate, tartrate, malate, citrate, and mixtures thereof.

The N/P value is preferably at least about 4. In some embodiments, the N/P value ranges from 4 to 20, 4 to 12, 4 to 10, 4 to 8, or 5 to 7. In one embodiment, the N/P value is about 6.

In some embodiments, the nucleic acid (such as RNA) is present in the nucleic acid compositions (such as RNA compositions) described herein in a concentration from about 1 mg/i to about 500 mg/i, such as from about 1 mg/i to about 100 mg/i, about 5 mg/l to about 100 mg/l, or about 10 mg/i to about 100 mg/i. In some embodiments, in particular those, where the nucleic acid composition is in frozen form, the concentration of the nucleic acid in the composition is about 1 mg/i to about 50 mg/i. In some embodiments, in particular those, where the nucleic acid composition is in liquid form, the concentration of the nucleic acid in the composition is about 10 mg/i to about 100 mg/i.

Compositions Comprising Nucleic Acid (Such as RNA, Preferably mRNA) Particles

The nucleic acid (such as RNA) compositions described herein may comprise nucleic acid particles (such as RNA particles, like RNA LNPs), preferably a plurality of nucleic acid particles (such as a plurality of RNA particles). The term "plurality of nucleic acid particles" or "plurality of nucleic acid-lipid particles" refers to a population of a certain number of particles. In certain embodiments, the term refers to a population of more than 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, $10^{21}$, $10^{22}$, or $10^{23}$ or more particles.

Nucleic acid particles (such as RNA particles, like LNPs comprising RNA (or "RNA LNPs")) described herein have an average diameter that in some embodiments ranges from about 30 nm to about 1000 nm, from about 30 nm to about 800 nm, from about 30 nm to about 700 nm, from about 30 nm to about 600 nm, from about 30 nm to about 500 nm, from about 30 nm to about 450 nm, from about 30 nm to about 400 nm, from about 30 nm to about 350 nm, from about 30 nm to about 300 nm, from about 30 nm to about 250 nm, from about 30 nm to about 200 nm, from about 30 nm to about 190 nm, from about 30 nm to about 180 nm, from about 30 nm to about 170 nm, from about 30 nm to about 160 nm, from about 30 nm to about 150 nm, from about 50 nm to about 500 nm, from about 50 nm to about 450 nm, from about 50 nm to about 400 nm, from about 50 nm to about 350 nm, from about 50 nm to about 300 nm, from about 50 nm to about 250 nm, from about 50 nm to about 200 nm, from about 50 nm to about 190 nm, from about 50 nm to about 180 nm, from about 50 nm to about 170 nm, from about 50 nm to about 160 nm, or from about 50 nm to about 150 nm.

In certain embodiments, nucleic acid particles (such as RNA particles, like RNA LNPs) described herein have an average diameter that ranges from about 40 nm to about 800 nm, from about 50 nm to about 700 nm, from about 60 nm to about 600 nm, from about 70 nm to about 500 nm, from about 80 nm to about 400 nm, from about 150 nm to about 800 nm, from about 150 nm to about 700 nm, from about 150 nm to about 600 nm, from about 200 nm to about 600 nm, from about 200 nm to about 500 nm, or from about 200 nm to about 400 nm.

In certain embodiments, nucleic acid particles (such as RNA particles, like RNA LNPs) described herein may have an average diameter that in some embodiments ranges from about 30 nm to about 500 nm, such as from about 30 nm to about 200 nm, or from about 50 nm to about 150 nm.

In some embodiments, the nucleic acid (such as RNA) compositions described herein comprise particles with a size of at least 10 μm in an amount of less than 4000/ml, preferably at most 3500/ml, such as at most 3400/ml, at most 3300/ml, at most 3200/ml, at most 3100/ml, or at most 3000/ml.

It will be apparent to those of skill in the art that the plurality of particles can include any fraction of the foregoing ranges or any range therein.

Nucleic acid particles (such as RNA particles, like RNA LNPs) described herein, e.g. prepared by the methods described herein, exhibit a polydispersity index less than about 0.5, less than about 0.4, less than about 0.3, less than about 0.2, less than about 0.1 or about 0.05 or less. By way of example, the nucleic acid particles (such as RNA LNPs) can exhibit a polydispersity index in a range of about 0.05 to about 0.2, such as about 0.05 to about 0.1.

Generally, the nucleic acid particles (such as RNA particles, like RNA LNPs) described herein are "nucleic acid-lipid particles" (such as "RNA-lipid particles") that can be used to deliver the nucleic acid to a target site of interest (e.g., cell, tissue, organ, and the like). A nucleic acid-lipid particle is typically formed from a cationic or cationically ionizable lipid (such as the cationic or cationically ionizable lipids disclosed herein), one or more additional lipids (such as a phospholipid as disclosed herein (e.g., DSPC), and a steroid (e.g., cholesterol or analogues thereof)), and a multivalent anion (such as an inorganic polyphosphate) disclosed herein (e.g., the multivalent anion may be an inorganic polyphosphate such as triphosphate, tetraphosphate, pentaphosphate, hexaphosphate, heptaphosphate, and mixtures thereof, preferably triphosphate, or the multivalent anion may be an inorganic phosphate, sulfate, succinate, glutarate, tartrate, malate, citrate, or mixtures thereof).

Without intending to be bound by any theory, it is believed that the cationic or cationically ionizable lipid and the one or more additional lipids combine together with the nucleic acid (such as RNA) to form particles, which become colloidally stable upon addition of the multivalent anion (such as the inorganic polyphosphate or inorganic phosphate, sulfate, succinate, glutarate, tartrate, malate, citrate, or mixtures thereof) (due to the association of the multivalent anion (such as the inorganic polyphosphate, or inorganic phosphate, sulfate, succinate, glutarate, tartrate, malate, citrate, or mixtures thereof) to the surface of the particles thereby neutralizing the surface charge on the particles or even forming anionic particles), wherein the nucleic acid is bound to the lipid matrix.

In some embodiments, nucleic acid-lipid particles (such as RNA-lipid particles) comprise more than one type of nucleic acid molecules (such as more than one type of RNA molecules), where the molecular parameters of the nucleic acid molecules may be similar or different from each other, like with respect to molar mass or fundamental structural elements such as molecular architecture, capping, coding regions or other features.

In some embodiments (in particular those having higher relative amounts of ionizable and neutral lipids and a lower relative amount of steroid), nucleic acid-lipid particles (such as RNA-lipid particles, like RNA LNPs) in addition to (i) nucleic acid comprise (ii) a cationic or cationically ionizable lipid which may comprise from about 40 mol % to about 70 mol % (such as from about 25 mol % to about 40 mol % or from about 25 mol % to about 35 mol %) of the total lipids present in the particle; (iii) a steroid which may comprise from about 15 mol % to about 40 mol % (such as from about 20 mol % to about 35 mol %, or from about 20 mol % to about 30 mol %) of the total lipids present in the particle; (iv) a neutral lipid which may comprise from about 15 mol % to about 25 mol % (such as from about 7 mol % to about 14 mol %) of the total lipids present in the particle; and (v) a multivalent anion (such as an inorganic polyphosphate), wherein the molar ratio of multivalent anion (such as inorganic polyphosphate) to the cationic or cationically ionizable lipid is at least about 1:2, preferably at least about 2:3, such as at least about 4:3. In some embodiments, the molar ratio of steroid to neutral lipid is at most 2.5, preferably said ratio is between 1 and 2.5. In some embodiments, the steroid is cholesterol; and the neutral lipid is selected from the group consisting of DSPC, DPPC, DSPE, and DPPE. In any of the above embodiments, the multivalent anion may be as disclosed herein, e.g., an inorganic polyphosphate or an inorganic phosphate, sulfate, succinate, glutarate, tartrate, malate, citrate, or mixtures thereof. For example, the inorganic polyphosphate may be selected from the group consisting of triphosphate, tetraphosphate, pentaphosphate, hexaphosphate, heptaphosphate, and mixtures thereof. Preferably, the inorganic polyphosphate is selected from the group consisting of triphosphate, tetraphosphate, pentaphosphate, and mixtures thereof. In some preferred embodiments, the inorganic polyphosphate is triphosphate. In some embodiments, the steroid is cholesterol; the neutral lipid is selected from the group consisting of DSPC, DPPC, DSPE, and DPPE; and the inorganic polyphosphate is selected from the group consisting of triphosphate, tetraphosphate, pentaphosphate, hexaphosphate, heptaphosphate, and mixtures thereof, preferably the inorganic polyphosphate is triphosphate.

In some other embodiments, nucleic acid-lipid particles (such as RNA-lipid particles, like RNA LNPs, e.g., mRNA-lipid LNPs) in addition to (i) nucleic acid comprise (ii) a cationic or cationically ionizable lipid which may comprise from about 20 mol % to about 40 mol % (such as from about 25 mol % to about 40 mol % or from about 25 mol % to about 35 mol %) of the total lipids present in the particle; (iii) a steroid which may comprise from about 35 mol % to about 60 mol % (such as from about 40 mol % to about 60 mol % or from about 45 mol % to about 60 mol %) of the total lipids present in the particle; (iv) a neutral lipid which may comprise from about 5 mol % to about 15 mol % (such as from about 7 mol % to about 14 mol %) of the total lipids present in the particle; and (v) a multivalent anion (such as an inorganic polyphosphate), wherein the molar ratio of multivalent anion (such as inorganic polyphosphate) to the cationic or cationically ionizable lipid is at least about 1:2, preferably at least about 2:3, such as at least about 4:3. In some embodiments, the molar ratio of steroid to neutral lipid is at least 3.0, preferably said ratio is between 3.0 and 10.0, such as between 5.0 and 7.0. In some embodiments, the steroid is cholesterol; and the neutral lipid is selected from the group consisting of DSPC, DPPC, DSPE, and DPPE. In any of the above embodiments, the multivalent anion may be as disclosed herein, e.g., an inorganic polyphosphate or an inorganic phosphate, sulfate, succinate, glutarate, tartrate, malate, citrate, or mixtures thereof. For example, the inorganic polyphosphate may be selected from the group consisting of triphosphate, tetraphosphate, pentaphosphate, hexaphosphate, heptaphosphate, and mixtures thereof. Preferably, the inorganic polyphosphate is selected from the group consisting of triphosphate, tetraphosphate, pentaphosphate, and mixtures thereof. In some preferred embodiments, the inorganic polyphosphate is triphosphate. In some embodiments, the steroid is cholesterol; the neutral lipid is selected from the group consisting of DSPC, DPPC, DSPE, and DPPE; and the inorganic polyphosphate is selected from the group consisting of triphosphate, tetraphosphate, pentaphosphate, hexaphosphate, heptaphosphate, and mixtures thereof, preferably the inorganic polyphosphate is triphosphate.

In some of the above described embodiments of the nucleic acid-lipid particles (such as RNA-lipid particles, like RNA LNPs, e.g., mRNA-lipid LNPs) (in particular those having higher relative amounts of ionizable and neutral lipids and a lower relative amount of steroid or those having lower relative amounts of ionizable and neutral lipids and a higher relative amount of steroid), the nucleic acid-lipid particles are substantially free of a lipid comprising PEG (such as substantially free of any compound comprising PEG, substantially free of PEG, or substantially free of any polymer-conjugated lipid). In these embodiments, the multivalent anion may be as defined herein, e.g., selected from the group consisting of an inorganic polyphosphate, inorganic phosphate, sulfate, succinate, glutarate, tartrate, malate, citrate, and mixtures thereof.

In some embodiments, the composition described herein is a liquid or a solid, with a solid referring to a frozen form.

Figure 5A:
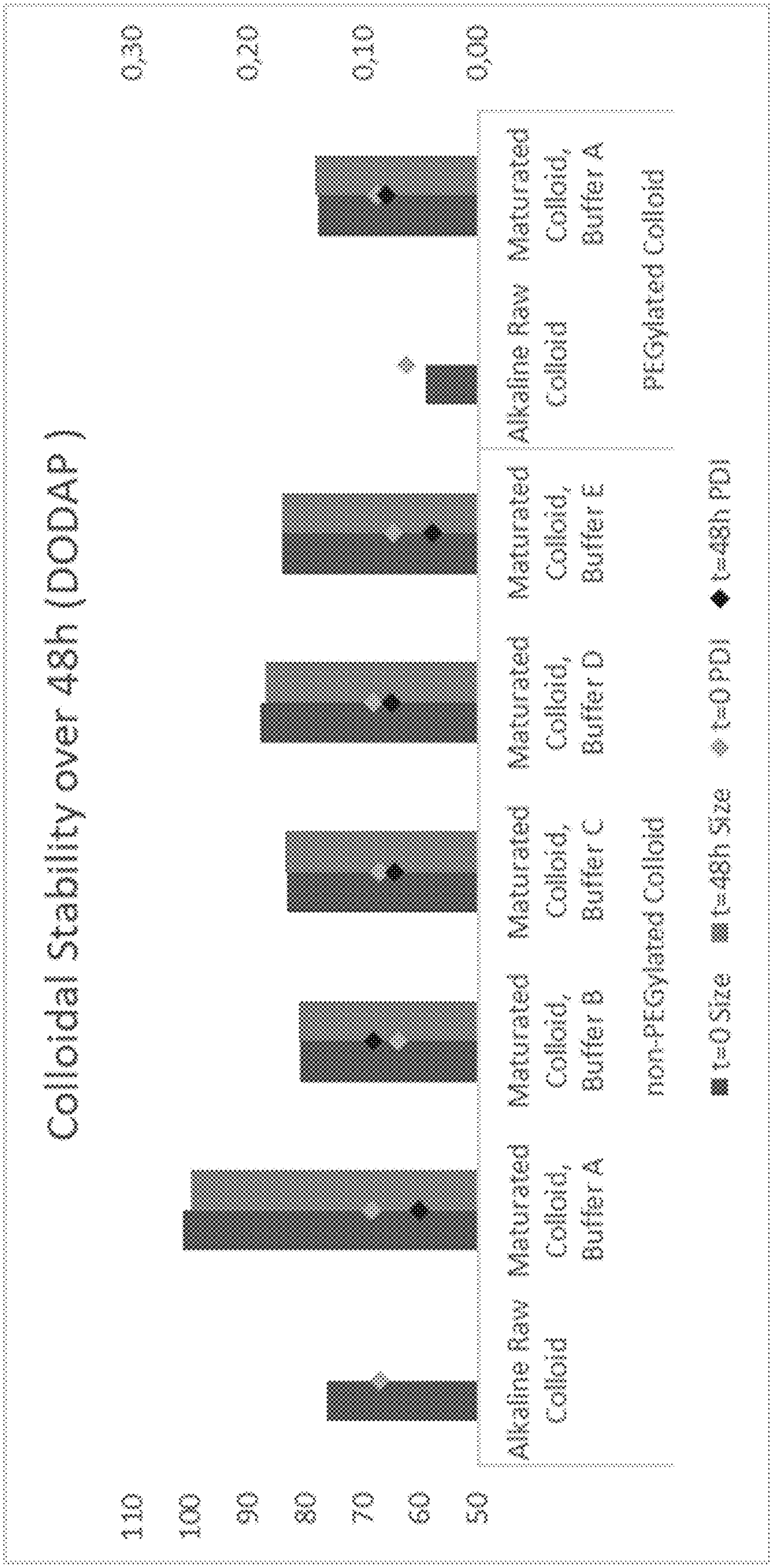
FIG. 5: Stabilization of lipid particle compositions using multivalent anions. An alkaline raw colloid was produced using (A) DODAP, (B) lipid D, or (C) lipid XIV-2 as ionizable lipid component and being devoid of a stealth lipid. The materials were dialyzed against buffer A (HEPES pH 7.4), buffer B (as buffer A plus 5 mM sodium triphosphate), buffer C (as buffer A plus 5 mM sodium diphosphate), buffer D (as buffer A plus 5 mM sodium phosphate) or buffer E (as buffer A plus 5 mM sodium citrate) resulting in the matured colloid. A control material comprising PEG-lipid was processed in the same way. Particle size and polydispersity of the matured colloid were monitored over 48 hours.
Figure 5B:
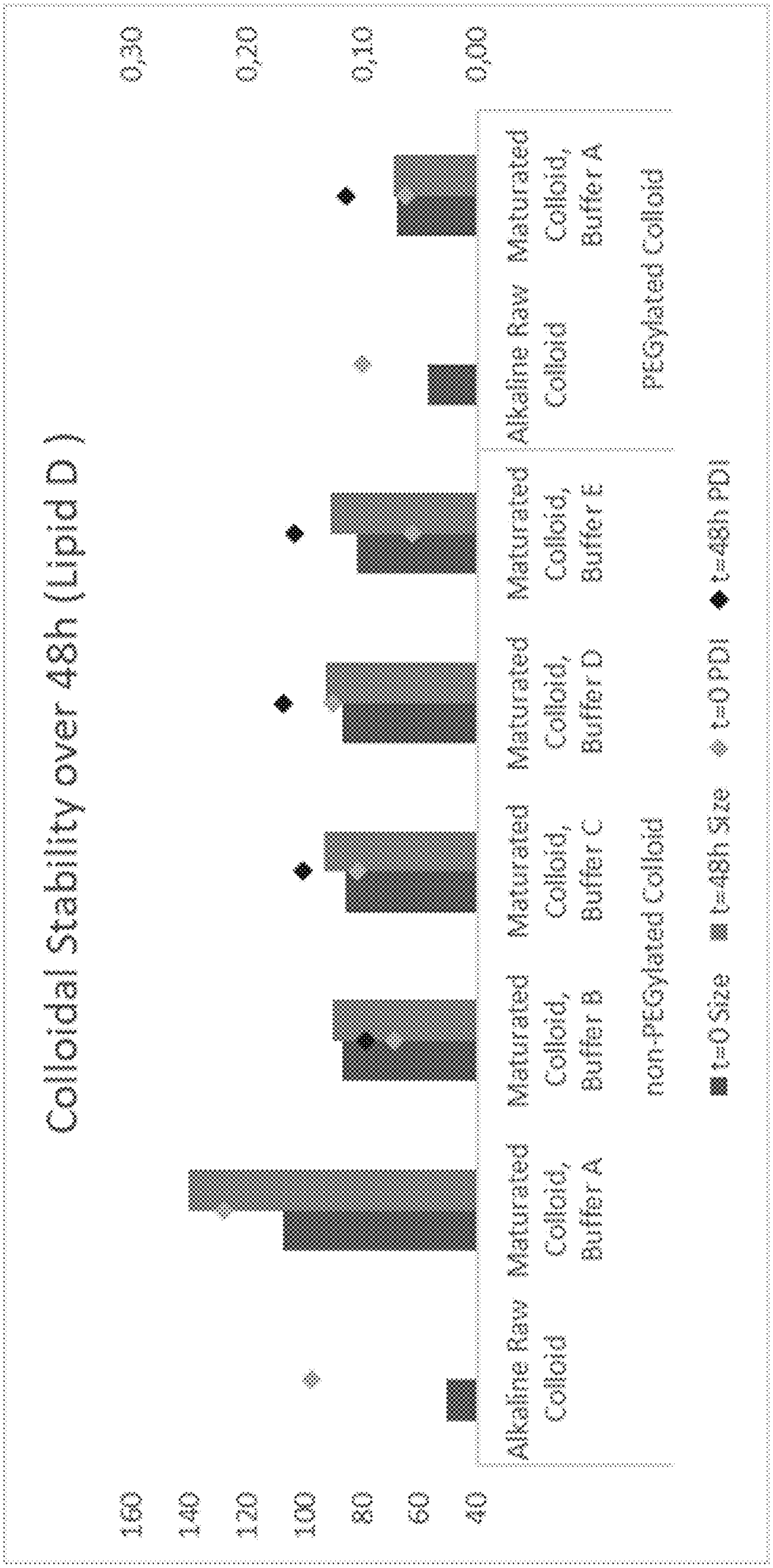
Figure 5C:
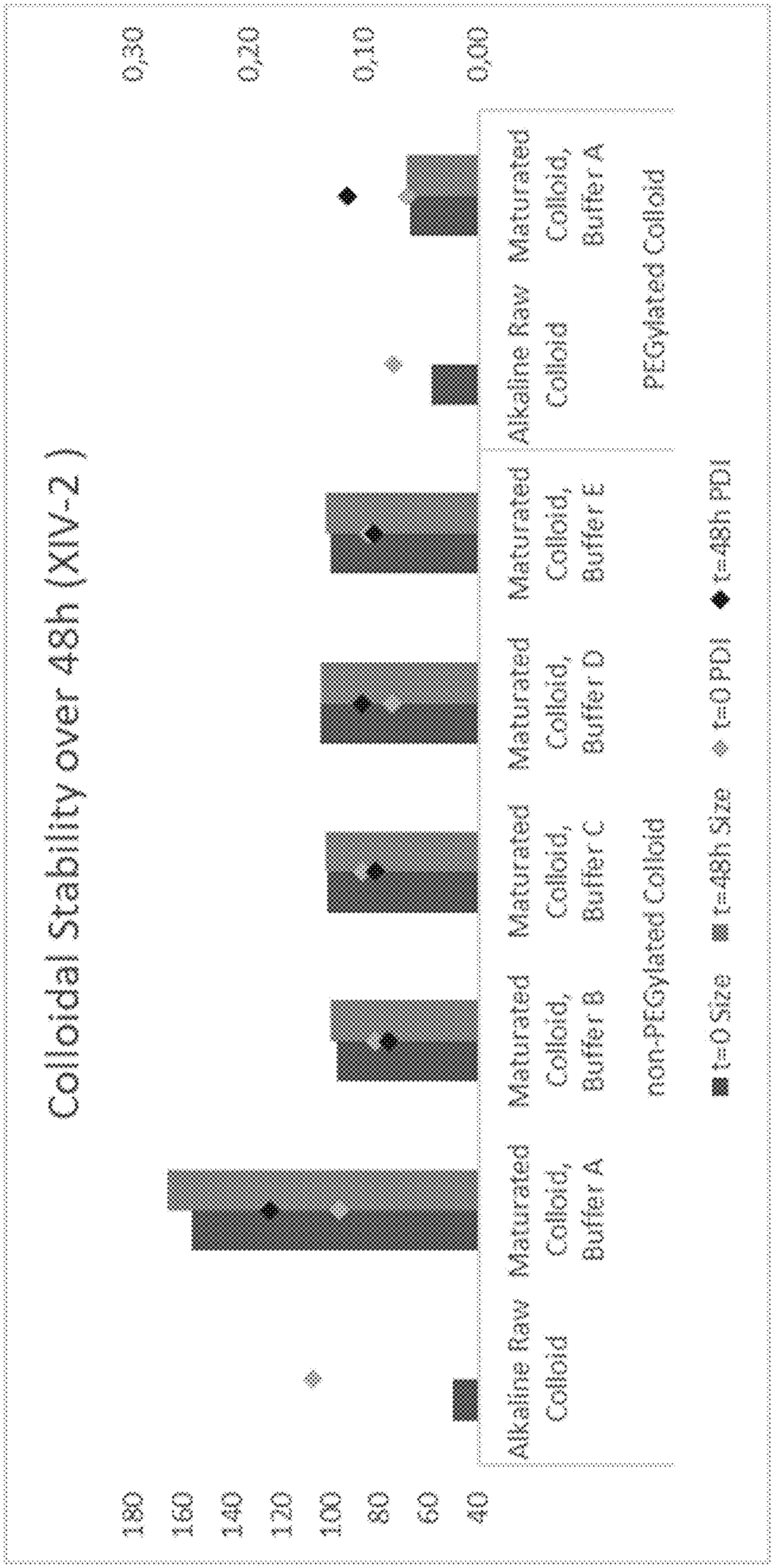

The present inventors have found that nucleic acid compositions which contain particles formed from the nucleic acid and lipids but which to not a stealth lipid (such as a PEG-lipid) are not stable, since the particles aggregate within minutes or hours. Surprisingly, the present inventors have found that by adding a multivalent anion as disclosed herein (e.g., inorganic polyphosphate, or inorganic phosphate, sulfate, succinate, glutarate, tartrate, malate, citrate, or mixtures thereof), or a salt thereof to such nucleic acid particles results in stable compositions. See also example 6 and FIG. 5.

Furthermore, the present application demonstrates that, surprisingly, by including a multivalent anion, it is possible to obtain nucleic acid compositions having colloidal stability in liquid or frozen form. Thus, the compositions prepared by the claimed method provides sufficient stability, can be stored in a temperature range compliant to regular technologies in pharmaceutical practice, and provides a ready-to-use preparation.

Moreover, present inventors have surprisingly found that by adjusting the amount of lipids used for the formation of the nucleic acid particles (in particular by increasing the amount of certain lipids (i.e., the cationic or cationically ionizable lipid and the neutral lipid) and decreasing the amount of other lipids (i.e., cholesterol)), the biological performance can be altered: when used for transfecting cells, nucleic acid compositions containing higher relative amounts of ionizable and neutral lipids and a lower relative amount of steroid result in higher expression of the nucleic acid in the transfected cells if the transfection is carried out in the presence of serum compared to the expression obtained if the transfection is carried out in the absence of serum. In contrast, nucleic acid compositions containing lower relative amounts of ionizable and neutral lipids and a higher relative amount of steroid and used for transfecting cells result in comparable or reduced expression of the nucleic acid in the transfected cells if the transfection is carried out in the presence of serum (i.e., these compositions show some or no serum inhibition, but do not show serum stimulation).

The expression "essentially equal to", as used herein with respect to the size ($Z_{average}$) of particles (such as LNPs), means that the size ($Z_{average}$) value of the particles contained in a composition after a processing step (e.g., after a freeze/thaw cycle) corresponds to the size ($Z_{average}$) value of the particles before the processing step (e.g., before the freeze/thaw cycle) ±30% (preferably, ±25%, more preferably ±24%, such as ±20%, ±15%, ±10%, ±5%, or ±1%). For example, if the size ($Z_{average}$) value of particles (such as LNPs) contained in a composition not yet subjected to a freeze/thaw cycle is 90 nm, and the size ($Z_{average}$) value of particles (such as LNPs) contained in the composition subjected to a freeze/thaw cycle is 115 nm, then the size ($Z_{average}$) of particles after the freeze/thaw cycle, i.e., after thawing the frozen composition, is considered being essentially equal to the size ($Z_{average}$) of particles before the freeze/thaw cycle, i.e., before freezing the composition. The expression "essentially equal to", as used herein with respect to the size distribution or PDI of particles (such as LNPs), is to be interpreted accordingly. For example, if the PDI value of particles (such as LNPs) contained in a composition not yet subjected to a freeze/thaw cycle is 0.30, and the PDI value of particles (such as LNPs) contained in the composition subjected to a freeze/thaw cycle is 0.38, then the PDI of particles after the freeze/thaw cycle, i.e., after thawing the frozen composition, is considered being essentially equal to the PDI of particles before the freeze/thaw cycle, i.e., before freezing the composition.

Compositions described herein may also comprise a cryoprotectant and/or a surfactant as stabilizer to avoid substantial loss of the product quality and, in particular, substantial loss of nucleic acid (e.g., RNA) activity during storage and/or freezing, for example to reduce or prevent aggregation, particle collapse, nucleic acid (such as RNA) degradation and/or other types of damage.

In some embodiments, the cryoprotectant is a carbohydrate. The term "carbohydrate", as used herein, refers to and encompasses monosaccharides, disaccharides, trisaccharides, oligosaccharides and polysaccharides.

In some embodiments, the cryoprotectant is a monosaccharide. The term "monosaccharide", as used herein refers to a single carbohydrate unit (e.g., a simple sugar) that cannot be hydrolyzed to simpler carbohydrate units. Exemplary monosaccharide cryoprotectants include glucose, fructose, galactose, xylose, ribose and the like.

In some embodiments, the cryoprotectant is a disaccharide. The term "disaccharide", as used herein refers to a compound or a chemical moiety formed by 2 monosaccharide units that are bonded together through a glycosidic linkage, for example through 1-4 linkages or 1-6 linkages. A disaccharide may be hydrolyzed into two monosaccharides. Exemplary disaccharide cryoprotectants include sucrose, trehalose, lactose, maltose and the like.

The term "trisaccharide" means three sugars linked together to form one molecule. Examples of a trisaccharides include raffinose and melezitose.

In some embodiments, the cryoprotectant is an oligosaccharide. The term "oligosaccharide", as used herein refers to a compound or a chemical moiety formed by 3 to about 15, preferably 3 to about 10 monosaccharide units that are bonded together through glycosidic linkages, for example through 1-4 linkages or 1-6 linkages, to form a linear, branched or cyclic structure. Exemplary oligosaccharide cryoprotectants include cyclodextrins, raffinose, melezitose, maltotriose, stachyose, acarbose, and the like. An oligosaccharide can be oxidized or reduced.

In some embodiments, the cryoprotectant is a cyclic oligosaccharide. The term "cyclic oligosaccharide", as used herein refers to a compound or a chemical moiety formed by 3 to about 15, preferably 6, 7, 8, 9, or 10 monosaccharide units that are bonded together through glycosidic linkages, for example through 1-4 linkages or 1-6 linkages, to form a cyclic structure. Exemplary cyclic oligosaccharide cryoprotectants include cyclic oligosaccharides that are discrete compounds, such as a cyclodextrin, p cyclodextrin, or γ cyclodextrin.

Other exemplary cyclic oligosaccharide cryoprotectants include compounds which include a cyclodextrin moiety in a larger molecular structure, such as a polymer that contains a cyclic oligosaccharide moiety. A cyclic oligosaccharide can be oxidized or reduced, for example, oxidized to dicarbonyl forms. The term "cyclodextrin moiety", as used herein refers to cyclodextrin (e.g., an α, β, or γ cyclodextrin) radical that is incorporated into, or a part of, a larger molecular structure, such as a polymer. A cyclodextrin moiety can be bonded to one or more other moieties directly, or through an optional linker. A cyclodextrin moiety can be oxidized or reduced, for example, oxidized to dicarbonyl forms.

Carbohydrate cryoprotectants, e.g., cyclic oligosaccharide cryoprotectants, can be derivatized carbohydrates. For example, in an embodiment, the cryoprotectant is a derivatized cyclic oligosaccharide, e.g., a derivatized cyclodextrin, e.g., 2-hydroxypropyl-β-cyclodextrin, e.g., partially etherified cyclodextrins (e.g., partially etherified β cyclodextrins).

An exemplary cryoprotectant is a polysaccharide. The term "polysaccharide", as used herein refers to a compound or a chemical moiety formed by at least 16 monosaccharide units that are bonded together through glycosidic linkages, for example through 1-4 linkages or 1-6 linkages, to form a linear, branched or cyclic structure, and includes polymers that comprise polysaccharides as part of their backbone structure. In backbones, the polysaccharide can be linear or cyclic. Exemplary polysaccharide cryoprotectants include glycogen, amylase, cellulose, dextran, maltodextrin and the like.

In some embodiments, the cryoprotectant is a sugar alcohol. The term "sugar alcohol", as used herein, refers to organic compounds containing at least two carbon atoms and one hydroxyl group attached to each carbon atom. Typically, sugar alcohols are derived from sugars (e.g., by hydrogenation of sugars) and are water-soluble solids. The term "sugar", as used herein, refers sweet-tasting, soluble carbohydrates. Examples of sugar alcohols include ethylene glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, and polyglycitol. In one embodiment, the sugar alcohol has the formula $HOCH_2(CHOH)_nCH_2OH$, wherein n is 0 to 22 (e.g., 0, 1, 2, 3, or 4), or a cyclic variant thereof (which can formally be derived by dehydration of the sugar alcohol to give cyclic ethers; e.g. isosorbide is the cyclic dehydrated variant of sorbitol).

In some embodiments, the cryoprotectant is glycerol and/or sorbitol.

In some embodiments, the nucleic acid (such as RNA) compositions (such as RNA LNP compositions) described herein may include sucrose as cryoprotectant. Without wishing to be bound by theory, sucrose functions to promote cryoprotection of the compositions, thereby preventing nucleic acid (especially RNA) particle aggregation and maintaining chemical and physical stability of the composition. Certain embodiments contemplate alternative cryoprotectants to sucrose in the present disclosure. Alternative stabilizers include, without limitation, glucose, glycerol, and sorbitol.

A preferred cryoprotectant is selected from the group consisting of sucrose, glucose, glycerol, sorbitol, and a combination thereof. In a preferred embodiment, the cryoprotectant comprises sucrose and/or glycerol. In a more preferred embodiment, the cryoprotectant is sucrose.

Preferably, the nucleic acid (such as RNA) compositions (such as RNA LNP compositions) described herein comprise the cryoprotectant in a concentration resulting in an osmolality of the composition in the range of from about $50\times10^{-3}$ osmol/kg to about 1 osmol/kg (such as from about $100\times10^{-3}$ osmol/kg to about $900\times10^{-3}$ osmol/kg, from about $120\times10^{-3}$ osmol/kg to about $800\times10^{-3}$ osmol/kg, from about $140\times10^{-3}$ osmol/kg to about $700\times10^{-3}$ osmol/kg, from about $160\times10^{-3}$ osmol/kg to about $600\times10^{-3}$ osmol/kg, from about $180\times10^{-3}$ osmol/kg to about $500\times10^{-3}$ osmol/kg, or from about $200\times10^{-3}$ osmol/kg to about $400\times10^{-3}$ osmol/kg), for example, from about $50\times10^{-3}$ osmol/kg to about $400\times10^{-3}$ osmol/kg (such as from about $50\times10^{-3}$ osmol/kg to about $390\times10^{-3}$ osmol/kg, from about $60\times10^{-3}$ osmol/kg to about $380\times10^{-3}$ osmol/kg, from about $70\times10^{-3}$ osmol/kg to about $370\times10^{-3}$ osmol/kg, from about $80\times10^{-3}$ osmol/kg to about $360\times10^{-3}$ osmol/kg, from about $90\times10^{-3}$ osmol/kg to about $350\times10^{-3}$ osmol/kg, from about $100\times10^{-3}$ osmol/kg to about $340\times10^{-3}$ osmol/kg, from about $120\times10^{-3}$ osmol/kg to about $330\times10^{-3}$ osmol/kg, from about $140\times10^{-3}$ osmol/kg to about $320\times10^{-3}$ osmol/kg, from about $160\times10^{-3}$ osmol/kg to about $310\times10^{-3}$ osmol/kg, from about $180\times10^{-3}$ osmol/kg to about $300\times10^{-3}$ osmol/kg, or from about $200\times10^{-3}$ osmol/kg to about $300\times10^{-3}$ osmol/kg), based on the total weight of the composition.

In some embodiments, the nucleic acid (such as RNA) compositions (such as RNA LNP compositions) described herein comprise sucrose as cryoprotectant and a multivalent anion (such as an inorganic polyphosphate, inorganic phosphate, sulfate, succinate, glutarate, tartrate, malate, citrate, or mixtures thereof), preferably in the amounts/concentrations specified herein. For example, in some embodiments, the nucleic acid (such as RNA) compositions (such as RNA LNP compositions) described herein comprise sucrose as cryoprotectant and a linear inorganic polyphosphate (preferably from the group consisting of diphosphate, triphosphate, tetraphosphate, pentaphosphate, and mixtures thereof, more preferably from the group consisting of triphosphate, tetraphosphate, pentaphosphate, and mixtures thereof) as multivalent anion, preferably in the amounts/concentrations specified herein. In some embodiments, the inorganic polyphosphate is triphosphate.

In some alternative embodiments, the nucleic acid (such as RNA) compositions (such as RNA LNP compositions) described herein are substantially free of a cryoprotectant, for example they do not contain any cryoprotectant, and may comprise an inorganic polyphosphate, inorganic phosphate, sulfate, succinate, glutarate, tartrate, malate, citrate, or mixtures thereof as multivalent anion. For example, in some alternative embodiments, the nucleic acid (such as RNA) compositions (such as RNA LNP compositions) described herein are substantially free of a cryoprotectant, for example they do not contain any cryoprotectant, and comprise a linear inorganic polyphosphate (preferably from the group consisting of triphosphate, tetraphosphate, pentaphosphate, and mixtures thereof), preferably in the amounts/concentrations specified herein. In some embodiments, the inorganic polyphosphate is triphosphate.

Certain embodiments of the present disclosure contemplate the use of a chelating agent in a nucleic acid (such as RNA) composition (such as an RNA LNP composition) described herein. Chelating agents refer to chemical compounds that are capable of forming at least two coordinate covalent bonds with a metal ion, thereby generating a stable, water-soluble complex. Without wishing to be bound by theory, chelating agents reduce the concentration of free divalent ions, which may otherwise induce accelerated RNA degradation in the present disclosure. Examples of suitable chelating agents include, without limitation, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid (DTPA), and bis(aminoethyl)glycolether-N,N,N',N'-tetraacetic acid. In certain embodiments, the chelating agent is EDTA or a salt of EDTA. In an exemplary embodiment, the chelating agent is EDTA disodium dihydrate. In some embodiments, the EDTA is at a concentration from about 0.05 mM to about 5 mM, from about 0.1 mM to about 2.5 mM or from about 0.25 mM to about 1 mM.

In some embodiments, the aqueous phase of the nucleic acid (such as RNA) compositions (such as RNA LNP compositions) described herein do not comprise a chelating agent. For example, it is preferred that if the nucleic acid (such as RNA) compositions (such as RNA LNP compositions) described herein comprise a chelating agent, said chelating agent is only present in the particles, if present.

Pharmaceutical Compositions

The nucleic acid (such as RNA) compositions described herein are useful as or for preparing pharmaceutical compositions or medicaments for therapeutic or prophylactic treatments.

The nucleic acid (such as RNA) compositions described herein may be administered in the form of any suitable pharmaceutical composition.

The term "pharmaceutical composition" relates to a composition comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. In the context of the present disclosure, the pharmaceutical composition comprises RNA as described herein.

The pharmaceutical compositions of the present disclosure may comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cytokines, such as monokines, lymphokines, interleukins, chemokines. The chemokines may be IL-1, IL-2, IL-3, IL-4, IL-5, IL-6, IL-7, IL-8, IL-9, IL-10, IL-12, INFa, INF-γ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys, as well as lipophilic components, such as saponins, trehalose-6,6-dibehenate (TDB), monophosphoryl lipid-A (MPL), monomycoloyl glycerol (MMG), or glucopyranosyl lipid adjuvant (GLA).

The pharmaceutical compositions of the present disclosure may be in in a frozen form or in a "ready-to-use form" (i.e., in a form, in particular a liquid form, which can be immediately administered to a subject, e.g., without any processing such as thawing, reconstituting or diluting). Thus, prior to administration of a storable form of a pharmaceutical composition, this storable form has to be processed or transferred into a ready-to-use or administrable form. E.g., a frozen pharmaceutical composition has to be thawed. Ready to use injectables can be presented in containers such as vials, ampoules or syringes wherein the container may contain one or more doses.

In some embodiments, the pharmaceutical composition is in frozen form and can be stored at a temperature of about −90° C. or higher, such as about −90° C. to about −10° C. For example, the frozen pharmaceutical compositions described herein (such as the frozen compositions prepared by the methods of the second, third or sixth aspect, or the frozen compositions of the first, fifth, eighth, ninth, or tenth aspect) can be stored at a temperature ranging from about −90° C. to about −10° C., such as from about −905° C. to about −40° C. or from about −40° C. to about −25° C., or from about −25° C. to about −10° C., or a temperature of about −20° C.

In some embodiments of the pharmaceutical compositions in frozen form, the pharmaceutical composition can be stored for at least 1 week, such as at least 2 weeks, at least 3 weeks, at least 4 weeks, at least 1 month, at least 2 months, at least 3 months, at least 6 months, at least 12 months, at least 24 months, or at least 36 months, preferably at least 4 weeks. For example, the frozen pharmaceutical composition can be stored for at least 4 weeks, preferably at least 1 month, more preferably at least 2 months, more preferably at least 3 months, more preferably at least 6 months at −20° C.

In some embodiments of the pharmaceutical compositions in frozen form, the nucleic acid (such as RNA) integrity after thawing the frozen pharmaceutical composition is at least 90%, at least 95%, at least 97%, at least 98%, or substantially 100%, e.g., after thawing the frozen composition which has been stored (for at least 1 week, such as at least 2 weeks, at least 3 weeks, at least 4 weeks, at least 1 month, at least 2 months, at least 3 months, at least 6 months, at least 12 months, at least 24 months, or at least 36 months, preferably at least 4 weeks) at −20° C.

In some embodiments, the initial nucleic acid integrity (such as the initial RNA integrity) of the pharmaceutical composition (i.e., after its preparation but before freezing) is at least 50% and the nucleic acid (such as RNA) integrity of the composition after thawing the frozen composition is at least 90%, preferably at least 95%, more preferably at least 97%, more preferably at least 98%, more preferably substantially 100%, of the initial nucleic acid integrity (such as the initial RNA integrity).

In some embodiments of the pharmaceutical compositions in frozen form, the size ($Z_{average}$) and/or size distribution and/or PDI of the particles after thawing the frozen pharmaceutical composition is essentially equal to the size ($Z_{average}$) and/or size distribution and/or PDI of the particles before freezing.

For example, if a ready-to-use pharmaceutical composition is prepared from a frozen pharmaceutical composition as described herein, it is preferred that the size ($Z_{average}$) and/or size distribution and/or PDI of the particles contained in the ready-to-use pharmaceutical composition is essentially equal to the size ($Z_{average}$) and/or size distribution and/or PDI of the particles contained in the frozen pharmaceutical composition before freezing (such as contained in the formulation prepared in step (I) of the method of the second aspect).

In some embodiments, the size of the nucleic acid (such as RNA) particles and the nucleic acid (such as RNA) integrity of the pharmaceutical composition after one freeze/thaw cycle, preferably after two freeze/thaw cycles, more preferably after three freeze/thaw cycles, more preferably after four freeze/thaw cycles, more preferably after five freeze/thaw cycles or more, are essentially equal to the size of the nucleic acid (such as RNA) particles and the nucleic acid (such as RNA) integrity of the initial pharmaceutical composition (i.e., before the pharmaceutical composition has been frozen for the first time).

In some embodiments, the pharmaceutical composition is in liquid form and can be stored at a temperature ranging from about 0° C. to about 20° C. For example, the liquid pharmaceutical compositions described herein (such as the liquid compositions prepared by the methods of the second, fourth or seventh aspect, or the liquid compositions of the first, fifth, eighth, ninth, or tenth aspect) can be stored at a temperature ranging from about 1° C. to about 15° C., such as from about 2° C. to about 10° C., or from about 2° C. to about 8° C., or at a temperature of about 5° C.

In some embodiments of the pharmaceutical compositions in liquid form, the pharmaceutical composition can be stored for at least 1 week, such as at least 2 weeks, at least 3 weeks, at least 4 weeks, at least 1 month, at least 2 months, at least 3 months, at least 6 months, at least 12 months, or at least 24 months, preferably at least 4 weeks. For example, the liquid pharmaceutical composition can be stored for at least 4 weeks, preferably at least 1 month, more preferably at least 2 months, more preferably at least 3 months, more preferably at least 6 months at 5° C.

In some embodiments of the pharmaceutical composition in liquid form, the nucleic acid (such as RNA) integrity of the liquid composition, when stored, e.g., at 0° C. or higher for at least one week, is such that the desired effect, e.g., to induce an immune response, can be achieved. For example, the nucleic acid (such as RNA) integrity of the liquid composition, when stored, e.g., at 0° C. or higher for at least one week (such as for at least 2 weeks, at least three weeks, at least four weeks, at least one month, at least two months, at least three months, at least 4 months, or at least 6 months), may be at least 90%, compared to the nucleic acid (such as RNA) integrity of the initial composition, i.e., the nucleic acid (such as RNA) integrity before the composition has been stored. In some embodiments, the nucleic acid (such as RNA) integrity of the composition after storage for at least four weeks (e.g., for at least three months), preferably at a temperature of 0° C. or higher, such as about 2° C. to about 8° C., is at least 90%, compared to the nucleic acid (such as RNA) integrity before storage.

In some embodiments, the initial nucleic acid integrity (such as the initial RNA integrity) of the pharmaceutical composition (i.e., after its preparation but before storage) is at least 50% and the nucleic acid (such as RNA) integrity of the pharmaceutical composition after storage for at least one week (such as for at least 2 weeks, at least three weeks, at least four weeks, at least one month, at least two months, or at least 3 months), preferably at a temperature of 0° C. or higher, such as about 2° C. to about 8° C., is at least 90% of the initial nucleic acid integrity (such as the initial RNA integrity). 35 In some embodiments of the pharmaceutical composition in liquid form, the size ($Z_{average}$) (and/or size distribution and/or polydispersity index (PDI)) of the particles of the pharmaceutical composition, when stored, e.g., at 0° C. or higher for at least one week, is such that the desired effect, e.g., to induce an immune response, can be achieved. For example, the size ($Z_{average}$) (and/or size distribution and/or polydispersity index (PDI)) of the particles of the pharmaceutical composition, when stored, e.g., at 0° C. or higher for at least one week, is essentially equal to the size ($Z_{average}$) (and/or size distribution and/or PDI) of the particles of the initial pharmaceutical composition, i.e., before storage. In some embodiments, the size ($Z_{average}$) of the particles after storage of the pharmaceutical composition, e.g., at 0° C. or higher for at least one week is between about 50 nm and about 500 nm, preferably between about 40 nm and about 200 nm, more preferably between about 40 nm and about 120 nm. In some embodiments, the PDI of the particles after storage of the pharmaceutical composition, e.g., at 0° C. or higher for at least one week is less than 0.3, preferably less than 0.2, more preferably less than 0.1. In some embodiments, the size ($Z_{average}$) of the particles after storage of the pharmaceutical composition, e.g., at 0° C. or higher for at least one week is between about 50 nm and about 500 nm, preferably between about 40 nm and about 200 nm, more preferably between about 40 nm and about 120 nm, and the size ($Z_{average}$) (and/or size distribution and/or PDI) of the particles after storage of the pharmaceutical composition, e.g., at 0° C. or higher for at least one week is essentially equal to the size ($Z_{average}$) (and/or size distribution and/or PDI) of the particles before storage. In some embodiments, the size ($Z_{average}$) of the particles after storage of the pharmaceutical composition, e.g., at 0° C. or higher for at least one week is between about 50 nm and about 500 nm, preferably between about 40 nm and about 200 nm, more preferably between about 40 nm and about 120 nm, and the PDI of the particles after storage of the pharmaceutical composition, e.g., at 0° C. or higher for at least one week is less than 0.3 (preferably less than 0.2, more preferably less than 0.1).

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the particles or pharmaceutical compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the particles or pharmaceutical compositions described herein may depend on various of such parameters. In the case that a reaction in a patient is insufficient with an initial dose, higher doses (or effectively higher doses achieved by a different, more localized route of administration) may be used.

In particular embodiments, a pharmaceutical composition of the present disclosure (e.g., an immunogenic composition, i.e., a pharmaceutical composition which can be used for inducing an immune response) is formulated as a single-dose in a container, e.g., a vial. In some embodiments, the immunogenic composition is formulated as a multi-dose formulation in a vial. In some embodiments, the multi-dose formulation includes at least 2 doses per vial. In some embodiments, the multi-dose formulation includes a total of 2-20 doses per vial, such as, for example, 2, 3, 4, 5, 6, 7, 8, 9, 10, 11, or 12 doses per vial. In some embodiments, each dose in the vial is equal in volume. In some embodiments, a first dose is a different volume than a subsequent dose.

A "stable" multi-dose formulation preferably exhibits no unacceptable levels of microbial growth, and substantially no or no breakdown or degradation of the active biological molecule component(s). As used herein, a "stable" immunogenic composition includes a formulation that remains capable of eliciting a desired immunologic response when administered to a subject.

The pharmaceutical compositions of the present disclosure may contain buffers (in particular, derived from the nucleic acid (such as RNA) compositions with which the pharmaceutical compositions have been prepared), preservatives, and optionally other therapeutic agents. In one embodiment, the pharmaceutical compositions of the present disclosure, in particular the ready-to-use pharmaceutical compositions, comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants "Pharmaceutically acceptable salts" comprise, for example, acid addition salts which may, for example, be formed by using a pharmaceutically acceptable acid such as hydrochloric acid, acetic acid, lactic acid, 2-(N-morpholino)ethanesulfonic acid (MES), 3-(N-morpholino)propanesulfonic acid (MOPS), 2-[4-(2-hydroxyethyl)piperazin-1-yl]ethanesulfonic acid (HEPES) or benzoic acid. Furthermore, suitable pharmaceutically acceptable salts may include alkali metal salts (e.g., sodium or potassium salts); alkaline earth metal salts (e.g., calcium or magnesium salts); ammonium ($NH_4$); and salts formed with suitable organic ligands (e.g., quaternary ammonium and amine cations). Illustrative examples of pharmaceutically acceptable salts can be found in the prior art; see, for example, S. M. Berge et al., "Pharmaceutical Salts", J. Pharm. Sci., 66, pp. 1-19 (1977)). Salts which are not pharmaceutically acceptable may be used for preparing pharmaceutically acceptable salts and are included in the present disclosure.

The term "diluent" relates a diluting and/or thinning agent. Moreover, the term "diluent" includes any one or more of fluid, liquid or solid suspension and/or mixing media. Examples of suitable diluents include ethanol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carriers include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

Routes of Administration of Pharmaceutical Compositions

In one embodiment, the compositions described herein, such as the pharmaceutical compositions or ready-to-use pharmaceutical compositions described herein, may be administered intravenously, intraarterially, subcutaneously, intradermally, dermally, intranodally, intramuscularly or intratumorally. In certain embodiments, the (pharmaceutical) composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the (pharmaceutical) compositions, in particular the ready-to-use pharmaceutical compositions, are formulated for systemic administration. In another preferred embodiment, the systemic administration is by intravenous administration. In another preferred embodiment, the (pharmaceutical) compositions, in particular the ready-to-use pharmaceutical compositions, are formulated for intramuscular administration.

Use of Pharmaceutical Compositions

Nucleic acid (such as RNA) compositions described herein may be used in the therapeutic or prophylactic treatment of various diseases, in particular diseases in which provision of a peptide or protein to a subject results in a therapeutic or prophylactic effect. For example, provision of an antigen or epitope which is derived from a virus may be useful in the treatment or prevention of a viral disease caused by said virus. Provision of a tumor antigen or epitope may be useful in the treatment of a cancer disease wherein cancer cells express said tumor antigen. Provision of a functional protein or enzyme may be useful in the treatment of genetic disorder characterized by a dysfunctional protein, for example in lysosomal storage diseases (e.g. Mucopolysaccharidoses) or factor deficiencies. Provision of a cytokine or a cytokine-fusion may be useful to modulate tumor microenvironment.

The term "disease" (also referred to as "disorder" herein) refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "infectious disease" refers to any disease which can be transmitted from individual to individual or from organism to organism, and is caused by a microbial agent. Infectious diseases are known in the art and include, for example, a viral disease, a bacterial disease, or a parasitic disease, which diseases are caused by a virus, a bacterium, and a parasite, respectively. In this regard, the infectious disease can be, for example, sexually transmitted diseases (e.g., *chlamydia*, gonorrhea, or syphilis), SARS, acquired immune deficiency syndrome (AIDS), measles, chicken pox, cytomegalovirus infections, genital herpes, hepatitis (such as hepatitis B or C), influenza (flu, such as human flu, swine flu, dog flu, horse flu, and avian flu), HPV infection, shingles, rabies, common cold, gastroenteritis, rubella, mumps, anthrax, cholera, diphtheria, foodborne illnesses, leprosy, meningitis, peptic ulcer disease, pneumonia, sepsis, septic shock, tetanus, tuberculosis, typhoid fever, urinary tract infection, Lyme disease, Rocky Mountain spotted fever, *chlamydia*, pertussis, tetanus, meningitis, scarlet fever, malaria, trypanosomiasis, Chagas disease, leishmaniasis, trichomoniasis, dientamoebiasis, giardiasis, amebic dysentery, coccidiosis, toxoplasmosis, sarcocystosis, rhinosporidiosis, and balantidiasis.

In some embodiments, nucleic acid (such as RNA) compositions described herein may be used in the therapeutic or prophylactic treatment of an infectious disease.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g., mouse, rat, rabbit, dog, cat, cattle, swine, sheep, horse or primate), or any other non-mammal-animal, including birds (chicken), fish or any other animal species that can be afflicted with or is susceptible to a disease or disorder (e.g., cancer, infectious diseases) but may or may not have the disease or disorder, or may have a need for prophylactic intervention such as vaccination, or may have a need for interventions such as by protein replacement. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In some embodiments of the disclosure, the aim is to provide protection against an infectious disease by vaccination.

In some embodiments of the disclosure, the aim is to provide secreted therapeutic proteins, such as antibodies, bispecific antibodies, cytokines, cytokine fusion proteins, enzymes, to a subject, in particular a subject in need thereof.

In some embodiments of the disclosure, the aim is to provide a protein replacement therapy, such as production of erythropoietin, Factor VII, Von Willebrand factor, β-galactosidase, Alpha-N-acetylglucosaminidase, to a subject, in particular a subject in need thereof.

In some embodiments of the disclosure, the aim is to modulate/reprogram immune cells in the blood.

In some embodiments of the disclosure (in particular those relating to inhibitory RNA), the aim is to reduce or inhibit the expression of a peptide or polypeptide (such as the transcription and/or translation of a target mRNA). In some embodiments, the target mRNA comprises an ORF encoding a pharmaceutically active peptide or polypeptide, in particular a pharmaceutically active peptide or polypeptide whose expression (in particular increased expression, e.g., compared to the expression in a healthy subject) is associated with a disease. In some embodiments, the target mRNA comprises an ORF encoding a pharmaceutically active peptide or polypeptide whose expression (in particular increased expression, e.g., compared to the expression in a healthy subject) is associated with cancer.

In some embodiments, the nucleic acid (such as RNA) compositions described herein which contain nucleic acid (such as RNA) encoding a SARS-CoV-2 S protein, an immunogenic variant thereof, or an immunogenic fragment of the SARS-CoV-2 S protein or the immunogenic variant thereof (in the following simply "SARS-CoV-2 S nucleic acid compositions" which explicitly include SARS-CoV-2 S RNA compositions) following administration to a subject induce an antibody response, in particular a neutralizing antibody response, in the subject that targets a panel of different S protein variants such as SARS-CoV-2 S protein variants, in particular naturally occurring S protein variants. In some embodiments, the panel of different S protein variants comprises at least 5, at least 10, at least 15, or even more S protein variants. In some embodiments, such S protein variants comprise variants having amino acid modifications in the RBD domain and/or variants having amino acid modifications outside the RBD domain. In some embodiments, the SARS-CoV-2 S nucleic acid compositions described herein following administration to a subject induce an immune response (cellular and/or antibody response, in particular a neutralizing antibody response) in the subject that targets VOC-202012/01.

In some embodiments, the SARS-CoV-2 S nucleic acid compositions described herein following administration to a subject induce an immune response (cellular and/or antibody response, in particular a neutralizing antibody response) in the subject that targets 501.V2.

In some embodiments, the SARS-CoV-2 S nucleic acid compositions described herein following administration to a subject induce an immune response (cellular and/or antibody response, in particular a neutralizing antibody response) in the subject that targets "Cluster 5".

In some embodiments, the SARS-CoV-2 S nucleic acid compositions described herein following administration to a subject induce an immune response (cellular and/or antibody response, in particular a neutralizing antibody response) in the subject that targets "B.1.1.28".

In some embodiments, the SARS-CoV-2 S nucleic acid compositions described herein following administration to a subject induce an immune response (cellular and/or antibody response, in particular a neutralizing antibody response) in the subject that targets "B.1.1.248".

In some embodiments, the SARS-CoV-2 S nucleic acid compositions described herein following administration to a subject induce an immune response (cellular and/or antibody response, in particular a neutralizing antibody response) in the subject that targets the Omicron (B.1.1.529) variant.

A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

The terms "immunization" or "vaccination" describe the process of administering an antigen to an individual with the purpose of inducing an immune response, for example, for therapeutic or prophylactic reasons.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The description (including the following examples) is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Materials

The following materials have been used in the experiments and have been received by the respective suppliers indicated in the tables below.

| Solvent/Chemical/Solution | Supplier |
|---|---|
| Ethanol absolute | Merck KGaA, Darmstadt, Germany |
| Hydrochloric acid, 37% | Merck KGaA, Darmstadt, Germany |
| Acetic acid 100% | Merck KGaA, Darmstadt, Germany |
| penta-Sodium triphosphate | Sigma-Aldrich, Missouri, USA |
| Sucrose | Sigma-Aldrich, Missouri, USA |
| Sodium hydroxide solution 2M | Sigma-Aldrich, Missouri, USA |
| dH20 | Generated by Arium ® mini Ultrapure |
| TRIS | Merck KGaA, Darmstadt, Germany |
| Human Male AB Serum | Sigma-Aldrich, Missouri, USA |
| Beetle Lysis Juice | PJK GmbH, Germany |

| Kits | Supplier |
|---|---|
| Luciferase Assay System | Promega, Fitchburg, USA |

| Article | Supplier |
|---|---|
| 2 ml - 2R Injection vial | APG Europe, Uitoorn, Niederlande |
| Slide-A-Lyzer ™ Dialysis Cassettes, 10K MWCO, 3 mL | Thermo Fisher Scientific, Massachusetts, USA |
| 1.0 and 2.0 ml DeepWell ™ Plates | Thermo Fisher Scientific, Massachusetts, USA |
| Nunc 96-Well Flat Bottom, clear | Thermo Fisher Scientific, Massachusetts, USA |
| Nunc 96-Well Flat Bottom, white | Thermo Fisher Scientific, Massachusetts, USA |
| MICROPLATE, 96 WELL, PS, F-BOTTOM (transparent bottom for HT-DLS) | Greiner bio-one, Frickenhausen, Germany |
| Sterile PES Syringe Filter (0.2 μm) | Thermo Fisher Scientific, Massachusetts, USA |
| Cell culture flasks | Thermo Fisher Scientific, Massachusetts, USA |
| Pipetting tips | BRAND GMBH + CO KG, Wertheim, Germany |
| Syringes | BD, Heidelberg, Germany |
| 15 mL and 50 mL Conical Sterile Polypropylene Centrifuge Tubes | Thermo Fisher Scientific, Massachusetts, USA |
| Sterile Microcentrifuge Tube 1.5 mL | Eppendorf, Hamburg, Germany |
| GREEN CHOICE 96 300 μl tips | INTEGRA Biosciences, Zizers, Swisse |
| DMEM/F12 + GlutaMAX | Thermo Fisher Scientific, Massachusetts, USA |
| RPMI 1640 | Merck KGaA, Darmstadt, Germany |
| Pen Strep | Thermo Fisher Scientific, Massachusetts, USA |
| Trypsin-EDTA | Capricorn Scientific GmbH, Ebsdorfergrund, Germany |
| FBS Superior | Sigma-Aldrich, Missouri, USA |
| DPBS | Thermo Fisher Scientific, Massachusetts, USA |

| Components | % Volume | Volumes ml |
|---|---|---|
| Medium for adherent cells | | |
| DMEM + F12 | | 500 ml |
| FBS | 10% | 55 ml |
| Pen-Strep | 1% | 5.5 ml |
| Medium for suspension cells | | |
| RPMI 1640 | | 500 ml |
| FBS | 10% | 55 ml |
| Pen-Strep | 1% | 5.5 ml |
| Medium for MOLT-4 cells | | |
| RPMI 1640 | | 500 ml |
| FBS | 20% | 110 ml |
| Pen-Strep | 1% | 6.1 ml |

| Name | Chemical Structure | Supplier |
|---|---|---|
| DSPC | 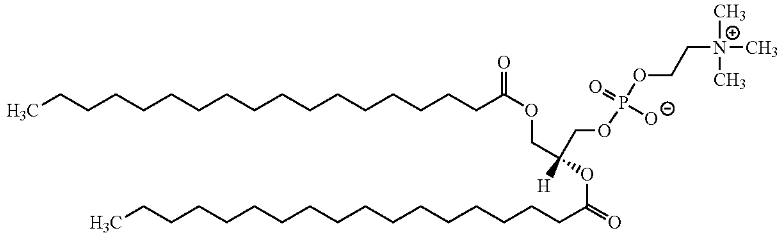 [SMILES: CCCCCCCCCCCCCCCCCC(=O)OC[C@H](COP(=O)([O-])OCC[N+](C)(C)C)OC(=O)CCCCCCCCCCCCCCCCC] | Avanti, Alabama, USA |

-continued

| Name | Chemical Structure | Supplier |
|---|---|---|
| CHOL | 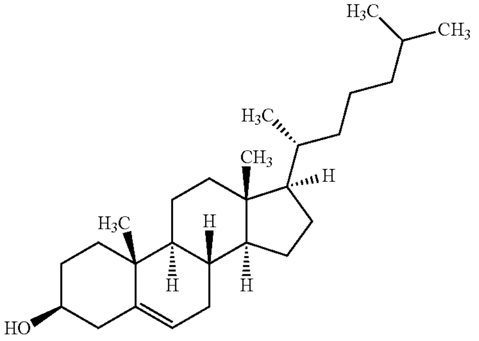 | Avanti, Alabama, USA |

| Device | Supplier |
|---|---|
| CERTUS FLEX | Fritz Gyger AG, Gwatt, Switzerland |
| DynaPro Plate Reader III | Wyatt, Santa Barbara, USA |
| ViaFlo96 | INTEGRA Biosciences, Zizers, Switzerland |
| Spark Plate Reader | Tecan Group Ltd., Mannedorf, Switzerland |
| Zetasizer Ultra | Malvern Instruments, Malvern, UK |

Luciferase mRNA was provided by BioNTech SE (Mainz, Germany)

Following cell lines were provided by ATCC (Virginia, USA): HEK293, HepG2, THP1, J774, Jurkat, MOLT-4, K-562, HL-60, C2C12

Methods

Formulation by JetMix

LNPs Comprising PEG

An organic phase comprising lipids in Table 2, further comprising 1.5 eq. acetic acid (relative to the cationically ionizable lipid), is provided using ethanol as solvent, lipid concentration is 47 mM. An RNA phase is provided having 0.4 mg/ml of RNA in water (diluted from 2 mg/mL RNA in 10H pH 7.1). Water was used to dilute the mixture. RNA phase, organic phase and water are continuously mixed in a ratio 3:1:1.5 (v/v) using a flow of 225 ml/min. Mixing is achieved in a mixing T having 0.5 mm bore using the Nemesys Flow System (CETONI, Germany). Formulation volumes ranged from 15 to 50 ml. The first 7 ml of each formulation were discarded prior collection of the LNPs.

TABLE 2

Lipid composition shown in percent of the LNPs

| Lipid | | Percent (%) |
|---|---|---|
| cationically ionizable lipid | cation | 47.5 |
| DSPC | neutral | 10 |
| Chol | Chol | 40.7 |
| PEG lipid | PEG | 1.8 |

PEG-Free LNPs Comprising Triphosphate (3P)

3P LNPs were formulated as described above excluding the PEG lipid from the organic phase. The mixture was quenched in a beaker under stirring with a 250 mM triphosphate solution to obtain final concentrations of 2.5, 5, 7.5 or 10 mM triphosphate.

Dialysis

Samples were dialyzed for 2×12 h against final buffer (35 mM Tris pH 7.4) using a Slide A Lyzer dialysis cassette with 10 kDa MWCO dialyzer (Thermo Fisher Scientific, Massachusetts, USA).

SpotMix Formulation and 3P Quenching by Dispenser

LNPs Comprising PEG

For screening purposes, the CERTUS FLEX (Fritz Gyger AG, Gwatt Switzerland) dispenser was used to formulate LNPs in 96 well plates. The organic phase, the RNA phase and water was dispensed in a sequential manner using the same concentrations and the same ratios as described above to a total volume of 200 μl.

PEG-Free LNPs Comprising 3P

In case of 3P LNPs the formulation was performed as described above excluding PEG from the organic phase. LNPs were quenched with 16 μl of a 250 mM triphosphate solution to achieve a final concentration of 20 mM triphosphate.

Buffer Dilution Instead of Dialysis

20 μl of the formulation was transferred into a new 96 well plate using the ViaFlo96 (INTEGRA Biosciences, Zizers, Switzerland). Ten steps of 20 μl were added with the CERTUS FLEX dispenser with a pause of 60s in-between, shifting the pH to 7.4.

Compounding:

For stability experiments 3P LNPs samples were added 1.2M trehalose as cryoprotectant to a final concentration of 300 mM. The experiments included storage at 4° C., one freeze thaw cycle (1 ft) at −20° C. and −70° C. with a final mRNA concentration of the samples of 10 μg/ml and 70 μg/ml. Dilutions were performed in the target buffer always in the presence of the indicated amount of triphosphate.

Determination of Size and Polydispersity Index (PDI) with Dynamic Light Scattering (DLS)

Mean particle size and size distribution of LNP in a sample is evaluated by dynamic light scattering (DLS). The method employs the Zetasizer Ultra (Malvern Instruments, Malvern, UK) that uses back-scatter at 1730 to determine particle size. The results are reported as the Z-average size of the particles and the polydispersity index. The polydispersity values are used to describe the width of fitted log-normal distribution around the measured Z-average size and are generated using proprietary mathematical calculations within the particle sizing software. Results for size and polydispersity are reported as nm and polydispersity index value, respectively.

SERUM Incubation

A portion of the LNPs was incubated with human serum in a 1:1 (v/v) ratio for 30 min at room temperature. The other portion of the LNP was left untreated.

Transfection and Luciferase Readout

Transfection of the LNPs was performed in 96 well format using the ViaFlo96 with 10 μl sample at a concentration of 10 ng/μl resulting in 100 ng mRNA per well. If needed, samples were diluted in target buffer (35 mM Tris pH7.4). For LNP incubated with human serum 20 μl were used for transfection, also providing 100 ng of RNA per well.

The quantification of the firefly luciferase activity as a bioluminescent reporter is a method to quantify the transfection of the LNPs. A high luciferase mRNA expression is the result of a high transfection performance of the LNPs. The expressed luciferase catalyses the ATP-dependent luciferin oxidation into oxyluciferin leading to light emission with a maximum at 560 nm. 24 h after the culture medium was discarded, cells were washed once with phosphate-buffered saline and lysed using 100 μl of 1× Beetle Lysis Juice (PJK GmbH, Germany). Luminescence was measured 10 min later.

Example 1

We compared the aggregation behavior of non-PEG lipid particle compositions vs. polyphosphate lipid particle compositions.

To this end lipid particle compositions comprising a cationically ionizable lipid, a steroid, and a neutral lipid but being free of PEG and inorganic polyphosphate were prepared and their size (diameter ($Z_{ave.}$) in nm) was measured over time (up to 30 min). Furthermore, lipid particle compositions comprising a cationically ionizable lipid, a steroid, a neutral lipid, and an inorganic polyphosphate (triphosphate (3P)) in different concentrations (0-10 mM) but being free of PEG were prepared and their size (diameter ($Z_{ave}$) in nm) was measured 16 h after their preparation.

As can be seen in FIG. 2A, the lipid particle compositions which were free of PEG and inorganic polyphosphate aggregated within about 20 min. In contrast, FIG. 2B shows that lipid particle compositions comprising inorganic polyphosphate but being free of PEG were colloidally stable for at least 16 h.

Thus, this example demonstrates that by using an inorganic polyphosphate, it is possible to prepare nucleic acid particle compositions which are colloidally stable even in the absence of any stealth lipid (such as PEG lipid).

Example 2

Next, we analyzed the stability of the lipid particle compositions under various conditions.

To this end, lipid particle compositions comprising RNA (in two different concentrations: 10 or 70 mg/l), a cationically ionizable lipid, a steroid, a neutral lipid, an inorganic polyphosphate (triphosphate (3P), added at a concentration of 2.5 mM after formation of the particles, optionally also present in the final filtration (dialysis) step) with a PEG lipid (+PEG) or without PEG lipid (−PEG) were prepared. After storing under various conditions (5° C., −20° C., or −70° C.), the colloidal parameters (diameter in nm and polydispersity index (PDI)) of the particle compositions were measured.

As indicated by a constant size (cf, FIG. 3A) and low PDI (cf., FIG. 3B), the resulting particle compositions were stable for 1 day in liquid form in the presence or absence of inorganic polyphosphate in the dialysis buffer. Thus, this example shows that the presence of an inorganic polyphosphate in the final filtration (dialysis) step is not required.

Furthermore, as can be seen from FIGS. 3A and B, particle compositions can be frozen while maintaining the colloidal properties; to improve the stability of the particle compositions, inorganic polyphosphate should be present in the aqueous phase and/or the RNA concentration should be below about 70 mg/l.

In summary, this example demonstrates that the compositions of the present disclosure are stable and can be stored in a temperature range compliant to regular technologies in pharmaceutical practice.

Example 3

In this example, we analyzed the influence of different molar ratios of the cationically ionizable lipid, a steroid, and a neutral lipid in the absence or presence of serum on the expression level.

Lipid particle compositions comprising RNA (encoding luciferase), a cationically ionizable lipid (FIG. 4A: lipid XIV-3; FIG. 4B: lipid XIV-1; FIG. 4C: lipid XIV-2; FIG. 4D: lipid G (DPL-14)), a steroid (cholesterol), a neutral lipid (DSPC), and an inorganic polyphosphate (triphosphate (3P)) were prepared using compositions having the molar percentage of DSPC as provided in the figures, the remainder of the lipid composition being the ionizable lipid and cholesterol in the molar ratio as provided in the figures.

Cells were transfected with either of the compositions in the presence of serum (+Serum (+S)) or in the absence of serum (−Serum (−S)). Luciferase expression was determined and the serum stimulation was calculated based on the ratio of the luciferase expression in the presence of serum (+S) to the luciferase expression in the absence of serum (−S) (ratio+S/−S).

FIG. 4 shows the results for the luciferase expression, the serum stimulation (expressed as $\log_{10}$ (ratio+S/−S) values). As can be seen from FIG. 4, changes to the lipid ratio of the RNA particle compositions resulted in serum stimulation or serum inhibition of the transfection reaction. The ratio+S/−S corresponds with the molar ratio of cholesterol to DSPC as provided in Table 3.

TABLE 3

| Ratios of cholesterol to DSPC in the lipid compositions DSPC [mol %] | | | |
|---|---|---|---|
| 10 | 14 | 17 | 21 |
| 6.0 | 4.0 | 3.0 | 2.4 |
| 5.6 | 3.7 | 2.8 | 2.2 |
| 5.1 | 3.4 | 2.6 | 2.1 |
| 4.7 | 3.1 | 2.4 | 1.9 |
| 4.3 | 2.9 | 2.1 | 1.7 |
| 3.9 | 2.6 | 1.9 | 1.5 |
| 3.4 | 2.3 | 1.7 | 1.4 |
| 3.0 | 2.0 | 1.5 | 1.2 |
| 2.6 | 1.7 | 1.3 | 1.0 |

Lipid compositions having a cholesterol:DSPC ratio of at most 2.5 display an enhanced activity upon incubation with serum, the coefficient of log(+S/−S) is greater 0. Lipid compositions having a cholesterol:DSPC ratio of at least 3 display a reduced activity upon incubation with serum, the coefficient of log(+S/−S) is below 0.

As this effect is achieved with several different cationically ionizable lipids, it appears to be independent from the type of cationically ionizable lipid used and a general feature of lipid nanoparticles comprising ionizable cationic lipid, a steroid (such as cholesterol) and a neutral lipid (such as DSPC).

Example 4

In this example, we analyzed the influence of two LNP preparation processes on LNP attributes.

Production 3P LNP Using Addition of 3P to Acidic Raw Colloid

LNPs were prepared using an aqueous-ethanol mixing protocol in a volume part ratio of 3:1:2 (acidified mRNA: organic phase: quench buffer). For that, mRNA having a concentration of 0.4 mg/mL was provided in 50 mM sodium acetate pH 5.5. The organic phase comprising 47.4 mM of total lipids (49.1 mol % lipid XIV-3, 17.4 mol % DSPC and 33.5 mol % cholesterol) was provided in ethanol. Quench buffer was 15 mM 3P (sodium triphosphate) acidified with 34.97 mM acetic acid to pH 5.1. A raw colloid was produced by continuous mixing of the acidified mRNA with the organic phase, followed by inline addition of quench buffer.

The acidic colloid was dialyzed against 50 mM HEPES 5 mM sodium triphosphate pH 7.7 (NaOH) followed by up-concentration using a cross-flow membrane (MikroKros 20 $cm^2$ 100K MPES 0.5 mm (C02-E100-05)).

Eventually, HEPES 3P buffer solution and sucrose were added to arrive at a final product having 0.1 mg/mL of RNA, 50 mM HEPES, 5 mM 3P, 300 mM sucrose, pH 7.4.

TABLE 4

Quality attributes of resulting 3P LNP (XIV-3#1d001) and stability data over 21 days at 4° C.

| Particle attribute | t0 (RT) | 2 days | 5 days | 14 days | 21 days |
|---|---|---|---|---|---|
| Size [nm] | 64 | 81 | 81 | 82 | 81 |
| PDI | 0.020 | 0.029 | 0.016 | 0.011 | 0.025 |
| RNA integrity [%] | 86 | 82 | 87 | 81 | 79 |
| RNA content [mg/ml] | 0.081 | n.a. | n.a. | n.a. | n.a. |
| Encapsulation efficacy [%] | 97 | 97 | 96 | 96 | 96 |

Production of 3P LNP Using Addition of 3P to Neutralize Raw Colloid LNPs were prepared using an aqueous-ethanol mixing protocol in a volume part ratio of 3:1:2 (acidified mRNA: organic phase: quench buffer). For that, mRNA having a concentration of 0.4 mg/mL was provided in 50 mM sodium acetate pH 5.5. The organic phase comprising 47.4 mM of total lipids (29.2 mol % lipid XIV-3, 20.8 mol % DSPC and 50.0 mol % cholesterol) was provided in ethanol. Quench buffer was water. A raw colloid was produced by continuous mixing of the acidified mRNA with the organic phase, immediately followed by quenching. The raw colloid was collected and a solution of 250 mM 3P (sodium triphosphate) was added to arrive at a concentration of 5 mM 3P.

The resulting colloid was dialyzed against 50 mM HEPES, 5 mM sodium triphosphate pH 7.4 (NaOH) followed by up-concentration using a cross-flow membrane (MikroKros 20 cm 100K MPES 0.5 mm (C02-E100-05)).

Eventually, HEPES 3P buffer solution and sucrose were added to arrive at a final product having 0.1 mg/mL of RNA, 50 mM HEPES, 5 mM 3P, 300 mM sucrose, pH 7.4.

TABLE 5

Quality attributes of resulting 3P LNP (XIV-3#3d003) and stability data over 21 days at 4° C.

| Particle attribute | t0 (RT) | 2 days | 5 days | 14 days | 21 days |
|---|---|---|---|---|---|
| Size [nm] | 62 | 72 | 75 | 77 | 79 |
| PDI | 0.064 | 0.049 | 0.035 | 0.057 | 0.062 |
| RNA integrity [%] | 87 | 85 | 87 | 76 | 73 |
| RNA content [mg/ml] | 0.091 | n.a. | n.a. | n.a. | n.a. |
| Encapsulation efficacy [%] | 99 | 98 | 98 | 98 | 98 |

In summary, a first process of manufacturing was used where the 3P anion was adjusted to an acidic pH and combined with an acidic first colloid in presence of 25% ethanol. Adjustment of pH to about neutral conditions was achieved by dialysis which is a slow process.

A second process of manufacturing was used where the first colloid having 25% ethanol was diluted with water and the 3P anion was added in its alkaline state, resulting in an immediate adjustment of the pH to about neutral conditions. Further buffer exchange and removal of solvent was then achieved by dialysis.

Both methods resulted in the formation of a highly homogeneous colloid, encapsulation of mRNA and maintenance of RNA integrity. The material was stable over time.

Example 5

In this example, we analyzed the functional properties of 3P LNP formulations after i.m. injection.

Test items were manufactured as described in Example 4. Balb/c mice (female, n=3), in the age of 8 weeks, were injected intramuscularly (i.m.) into the gastrocnemius at both sides with 3P-LNPs loaded with Luciferase encoding mRNA. A total dose of 2 μg mRNA was administered per mouse using a volume of 20 μl per injection (c=0.05 mg/mL). After 6 h, 24 h, 48 h, 96 h and d7 post-injection in-vivo imaging from all groups was performed. Mice were imaged from dorsal side. At the end of the study (d7) the animals were sacrificed by exsanguination and subsequent cervical dislocation.

To characterize the anti-LUC immune response elicited by the novel materials, an ELISpot analysis was performed. Spleen-derived lymphocytes were isolated. For identification of IFN-γ secreting T-cells the Mouse IFN-γ ELISpot kit from Mabtech was used according to the manufacturer's instructions. Cells isolated from different animals were seeded into the ELISpot plate with a concentration of $1\cdot10^5$ and $2\cdot10^5$ cells per well. Each concentration was analyzed in duplicates. For activation of the cells a Luc-specific peptide pool was added to each well to obtain a final concentration of 2 μg/mL. The negative controls (w/o stimulation of Luc-peptide) were seeded with a concentration of $2\cdot10^5$ cells per well.

The materials tested here both mediate a potent expression of the luciferase protein and also mounted an immune response specific to this foreign protein. The results are shown in Tables 6 and 7.

TABLE 6

| Time-resolved LUC expression for PEG-free 3P-LNP formulations. | | | | | |
|---|---|---|---|---|---|
| Mean counts/s/cm$^2$ | 6 h | 24 h | 48 h | 96 h | d 7 |
| XIV-3d001 (#6) | 9.052 | 5.540 | 2.936 | 443 | 60 |
| XIV-3d003 (#7) | 10.635 | 6.888 | 3.270 | 414 | 61 |

TABLE 7

| ELISpot analysis upon luciferase expression in mice | |
|---|---|
| Group | Group Mean Count (±SD) |
| 3P-LNP (#6) | 704 (±338) |
| 3P-LNP (#7) | 369 (±217) |

It was found that 3P LNPs show expression of luciferase in muscle, mostly at the site of injection. No signal is detected outside the actual injection site.

It is concluded that 3P LNPs are able to mediate an immune response against Luciferase, after a single dose.

Example 6

In this example, we analyzed the stabilization of LNP formulations using different multivalent anions.

Materials were prepared using an aqueous-ethanol mixing protocol in a volume part ratio of 3:1:2 (acidified mRNA: organic phase: quench solvent). For that, mRNA having a concentration of 0.4 mg/mL was provided in 50 mM sodium acetate pH 5.5. For non-PEGylated variants the organic phase comprising 47.4 mM of total lipids (48.4 mol % ionizable lipid, 10 mol % DSPC and 41.6 mol % cholesterol) was provided in ethanol and quench was $dH_2O$. A first mixture was produced by continuous mixing of the acidified mRNA with the organic phase, followed by inline addition of $dH_2O$ as quench solvent, said mixture being the "raw colloid". Ionizable lipids tested were DODAP, lipid D or lipid XIV-2.

In control experiments, PEG-lipid was added and the same aqueous-ethanol mixing protocol was applied to an organic phase comprising 47.4 mM of total lipids (48.4 mol % ionizable lipid, 10 mol % DSPC, 39.8 mol % cholesterol and 1.8 mol % DMG-PEG 2000).

After initial mixing and quench, the pH of the raw colloid was rapidly shifted to about pH 8.5 by adding one volume part HEPES 500 mM pH 8.5 to nine parts raw colloid, resulting in the "alkaline raw colloid".

To obtain "matured colloids" at about neutral pH, the alkaline raw colloid was dialyzed against following buffers:

- Buffer A: 50 mM HEPES, pH 7.4 (NaOH)
- Buffer B: 50 mM HEPES, 5 mM sodium triphosphate, pH 7.4 (NaOH)
- Buffer C: 50 mM HEPES, 5 mM sodium diphosphate, pH 7.4 (NaOH)
- Buffer D: 50 mM HEPES, 5 mM sodium phosphate, pH 7.4 (NaOH)
- Buffer E: 50 mM HEPES, 5 mM sodium citrate, pH 7.4 (NaOH)

Figure 6:
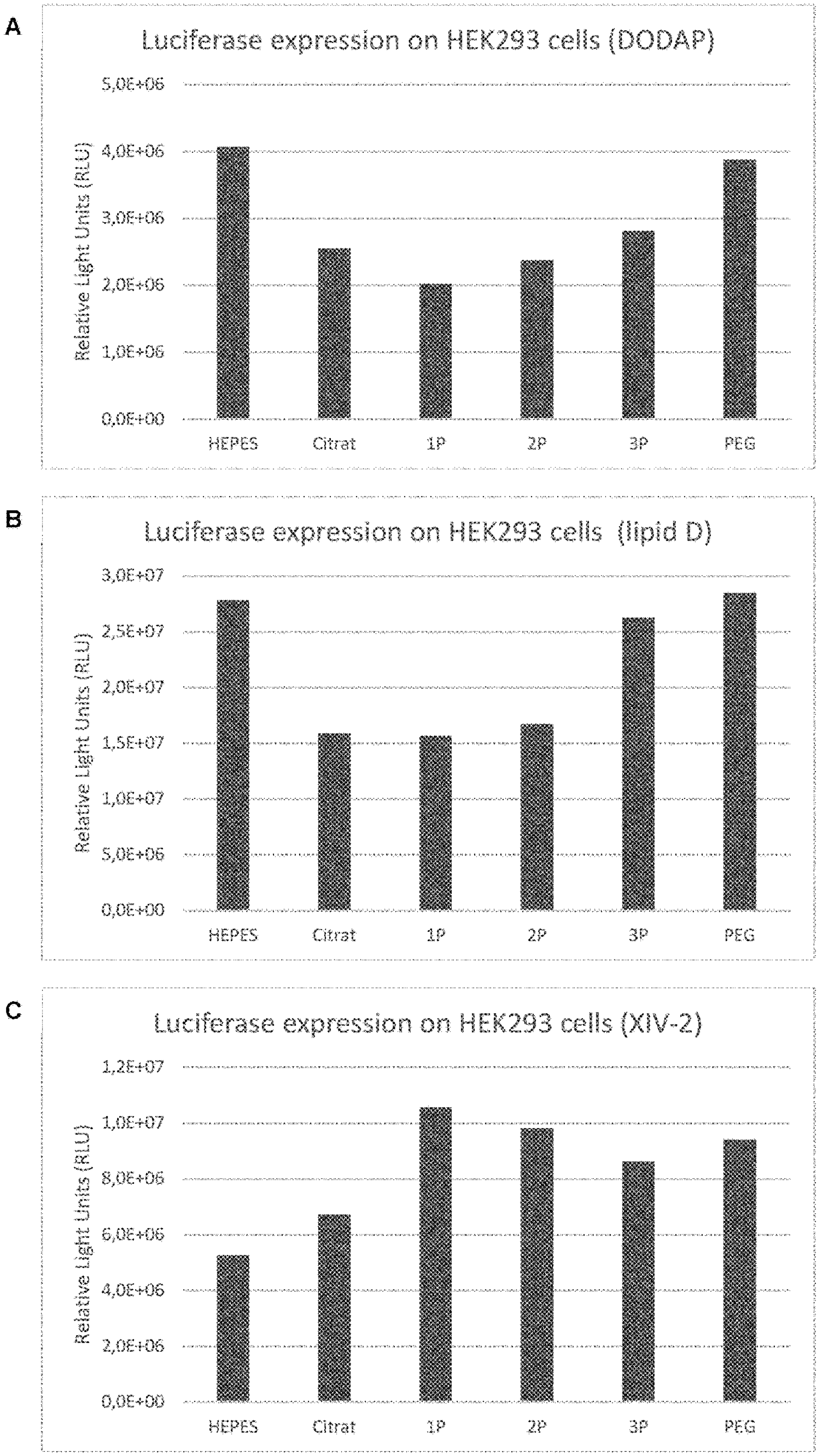
FIG. 6: Activity of lipid particle compositions using multivalent anions. The matured colloids as described in FIG. 5 were tested for their ability to transfect mRNA into HEK cells. The ionizable lipid was (A) DODAP, (B) lipid D, or (C) lipid XIV-2.

After dialysis an mRNA concentration of approximately 0.15 mg/mL was obtained. The colloidal stability of the matured colloids was followed over 48 hours and results are presented in FIGS. 5A-C. The functional expression of mRNA was tested in HEK293 cells and is presented in FIGS. 6A-C.

The findings can be summarized as follows:

- LNP formulations not comprising a stealth lipid can be obtained from various and structurally different ionizable lipids.
- The LNP formulations not comprising a stealth lipid can be stabilized using multivalent anions such as inorganic polyphosphate anions, inorganic phosphate anions, or citrate anions, but not using zwitterionic species.
- The LNP formulations not comprising stealth lipid and stabilized using multivalent anions are active carriers having comparable efficacy to PEGylated carrier controls.

The invention claimed is:

1. A composition comprising (i) a nucleic acid; (ii) a cationically ionizable lipid; (iii) a steroid; (iv) a neutral lipid; and (v) an inorganic polyphosphate.

2. The composition of claim 1, wherein (i) the inorganic polyphosphate comprises the formula $[P_xO_{(3x+1)}]^y$, wherein x is an integer and is at least 3; and y is the anionic charge;

(ii) the inorganic polyphosphate is selected from the group consisting of triphosphate, tetraphosphate, pentaphosphate, hexaphosphate, heptaphosphate, and mixtures thereof;

(iii) the inorganic polyphosphate is a linear inorganic polyphosphate; and/or (iv) the molar ratio of the inorganic polyphosphate to the cationically ionizable lipid is at least 1:2.

3. The composition of claim 1, wherein the inorganic polyphosphate is triphosphate.

4. The composition of claim 1, wherein (i) the composition is free of a lipid comprising polyethyleneglycol (PEG), or free of any compound comprising PEG, or free of PEG; or (ii) the composition comprises a lipid comprising polyethyleneglycol (PEG), or any compound comprising PEG, or PEG in an amount of less than 1% by weight based on the total weight of the composition;

(ii) the pH of the composition is between 4.0 and 8.0;

(iii) water is the main component in the composition and/or the total amount of solvent(s) other than water contained in the composition is less than 0.5% (v/V);

(iv) the osmolality of the composition is at most $1000\times10^{-3}$ osmol/kg; and/or (v) the concentration of the nucleic acid in the composition is 1 mg/l to 500 mg/l.

5. The composition of claim 1, wherein (i) the cationically ionizable lipid comprises a head group which includes at least one tertiary amine moiety;

(ii) the cationically ionizable lipid has the structure of Formula (X)

(X)

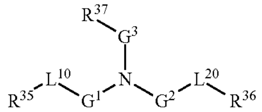

or a pharmaceutically acceptable salt, tautomer, prodrug or stereoisomer thereof, wherein:

one of $L^{10}$ and $L^{20}$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, $NR^aC$(═O)$NR^a$—, —OC(═O)$NR^a$— or —$NR^aC$(═O)O—, and the other of $L^{10}$ and $L^{20}$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, $NR^aC$(═O)$NR^a$—, —OC(═O)$NR^a$— or —$NR^aC$(═O)O— or a direct bond;

$G^1$ and $G^2$ are each independently unsubstituted $C_1$-$C_{12}$ alkylene or $C_{2-12}$ alkenylene;

$G^3$ is $C_{1-24}$ alkylene, $C_{2-24}$ alkenylene, $C_{3-8}$ cycloalkylene, or $C_{3-8}$ cycloalkenylene;

$R^a$ is H or $C_{1-12}$ alkyl;

$R^{35}$ and $R^{36}$ are each independently $C_{6-24}$ alkyl or $C_{6-24}$ alkenyl;

$R^{37}$ is H, $OR^{50}$, CN, —C(═O)$OR^{40}$, —OC(═O)$R^{40}$ or —$NR^{50}C$(═O)$R^{40}$;

$R^{40}$ is $C_{1-12}$ alkyl;

$R^{50}$ is H or $C_{1-6}$ alkyl; and x is 0, 1 or 2;

(iii) the cationically ionizable lipid has the structure of Formula (XI):

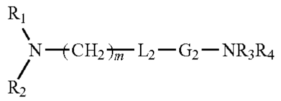

wherein each of $R_1$ and $R_2$ is independently $R_5$ or -$G_1$-$L_1$-$R_6$, wherein at least one of $R_1$ and $R_2$ is -$G_1$-$L_1$-$R_6$;

each of $R_3$ and $R_4$ is independently selected from the group consisting of $C_{1-6}$ alkyl, $C_{2-6}$ alkenyl, aryl, and $C_{3-10}$ cycloalkyl;

each of $R_5$ and $R_6$ is independently a non-cyclic hydrocarbyl group having at least 10 carbon atoms;

each of $G_1$ and $G_2$ is independently unsubstituted $C_{1-12}$ alkylene or $C_{2-12}$ alkenylene;

each of $L_1$ and $L_2$ is independently selected from the group consisting of —O(C═O)—, —(C═O)O—, —C(═O)—, —O—, —$S(O)_x$—, —S—S—, —C(═O)S—, —SC(═O)—, —NRaC(═O)—, —C(═O)$NR^a$—, —NRaC(═O)$NR^a$—, —OC(═O)$NR^a$— and —NRaC(═O)O—;

Ra is H or $C_{1-12}$ alkyl;

m is 0, 1, 2, 3, or 4; and x is 0, 1 or 2;

(iv) the cationically ionizable lipid comprises from 20 mol % to 75 mol % of the total lipid present in the composition;

(v) the steroid comprises a sterol or cholesterol;

(vi) the steroid comprises from 15 mol % to 60 mol % of the total lipid present in the composition;

(vii) the neutral lipid is a phospholipid selected from the group consisting of phosphatidylcholines, phosphatidylethanolamines, phosphatidylglycerols, phosphatidic acids, phosphatidylserines and sphingomyelins, or selected from the group consisting of distearoylphosphatidylcholine (DSPC), dipalmitoylphosphatidylcholine (DPPC), distearoyl-phosphatidylethanolamine (DSPE), and dipalmitoyl-phosphatidylethanolamine (DPPE);

(viii) the neutral lipid comprises from 5 mol % to 25 mol % of the total lipid present in the composition;

(ix) the cationically ionizable lipid comprises from 20 mol % to 70 mol % of the total lipid present in the composition; the steroid comprises from 15 mol % to 60 mol % of the total lipid present in the composition; and the neutral lipid comprises from 5 mol % to 25 mol % of the total lipid present in the composition; and/or (x) the cationically ionizable lipid comprises from 40 mol % to 70 mol % of the total lipid present in the composition; the steroid comprises from 15 mol % to 40 mol % of the total lipid present in the composition; and the neutral lipid comprises from 15 mol % to 25 mol % of the total lipid present in the composition, wherein the molar ratio of steroid to neutral lipid is at most 2.5, or said ratio is between 1 and 2.5; or the cationically ionizable lipid comprises from 20 mol % to 40 mol % of the total lipid present in the composition; the steroid comprises from 35 mol % to 60 mol % of the total lipid present in the composition; and the neutral lipid comprises from 5 mol % to 15 mol % of the total lipid present in the composition, wherein the molar ratio of steroid to neutral lipid is at least 3.0, or said ratio is between 3.0 and 10.0.

6. The composition of claim 1, wherein the composition comprises particles dispersed in an aqueous phase, wherein the particles comprise at least a portion of the nucleic acid, at least a portion of the cationically ionizable lipid, at least a portion of the steroid, and at least a portion of the neutral lipid; and wherein at least a portion of the inorganic polyphosphate is associated with the particles.

7. The composition of claim 6, wherein (i) the particles are selected from lipid nanoparticles (LNPs), liposomes, lipoplexes (LPXs), and mixtures thereof;

(ii) the the particles comprise at least 50% of the nucleic acid present in the composition;

(iii) at least 10% or at least 50% of the polyphosphate present in the composition is associated with the particles; and/or (iv) the particles have a size of from 30 nm to 500 nm.

8. The composition of claim 1, wherein the nucleic acid is RNA or mRNA.

9. The composition of claim 8, wherein (i) the RNA (1) comprises a modified nucleoside in place of uridine, wherein the modified nucleoside is selected from pseudouridine (ψ), N1-methyl-pseudouridine (m1ψ), and 5-methyl-uridine (m5U); (2) has a coding sequence which is codon-optimized; and/or (3) has a coding sequence whose G/C content is increased compared to the wild-type coding sequence; and/or (ii) the RNA comprises at least one of the following, or all of the following: a 5' cap; a 5' UTR; a 3' UTR; and a poly-A sequence.

10. The composition of claim 8, wherein the RNA encodes one or more polypeptides, wherein the one or more polypeptides are pharmaceutically active polypeptides and/or comprise an epitope for inducing an immune response against an antigen in a subject.

11. The composition of claim 10, wherein (i) the pharmaceutically active polypeptide and/or the antigen or epitope is derived from or is a protein of a pathogen, an immunogenic variant of the protein, or an immunogenic fragment of the protein or the immunogenic variant thereof; and/or (ii) the pharmaceutically active polypeptide and/or the antigen or epitope is derived from or is a SARS-COV-2 spike(S) protein, an immunogenic variant thereof, or an immunogenic fragment of the SARS-COV-2 S protein or the immunogenic variant thereof.

12. The composition of claim 1, wherein the composition is (i) in liquid form;

(ii) in liquid form at a temperature of 2° C. to 10° C.; or (iii) in frozen form.

13. A method of preparing a composition comprising particles dispersed in a final aqueous phase, wherein the composition comprises (i) a nucleic acid; (ii) a cationically ionizable lipid; (iii) a steroid; (iv) a neutral lipid; and (v) an inorganic polyphosphate; wherein the particles comprise at least a portion of the nucleic acid, at least a portion of the cationically ionizable lipid, and at least a portion of the steroid; wherein at least a portion of the inorganic polyphosphate is associated with the particles; and wherein the final aqueous phase comprises a final buffer system;

wherein the method comprises:

(I) preparing a formulation comprising particles dispersed in the final aqueous phase, wherein the particles comprise at least a portion of the nucleic acid, at least a portion of the cationically ionizable lipid, at least a portion of the steroid, and at least a portion of the neutral lipid, and wherein at least a portion of the inorganic polyphosphate is associated with the particles; and (II) optionally freezing the formulation to about-10° C. or below, thereby obtaining the composition, wherein step (I) comprises:

(a) providing a nucleic acid solution containing water and a first buffer system;

(b) providing an organic solution comprising the cationically ionizable lipid, the steroid, and the neutral lipid;

(c) mixing the nucleic acid solution provided under (a) with the organic solution provided under (b), thereby preparing a first intermediate formulation comprising the particles dispersed in a first aqueous phase comprising the first buffer system;

(d) mixing the first intermediate formulation prepared under (c) with an inorganic polyphosphate or a salt thereof, thereby preparing a second intermediate formulation comprising the particles dispersed in a second aqueous phase comprising a second buffer system, wherein at least a portion of the inorganic polyphosphate is associated with the particles; and (e) filtrating and/or diluting the second intermediate formulation prepared under (d) using a final aqueous buffer solution comprising the final buffer system, thereby preparing the formulation comprising the particles dispersed in the final aqueous phase.

14. The method of claim 13, wherein (i) step (I) further comprises one or more steps selected from diluting and filtrating:

(ii) step (I) comprises:

(a') providing an aqueous nucleic acid solution;

(b') providing a first aqueous buffer solution comprising a first buffer system;

(c') mixing the aqueous nucleic acid solution provided under (a') with the first aqueous buffer solution provided under (b') thereby preparing a nucleic acid solution containing water and the first buffer system;

(d') providing an organic solution comprising the cationically ionizable lipid, the steroid, and the neutral lipid;

(e') mixing the nucleic acid solution prepared under (c') with the organic solution provided under (d'), thereby preparing a first intermediate formulation comprising particles dispersed in a first aqueous phase comprising the first buffer system;

(f') optionally diluting the first intermediate formulation prepared under (e') using water or a further aqueous buffer solution comprising a further buffer system, thereby preparing a further intermediate formulation comprising the particles dispersed in a further aqueous phase comprising the first or further buffer system, wherein the further aqueous buffer solution may be identical to or different from the first aqueous buffer solution;

(g') mixing the first intermediate formulation obtained in step (e'), if step (f') is absent, or the further intermediate formulation obtained in step (f'), if step (f) is present, with an inorganic polyphosphate or a salt thereof, thereby preparing a second intermediate formulation comprising the particles dispersed in a second aqueous phase, wherein at least a portion of the inorganic polyphosphate is associated with the particles;

(h') optionally filtrating the second first intermediate formulation prepared under (g') using a further aqueous buffer solution comprising a further buffer system, thereby preparing a further intermediate formulation comprising the particles dispersed in a further aqueous phase comprising the further buffer system, wherein the further aqueous buffer solution may be identical to or different from the first and/or second aqueous buffer solution;

(i') optionally repeating step (h') once or two or more times, wherein the further intermediate formulation comprising the particles dispersed in the further aqueous phase comprising the further buffer system obtained after step (h') of one cycle is used as the second intermediate formulation of the next cycle, wherein in each cycle the further aqueous buffer solution may be identical to or different from the first and/or second aqueous buffer solution;

(i') filtrating the second intermediate formulation obtained in step (g'), if step (h') is absent, or the further intermediate formulation obtained in step (h'), if step (h') is present and step (i') is not present, or the further intermediate formulation obtained after step (i'), if steps (h') and (i') are present, using a final aqueous buffer solution comprising the final buffer system; and (k') optionally diluting the formulation obtained in step (i') with a dilution solution;

thereby preparing the formulation comprising the particles dispersed in the final aqueous phase; and/or (iii) filtrating is dialyzing, tangential flow filtrating or diafiltrating.

15. The method of claim 12, wherein (i) the inorganic polyphosphate or a salt thereof comprises or has the formula $P_xO_{(3x+1)}M_{y'}$, wherein x is an integer and is at least 3; each M is independently $H^+$ or a cation; and y' is the number of cations needed for charge equalization; or the inorganic polyphosphate or a salt thereof comprises or has the formula $P_xO_{(3x+1)}M_{y'}$, wherein x is an integer and is at least 3;

each M is independently selected from the group consisting of $H^+$, an alkaline cation, ammonium, and a monovalent organic cation, or each M is independently selected from the group consisting of $H^+$, $Na^+$, $K^+$, $Li^+$, and $NH_4^+$;

(ii) the inorganic polyphosphate or a salt thereof is selected from the group consisting of triphosphate, tetraphosphate, pentaphosphate, hexaphosphate, heptaphosphate, salts and mixtures thereof;

(iii) the inorganic polyphosphate or a salt thereof is triphosphate or a salt thereof;

(iv) the inorganic polyphosphate or a salt thereof is a linear inorganic polyphosphate or a salt thereof;

(v) the molar ratio of the inorganic polyphosphate to the cationically ionizable lipid is at least 1:2;

(vi) the composition is free of a lipid comprising PEG, or free of any compound comprising PEG, or free of PEG, or the composition comprises a lipid comprising polyethyleneglycol (PEG), or any compound comprising PEG, or PEG in an amount of less than 1% by weight based on the total weight of the composition;

(vii) (1) the nucleic acid solution obtained in step (a) has a pH of below 6.0; or (2) the first aqueous buffer solution has a pH of below 6.0;

(viii) the pH of the composition is between 4.0 and 8.0;

(ix) water is the main component in the formulation and/or composition and/or the total amount of solvent (s) other than water contained in the composition is less than 0.5% (v/v);

(x) the osmolality of the composition is at most $1000\times10^{-3}$ osmol/kg;

(xi) the concentration of the nucleic acid in the composition is 1 mg/l to 500 mg/l;

(xii) the cationically ionizable lipid comprises a head group which includes at least one tertiary amine moiety;

(xiii) the cationically ionizable lipid, the steroid, and the neutral lipid are present in the organic solution in a molar ratio of 20 mol % to 70 mol % of the cationically ionizable lipid; 15 mol % to 60 mol % of the steroid; and from 5 mol % to 25 mol % of the neutral lipid; and/or (xiv) the cationically ionizable lipid, the steroid, and the neutral lipid are present in the organic solution in a molar ratio of 40 mol % to 70 mol % of the cationically ionizable lipid; 15 mol % to 40 mol % of the steroid; and from 15 mol % to 25 mol % of the neutral lipid, wherein the molar ratio of steroid to neutral lipid in the organic solution is at most 2.5, or said ratio is between 1 and 2.5; or the cationically ionizable lipid, the steroid, and the neutral lipid are present in the organic solution in a molar ratio of 20 mol % to 40 mol % of the cationically ionizable lipid; 35 mol % to 60 mol % of the steroid; and from 5 mol % to 15 mol % of the neutral lipid, wherein the molar ratio of steroid to neutral lipid is at least 3.0, or said ratio is between 3.0 and 10.0.

16. The method of claim 13, wherein (i) the particles have a size of from 30 nm to 500 nm;

(ii) the particles are selected from the group consisting of lipid nanoparticles (LNPs), liposomes, lipoplexes (LPXs), and mixtures of two or more thereof; and/or (iii) the nucleic acid is as defined in claim 8.

17. The method of claim 13, which comprises (II) freezing the formulation to −10° C. or below.

18. The method of claim 13, which does not comprise step (II).

19. A composition preparable by the method of claim 13, which is (i) in frozen form; or (ii) in liquid form.

20. A ready-to-use pharmaceutical composition preparable by (i) a method comprising the steps of providing a frozen composition prepared by the method of claim 17, and thawing the frozen composition thereby obtaining the ready-to-use pharmaceutical composition; or (ii) a method comprising the step of providing a liquid composition prepared by the method of claim 18, thereby obtaining the ready-to-use pharmaceutical composition.

21. A method for inducing an immune response in a subject using the composition of claim 1.

22. A method of using a composition of claim 1 for transfecting cells.

* * * * *